US012205677B2

(12) United States Patent
Oved et al.

(10) Patent No.: US 12,205,677 B2
(45) Date of Patent: Jan. 21, 2025

(54) SYSTEM AND METHOD FOR ANALYSIS OF BIOLOGICAL DATA

(71) Applicant: MeMed Diagnostics Ltd., Tirat HaCarmel (IL)

(72) Inventors: Kfir Oved, Hof HaCarmel (IL); Eran Eden, Haifa (IL); Roy Navon, Tel-Aviv (IL); Assaf Cohen-Dotan, Natania (IL); Gali Kronenfeld, Tirat Carmel (IL); Olga Boico, Haifa (IL)

(73) Assignee: MeMed Diagnostics Ltd., Tirat HaCarmel (IL)

( * ) Notice: Subject to any disclaimer, the term of this patent is extended or adjusted under 35 U.S.C. 154(b) by 1296 days.

(21) Appl. No.: 16/324,562

(22) PCT Filed: Aug. 10, 2017

(86) PCT No.: PCT/IL2017/050886
§ 371 (c)(1),
(2) Date: Feb. 10, 2019

(87) PCT Pub. No.: WO2018/029690
PCT Pub. Date: Feb. 15, 2018

(65) Prior Publication Data

US 2019/0180846 A1 Jun. 13, 2019

Related U.S. Application Data

(60) Provisional application No. 62/372,820, filed on Aug. 10, 2016.

(51) Int. Cl.
*G16B 40/20* (2019.01)
*G01N 33/569* (2006.01)
*G16H 10/40* (2018.01)

(52) U.S. Cl.
CPC ........... *G16B 40/20* (2019.02); *G01N 33/569* (2013.01); *G01N 2333/4737* (2013.01); *G01N 2333/91091* (2013.01); *G16H 10/40* (2018.01)

(58) Field of Classification Search
None
See application file for complete search history.

(56) References Cited

U.S. PATENT DOCUMENTS

| | | | |
|---|---|---|---|
| 8,021,836 | B2 | 9/2011 | Kolopp-Sarda et al. |
| 8,507,210 | B2 | 8/2013 | Bergmann et al. |
| 2005/0227223 | A1 | 10/2005 | Miyawaki |
| 2013/0196310 | A1 | 8/2013 | Sambursky et al. |

FOREIGN PATENT DOCUMENTS

| | | | |
|---|---|---|---|
| CN | 101410715 | 4/2009 | |
| CN | 103119444 | 5/2013 | |
| CN | 104204803 | 12/2014 | |
| WO | WO2011132086 | * 10/2011 | |
| WO | WO 2013/117746 | 8/2013 | |
| WO | WO2016024278 | * 2/2016 | ............... G09G 5/18 |
| WO | WO 2018/029690 | 2/2018 | |

OTHER PUBLICATIONS

Notification of Office Action and Search Report Dated Sep. 22, 2021 From the State Intellectual Property Office of the People's Republic of China Re. Application No. 201780062459.6 and Its Translation of Office Action Into English. (34 Pages).

Communication Pursuant to Article 94(3) EPC Dated Oct. 29, 2020 From the European Patent Office Re. Application No. 17838930.0. (5 Pages).

Supplementary European Search Report and the European Search Opinion Dated Mar. 11, 2020 From the European Patent Office Re. Application No. 17838930.0. (7 Pages).

Halminen et al. "Expression of MxA Protein in Blood Lymphocytes Discriminates Between Viral and Bacterial Infections in Febrile Children", Pediatric Research, XP008018242, 41(5): 647-650, May 1997.

International Preliminary Report on Patentability Dated Feb. 21, 2019 From the International Bureau of WIPO Re. Application No. PCT/IL2017/050886. (9 Pages).

International Search Report and the Written Opinion Dated Nov. 23, 2017 From the International Searching Authority Re. Application No. IL/2017/ 050886. (14 Pages).

Bhowmik et al. "Relation of Sputum Inflammatory Markers to Symptoms and Lung Function Changes in COPD Exacerbations", Thorax, 55(2): 114-120, Feb. 1, 2000.

Bossuyt et al. "The STARD Statement for Reporting Studies of Diagnostic Accuracy: Explanation and Elaboration", Annals of Internal Medicine, 138(1): W1-W12, Jan. 7, 2003.

Chieux et al. "Increased Levels of Antiviral MxA Protein in Peripheral Blood of Patients With A Chronic Disease of Unknown Etiology", Journal of Medical Virology, 65(2): 301-308, Oct. 2001.

Chieux et al. "MxA Protein in Capillary Blood of Children With Viral Infections", Journal of Medical Virology, 59(4): 547-551, Dec. 1999.

Chieux et al. "The MxA Protein Levels in Whole Blood Lysates of Patients With Various Viral Infections", Journal of Virological Methods, 70(2): 183-191, Feb. 1998.

Engelmann et al. "Diagnosis of Viral Infections Using Myxovirus Resistance Protein A (MxA)", Pediatrics, 135(4): e985-e993, Apr. 2015.

Forster et al. "MxA Protein in Infants and Children With Respiratory Tract Infection", Acta Paediatrica, 85(2): 163-167, Feb. 1996.

Haller et al. "Interferon-Induced Mx Proteins: Dynamin-Like GTPases With Antiviral Activity", Traffic, 3(10): 710-717, Oct. 2002.

Hoogendoorn-Lips "Economic Impact of COPD. Empirical and Model-Based Studies on the Cost-Effectiveness of Treatment Options", Dissertation, Erasmus University Rotterdam, NL, p. 1-221, Nov. 29, 2011.

(Continued)

Primary Examiner — Ann Montgomery

(57) ABSTRACT

A method of analyzing biological data is disclosed. The method comprises obtaining biological data containing at least an expression level of MX dynamin-like GTPase 1 (MX1) and an expression level of C-reactive protein (CRP) in the blood of a subject, calculating a distance between a segment of a curved line and an axis defined by a direction, the distance being calculated at a point over the curved line defined by a coordinate along the direction, and correlating the distance to the presence of, absence of, or likelihood that the subject has, a bacterial infection.

29 Claims, 19 Drawing Sheets

Specification includes a Sequence Listing.

(56) References Cited

OTHER PUBLICATIONS

Hurst et al. "Susceptibility to Exacerbation in Chronic Obstructive Pulmonary Disease", The New England Journal of Medicine, 363(12): 1128-1138, Sep. 16, 2010.
Jakschies et al. "Strong Transient Expression of the Type I Interferon-Induced MxA Protein in Hepatitis A But Not in Acute Hepatitis B and C", Hepatology, 19(4): 857-865, Apr. 1994.
Kim et al. "Airway Wall Thickness Is Increased in COPD Patients With Bronchodilator Responsiveness", Respiratory Research, 15(84): 1-9, Aug. 8, 2014.
Lin et al. "Mannose-Binding Lectin Gene Polymorphism Contributes to Recurrence of Infective Exacerbation in Patients With COPD", Chest, 139(1): 43-51, Jan. 2011.
Molyneaux et al. "Outgrowth of the Bacterial Airway Microbiome After Rhinovirus Exacerbation of Chronic Obstructive Pulmonary Disease", American Journal of Respiratory and Critical Care Medicine, 188(10): 1224-1231, Nov. 15, 2013.
Nakabayashi et al. "MxA-Based Recognition of Viral Illness in Febrile Children by A Whole Blood Assay", Pediatric Research, 60(6): 770-774, Published Online Oct. 25, 2006.
Oved et al. "A Novel Host-Proteome Signature for Distinguishing Between Acute Bacterial and Viral Infections", PLOS ONE, 10(3): e0120012-1-e0120012-18, Mar. 18, 2015.
Rutjes et al. "Evaluation of Diagnostic Test When There Is No Gold Standard. A Review of Methods", Health Technology Assessment, 11(50): Executive Summary, 4 P., Dec. 2007.
Salvi "The Silent Epidemic of COPD in Africa", The Lancet, 3(1): e6-e7, Jan. 2015.
Sambursky et al. "Evaluation of A Combined MxA and CRP Point-of-Care Immunoassay to Identify Viral and/or Bacterial Immune Response in Patients With Acute Febrile Respiratory Infection", European Clinical Respiratory Journal, 2: 28245-1-28245-9, Dec. 10, 2015.
Sethi et al. "New Strains of Bacteria and Exacerbations of Chronic Obstructive Pulmonary Disease", The New England Journal of Medicine, 347(7): 465-471, Aug. 15, 2002.
Taylor et al. "Defective Macrophage Phagocytosis of Bacteria in COPD", European Respiratory Journal, 35(5): 1039-1047, Published Online Nov. 6, 2009.
Toivonen et al. "Blood MxA Protein as A Marker for Respiratory Virus Infections in Young Children", Journal of Clinical Virology, 62: 8-13, Published Online Nov. 18, 2014.
Wirth et al. "Post-Translational Modification Detection Using Metastable Ions in Refelctor Matrix-Assisted Laser Desorption/Ionization-Time of Flight Mass Spectrometry", Proteomics, 2(10): 1445-1451, Oct. 2002.
Woodhead et al. "Guidelines for the Management of Adult Lower Respiratory Tract Infections—Full Version", Clinial Microbiology and Infection, 17(Suppl.6): E1-E59, Nov. 1, 2011.
Xu et al. "Lipocalins as Biochemical Markers of Disease", Biochimica et Biophysica Acta, 1482(1): 298-307, Oct. 18, 2000.
Zhang et al. "The Accuracy of Presepsin (sCD14-ST) for the Diagnosis of Sepsis in Adults: A Meta-Analysis", Critical Care, 19(323): 1-11, Sep. 11, 2015.
European Search Report (Rule 61 EPC) Dated Jun. 8, 2022 From the European Patent Office Re. Application No. 22161612.1. (7 Pages).

* cited by examiner

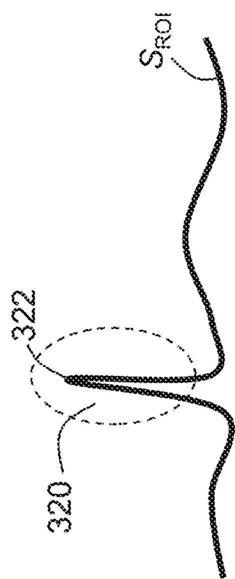
FIG. 12A
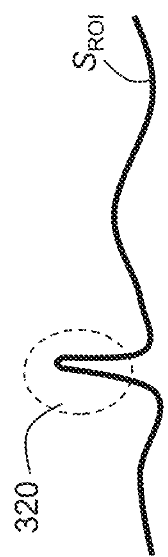
FIG. 12B
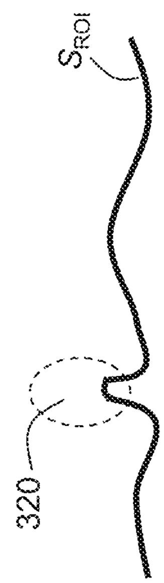
FIG. 12C
FIG. 12D

SEQUENCE LISTING

```
<160> NUMBER OF SEQ ID NOS: 42

<210> SEQ ID NO 1
<211> LENGTH: 1953
<212> TYPE: DNA
<213> ORGANISM: Homo sapiens

<400> SEQUENCE: 1

acagaaccca gaaaaacaac tcattcgctt tcatttcctc actgactata aaagaataga     60

gaaggaaggg cttcagtgac cggctgcctg gctgacttac agcagtcaga ctctgacagg    120

atcatggcta tgatggaggt ccagggggga cccagcctgg gacagacctg cgtgctgatc    180

gtgatcttca cagtgctcct gcagtctctc tgtgtggctg taacttacgt gtactttacc    240

aacgagctga agcagatgca ggacaagtac tccaaaagtg gcattgcttg tttcttaaaa    300

gaagatgaca gttattggga ccccaatgac gaagagagta tgaacagccc ctgctggcaa    360

gtcaagtggc aactccgtca gctcgttaga aagatgattt tgagaacctc tgaggaaacc    420
```

```
atttctacag ttcaagaaaa gcaacaaaat atttctcccc tagtgagaga aagaggtcct    480

cagagagtag cagctcacat aactgggacc agaggaagaa gcaacacatt gtcttctcca    540

aactccaaga atgaaaaggc tctgggccgc aaaataaact cctgggaatc atcaaggagt    600

gggcattcat tcctgagcaa cttgcacttg aggaatggtg aactggtcat ccatgaaaaa    660

gggtttttact acatctattc ccaaacatac tttcgatttc aggaggaaat aaaagaaaac    720

acaaagaacg acaaacaaat ggtccaatat atttacaaat acacaagtta tcctgaccct    780

atattgttga tgaaaagtgc tagaaatagt tgttggtcta aagatgcaga atatggactc    840

tattccatct atcaaggggg aatatttgag cttaaggaaa atgacagaat tttgtttct    900

gtaacaaatg agcacttgat agacatggac catgaagcca gtttttttgg ggcctttta    960

gttggctaac tgacctggaa agaaaaagca ataacctcaa agtgactatt cagttttcag   1020

gatgatacac tatgaagatg tttcaaaaaa tctgaccaaa acaaacaaac agaaaacaga   1080

aaacaaaaaa acctctatgc aatctgagta gagcagccac aaccaaaaaa ttctacaaca   1140

cacactgttc tgaaagtgac tcacttatcc caagagaatg aaattgctga aagatctttc   1200

aggactctac ctcatatcag tttgctagca gaaatctaga agactgtcag cttccaaaca   1260

ttaatgcaat ggttaacatc ttctgtcttt ataatctact ccttgtaaag actgtagaag   1320

aaagagcaac aatccatctc tcaagtagtg tatcacagta gtagcctcca ggtttcctta   1380

agggacaaca tccttaagtc aaaagagaga agaggcacca ctaaaagatc gcagtttgcc   1440

tggtgcagtg gctcacacct gtaatcccaa cattttggga acccaaggtg ggtagatcac   1500

gagatcaaga gatcaagacc atagtgacca acatagtgaa accccatctc tactgaaagt   1560

acaaaaatta gctgggtgtg ttggcacatg cctgtagtcc cagctacttg agaggctgag   1620

gcaagagaat tgtttgaacc cgggaggcag aggttgcagt gtggtgagat catgccacta   1680

cactccagcc tggcgacaga gcgagacttg gtttcaaaaa aaaaaaaaaa aaaaacttca   1740

gtaagtacgt gttatttttt tcaataaaat tctattacag tatgtcatgt ttgctgtagt   1800

gctcatattt attgttgttt ttgttttagt actcacttgt ttcataatat caagattact   1860

aaaaatgggg gaaaagactt ctaatctttt tttcataata tctttgacac atattacaga   1920

agaaataaat ttcttacttt taatttaata tga                                1953
```

```
<210> SEQ ID NO 2
<211> LENGTH: 1805
<212> TYPE: DNA
<213> ORGANISM: Homo sapiens

<400> SEQUENCE: 2
```

```
acagaaccca gaaaaacaac tcattcgctt tcatttcctc actgactata aaagaataga     60

gaaggaaggg cttcagtgac cggctgcctg gctgacttac agcagtcaga ctctgacagg    120

atcatggcta tgatggaggt ccaggggggga cccagcctgg gacagacctg cgtgctgatc    180

gtgatcttca cagtgctcct gcagtctctc tgtgtggctg taacttacgt gtactttacc    240

aacgagctga agcagatgca ggacaagtac tccaaaagtg gcattgcttg tttcttaaaa    300

gaagatgaca gttattggga ccccaatgac gaagagagta tgaacagccc ctgctggcaa    360

gtcaagtggc aactccgtca gctcgttaga aagactccaa gaatgaaaag gctctgggcc    420

gcaaaataaa ctcctgggaa tcatcaagga gtgggcattc attcctgagc aacttgcact    480

tgaggaatgg tgaactggtc atccatgaaa aagggtttta ctacatctat tcccaaacat    540
```

```
actttcgatt tcaggaggaa ataaaagaaa acacaaagaa cgacaaacaa atggtccaat     600

atatttacaa atacacaagt tatcctgacc ctatattgtt gatgaaaagt gctagaaata     660

gttgttggtc taaagatgca gaatatggac tctattccat ctatcaaggg ggaatatttg     720

agcttaagga aaatgacaga atttttgttt ctgtaacaaa tgagcacttg atagacatgg     780

accatgaagc cagttttttt ggggcctttt tagttggcta actgacctgg aaagaaaaag     840

caataacctc aaagtgacta ttcagttttc aggatgatac actatgaaga tgtttcaaaa     900

aatctgacca aaacaaacaa acagaaaaca gaaaacaaaa aaacctctat gcaatctgag     960

tagagcagcc acaaccaaaa aattctacaa cacacactgt tctgaaagtg actcacttat    1020

cccaagagaa tgaaattgct gaaagatctt tcaggactct acctcatatc agtttgctag    1080

cagaaatcta gaagactgtc agcttccaaa cattaatgca atggttaaca tcttctgtct    1140

ttataatcta ctccttgtaa agactgtaga agaaagagca acaatccatc tctcaagtag    1200

tgtatcacag tagtagcctc caggtttcct taagggacaa catccttaag tcaaaagaga    1260

gaagaggcac cactaaaaga tcgcagtttg cctggtgcag tggctcacac ctgtaatccc    1320

aacattttgg gaacccaagg tgggtagatc acgagatcaa gagatcaaga ccatagtgac    1380

caacatagtg aaaccccatc tctactgaaa gtacaaaaat tagctgggtg tgttggcaca    1440

tgcctgtagt cccagctact tgagaggctg aggcaagaga attgtttgaa cccgggaggc    1500

agaggttgca gtgtggtgag atcatgccac tacactccag cctggcgaca gagcgagact    1560

tggtttcaaa aaaaaaaaaa aaaaaaactt cagtaagtac gtgttatttt tttcaataaa    1620

attctattac agtatgtcat gtttgctgta gtgctcatat ttattgttgt ttttgtttta    1680

gtactcactt gtttcataat atcaagatta ctaaaaatgg gggaaaagac ttctaatctt    1740

tttttcataa tatctttgac acatattaca gaagaaataa atttcttact tttaatttaa    1800

tatga                                                                1805
```

<210> SEQ ID NO 3
<211> LENGTH: 1334
<212> TYPE: DNA
<213> ORGANISM: Homo sapiens

<400> SEQUENCE: 3

```
atttcctcac tgactataaa agaatagaga aggaagggct tcagtgaccg gctgcctggc      60

tgacttacag cagtcagact ctgacaggat catggctatg atggaggtcc aggggggacc     120

cagcctggga cagacctgcg tgctgatcgt gatcttcaca gtgctcctgc agtctctctg     180

tgtggctgta acttacgtgt actttaccaa cgagctgaag cagtttgcag aaaatgattg     240

ccagagacta atgtctgggc agcagacagg gtcattgctg ccatcttgaa gtctaccttg     300

ctgagtctac cctgctgacc tcaagcccca tcaaggactg gttgaccctg gcctagacaa     360

ccaccgtgtt tgtaacagca ccaagagcag tcaccatgga aatccacttt tcagaaccaa     420

gggcttctgg agctgaagaa caggcaccca gtgcaagagc tttcttttca gaggcacgca     480

aatgaaaata atccccacac gctaccttct gcccccaatg cccaagtgtg gttagttaga     540

gaatatagcc tcagcctatg atatgctgca ggaaactcat attttgaagt ggaaaggatg     600

ggaggaggcg ggggagacgt atcgtattaa ttatcattct tggaataacc acagcacctc     660

acgtcaaccc gccatgtgtc tagtcaccag cattggccaa gttctatagg agaaactacc     720

aaaattcatg atgcaagaaa catgtgaggg tggagagagt gactggggct tcctctctgg     780

atttctattg ttcagaaatc aatatttatg cataaaaagg tctagaaaga gaaacaccaa     840
```

```
aatgacaatg tgatctctag atggtatgat tatgggtact tttttccctt tttatttttc    900

tatattttac aaattttcta cagggaatgt tataaaaata tccatgctat ccatgtataa    960

ttttcataca gatttaaaga acacagcatt tttatatagt cttatgagaa aacaaccata   1020

ctcaaaatta tgcacacaca cagtctgatc tcacccctgt aaacaagaga tatcatccaa   1080

aggttaagta ggaggtgaga atatagctgc tattagtggt tgttttgttt tgtttttgtg   1140

atttacttat ttagtttttg gagggttttt tttttctttt agaaaagtgt tctttacttt   1200

tccatgcttc cctgcttgcc tgtgtatcct gaatgtatcc aggctttata aactcctggg   1260

taataatgta gctacattaa cttgttaacc tcccatccac ttatacccag gaccttactc   1320

aattttccag gttc                                                     1334
```

```
<210> SEQ ID NO 4
<211> LENGTH: 281
<212> TYPE: PRT
<213> ORGANISM: Homo sapiens

<400> SEQUENCE: 4

Met Ala Met Met Glu Val Gln Gly Gly Pro Ser Leu Gly Gln Thr Cys
1               5                   10                  15

Val Leu Ile Val Ile Phe Thr Val Leu Leu Gln Ser Leu Cys Val Ala
            20                  25                  30

Val Thr Tyr Val Tyr Phe Thr Asn Glu Leu Lys Gln Met Gln Asp Lys
        35                  40                  45

Tyr Ser Lys Ser Gly Ile Ala Cys Phe Leu Lys Glu Asp Asp Ser Tyr
    50                  55                  60

Trp Asp Pro Asn Asp Glu Glu Ser Met Asn Ser Pro Cys Trp Gln Val
65                  70                  75                  80

Lys Trp Gln Leu Arg Gln Leu Val Arg Lys Met Ile Leu Arg Thr Ser
                85                  90                  95

Glu Glu Thr Ile Ser Thr Val Gln Glu Lys Gln Gln Asn Ile Ser Pro
            100                 105                 110

Leu Val Arg Glu Arg Gly Pro Gln Arg Val Ala Ala His Ile Thr Gly
        115                 120                 125

Thr Arg Gly Arg Ser Asn Thr Leu Ser Ser Pro Asn Ser Lys Asn Glu
    130                 135                 140

Lys Ala Leu Gly Arg Lys Ile Asn Ser Trp Glu Ser Ser Arg Ser Gly
145                 150                 155                 160

His Ser Phe Leu Ser Asn Leu His Leu Arg Asn Gly Glu Leu Val Ile
                165                 170                 175

His Glu Lys Gly Phe Tyr Tyr Ile Tyr Ser Gln Thr Tyr Phe Arg Phe
            180                 185                 190

Gln Glu Glu Ile Lys Glu Asn Thr Lys Asn Asp Lys Gln Met Val Gln
        195                 200                 205

Tyr Ile Tyr Lys Tyr Thr Ser Tyr Pro Asp Pro Ile Leu Leu Met Lys
    210                 215                 220

Ser Ala Arg Asn Ser Cys Trp Ser Lys Asp Ala Glu Tyr Gly Leu Tyr
225                 230                 235                 240

Ser Ile Tyr Gln Gly Gly Ile Phe Glu Leu Lys Glu Asn Asp Arg Ile
                245                 250                 255
```

```
Phe Val Ser Val Thr Asn Glu His Leu Ile Asp Met Asp His Glu Ala
            260                 265                 270

Ser Phe Phe Gly Ala Phe Leu Val Gly
        275                 280


<210> SEQ ID NO 5
<211> LENGTH: 101
<212> TYPE: PRT
<213> ORGANISM: Homo sapiens

<400> SEQUENCE: 5

Met Ala Met Met Glu Val Gln Gly Gly Pro Ser Leu Gly Gln Thr Cys
1               5                   10                  15

Val Leu Ile Val Ile Phe Thr Val Leu Leu Gln Ser Leu Cys Val Ala
            20                  25                  30

Val Thr Tyr Val Tyr Phe Thr Asn Glu Leu Lys Gln Met Gln Asp Lys
        35                  40                  45

Tyr Ser Lys Ser Gly Ile Ala Cys Phe Leu Lys Glu Asp Asp Ser Tyr
    50                  55                  60

Trp Asp Pro Asn Asp Glu Glu Ser Met Asn Ser Pro Cys Trp Gln Val
65                  70                  75                  80

Lys Trp Gln Leu Arg Gln Leu Val Arg Lys Thr Pro Arg Met Lys Arg
                85                  90                  95

Leu Trp Ala Ala Lys
            100


<210> SEQ ID NO 6
<211> LENGTH: 65
<212> TYPE: PRT
<213> ORGANISM: Homo sapiens

<400> SEQUENCE: 6

Met Ala Met Met Glu Val Gln Gly Gly Pro Ser Leu Gly Gln Thr Cys
1               5                   10                  15

Val Leu Ile Val Ile Phe Thr Val Leu Leu Gln Ser Leu Cys Val Ala
            20                  25                  30

Val Thr Tyr Val Tyr Phe Thr Asn Glu Leu Lys Gln Phe Ala Glu Asn
        35                  40                  45

Asp Cys Gln Arg Leu Met Ser Gly Gln Gln Thr Gly Ser Leu Leu Pro
    50                  55                  60

Ser
65


<210> SEQ ID NO 7
<211> LENGTH: 223
<212> TYPE: PRT
<213> ORGANISM: Homo sapiens

<400> SEQUENCE: 7

Gln Asp His Gly Tyr Asp Gly Gly Pro Gly Gly Thr Gln Pro Gly Thr
1               5                   10                  15

Asp Leu Arg Ala Asp Arg Asp Leu His Ser Ala Pro Ala Val Ser Leu
            20                  25                  30

Cys Gly Cys Asn Leu Arg Val Leu Tyr Gln Arg Ala Glu Ala Glu Lys
        35                  40                  45

Gln Gln Asn Ile Ser Pro Leu Val Arg Glu Arg Gly Pro Gln Arg Val
    50                  55                  60
```

```
Ala Ala His Ile Thr Gly Thr Arg Gly Arg Ser Asn Thr Leu Ser Ser
65                  70                  75                  80

Pro Asn Ser Lys Asn Glu Lys Ala Leu Gly Arg Lys Ile Asn Ser Trp
                85                  90                  95

Glu Ser Ser Arg Ser Gly His Ser Phe Leu Ser Asn Leu His Leu Arg
            100                 105                 110

Asn Gly Glu Leu Val Ile His Glu Lys Gly Phe Tyr Tyr Ile Tyr Ser
        115                 120                 125

Gln Thr Tyr Phe Arg Phe Gln Glu Glu Ile Lys Glu Asn Thr Lys Asn
    130                 135                 140

Asp Lys Gln Met Val Gln Tyr Ile Tyr Lys Tyr Thr Ser Tyr Pro Asp
145                 150                 155                 160

Pro Ile Leu Leu Met Lys Ser Ala Arg Asn Ser Cys Trp Ser Lys Asp
                165                 170                 175

Ala Glu Tyr Gly Leu Tyr Ser Ile Tyr Gln Gly Gly Ile Phe Glu Leu
            180                 185                 190

Lys Glu Asn Asp Arg Ile Phe Val Ser Val Thr Asn Glu His Leu Ile
        195                 200                 205

Asp Met Asp His Glu Ala Ser Phe Phe Gly Ala Phe Leu Val Gly
    210                 215                 220


<210> SEQ ID NO 8
<211> LENGTH: 178
<212> TYPE: PRT
<213> ORGANISM: Homo sapiens

<400> SEQUENCE: 8

Lys Glu Lys Gln Gln Asn Ile Ser Pro Leu Val Arg Glu Arg Gly Pro
1               5                   10                  15

Gln Arg Val Ala Ala His Ile Thr Gly Thr Arg Gly Arg Ser Asn Thr
            20                  25                  30

Leu Ser Ser Pro Asn Ser Lys Asn Glu Lys Ala Leu Gly Arg Lys Ile
        35                  40                  45

Asn Ser Trp Glu Ser Ser Arg Ser Gly His Ser Phe Leu Ser Asn Leu
    50                  55                  60

His Leu Arg Asn Gly Glu Leu Val Ile His Glu Lys Gly Phe Tyr Tyr
65                  70                  75                  80

Ile Tyr Ser Gln Thr Tyr Phe Arg Phe Gln Glu Glu Ile Lys Glu Asn
                85                  90                  95

Thr Lys Asn Asp Lys Gln Met Val Gln Tyr Ile Tyr Lys Tyr Thr Ser
            100                 105                 110

Tyr Pro Asp Pro Ile Leu Leu Met Lys Ser Ala Arg Asn Ser Cys Trp
        115                 120                 125

Ser Lys Asp Ala Glu Tyr Gly Leu Tyr Ser Ile Tyr Gln Gly Gly Ile
    130                 135                 140

Phe Glu Leu Lys Glu Asn Asp Arg Ile Phe Val Ser Val Thr Asn Glu
145                 150                 155                 160

His Leu Ile Asp Met Asp His Glu Ala Ser Phe Phe Gly Ala Phe Leu
                165                 170                 175

Val Gly


<210> SEQ ID NO 9
<211> LENGTH: 2421
<212> TYPE: DNA
<213> ORGANISM: Homo sapiens
```

<400> SEQUENCE: 9

```
caccctcatg agccccgggt acgtttaact attgagggcc aggaaattgc cttcctcctg     60
gacactggcg cagccttctc agggttaatc tcctgtcctg gatgactgtc ttcaaggtcc    120
gttaccaccc gaggaatcct gggacagcct ataaccaggt atttctccca catcctcagt    180
tgtaattgag agactttaat cttttcacat gccttttttg ttattcctga aagtcccaca    240
cccttattaa ggagggatat attagccaag gctggagcta ttatctacat gaatatgggg    300
aaaaagttac ccatttgctg tcccctactt gaggagggaa tcaaccctga agtctgggca    360
ttggaaggac aatttggaag ggcaaaaaat gcctgcccag tccaaatcag gttaaaagat    420
cccaccactt ttccgtatca aaggcaatat cccttaaggc ctgaagctca taaaggatta    480
tagaatattg ttaaacattt aaaagctcaa ggcttagtga ggaaatgcag cagtccctgc    540
aacaccccag ttctaggagt acaaaaacca aacagtcagt ggagactagt gcaagatctt    600
agactcatta atgaggcagt aattcctcta tatccagttg tacccaaccc ctataccctg    660
ctctctcaaa taccagggga agcagaatgg ttcacggttc tggacctcaa ggatgccttc    720
ttctttattc ccctgcactc tgactcccag tttctctttg cttttgagga tcccacagac    780
cacacgtccc aacttacaca gatggtcttg ccccaagggt ttagggatag ccctcatctg    840
tttggtcagg cactggccca agatctatag gccacttctc aagtccaggc actctggtcc    900
ttcaatatgt ggatgattta cttttggcta ccagtttgga agcctcgtgc cagcaggcta    960
ctctggatct cttgaacttt ctggctaatc aagggtacaa ggtgtctagg tcgaaggccc   1020
agctttgcct acagcaggtt aaatatctaa gcctaatctt agccaaaggg accagggccc   1080
tcagcaagga atgaatacag cctatactgg cttatcctca ccctaagaca ttaaaacagt   1140
tgcggggatt ccttggaatt actggctttt gctgactatg gatctccaga tacagcgaga   1200
cagccaggcc cctctatact ctaatcaagg aaacccagag ggcaaatact catctagtcg   1260
aaagggaacc agaggcagaa acagccttca aaagcttaaa gcaggctcta gtacaagctc   1320
cagctttaag ccttcccaca ggacagaact tctctttata catcacagag agagccaaga   1380
tagctcttgg agtccttaga ctcgtgggac aaccccacaa ccagtggcat acctaagtaa   1440
ggaaattgat gtagtagcaa aaggctggcc tcactgttta agggtagttg cagcagcggc   1500
cgtcttagcg tcagaggcta tcagaataat acaaggaaag gatctcactg tctggactac   1560
tcatgatgta aatggcatac taggtgccaa aggaagttta tggctatcag acaaccgcct   1620
cttagatgcc aggcactact ccttgaggga ctggtgctta aaatatgcac gtgcgtggcc   1680
ctcaaccctg ccacttttct cccagaggat ggggaaccaa ttgagcatga ctgccaacaa   1740
attatagtcc agacttatgc cgcccgagat gatctcttag aagtcccctt aactaatcct   1800
gaccttaacc tatataccga cggaagttca tttgtggaga atgggatacg aagggcaggt   1860
tacgccatag tgatgtaacc acacttgaaa gcaagcctct tcccccaggg accagtgccc   1920
agttagcaga actagtggca cttacccgag ccttagaact gggaaaggga aaaagaataa   1980
atgtgtatac agataacaag tatgcttatc taatcctaca tgcccatgct gcaatatgga   2040
aagaatggga gttcctaacc tctgggaacc cccgctggat gccacaggga agttatggag   2100
ttattgcaca tggtgcagga acccaaagag gtgggagtct tacactacca aggccatcaa   2160
aatgggaagg agaggggaga acagcagcat aagcggctgg cagaggtagg gaaagaccag   2220
caagaaggaa agagagaaag agaaagtcag agaaagagac agagagagga agagacagag   2280
agacagaacg ttaaagaggg tgtcagaaac agagacaaac aaaaggagtc agaaagaagg   2340
```

acagacacag aaagtcaaag agagagttaa aaagagagga agagacaaag aagtcgaaga 2400
gagaaagaga gagatggaag t 2421

<210> SEQ ID NO 10
<211> LENGTH: 2421
<212> TYPE: DNA
<213> ORGANISM: Homo sapiens

<400> SEQUENCE: 10
ctttgcagat aaatatggca cactagcccc acgttttctg agacattcct caattgctta 60
gacatattct gagcctacag cagaggaacc tccagtctca gcaccatgaa tcaaactgcc 120
attctgattt gctgccttat ctttctgact ctaagtggca ttcaaggtaa ggaacatcaa 180
aggatactta atttgtaaaa tgagaaatag gaataggtat aaattctaaa aatacagaaa 240
taatgtattt gtaaaagttt cactgcatgc ttataaataa gagggaaata aatagagatt 300
ccctcagatc ataaaactta tatgaattga agtgagagaa acaaatagaa taagagaaag 360
agaaggaaaa agggaaggag gacagaagag atggggaaga gggaggatag agagagaaaa 420
tgtgagggaa tgcggacaga gatgagatac agatacttcc ttacctaact aagctcaatg 480
aaccacatga actgtgctta agggtttgac tttataatca acaagctgca attcttttct 540
tccagataat caactcttta atcatttaca gttgtgttat gatgtgatcc attcctcctc 600
agattaagtg actatttgct gatatgggga tataggttct gctaaatacc accagtctac 660
attaaatgcc taaaatgaac actgtgctaa ccttctctgc tgttcctctt ttcctacagg 720
agtacctctc tctagaactg tacgctgtac ctgcatcagc attagtaatc aacctgttaa 780
tccaaggtct ttagaaaaac ttgaaattat tcctgcaagc caattttgtc cacgtgttga 840
gatcatgtga gtgaaatccc atctgattat cacttccctg gttgtaatta tatactgtat 900
taaatatgta atgataataa aaaaagatca gtaaagggtt tgtgatgatt ctaaaactaa 960
tgtacagcaa acaaaaacat gcagagtgaa acttaaatgt ctgacttcag aactgcgtat 1020
gccatctgtt ttattgaccc aacacagttt taaatatttt catccctatt tatttctaca 1080
gtgctacaat gaaaaagaag ggtgagaaga gatgtctgaa tccagaatcg aaggccatca 1140
agaatttact gaaagcagtt agcaaggaaa ggtaggtttg ctgttgcctg cagaagaatt 1200
gctctttagg aaacggcaat cttgggagtc agaaatactt gcattgtggt ttgctgtgca 1260
atcgctggtt taaaagtatg ttaccaccac gccctcccct acctccattt atttaaatgc 1320
tgaggcacca tcttgtgtga taagtatcag aagttaccct gattaccagt caaccttgaa 1380
gtacagctat aactatctaa gcaaaactga caacattttc cccaagtctt tcatggttga 1440
aaaaagcaac ccctataatc cataatgaat gcatagcagc aggaaagctc agttatctat 1500
tctatgaact cggtactttc caaacacaac ccaatctgaa gccagagtca gactatcaca 1560
cttttatatc ccctttctct tcttacaggt ctaaaagatc tccttaaaac cagaggggag 1620
caaaatcgat gcagtgcttc caaggatgga ccacacagag gctgcctctc ccatcacttc 1680
cctacatgga gtatatgtca agccataatt gttcttagtt tgcagttaca ctaaaaggtg 1740
accaatgatg gtcaccaaat cagctgctac tactcctgta ggaaggttaa tgttcatcat 1800
cctaagctat tcagtaataa ctctaccctg gcactataat gtaagctcta ctgaggtgct 1860
atgttcttag tggatgttct gaccctgctt caaatatttc cctcaccttt cccatcttcc 1920
aagggtacta aggaatcttt ctgctttggg gtttatcaga attctcagaa tctcaaataa 1980

```
ctaaaaggta tgcaatcaaa tctgcttttt aaagaatgct ctttacttca tggacttcca   2040

ctgccatcct cccaaggggc ccaaattctt tcagtggcta cctacataca attccaaaca   2100

catacaggaa ggtagaaata tctgaaaatg tatgtgtaag tattcttatt taatgaaaga   2160

ctgtacaaag tagaagtctt agatgtatat atttcctata ttgttttcag tgtacatgga   2220

ataacatgta attaagtact atgtatcaat gagtaacagg aaaattttaa aaatacagat   2280

agatatatgc tctgcatgtt acataagata aatgtgctga atggttttca aaataaaaat   2340

gaggtactct cctggaaata ttaagaaaga ctatctaaat gttgaaagat caaaaggtta   2400

ataaagtaat tataactaag a                                             2421


<210> SEQ ID NO 11
<211> LENGTH: 2421
<212> TYPE: DNA
<213> ORGANISM: Homo sapiens

<400> SEQUENCE: 11

agatgacttt tttctattta tatttaataa gatgatgaac ccttcttgca ttcccgaaat     60

aaacctcaac tgttacagtg ttttattctt ttaatatgta cgaagtacat gttaagcaag    120

ttatttccta agcagcccca caaactgggc actactacca tcctgctctg cccctccctc    180

actctacttc agccacttca gccacaatgg cctctcctca ctgcccctct gatgcaccaa    240

gcttgttctc acctcaggaa tgtgcaacac ctgccagact tgctgttccc cggagcctcc    300

atccccagat atcctcatat atcatcctcc tcttcatttg tgtctctgct tacatatgac    360

ctatttacag aagcctttcc tgtctacccc ccatgaaata gaaatcgcat tccaatcttg    420

tctctacccc aatgctgttt cattttgtct gtagcaattg tcatcatctc atatatattc    480

acatgtggaa aatacacaaa atgtttaact tcttttaatt tacattccat ttccccatga    540

attgaagctc catgacagcg gagatttttc tctgctttcc ctgttgctca cttcccagca    600

ccaagagcag gcctggcaca tgggaagtac ttactattta ttgaatggat gaatgaacaa    660

atgaatgaat ggatacttat tttacacata agaaaactga agcttataga aattaagtaa    720

ctaaaatcac acagaagcac agctgaaact aaaacctacg tctaactttc aattcctgac    780

ccttaaccat taaaacaaat gacaggtgac tttaggccac tgaaaatgct catataatct    840

tatgaattct aaagcacaag ttaatcacac cattgattga aagtctgagg aatactgtat    900

agacaagccc ctgtacaagg taagcaaaag aatcagagga tggcctccaa agaattccct    960

ggacattatg ggaattacat tgttagcctt cctactgata cccataagcc tcacagcaag   1020

catcatgaag ctgtgacctt catctgcaca tgcccttgta tacccaaaag ataaaactgg   1080

atgcttcagg gccgaatggc caataaacac gtgtttatta ctggcatggg cagacacaca   1140

tactgaaagt accatttccc agcggactag ccatattatg atcagtacag acactaaaga   1200

tttagctttg aaaaaactat ttgctcttcc aaagctgaag aatcttctgt gatttcaaca   1260

ggcaagttac agtcaggtat tcttaatgtt cttttcctcc tctctcactg ggatactttc   1320

tttccttcag acaacgtcaa gcgaaaaaca aaatttcaca aatctccatt tctgacacta   1380

aacagtacag tatctttatt ttttttataa tttaatcaaa ccctgtattt tagaactgtg   1440

gggctgatcc aacattgcaa tgtgtcacat ttaattccat caatgtaaag cataatgagc   1500

aaagattaag gtagtgaggc ataactaaat gttttgaacc tgtgaatttc aaaagcaagg   1560

cccatttgtg ttattttcta aatagtaaat aaaatcattt tccaacattt cactatcaaa   1620

ttacagtaat ttttccacca gtacacactt gaggaaagcc acaaaaagac ttttccaaca   1680
```

```
gttcattctg ttattgctca taaccttcta aatacttctc ctcattggct tctattcaaa   1740

ggtaaatgga aagcagtaaa atttatggaa aatatattca actgcttaaa atacatcaac   1800

caaaaaaaag attttagagc tgtattatga gttgtgaaat tgcattgcct tcacttacct   1860

ttcagtttca ctggtaggta acaaaactga cagactggtc aagttccaaa acatccccta   1920

tatagagcct gactcttcca tctcaaattc tcaccttggt caaggccaga gtaaacacct   1980

gtccttcaca tttttacaca acatcacttt gtatgctaca aatataagct ttcataccag   2040

ggaggaagca aattccagga cactggaaac atttctgctc tcttaaacca gtctgttgat   2100

tgttcccttg actttctcag ctgtcaggat agtgaaagga ggaaaactgc aaaactgtaa   2160

agtataacct gataagtttg ccctttaagc ttttcacaca gagagaggta aaataaaact   2220

caagtctaag gtttaaaatt gagctatgaa tattatattc tagcactaga caaaaatgtt   2280

gcaagatttt aataaaataa gattattaaa atcaattttt acatttcatg ggccaaggag   2340

agacatcaaa gaatgtttaa ctaacatttt aaagatacta tactttataa agttaagaag   2400

aaaaatgaca actgcaccag t                                             2421
```

<210> SEQ ID NO 12
<211> LENGTH: 1227
<212> TYPE: DNA
<213> ORGANISM: Homo sapiens

<400> SEQUENCE: 12

```
ctttgcagat aaatatggca cactagcccc acgttttctg agacattcct caattgctta     60

gacatattct gagcctacag cagaggaacc tccagtctca gcaccatgaa tcaaactgcc    120

attctgattt gctgccttat ctttctgact ctaagtggca ttcaaggagt acctctctct    180

agaactgtac gctgtacctg catcagcatt agtaatcaac ctgttaatcc aaggtcttta    240

gaaaaacttg aaattattcc tgcaagccaa ttttgtccac gtgttgagat cattgctaca    300

atgaaaaaga agggtgagaa gagatgtctg aatccagaat cgaaggccat caagaattta    360

ctgaaagcag ttagcaagga aaggtctaaa agatctcctt aaaaccagag gggagcaaaa    420

tcgatgcagt gcttccaagg atggaccaca cagaggctgc ctctcccatc acttccctac    480

atggagtata tgtcaagcca taattgttct tagtttgcag ttacactaaa aggtgaccaa    540

tgatggtcac caaatcagct gctactactc ctgtaggaag gttaatgttc atcatcctaa    600

gctattcagt aataactcta ccctggcact ataatgtaag ctctactgag gtgctatgtt    660

cttagtggat gttctgaccc tgcttcaaat atttccctca cctttcccat cttccaaggg    720

tactaaggaa tctttctgct ttggggttta tcagaattct cagaatctca aataactaaa    780

aggtatgcaa tcaaatctgc tttttaaaga atgctcttta cttcatggac ttccactgcc    840

atcctcccaa ggggcccaaa ttctttcagt ggctacctac atacaattcc aaacacatac    900

aggaaggtag aaatatctga aaatgtatgt gtaagtattc ttatttaatg aaagactgta    960

caaagtagaa gtcttagatg tatatatttc ctatattgtt ttcagtgtac atggaataac   1020

atgtaattaa gtactatgta tcaatgagta acaggaaaat tttaaaaata cagatagata   1080

tatgctctgc atgttacata agataaatgt gctgaatggt tttcaaaata aaaatgaggt   1140

actctcctgg aaatattaag aaagactatc taaatgttga aagatcaaaa ggttaataaa   1200

gtaattataa ctaagaaaaa aaaaaaa                                       1227
```

<210> SEQ ID NO 13

<211> LENGTH: 98
<212> TYPE: PRT
<213> ORGANISM: Homo sapiens

<400> SEQUENCE: 13

```
Met Asn Gln Thr Ala Ile Leu Ile Cys Cys Leu Ile Phe Leu Thr Leu
1               5                   10                  15

Ser Gly Ile Gln Gly Val Pro Leu Ser Arg Thr Val Arg Cys Thr Cys
            20                  25                  30

Ile Ser Ile Ser Asn Gln Pro Val Asn Pro Arg Ser Leu Glu Lys Leu
        35                  40                  45

Glu Ile Ile Pro Ala Ser Gln Phe Cys Pro Arg Val Glu Ile Ile Ala
    50                  55                  60

Thr Met Lys Lys Lys Gly Glu Lys Arg Cys Leu Asn Pro Glu Ser Lys
65                  70                  75                  80

Ala Ile Lys Asn Leu Leu Lys Ala Val Ser Lys Glu Arg Ser Lys Arg
                85                  90                  95

Ser Pro
```

<210> SEQ ID NO 14
<211> LENGTH: 2301
<212> TYPE: DNA
<213> ORGANISM: Homo sapiens

<400> SEQUENCE: 14

```
aaggcaagag atctaggact tctagcccct gaactttcag ccgaatacat cttttccaaa     60

ggagtgaatt caggcccttg tatcactggc agcaggacgt gaccatggag aagctgttgt    120

gtttcttggt cttgaccagc ctctctcatg cttttggcca gacaggtaag ggccacccca    180

ggctatggga gagatttgat ctgaggtatg gggtggggt ctaagactgc atgaacagtc     240

tcaaaaaaaa aaaaaaaaga ctgtatgaac agaacagtgg agcatccttc atggtgtgtg    300

tgtgtgtgtg tgtgtgtgtg tgtgtgtgtg tggtgtgtaa ctggagaagg ggtcagtctg    360

tttctcaatc ttaaattcta tacgtaagtg aggggataga tctgtgtgat ctgagaaacc    420

tctcacattt gcttgttttt ctggctcaca gacatgtcga ggaaggcttt tgtgtttccc    480

aaagagtcgg atacttccta tgtatccctc aaagcaccgt taacgaagcc tctcaaagcc    540

ttcactgtgt gcctccactt ctacacggaa ctgtcctcga cccgtgggta cagtattttc    600

tcgtatgcca ccaagagaca agacaatgag attctcatat tttggtctaa ggatatagga    660

tacagtttta cagtgggtgg gtctgaaata ttattcgagg ttcctgaagt cacagtagct    720

ccagtacaca tttgtacaag ctgggagtcc gcctcaggga tcgtggagtt ctgggtagat    780

gggaagccca gggtgaggaa gagtctgaag aagggataca ctgtgggggc agaagcaagc    840

atcatcttgg ggcaggagca ggattccttc ggtgggaact ttgaaggaag ccagtccctg    900

gtgggagaca ttggaaatgt gaacatgtgg gactttgtgc tgtcaccaga tgagattaac    960

accatctatc ttggcgggcc cttcagtcct aatgtcctga actggcgggc actgaagtat   1020

gaagtgcaag gcgaagtgtt caccaaaccc cagctgtggc cctgaggccc agctgtgggt   1080

cctgaaggta cctcccggtt ttttacaccg catgggcccc acgtctctgt ctctggtacc   1140

tcccgctttt ttacactgca tggttcccac gtctctgtct ctgggccttt gttcccctat   1200

atgcattgca ggcctgctcc accctcctca gcgcctgaga atggaggtaa agtgtctggt   1260

ctgggagctc gttaactatg ctgggaaacg gtccaaaaga atcagaattt gaggtgtttt   1320

gttttcattt ttatttcaag ttggacagat cttggagata atttcttacc tcacatagat   1380
```

```
gagaaaacta acacccagaa aggagaaatg atgttataaa aaactcataa ggcaagagct   1440

gagaaggaag cgctgatctt ctatttaatt ccccacccat gacccccaga aagcaggagg   1500

gcattgccca cattcacagg gctcttcagt ctcagaatca ggacactggc caggtgtctg   1560

gtttgggtcc agagtgctca tcatcatgtc atagaactgc tgggcccagg tctcctgaaa   1620

tgggaagccc agcaatacca cgcagtccct ccactttctc aaagcacact ggaaaggcca   1680

ttagaattgc cccagcagag cagatctgct tttttccag agcaaaatga agcactaggt    1740

ataaatatgt tgttactgcc aagaacttaa atgactggtt tttgtttgct tgcagtgctt   1800

tcttaatttt atggctcttc tgggaaactc ctcccctttt ccacacgaac cttgtggggc   1860

tgtgaattct ttcttcatcc ccgcattccc aatataccca ggccacaaga gtggacgtga   1920

accacagggt gtcctgtcag aggagcccat ctcccatctc cccagctccc tatctggagg   1980

atagttggat agttacgtgt tcctagcagg accaactaca gtcttcccaa ggattgagtt   2040

atggactttg ggagtgagac atcttcttgc tgctggattt ccaagctgag aggacgtgaa   2100

cctgggacca ccagtagcca tcttgtttgc cacatggaga gagactgtga ggacagaagc   2160

caaactggaa gtggaggagc caagggattg acaaacaaca gagccttgac cacgtggagt   2220

ctctgaatca gccttgtctg gaaccagatc tacacctgga ctgcccaggt ctataagcca   2280

ataaagcccc tgtttacttg a                                              2301
```

```
<210> SEQ ID NO 15
<211> LENGTH: 2301
<212> TYPE: DNA
<213> ORGANISM: Homo sapiens

<400> SEQUENCE: 15
```

```
aggaattgaa ctcagctctg ccccaagcgg acctaataga catctacaga actctccacc     60

ccaaatcaac agaatataca tttttttcag caccacacca cacctattcc aaaattgatc    120

acatagttgg cagtaaagct ctcctcagca aatgtaaagg aacagaaatt ataacaaact    180

atctctcaga ccacagtgca atcaaattag aactcagaat taagaatctc actcaaaacc    240

gcacaactac atggaaactg aacaacctgc ttctgaatga ctactgggta cataatgaaa    300

tgaaggcaga aataaagatg ttctttgaaa tgaacaagaa caaacacaca acataccaga    360

atctctggga cgcattcaaa gcagtgtgta gagggaaatt tatagcacta aatgcccaca    420

agagaaagca ggaaacatcc aaaattgaca tcctaacatc acagttaaaa gaactagaaa    480

agcaagagca aacacattca aaagctagca gaaggcaaga gataactaaa atcagagcag    540

aactgaagga aatagagaca caaaaaccct tcaaaaaatt aatgaatcca ggagctggtt    600

ttttgaaagg atcaacaaaa tagatagacc actagcaaga ctaataaaga aaaaaagaga    660

gaagaatcaa atagacacaa taaaaaaatg ataaagggga tatcaccacc gatcccacgg    720

aaatacaaac taccatcaga gaatactaca aacacctcta cgcaaataaa ctagaaaatc    780

aagaagaaat ggataaattc ctcgacacat acactctccc aagactaaac caggaagaag    840

ttgaatctct gaatagacca ataacaggat atgaaattgt ggcaataatc aataccttac    900

caacaaaaaa gagtccagga ccagatggat tcacagccga attctaccag aggtacaagg    960

aggaactggt accattcctt ctgaaactat tccaatcaat agaaaaagag ggaatcctcc   1020

ctaactcatt ttatgaggcc agcatcattc tgataccaaa gccgggcaga gacacaacca   1080

aaaaagagaa ttttagacca atcaatatcc ttgatgaaca ttgatgcaaa aatcctcaat   1140
```

```
aaaatactgc caaaccaaat ccagcagcac atcaaaaagc ttatccacca tgatcaagtg   1200

ggcttcatcc ctgggatgca aggctggttc aatatacgca aatcaataaa tgtaatccag   1260

catataaaca gagccaaaga caaaaaccac atgattatct caatagatgc agaaaagacc   1320

tttgacaaaa ttcaacaacc cttcatgctc aaaactctca ataaattagg tattgatggg   1380

acgtatttca aaataataag agctatctat gacaaaccca cagccaatat catactgaat   1440

gggcaaaaac tggaagtatt cactttgaaa actggcacaa gacagggatg ccctctctca   1500

ccactcctat tcaacatagt gttggaagtt ctggccaggg caattaggca ggagaaggaa   1560

ataaagggta ttcaattagg aaaagaggaa gtcaaattgt ccctgtttgc agacgacatg   1620

attgtatatc tagaaaaccc cattgtctca gcccaaaatc tccttaagca gataagcaac   1680

ttcagcaaaa tctcaggata caaaatcaat gtacaaaaat cacaagcatt cttatacacc   1740

aacaacagac aaacagagag ccaaatcatg agtgaaatcc cattcacaat tgctttaaag   1800

agaataaaat acctaggaat ccaacttaca agggatgtga aggacctctt caaggagaac   1860

tacaaaccac tgctcaatga aataaaagag gataaaaaca aatggaagaa cattccatgc   1920

tcatgggtag gaagaatcaa tatcatgaaa atggccatac tgcccaaggt aatttacaga   1980

ttcaatgcca tccccatcaa gctaccaatg cctttcttca cagaattgga aaaaactatt   2040

tttagttcat atggaaccaa aaaagagccc gcattgccaa gtcaatccta agccaaaaga   2100

acaaagctgg aggcatcaca ctacctgact tcaaactata ctacaaggct acagtaacca   2160

aaacagcatg gtactggaac caaaacagag atatagatca atggaacaga acagagccct   2220

caaaattaat gccacatatc tacaactatc tgatctttga caaacctgag aaaaaccagc   2280

aatggggaaa ggattcccca t                                             2301
```

```
<210> SEQ ID NO 16
<211> LENGTH: 2024
<212> TYPE: DNA
<213> ORGANISM: Homo sapiens

<400> SEQUENCE: 16
```

```
aaggcaagag atctaggact tctagcccct gaactttcag ccgaatacat cttttccaaa     60

ggagtgaatt caggcccttg tatcactggc agcaggacgt gaccatggag aagctgttgt    120

gtttcttggt cttgaccagc ctctctcatg cttttggcca gacagacatg tcgaggaagg    180

cttttgtgtt tcccaaagag tcggatactt cctatgtatc cctcaaagca ccgttaacga    240

agcctctcaa agccttcact gtgtgcctcc acttctacac ggaactgtcc tcgacccgtg    300

ggtacagtat tttctcgtat gccaccaaga gacaagacaa tgagattctc atattttggt    360

ctaaggatat aggatacagt tttacagtgg gtgggtctga aatattattc gaggttcctg    420

aagtcacagt agctccagta cacatttgta caagctggga gtccgcctca gggatcgtgg    480

agttctgggt agatgggaag cccagggtga ggaagagtct gaagaaggga tacactgtgg    540

gggcagaagc aagcatcatc ttggggcagg agcaggattc cttcggtggg aactttgaag    600

gaagccagtc cctggtggga gacattggaa atgtgaacat gtgggacttt gtgctgtcac    660

cagatgagat taacaccatc tatcttggcg ggcccttcag tcctaatgtc ctgaactggc    720

gggcactgaa gtatgaagtg caaggcgaag tgttcaccaa accccagctg tggccctgag    780

gcccagctgt gggtcctgaa ggtacctccc ggtttttttac accgcatggg ccccacgtct    840

ctgtctctgg tacctcccgc ttttttacac tgcatggttc ccacgtctct gtctctgggc    900

ctttgttccc ctatatgcat tgcaggcctg ctccaccctc ctcagcgcct gagaatggag    960
```

```
gtaaagtgtc tggtctggga gctcgttaac tatgctggga aacggtccaa aagaatcaga   1020

atttgaggtg ttttgttttc atttttattt caagttggac agatcttgga gataatttct   1080

tacctcacat agatgagaaa actaacaccc agaaaggaga aatgatgtta taaaaaactc   1140

ataaggcaag agctgagaag gaagcgctga tcttctattt aattccccac ccatgacccc   1200

cagaaagcag gagggcattg cccacattca cagggctctt cagtctcaga atcaggacac   1260

tggccaggtg tctggtttgg gtccagagtg ctcatcatca tgtcatagaa ctgctgggcc   1320

caggtctcct gaaatgggaa gcccagcaat accacgcagt ccctccactt tctcaaagca   1380

cactggaaag gccattagaa ttgccccagc agagcagatc tgcttttttt ccagagcaaa   1440

atgaagcact aggtataaat atgttgttac tgccaagaac ttaaatgact ggtttttgtt   1500

tgcttgcagt gctttcttaa ttttatggct cttctgggaa actcctcccc ttttccacac   1560

gaaccttgtg gggctgtgaa ttctttcttc atccccgcat tcccaatata cccaggccac   1620

aagagtggac gtgaaccaca gggtgtcctg tcagaggagc ccatctccca tctccccagc   1680

tccctatctg gaggatagtt ggatagttac gtgttcctag caggaccaac tacagtcttc   1740

ccaaggattg agttatggac tttgggagtg agacatcttc ttgctgctgg atttccaagc   1800

tgagaggacg tgaacctggg accaccagta gccatcttgt ttgccacatg gagagagact   1860

gtgaggacag aagccaaact ggaagtggag gagccaaggg attgacaaac aacagagcct   1920

tgaccacgtg gagtctctga atcagccttg tctggaacca gatctacacc tggactgccc   1980

aggtctataa gccaataaag cccctgttta cttgaaaaaa aaaa                    2024
```

<210> SEQ ID NO 17
<211> LENGTH: 224
<212> TYPE: PRT
<213> ORGANISM: Homo sapiens

<400> SEQUENCE: 17

```
Met Glu Lys Leu Leu Cys Phe Leu Val Leu Thr Ser Leu Ser His Ala
1               5                   10                  15

Phe Gly Gln Thr Asp Met Ser Arg Lys Ala Phe Val Phe Pro Lys Glu
            20                  25                  30

Ser Asp Thr Ser Tyr Val Ser Leu Lys Ala Pro Leu Thr Lys Pro Leu
        35                  40                  45

Lys Ala Phe Thr Val Cys Leu His Phe Tyr Thr Glu Leu Ser Ser Thr
    50                  55                  60

Arg Gly Tyr Ser Ile Phe Ser Tyr Ala Thr Lys Arg Gln Asp Asn Glu
65                  70                  75                  80

Ile Leu Ile Phe Trp Ser Lys Asp Ile Gly Tyr Ser Phe Thr Val Gly
                85                  90                  95

Gly Ser Glu Ile Leu Phe Glu Val Pro Glu Val Thr Val Ala Pro Val
            100                 105                 110

His Ile Cys Thr Ser Trp Glu Ser Ala Ser Gly Ile Val Glu Phe Trp
        115                 120                 125

Val Asp Gly Lys Pro Arg Val Arg Lys Ser Leu Lys Lys Gly Tyr Thr
    130                 135                 140

Val Gly Ala Glu Ala Ser Ile Ile Leu Gly Gln Glu Gln Asp Ser Phe
145                 150                 155                 160

Gly Gly Asn Phe Glu Gly Ser Gln Ser Leu Val Gly Asp Ile Gly Asn
                165                 170                 175
```

```
Val Asn Met Trp Asp Phe Val Leu Ser Pro Asp Glu Ile Asn Thr Ile
            180                 185                 190

Tyr Leu Gly Gly Pro Phe Ser Pro Asn Val Leu Asn Trp Arg Ala Leu
        195                 200                 205

Lys Tyr Glu Val Gln Gly Glu Val Phe Thr Lys Pro Gln Leu Trp Pro
    210                 215                 220
```

<210> SEQ ID NO 18
<211> LENGTH: 26803
<212> TYPE: DNA
<213> ORGANISM: Homo sapiens

<400> SEQUENCE: 18

```
cttgctctgt cacccaggct ggagtgcagt gctgtgatca tggttcactg cagccttgaa     60

ctcctgggct ctggcaatcc tcctgcctga gccttctgag tagctgagac tatagatatg    120

ggccaccaca cctggctaat ttttaatttt ttttagtaga gatgaagtct tgctatgttg    180

accaggcttg tgggagttca gtcaggctgg tggaaaaaat tttaaagata gttataagaa    240

atagacacaa accttcttgt aaggctggag agggtttaca ttgcttcagt aacagatttg    300

gctgaaagca gcctaatcct ctctaccttt agctgatagc aaaaatgaaa ataacaaggg    360

aatgtgagga agtttatcta aatagcttgc ttactcatgt ggtcctaaaa ccaaactttg    420

atcaacctca ggtgcataat tgctctctac tcagggggtg agcaatgtta attaccctct    480

agtggtgttt actcgagacc tttgtcattt aatctgtatt aaataaatgt gaactttgct    540

agcttattga ggtgatgctc cagatgcaga gcagagcccc ttagccagac tgacaggcaa    600

aatatctgtg tcagtgtatg tctctcatcc atcactggtt cagggtctgc gggctggatt    660

cctgcacagg ctggtcttga actcctgggc tcaagcaatc ctcccgcctg agccttctga    720

gtagctgaga ctacagatat gggccaccac acctggctat ttttaacatt ttttagtaga    780

gatgaagtct tgctgtgttg cccaggctgg tcttaaactc ctgggctcaa gagctcctcc    840

tgccttggcc tcccaaagtg ctgggagtac aggcatgagt catggtgccc agacggacat    900

tttttaaaaa ataaaggaat actcctgaaa cgctgaagtc ttctttgtac cctctgtga    960

taacatgaat agcctcttaa tgacaccaag gagcaagaca agttagtccc aaagtagctc   1020

acatagatga tgataaagga atgaggggtg ggtgtgatct atgcaaaaaa cccttactct   1080

ttaatgggtt gctgtttcta acataattgc aacagtaccc tacattgcta taatgcatta   1140

tagttttcaa agtgcttttg tggcctccat aatagagagg ttgtgaggta agcttcaacc   1200

acggctgccc tactacccaa gagtggacac acaatgatga ataggtcaat ttctgcctct   1260

tagtttctta gctagggagg ggcacttact ggaacagcac agaaaacaga gtctttggcc   1320

cagttggaga atctttatca ggttatgcta cttcaagctt tcctcctgtt aaatgtgaga   1380

ggaataaatc cctgttcctt ggatcagtgt gactctgaaa cagctggagg agagacagct   1440

ttaggcaggt tgaaacagag agctccagca tatgtacttt tttttttttt ttgagatgga   1500

gtctcgctct gtctcccagg ctggagtgca gtggctcgat cttggctcac tgcaagctct   1560

gcctcccagg ttcatgccat tctcccgcct cagcctccct agtagctggg actacaggct   1620

cccgccacca cgcccggcta attttttgt atttttagta gagacagggt ttcaccatgt   1680

tggccaggcc agtcttgaac tcctgacctg aggtgatcca cctgcctcag tctcccaaag   1740

tgctgggatt acaggcgtga gccactgaac ttggccaagt gcactacttt taaaagttaa   1800

agtattatgc agccatgagg gaatattgtg caagaagaaa gcttttacaa gaaaaacttg   1860
```

```
aaacattggt atttttgcct ccttttttaac aactagagtc gttttgggag ttgtttcttg   1920
tcgaagaaac aacccatgtt tattttccca gtatggcagg accatgtagg aaagcaaaat   1980
taccccctcag gagaggaaat tctctgacac tctataaggc tccataaccc tcctctgaac   2040
tgtggccaac aagattgggt agcactttttt aaggtagttt aagaaaaata ggctgtgcat   2100
ggtggtttat gcctgtaatc ccagcacttt gggaggccga ggtgagtgga tcacctgagg   2160
tcaggagttt gagaccagcc tgaccaatat ggtgaaaccc catctctact gaaaatacaa   2220
aaattagccg ggtgtggtgg cgggcacctg tagtcccagc tactcgggag gctgaggcag   2280
gagaattgct tgaacctggg aggcggaggt tgcagtgagc cgagactgtg ccactgcact   2340
ccagcctggg tgacagagca ggactccatc tcaaaaaaaa aaaaaaaaaa aagaaagaaa   2400
gaaaaatata tagtgagccc aataaagctg tataatctaa atcaaacatg acttgcatgc   2460
ctggagactt tgcactagaa aaatatttct acctaaaaaa tcaaatttta ttttctttct   2520
cacaaatatt caatctgctt tcatctcagt tcttcctacc ttgtcaaacc tctccccaca   2580
tttcctattc tttttctctc cagcctgata tctctcatta tactgcttaa gagaaatgtt   2640
atgttactat tcttttctcc cagaactgtt tctctggttc tttaaggtgt ctgagtacac   2700
actgtgcctt cttcctttta gccctctctt ctccttgttc cctgagcctt acctttatga   2760
ccttagaact tcaagttccc actacaattt taaatataga ctattttgct tttcctccta   2820
ctagggagct taaattgcct ctaattacac tgtttttcccg agtccttcct ctcctttgca   2880
atttagatat agcacagaag cacattttgc ttgactgtcc tctgaactgt catgctgttt   2940
tgatgtggtt ctattgtcca agagtcttgg ttaaataata gcccagcatc ccacctgtgt   3000
ttaaaagaac tgcttcacag gcaaatcaaa aagcccatgg atccgaagtc acaatgggcg   3060
ttgctattca aacagcacca gattgctatt caacgcttgg ttgaaaaata aatttcagtt   3120
tcattcacct aatatatttc cttctatttt gtaggatggt atgctcttac ttcaatttgg   3180
acttgttcac aattgaacgt taacatagcc ttatagatta gcctgttttc attggtccag   3240
agtattctcc aaataaagca gggtctgtgc attttaagca actcccctga acaatttcat   3300
gggcattctc aaatttgaga actacctgaa aagctgtgtt ggagaaaaga acaaccaatg   3360
aatgtggcag gacagaatat tgaacattaa cttccctttt cctcttctcc catctgttct   3420
cttccattat ccctacccgt ccgctcagtc tcgttattca ggcaacagtt attttgccat   3480
tatttcctca agaaaggaac aaaagtaaac acaattgctt tctgattttt tttttttttt   3540
tgcattttaa aatggacttt gaaaccataa gcaaagaggt gtttaagagt ctttccaaag   3600
ccaaaaatga aggttttgaa atttcaaagt cactgccttg aagagactcg aggtttggag   3660
tgtgtacagt atgtcggagc tggacttttc tccttcctga gactagataa cggtctgaat   3720
ccaagacagt tttcatgatt tcagaggaag tggtcaagtg gtctgtgagg tagaccttct   3780
gcttaagagc agtcaggagg ccgggtgccg tggctcacgc ctgtaatccc agcactttgg   3840
gagaccgagg tgggcggatc acctgaggtc aggagttcaa gacaagcctg accaacatgc   3900
agaaaccctg tctctactaa aaatacaaaa aattggccgg gcacggtggc acatgcactc   3960
cagcctgggc aacaatagtg aaactccatc tcaaaaaaaa aacaaaaaaa agagaagaaa   4020
agaaaagaaa aggagcagtc aggatgtgtg cctccaaagc tgaggtagac aaaaagatac   4080
cagagttcta gaggcctgcc aggcacagca gcagcagcag aaggaaggtg tgggcgagaa   4140
cagggcagcc aggcgtgtgc cacctcccag acacaattat tgggaatgga gggcaagtgg   4200
```

-continued

```
tgatgggaga aaatcttgac ttaattgatg tcaagattaa agaaatgcca cctggtggca   4260
tttaagttca cacataggta aagaaagtta tgcatttact gtgaaagtca tcccactatt   4320
tagtagaaac aggagatctg gattctggtc aagagtctct tttgccaact gtggcaccac   4380
tgagcagcgg cacagctttt gtgaatcctg ggttcttcat tattaaaatg gggacattag   4440
cgttgggttg agtataagaa atggacattt ttgcaggtca aaaatggttg aatatttgca   4500
ttttcatatg attcaaccga atacttactt cacaggcata aggaaaaaaa tagaataaca   4560
tactaacaac tgtccctgga gtaagtactt aacaaataca tgatttataa agaagatatg   4620
tgaaagatat ttgtaagtac atgatttata gaaagatatg aaagtatgta aacccttgtg   4680
gtctaatggt cacagaataa tctgagctta atatccctgc tccctaccat acagaaggca   4740
aaatgcctat taggggtttt ctttcttcac cctctccttc tttttcctcc tcctcttgac   4800
tcctcctcat cctcctcttt cttcttcccc ttattaatgt ctaaaaaggg gctgagcatg   4860
gtggctcatg cctgtaatcc tagcactctg ggaagctgcg gcaggtggat cacctgaggc   4920
caggagtttg aaaccagcct ggtcaacatg gcaaaacccc atccctacta aaaatacaaa   4980
aattacccag gtgtggtggc aggcacctgt aattccaact acccgggagg ctgaggcagg   5040
agaatcgctt aaacccggga ggcagaggtt gcagtgagcc aagattgtgc cactgttgtc   5100
catcctgggt gacagaggga gactctgtct caagataaat aataataata ataataattt   5160
ctaaaaaggt aatacatttt catagttcaa aaaccaaaag gtataaaagg aaatacagta   5220
aaaaatttcc tatcatatca ctgtctagag tactattcct tatatatttt cctgattttt   5280
gagtatttta aaatgtgagt gttggatatg agtgttggat ttaaaaagtt ttatgataat   5340
ttgtgtatat ttgtgtgtgt gtgtgtgtgt gtgtgtgtgt atagtagtcc aagactatca   5400
gtttatgaat aataagagga gacccatgga aaaccagtcc ctttgaccaa gttcactcag   5460
ataatcagca gcagggcttg gacattaatt acagttatcc aacatccttt gaggtctcac   5520
atgacaaatt acaaatatgg agtgtaaatg taacccactt tgctaggcaa aaaaagccct   5580
gtttttttaa aaaatatata tttttggctt atgggcaaca gaagccaggg agacgtacag   5640
tcaaacctca tttctcatgg ctttcatatc tgcaaattct cctactcatt aaaagttatt   5700
tataactccc gaatcaatac ccacagcact tttgtgatca ttggcagaca tgtgcagaaa   5760
agaaaaaaaa attgagttgt tgattgcaca cattcccagc tgaatttcaa caaagcaaca   5820
ctctgccttc ccacttcagc tttcttacta tatgtgtgtc ctttttctgt ttatttagta   5880
ccatgttttt cacactttcg ttctttttgg tggtgatttt gctgtttaaa atggccaaca   5940
agtgtagtgc taagtgctgc gtagggttct taagcacaag aaggctatga tgtgccttat   6000
ggagaaaata cgtgtgttgg atcagtttca ctcaagcatg agttatggcg ctattagctg   6060
tgagttcaat gttaacaaat caacaatata tgctaaagtg tctttaaaca gaaacacaca   6120
taaaacaagg ttatatgttt ggttggcaaa aatgttataa ccagaagctt gcagaaacct   6180
aaccctgtat ttcccttaag agcaatggtt cattattcac taattcaatg tttacagcaa   6240
ctttataaac tataactacc atgaataatg agaattgact atgttttaga tcataatacc   6300
tgaagtgaag ttttccatca tggtttttag ttcttagagt ccatttaagt tttttaaaaa   6360
tatgatagct atcctatcac atcccacatt cttgagatta aaaaattaat cttttatttg   6420
gtacagaaaa ggctcctgcg tgcatttttg gaggggctgg accgctgagg aagtcatggt   6480
tggctcaagt ggtttaaatg cattgctaat ttcatagcct ctgaaccact tatgaaacaa   6540
tactgatgat atgtcagtag ctatgtttgc agctccttca ggaatgctta tatcttttac   6600
```

```
tgctggtaaa gaagaaattt atagtaatag attttttttt tttttagata gagtctcact   6660
ctgtcgccta ggctggatta cagcggcttg atcacggttt actgcagcct ggatctccca   6720
ggctctccta ctgtagcctc cccagtaact agggccccca cacaggcatc accacaccca   6780
gctcattttt ttatgtttta tagagacagg gtcttactat gttttccagg ctggtctcaa   6840
acttctgggc tcaagcaatc ctcctacttt ggcctcccaa agtgctgaaa ttacaggcat   6900
gaaccactgc acctggttta tggtcatctt aagtagagac ttatgagtgc gtatcattgt   6960
atcaccaatc tgagactcaa ttttatcttt ctgttaatag acaatgcagt tttctgtta    7020
attacaatga aaatcaaggg ttgcttagca agtttttact cataactcca agttttgtga   7080
cttatagtga gaaatgggta taattctttg tgatttgtta aaatgcagta tttcgaggag   7140
ggataacata taaaatttaa cagtttccta tcattatttt tatccttttg aaccactgta   7200
tactacagat agacaaaggc agctttggcc acttactcct cagtgtgact aagttgacca   7260
gatgttttcc agaccacagg ttctgtcaag agacagtgtg gagagaaatg ggtaggcagg   7320
tatggaaaga agagtcagaa acagatagtg agctaatctc tacaaatggc tcgttatggc   7380
ctgagctgtg ttctcctccc cgcaaaaaga tatgttggag tcgtaatccc cagtacctca   7440
gaatgtggcc ttatttggag attcgatatt tacagaggta agcaagttaa aatgagatca   7500
ctatagtggg tcctaattca atacgactgg tatccttaca aaaaagggga aatttaacca   7560
cagatacaga cacacacata gggagagtgc tagtgaaggt gaagtcagag attggaatga   7620
tgtagcagaa gcctaggaat gccaaagatt gccagcaaac caccagaagc tgggagagcc   7680
acatggaaca gattctcctt cacagtcccc tgaaagaacc aactctcctg acacctcgat   7740
ttcagacttc tagcctccag agctggggtc aatgagcttc tctcattaag ccatcatcca   7800
gtgtatggta ctttgttaca gcagtcttag caaatgcatg gttcctcact ggaaccatga   7860
atttccatgc atttatttca tttaaataat aaaacggatc ccctttgtgg cttgtagttc   7920
tgttccattt caaaaatcca gaaaaaagat ttgttcagaa gctagaaatg atgaactgga   7980
tcttgcccaa ggtcataaaa ccacaaaacc ctttacagag cacaaaagtc tgatttttca   8040
aagcttctct caaaagatgg gtcactcctt agtcatttag gccactgaca actgccctgg   8100
actctttatt tatttattta tttatttatt tatttaattt ttttgagaca gagtcttgct   8160
ttgtcgccca ggctggagtg cagtggcgtg atctgagctc actgcaagcc ctgcctcccg   8220
ggttgacgcc attctcctgc ctcagcctcc caagtagctg ggactacagg cacccgccac   8280
cacgcccggc taattttttg tattttgttt agtagagaca gggtttcacc atgttagcca   8340
ggatggtctc gaggtcctga ccttgtgatc cacccgcctt ggcctcccaa agtgctggga   8400
ttacaggcgt gagccactgc gcctggcctg gactcttaca tataataagc ttgacttatc   8460
gtacaactta taattgatgc tttcacgtca tgggaagatc aaattaatgc agagagcgac   8520
tacgtttctg gtgggagagc agcaggggtc ttgagaggaa cagcagtgtt gactgtttcg   8580
ctacctactc tgggtgctga ttacatcttt ctttcgtgca ggcaaatcca cttggagcta   8640
ttttgggctc actgtgggca tcattctttg tatactctgc tcctttcccc catagtttct   8700
ctattgatgg gggattacta aagaatgaag aaaagaacaa aatgaaagtg gcttttgaaa   8760
aattttaaat gactgtcact atgtaacata ttcattattt catgtctcca ctggacattt   8820
tggagatgtg agccttgcaa tacctacatg aatgcttcta tgattatgat tattgttttg   8880
ctcttcgcct aacaacttgc caagtattgt caacctcagt gtgtgagatg gggtccactc   8940
```

```
aaacatcagg gccgaagtca ggtagttcag ttaagtgaat ttgataccag gaactagtta   9000
caaaggagtt ggaagggctg gaaagccaaa ctggagaaga aggggaaccc cagagtaaca   9060
atagcaggaa gcctctaccg tctacctcta gaactgggga ggagctgagt taacagagtc   9120
ctggagccat tgctggggaa gaagaacccc aactgcagag gaaaagtggc cattgtgaag   9180
aaggtgatgg tggagaagtc gtctgaatca aaggggagag gatatgttgg ctcctttatc   9240
tttttatctt tcattgtcct aattccttct gggcatggtt aaatgagccc aggaaatgca   9300
gttggcagga atcagcttcc tgtgacatag acagagtaag agaaggacaa aaataatgaa   9360
tctgagagca agcaggcaaa tgaccagcac attaagccta gcacacagta tgttatacgg   9420
gatttggggt agcaaaagat gaaggcaggt cagagaagcc acaactaggg gatgggcaag   9480
gtcaatgagg tatgacgggt attgtataca ggaagagggt cataaacagg agtggagtca   9540
atacaggaga ctaacatata cacatcataa atattagtag agaagcataa aatagtctcc   9600
tggagatcag ggaaacagga aattataggt tttcaggata attcagccat atccaggaaa   9660
cacacacagt gaagtaacaa agagtcaata ggcttagagt ggtacaattc attatgcaca   9720
tgtaggaatt cattccaaat aataggctga aatgtagaca tgagaatcca aaaaagatgt   9780
tttcttagtt tttgccaata tcttagctac gttttttttg gttcaacaaa gtaagttaac   9840
agtcatatct gcttggaaat tgtatttagg ccaggtgcag tgtctcacgc ctgtaatccc   9900
agcacttggg gtggctgagg caggaggatc ccttgagccc aggagttaga ggctgcagtg   9960
agcgacaact acaccactgc attccagtct gggtgacaga acaaaaactt attaaaaaaa  10020
gaaaaaaaaa aggtcgggcg cggtggctca cgcctgtaat cccagcactt tgggaggtcg  10080
aggtgggcgg atcacgagtc aagagatgga gaccatcttg gtcaacatgg tgaaacccca  10140
tctctactaa aaatacaaaa attagctggg catggtggca tgcacctgta gtcccaccta  10200
ttcaggaggc tgaggcagga gaatcgcttg aacccgggaa gcggaggttg cagtgagctg  10260
agattgcacc actgcactcc atcctgtcga gactctgtct caaaaagaaa aaaaaggaaa  10320
agaaactatt gaaatagctg atattagttt gcttacttgt cgttactctt tttcatgatg  10380
gattataaag aaaagttata actatttgaa ttttctgctg atttgaagtc tctataaaca  10440
gtacattcct ttttggtaca cagagggcac ttatctgcaa gaaaggcaaa gaaaatggaa  10500
aagttaatga aagaggaatc atccaatcca cgaacagaat gaaaccacat acacagtgaa  10560
gaaacttgtc ttacattttc ttccttatat tacttatcat tcatggtagt gactactttg  10620
gggcttgagt aaagcttctc taatttattc catgtagcat catatgtgaa aaagacaaat  10680
agatacttta gacatgataa taacacttta ttttttattt atttgtttat tttgagacag  10740
agttttgctc ttgttgccca ggctggagtg caatggtgca atctcagctc actgcaacct  10800
ctgcctcctg ggttcaagcg actctcctga ctcagcctcc caagtagctg ggattacagg  10860
cacgcatcac cacgcccagc taattttttg taattttagt agagacaggg tttctccgtg  10920
ttggccgggc tggcctcaaa ctcctgacct caggtgatcc acccaccttg gtctcccgaa  10980
gtgctgggat tataggtgtg agccaccatg cctggcccat aacaccttat ttaaaaataa  11040
tctgtctgga tccatacaac ttgtctggat aactaaattg gaaattattc cttgttttaa  11100
agtaattcaa ttgaaaattt ttaaattttt ttgttaatca agcacttttt ggtggaatct  11160
aaattaacac atgtaggaga tgcctgtttc actaattaca caggcatctt gcagtaatta  11220
atgtctggga ggaaggaatg tcttttgctt actctcttct tcttcacaaa aatgtgaatt  11280
ttggaaagca ataatggaag catgtagaat tatagaaata caaatgtata taactatcac  11340
```

```
aaaaaaatga ggccaaagga ctattcagat ataattaggc tatggtagct gtaattatct  11400
aggaaattaa taaaattcat tcacctagaa attattagtg agcatcaaat atgtgtcagc  11460
actaggctag ggtctcagaa cgtacagata aatcatagtt ctggcttcag ggagttatat  11520
agattagaga taaaacctaa ctacaggggc tgggcacggt agctcatacc tgtaatccca  11580
ccactttggg aggccgaggc gggtggatcg cctgaggtca aggagtttga gaccagcctg  11640
gccaacatga taaaatcctg tcactactaa aaatacaaaa gttagccggg aggtagtatg  11700
tgcacctgta atcccagcta ctcgggaggc tgaggcagga gaatctcttg agcctgcggt  11760
ggaggttgtg gtgagctgag atcacgacac tgcactccaa tctgggcgag agagtgagac  11820
cctatctcaa aaccccaaac aaaacaaaca aaaaaaccaa acctaactac agggctatga  11880
gagatgacta ctggcaagga gccacaggta gaacaaaggg gatgtgtccc caggcaaagg  11940
gtagtcagca agcctgcaac ctcagggttc ccggatctga gcctctggct cttggctagg  12000
caggccccaa gcgttggcct cctgccatgg caagctccag cctggtctcc caccttgagc  12060
taacattcat atgttgtaga cacagccacg cttcctgctt acctgtcact tccagttctc  12120
gaaggcaccc ttttcaaatg aaaatccgcc ccttttcaca tcaaacagct catctggtcc  12180
tgtggattac atttctcaga aatgcctctg aacattcgcc tcctctccac ccccactgcc  12240
tctgctacag tgcaggtgct cgccatttct gatttgttct gtcacacact cgtttatcag  12300
gtctctccat ctcctgtttt gacatgctgt aaagcaattt gccactggaa aaaagggctc  12360
tctttttttt tttgagacgg agtctcgctc tgctgcccag gctggagtgc aatggcatga  12420
tctcggctca ctgcaacctc tgcctcccaa gttcaagtga ttctcctgcc tcagcctccc  12480
taaagtctgg gattacaggt gcacgccacc aagcccggct aatttttgta tttttagtag  12540
acgtggggtt tcaccatatt ggccaagctg gtctcgaact cctgacctca ggtgatccac  12600
ccgcctcggc ctcccaaagt gctgggattt caggtgtgag gcatcgtgcc cggcctctct  12660
ttccaaagta tgttattatt tttcccaaga ccctttgacg gatcctcatt tcctacacac  12720
agtggttctc aaacttggat gtactccaga attacatagg aaattcttca tttttttaga  12780
cgaggtcttg ctatgtttct caggttggtc tcaaactctt gacctcgtgt gatcctccgg  12840
ccgcagtctc ccaagtagct gagattatag gcgtgccact gagcccagct ggaaattttt  12900
ttaaaacaca gattcctctg aatcaaaatt tctagaagtg aggtctgagc aatctgtatt  12960
tttaacaagt tatccagatg gctctttact gtcagtctgg ttccagctga gggagtttta  13020
gaattacaag gcaaagtcca aacttagcac acaaagtcat tcacatcaac tcttcccctg  13080
tacacaccct atgtcatagc cagagttgta acccatttct taaacaccca gggttctttt  13140
aagtctctgt gtcattgtat gttattttct ctagaattgc ctttaacctc ctttccaccc  13200
tggaaagcat tccctaagcc atctttgaag ctttctttga tctctaactt agagtcctcc  13260
tctccttcta aagccctgtg ttaatcactt gtcatggtgt actttaattt ttacttgcct  13320
gtttctcttt acggtacttt gacttcaaag ggtggggctg caaattagtc atctccttag  13380
agtccagcct tgttcctagt tcctaactgg cacttaatat aaacgaatga atgaatggac  13440
aaatgaagag aatgctagtt atgataaaga attggccgtg tatgagacta cttctcttta  13500
tgaactaaat aattatatgc ctttcaataa aatactagta cacgtagcta gcacaagctc  13560
atcagcattt gagatgatat ggaaaccaaa ataaacaaat gctaccacaa aaacataatg  13620
actgctttcc ccagtgcagg actgatggaa tcatcaaaca ttgagattaa tgtaatgttt  13680
```

-continued

```
ggcagatgtc cagtgttttt atttttcatt tgcctttgtg ttcatttatg gactaacaat  13740
ataataaaca cacacatact cacagtacat cttttttttt ttttttttg caaagcccag  13800
ttttcttcat cgcatatctt tgttttcttc aagtatcccc ttacttaatg ttggtagtat  13860
ttttttaat gaaatataaa tccctaacca ccaagcaaga aatgagactc ttaattgcat  13920
cagtttacag tgcaatgtga gtgtaaatag tgtaaattga atttttaatg gactttttt  13980
tttcccgttt ttgcttgcct tacattcatt atccctccct gggtaataaa catttatttt  14040
tccctttgta accactcctc cccttctgtc catgtggttc tttttagtgg agctggtggt  14100
agggatgtgg catgagattc aagcttggcc acctggagtc actgtgttgt gctccagaag  14160
gacacctgat ccaagtcagc cagtaagagt gagccccagg atttttgctt ggaccactga  14220
ggaaaagtgt actctgccct gtggctgatc aaccattagg atataagcca ttgttgtagc  14280
tgtgtgagtc aagctacctg agaatgagga caacacagtg gcaagcaaca ccaagagaga  14340
aaaagaggca gattctgatg acatttttga gcctttgcat ccagctatgc ctgaatccaa  14400
tttatcccct ggaatttaca cttacttgag ctccacccac ttgaaagaaa acatttcttt  14460
ttattcttag cctgatttga atttggcctc tctcatttac tacccaaagt gtcttgacca  14520
ctagaatatt atgccagact ttacagcatc attgaatttg ccactttcca gaagagttgt  14580
gtgaattttc aatgtagctt ttaccttcta tgagtatcta gagatatatt taagtagaag  14640
tactccacta gtttgttgtg agatcttaag tcacttaatt tctctgtacc ctagttccct  14700
catttgctag acctagggag ctataatgtt ccttctgcaa aattcttatt ttgtgaaata  14760
ttctagaatg tctaactgat acactgctag aacaactgac tgctatttaa gaagagttga  14820
ctgctattta aggatcataa ttctctaggc ataagtgctg tgacggcaca gcgtgtgcat  14880
cggggctgag gggtggggtg gagcagaaag taggaggaga aagtttgata aacttccttt  14940
tggataaatt gaaaacagtc aaataattta taatttctta tattatcatt attagcttct  15000
tctataatta ggagacttgt tccaaaatgt gagaattgtc acaagttgtc aaattcatca  15060
aaggaagaaa atggatgtct cacaaaaaag tatgctcagt ccaatttctt ctcgtcacac  15120
tggaacaaac tgaacagttt tacacagaga tgagaagcct ggacattttt caaatatgtt  15180
ttgaagagaa tggcaatgcc tgagacagaa gtaggaaaaa gcaatgaata tttaaaaatc  15240
tgagctggtg taaaactaga aatagtttta gtaagaacaa tgtgatgtgc tacactaagt  15300
gaaatgtata cattgggcca cattataatc aaaaataaga atgtactttt attcatcttt  15360
tatttaaaca ataatcaagg tggcgggcgc ggtggctcat gcctgtaatc ccagcacttt  15420
gggaggccaa ggtgggtgga tcatgaggtc aggagttcaa gaccagcctg gacaacgtgg  15480
tgaaaccccg tctctactaa aaatacaaaa attagctggg tggggtggca tatgcctgta  15540
ataccagctg ctcgggggc tgaggcagga gaatcgcttg aacttgggaa gtggaggttg  15600
cagtcagcca agattgtgcc attgcgctcc agcctgggtg acagagcaag agactctgtc  15660
tcaaaaggaa aaaagaaaaa aaaaaaatca aggtaccatt tgtaccattt cctggaattt  15720
ctccaaagtg gcaaggtcac atgtttatac attagactcc cagtttaaca cacagcagac  15780
aataactttt tttttttttt tttgagatgg agtctcgctc tgtcacccag gctggagtgc  15840
agtggcacaa tcttggctga ctgcaacctc cgcttcccga gttcaagcga ttctcctgcc  15900
tcagcctccc gagtagctgg gattacaggc atatgccacc atgcccagct aatttttgta  15960
tttttagtgg agatggggtt tcaccacatt gtccaggctg gtctcaaact cctgacctca  16020
taatccagcc acctcagcct cccgaagtgc tggtccaccc ttccttcttt tctcccttcc  16080
```

```
atccttctcc cttttattcc atttttctaa atattagacc atagtacaaa tcaaaagtca  16140
caaactgata ggctgcaatg tagatacagc tgggaaaatg ttttgtttgc agaacactgg  16200
ggaaatttaa catgaaaaac tggaagatct caatccacat ggccacatgg taatattatt  16260
aatgttgcag ggctttccca attcaacatg tcctctgcat ccctactatt tatactgcca  16320
ctcatccacc tttctgtatt actggcctat cacctataca cgtttgagtt tatattcttc  16380
tggctttact tagcaactta ccttttatat ttaacattac aacatggtat tatcaattag  16440
tattcgattc agttgcatat aaccaaaaat gccaaattat actggcttaa acactaagga  16500
tttatttttc tgtcatataa aacaagtctg gaggtgggta gtccagggct aatatgacac  16560
tccagtgtca caaggtacct gggctccttc tatttatctt tttttttttt tttttgaga  16620
cggagtcttg ctctgtagcc caggctggag tgcagtggtg cgatctgggc tcactgcaag  16680
cttcgcctcc cgggttcaca ccattctcct gcctcagcct ccggagtagc tgggactaca  16740
ggcgcccgcc accacgcccg gctaattttt ttgttatttt taatagagac gaggtttaca  16800
ccgtgttagc caggatggtc tcgatctcct gacctcgtga tccactcatc tcggcctccc  16860
aaagtgctgg gattagaggc gtgagccacc gcgcctggcc ctatttatct tttataggac  16920
atggcttcca gtctcaagtt cagtttgtca cccataatgg ccaaagagca gtagtcacct  16980
tacctgtttc aggcaggaag ggcagagggc aagaaacaaa atggtgctcc tcctgattga  17040
gtcagcgttc tttaaagatg ttttccagat gttccaccca gccgcgtttt tttttttttg  17100
agagacaggg tcttgctctt gtcacccagg ctggagtaca gtggcatgat catggctcac  17160
tgaggcctca atctcccagg ctcaagcgat ccttccattt tagcctccca agtagctgga  17220
agtagctggg accacaggca catgccacca taccctgcta actttttcat tttgtgtaga  17280
gacaaggtgt cactgtgttc tccaggctgg tctgcagttt ccaactcctg agtgcaagtg  17340
atcctcctgc tttggcctcc caaagggctg ggattacagg tgtgagccac tgtgtctggc  17400
caagctactt ctacttatat ctcattggtc ataacttgat cacacagcca catccagcta  17460
caatggagat tgagaaatgt agtcttttgg ctgggtacac agcatctgaa taaaatccag  17520
gcattgttac taaggaagaa ggagtaagtg tcaatctctg ctccataact ctctaggtta  17580
atacacacag atggaggaga ttgctagttg cccctcaaga tccagccttg ccttctgggc  17640
taagaaagcc cctgagattt acctggccat agtggcactg ggaacaaaca atgtatttct  17700
aaatcttctg attttaaaat ctttcagaat cacgatttct ccgacatcag tatttttatg  17760
tctttagaat tcaacaaaat gaaattccta agtctaatat atgtgaatat taagttttag  17820
cagatactgc tacataactt tccagaaggg tgtggcaatt cacatctcca ccagtgatca  17880
gcatgttcat tttccataca gctctggata ttttgtctat tttaaaatat cttcttctaa  17940
tctataattt aaaaatgtaa cttagtagga atttaattgt tcatgtaacc aaatcttccc  18000
attaatggct atgggtttct tcttttactt cagaaagtcc tccccacctt cagagtatat  18060
aaacattttt ttctaaattc ccttctaatt tcttataatt tatagtttta tttttgttat  18120
ttgattcatt tattctctca acagatattt attgagcact tattatacgt caggctctct  18180
tcaaactctg gtgagagtat tttctaactg ggagagacaa ccctagttga taagaaacaa  18240
acaaaccaat aagtaaataa gacatttccc ccagataatt aatacttggt gacgggggaa  18300
gacagtgaga caggctactt tacactggca ggtcaggaaa ggcttctctg aggaggcaag  18360
tgattcagga ttaattgatg actggtggag aagtccgggg agtggacaca ggtgggaaca  18420
```

```
gcctggtggg tgtgaacagc aacaagaagg ttaatgtggc ttcatggaac agggtgaaga  18480
tgagacaagc tgaacactga ggtgggcacc agaacatgga gggctttgta ggtcccaata  18540
aggagtatgg attttattgt atactggaga tttgtcatcc atctagaatc tgtttttata  18600
tataagaaaa ggtgtatatg tttgcgcaag tgtgtgtgtg tgtgtttggg ggggcggggt  18660
gggggcagac agggcgtaac ttttctttaa attagagtca aaatttaatt aaactattca  18720
ttctttacag gcagtgaggg gattaggatc ttatcccaca gaatctcacc tcatttcaaa  18780
tgttgtacag atattatctg agatatattt tcaggccggg tgcggtggct cacgcctgta  18840
atctcagcac tttgggaagc cgaggcgggt ggatcatttg aggtcaggag ttcaagacca  18900
tcctggccaa catggtgaaa ccccatctct actaaaaata caaaaattag ccgggtgtgg  18960
tggtacacgt ctataatccc agctacttga gaggctgagg caggagaatc gcttgaatcc  19020
aggaggtgga gcttgcagtg agccgagaaa acgccactgc actccagcct gggcgacagg  19080
gcaagactct gtctcaaaaa aaaaaacgaa aaaagaaata tattttcaat gaaatcaagc  19140
atataatgac tatttttatc ccagcatctt ggcttcttca ggctgctata acaaagcatc  19200
cctagtggag catccctaat ctgaaaatcc aaaatccaaa acgttccaaa atctgaaacc  19260
ttctgaacac tgacatgaca ccacaaatgg aaaattctac atgtaaatac acgtaaatac  19320
aaactttgtt tcatgcacaa attaaaaata ttgtataaaa ttaccttcag gctatgcata  19380
taaggcatat atgaaatata aatgaatttt gtgtttaccc atgggtctca tccccaagat  19440
gtttcatttt gtatatgtgc atactcccaa atctgaaaaa atccaaaatc ttaaatatct  19500
gtagtcctaa gcattttaga taagggatat tcaatccctt atccataaac aatttattta  19560
taaacaacac aaatttaggc tttgtaaaaa atagaaattt ggccgggtgt ggtggctcac  19620
gcttgtaatc ccagcacttt gggaggccga ggcaggcaca tcacttgagc tcaggagttt  19680
gagaccagcc tggtcaacat ggtgaaacct tgtctctacc aaaaatacaa aaattagcag  19740
ggcttcgtgg catgcgcctg ttgtcccagc tactcgggag gctgaggcag gagaattgct  19800
tgaacccgga aggcagaggt tgcagtgagc caagattgag ccactgcact ccagcctggg  19860
ggacaagtga gactccacct caaaaaacaa acaatcaaac acaatataaa tttatttctc  19920
atagttctgc aagctgagaa gtccaagatc aagatgtgag cagatccacc tttggtgaag  19980
ggctgctttc catttgatag atggctgtct tcttgtgtcc tcacatggtg gaaagggtga  20040
ggcagttttt tgaggtctct tttaaaagag aactaatccc attcatgtgg gggtctgccc  20100
tcatgaccta atcactttcc aaaggcccca cttcctaata ccatcaccct gggggttaaa  20160
ttttcaacac acaaattggt tggagagtga gcgaacatag acattcagtc tatagccccc  20220
agggatgtag ccactgaata aaataatcta gaacttcatc tagaggcagt ttataagtca  20280
cataagaaaa ccagttttac ttatagtcac ataaaacttt tgataaaaaa caaccctagt  20340
tgataagcca tttgtttact ggacttggct ctgaagaaat gacttttggc taatcctcaa  20400
aatgaaatct actcacagag ggcaagatct gccaccagtg aagatgttta aaacaatgtg  20460
ctgtaggctt tgaaggcaag tctaaagaag agcttctaaa aatattttgc acaatggtag  20520
cattaaaaga gtaggcacat gggccccaag ataacatctg tgaagaggag gaccagtgtg  20580
tgtttccttt tgtatgttta agtactaagt cagtgattac tttataatta aaccatattc  20640
ctcttgatct gtccataata aggtcactct gtaatttata ataggcttct taccaaattc  20700
aagctttaca acaaccctat aggttaaata ttcctgtgaa ttttatagat gaagaaacag  20760
agtaagtgaa agagttcata ctcaattcaa gtctcttgag tctaaaatca gtgctctctc  20820
```

```
tacataagaa gttagttgct aagatcacac aacttgagaa gagagaagac agttttcaca  20880
gtccctcccc tctgaccact aggctgcttg ggtacttttt acaacttacc tgctctgaat  20940
taaggctctc tgtgaatctg attcatctgc caatttgcaa acagtcagcc ctgtagtacg  21000
tacctaagtt gatttttaaa atactatttc tcatcttaaa ataatggaaa ttgagtgaca  21060
taaatttcct ggacactttt taagatccaa agacaatttg ctaatttgtc gttacaatta  21120
aagagccccc caaaaggcgt aagaactgga ttttgacttg gacttctgtt ccttagtttc  21180
tttaacatat tgggggccgg gagtggtggc tcacacctgt aatcccagca ctttgggagg  21240
ccgaggcggg cagatcacga ggtcaggaga ttgagaccat cctggctaac acagtgaaac  21300
cccgtctcta caaaaaatac aaaaaaaaaa aaaaaaaatt agccgggtat ggtggcgggc  21360
gcctgtagtc ccagctactc aggaggctga ggtaggagaa tggcatgaac ccaggaggca  21420
gagcttgcag tgagccgaga tcgcactaca ctgcactcca gcctgggcga cagagcaaga  21480
ttccatctca aaaaaaaaaa gaaaaagata ttgggaaaac tcacttaaac tctatgggct  21540
tctgtaccac taaggcttct caaatttgat gcaagtaatg ggaacttgct gtggctaact  21600
tgagccacag gagaaggata ctgcaagact cacaaatgct tgaaagtttc ggaacaggtt  21660
tggaaatggg taagaaccaa ggaccgggtt gacctgaact gaaaggaaat tgaggtgcta  21720
ttagggacaa atatgaaatg aaggatgaac tgtctctgac atcctttgct tctgtgtttg  21780
gagatgagta agcagggagt gggtgcatat gcaaacaggg tggtcagaaa tgctttggcc  21840
ggatgtgtga ctgaaggcta tgtgcagctg aggaaggctg ggccaccaca gtagcagaga  21900
ggctgaccaa tttggcatgc agcaagcagg aagtagaagg gatcttaagc aagcaaagtg  21960
tttgggtaga caagattatg aggaatgagc accaatgaca tttccaacaa gcactgaaag  22020
cttccaaatg cttctaacag ttactgcctg tacaaacaca ggacagtctt gactatgtga  22080
gactgtgaca gtttcctcat gcctatgaaa tgagagacag tacttagcac tgacatgagc  22140
ttcatatttg aaggcagcaa actactgaac cacatgtagc ttccgaaatc aaaagatgca  22200
aactggcaga ccacaggtca gatatgacat gcagaaaaaa attagttact atcttagcct  22260
agtttgtgct gcttacagaa tatcagagac tgggtacttt atagagaaca caaattattt  22320
ttcatagttt tagaggctgg gaagtccaag atcaaagggc catcatctcg tgaaggcgtc  22380
cctgctgtgt caaaacatgg tggaaggcat cacatgggca aaagagagag agggaagcgg  22440
gggcaaactc ctttttatca ggcacccagt cctgtgattc attcatgaag acagtgtcct  22500
cctggcctaa tcacctctta aagctcccac ctctcagcac tgttgcactg gaaattatat  22560
ttctcacaca tgaactttgg ggaacacatt caaaccatta cagttaccaa agataaaaat  22620
gcagatttca gatttctctt ggggaagaaa aaaggctctg gcaataccag ggctgtattt  22680
ccacatggca acagttgtct gttgccttct gttgggttgt gggctctcac attgccatac  22740
cctcctcatg gccccccttca ctcataacag tacctgccta gacctcgaag cactagtttc  22800
caaccctgct tgagttaact acttccatga caactgtgca aggccagagt gtgggcagct  22860
accttgaggg ccaccggcat gggctgccca agtgaccgag ggcactaacc tctgctctcg  22920
aaacttcttt ggtaggatct cttcactcct gacttactac ttgtaactgc tggaaacaac  22980
catttattct acccctacta aaccacatct gtcttttctg tcagagccaa tcttcaagca  23040
tatgcttcct caaaagactt taattaccag gtagtagaag cggcagcaaa gagtccccat  23100
ctagcatctt ctaaaatgta gtggagaaac caacgacaac gaatctgaga caaccagttg  23160
```

```
tttgacttct ctgaaaacaa cctctaaaaa aagccttctc tcgtgaatag ctgcagacat  23220
gctgggcact aattgatgat gatgcccttt agtgagtctc ctctgcacat acctgattcc  23280
atttggatgc tggccctcac atacttctat ctgcgaactc cggaacacag aatatcatac  23340
aatgtatgat tcaatctgga ctctgctgga gccattctct acaaagcaga cacaactttt  23400
tcttgcctaa atcctttcaa gttgctttat ttttattttt aaactaatta ccataaatct  23460
aatttatcaa gctgctttta agataaactt taaaatgctt agagcagtct acaaattctt  23520
gcactgtttc actcttcctt atctctcagt cttcatctcc cattgcatct tctctgactc  23580
tttcatatgg atcttctttc aatttgtgga agaagccaag cttgttcctg cctcaggtcc  23640
ttgacacttg ctgttcactc tcctgggaga ctcttccccc catcttagct tttaaatacc  23700
agctggtcag actccttacc tgccttccac cttcctctca ttctcccact cctcgccttc  23760
atttctcaga gtcctccgct ctcttctttc tattgctctt aacacaattt gtctgttttc  23820
cgctaatctg taaactctac aagagcactt aactattttg catcccaccg aatattcgga  23880
gtcagcacag accccgtcat aatagagtag gtaagcaatg cttacctgtc aaatgaatga  23940
atgaaacacc cgattcatcc cccaagccag cttaatacat tagatgatct tatggactga  24000
ataagacatc cctcctttta aagaatattt ttgttttagc ttcacatcag caaaccccga  24060
acggttcatc ctaagataag cctggtagag aggaaagata ctaaccttct agggtcctaa  24120
agtggaacta ggaacttatt agatatgcac attctcaggc attatttccg atagcccagt  24180
cagagaattc tgggggtatg gcccagcaat ctgttttaac aaacctttca ggtaattctg  24240
atacacacta aagtttgaaa ggtttcttta aggctttcca gttttctttt ctttttttgga  24300
gggatggggg ggggtctccc catgttgccc aggctggtct cgaactccta gcctcaagct  24360
atcctatcct cccacctcgg ccttccaaag cattgaaatt acaggcatga cccactgcgg  24420
ctcgcctccg tttctaactt aaaaaaattt tctttggagg ggagccttaa tcctttctat  24480
tatcctgcta gtagaatctt actactcctg agggtaatct ttgtcataat ccaaaagcct  24540
tgaataaagg cctatttgta tagttatgca gaatatattc ctgggaggtt tgccttccta  24600
ggagcacagg tcggccctgg gaggtggggg ttggggggca gggctgcatt ctaaagtcct  24660
gtaacaacgc acaagtacaa ctgaatagaa ctcggaacaa aggcatcagg gccacggtgc  24720
aagtctttgt tcatccgttc cccgactgct caccctgtct gataccgctc ttttccaccc  24780
agaaaagcag ccactcaagt tttaagaatg gatgtatgcc gcggacgttt tcgattaggc  24840
cgttttctct caggcactgg aggatattcg tggctgcagg aggcgcttcc accctttcct  24900
caacctagca aagaagtaac tgaaactaac ccaagggtta caaccgaaaa gccccttcca  24960
gcttcagaag cagaactgga agctcggata gacttctccg cctctacact cctggaaaac  25020
ccgcagtgga tttcaccaac ttcaggatcg gagcccaggc aggcgaacgt accttattgc  25080
gcatgctcgc tagcccctcc cgctcggagc ggaaggggga gcgctggggg cctgggcctg  25140
gcctggccgg ggcgtcggca ccggcggcca tcttggcttc ccggggaaag gcggcgtgag  25200
gggaagaagt tgtagggtgg gggcaggagt gaggaggagg gaagagagag ggggaggagg  25260
ccgcggcggg gcagggcggg gactgcctgc ctgcctgggt tgcggaagtg atagccgccg  25320
accgagcctg ctgctttctt gctactgctt cggcttcccg gctacccccc ggacggtgaa  25380
ggcggcccag ctgtggatgg tcagatagcc cttgtctccc gccgccaatc tctggcccct  25440
agcagcacgg agcagacggc ggcagcagca gcagcaggcg aggaggaaga tggcgggacg  25500
gctgccggcc tgtgtggtgg actgtggcac ggggtaaggg ggcttacggg cgggggtggg  25560
```

```
gaaactgagg cggaggaagg aagatggcgg gggagggagg aggccgggaa atgaatggtg  25620
cggcgaggtg ccgccgccgg ctgtcagtcc tagacccgcc ggccagcgag gggtggggcc  25680
cgcagccagg gcctcgcggg tcccctcgtt tctccctcct gggactgggg cgggggcgcg  25740
ggcccgagat tcaaccccca accctcccag cggctttctc cgcgcgaccc ctcccggccc  25800
ttcccccact acggtgggca gcgccgccca aagggcgctg gggacggtcg tcttgggggt  25860
ggtccccggg cccgacccat ccggctttcc tttccctccg cgcccgtttt tgccagtcgg  25920
tttggggacc caggggccga gctcggggac tggcctggca ggggagctag aaaagagaag  25980
cgctcctggt aggtttgaca agatcgctgt gacaacattc tgcccagggt gtgggtgggg  26040
aaagggaaga atcggactct gaaaatggga acctacagtg gggctttcat ttgaccaccc  26100
accttctcct ttcgactcct ggtcatttcc atctccctct gcgttttaac cggtgaacca  26160
agtcacattt taattcgagg gagaaagatg tcatgtgtta cttctgtagc ctcaaaaaag  26220
tcccccagtg agcaagcgcg ctgcaacttc cttagttttg tcaaagccgc ttcctgcttt  26280
cagtctttta taccccttata aggtagtttt tagtttccaa cctgagcaca tcttactaga  26340
acttttaagc aggttttaaa gagactgaat taccggtgct tggtgtccat ttatatgact  26400
taaaaaaatg tacttatgtt tcatggagtg ggggaaagga agcaccctgg aaaataaact  26460
aatttaagtt gtattcgttc attctgtgat ggtatcttga aggaagcagg aaggtataga  26520
ggtatatagg agggtgttta agttgcaaat agttactcgt agatatgtag ggtagtttgc  26580
gaaaatgtag agtggcttta aagtgtggtc gttcattttg tattaataga cgttttagag  26640
agttgtacca cactcataac tgcatagaga atagactacc cttattttta tgtagaatca  26700
ctgcttcagg atgacatata ggaaagtggt tttttttttct gtgctgatga catctctcca  26760
attcccagaa cactcccagt tttttttttt tgagggggaa gtc                    26803
```

<210> SEQ ID NO 19
<211> LENGTH: 26803
<212> TYPE: DNA
<213> ORGANISM: Homo sapiens

<400> SEQUENCE: 19

```
gccgcaccta ccgctggcct cagacatcag caccccaaag ggtatgttgg agtcccatgg     60
tggaggtgcc ggccgctcct ccacgcactt gatgtatacc gaggatccca tgcttgacgt    120
cgcagggggc attagccagg agcacgttgc tgggatgcca gtccaggctg aggatggtgg    180
agccaatggg cttcttgatg tacttgcaca cccaccagtt attctcccgc tggaaataac    240
agatggcgat gacacacagc tgccgcccac agcaaacttg tcctgtgggc ccagcacaca    300
cagcaggcag tgggtgcggg cttaccctcc tggcccgtca gcgtccacac agaggccttg    360
tggcctgtgc cataggtcac gatgaggtta ctcttggagg cccagttgat gccttttacc    420
tgcccgttgt gctccttgag ctcgggcacc ttggcccact tggcccccact cttacagctt    480
cgtggttgtt gaggcagatg gtggccatct gggtgcggcc cttgctccag gtttggcagc    540
aatgggttcc tgcagtcagc tgtgggaggc tgtagttgct ctccttttca gagtacccca    600
gctgcagact ctgggcagga cgcacccaac cagtgctctg gttttttgaa gtaaaaaatg    660
cataatgcaa ttttaccatc ttaaccattt tttaattatg aaatccggta gtgttaagta    720
taattgtgtt gttgtgaaac agatctccac aactttttca ttttgcaaaa ctaaataact    780
cctctttccc cctactccca agctccaggc agctaccatt tctgtttcta tgaatttgac    840
```

```
tacttatatt acctcatata aaggggttca taagtatttg tcttttcttg cttggttaca    900
tcacttagca tgatttctta agtttcattc atgttgtagc acatgtcaag atttcctttt    960
tttttttaa aaaaaaggat gaagactatt cgtttgtatg tatatgccac attttgttta   1020
tccatccatt tttcttcaaa tgtttgagtt gtgtgatgtt taattatgtg tcaccttgac   1080
ggggcaaagg gttgcccaga cagctggtaa aacattattt ctgggtatgt tagtgaggct   1140
gtttccagaa gagattagca tttgaattgg caggctgaat aatgaagatc tgccctcatc   1200
aatgtggatg ggccagaaca aaccaaaaag gtggagaaag gaccagttat ctccccacca   1260
cccctgtgcc ctttagctgg gacatccatc ttctgccatc agacatcaga gcttctggtt   1320
ctcaggcctt cagactccag aagttatacc agtggcttcc ctggcttttg gactcagact   1380
ggggtttcac tgtatgtttc cctgattctc aggcctttgg acttgaattg aattacagca   1440
tgaactttcc tagttctcta gcttgcatat ggcatattgt gggacttctt gacctccata   1500
atcatgtgag ctaattccca taataaatct cctcttatgt atctataatt catatagata   1560
tgatatctat atatcaatcc catagataaa tagatgtctc atatatatat caatgtctct   1620
atatgtagat gtctcatata tggtatctat gtatctgtat catctctata tatctaatca   1680
tctaatatag atgtctcatg atatctatat agatatatct atatcataga tgcagagata   1740
tcatatatat gtctgtttct ttggagaatt ctgactgata caggttgctt ccgccttttg   1800
gctatcatga gtaatgccgc tgtaaccatg ggtatgcaaa tacttctttg agaccctgct   1860
ctgagttctt ttgggtaaat acccagaagt ggattgctgg atgatttggt ggttctactt   1920
ttaatttttt gaggaaatgc catactgttt tccataatgg ttgcaccatt ttataatctc   1980
accaagagtg cacagggttt caatttctct acatccatac caacacttat tagtgtgtgt   2040
gtgtgtgtgt gtgtgtgttt aatggctgtc ctaatgggtg tgaggtgaca tttcactgtg   2100
gttctgattt gcacatctct gataattgct ggtgttgagc atccttccat atgcttgttg   2160
gtcatttata tatcatcttt ggaaaaaatg tctattcaag tcttttgtct attttttttc   2220
cttccaactt ttattttagg tctgggggta catgtgcagg tttgttacat ggataaattg   2280
tgtgtcatgg gggtttggtg tacagattat ttggtcgcct aggtaaatga gcatagtacc   2340
tgataggtag tttttttgacc ctccccccttc tcccaccctc caccctgaag taggccccag   2400
tgtttattgt tcccttctta gcatctgtgt gtagtcaatg tttagctccc acttataagt   2460
gagaaaatgt ggtatttggt tttctgttct tacattaact tgcttagaat gatggcctcc   2520
agcagcatcc atgttgctgc aaaggacatg atttcgttct tcttatagct gtggtgtata   2580
tgtaccacat tttctttacc cagtccactg ctgatgggca tctaggttga ttccatgtct   2640
ttgatattgt gaatagtgct atgatgaaca tatgtgtgca tgtgtctttg tggcagaaca   2700
atttacattt ctttgggtat atatccagta atggggttgc taggtggaat gattaattca   2760
cttttaagtt ctttaagaaa tctctaaacc tctttcccca gtggctgaac taacttacat   2820
tcccaccagc agtgtccaag tgtttccttt tctgcacaac cttactaaca tctgttattt   2880
tttgactttt taatgatagc cattctgact catatgagat cgtatctctc tgtggttttg   2940
acttgcattt ctctgatgat tagtgatgta gagcattttt tcaaatgctt gttggccgca   3000
tgtgtcttct tttgagaagt gtctgctcct gtcatttgcc cactttttaa tgggcttgtt   3060
tgttttttgc ttgttaattt aagtttcatg tagattctgg atattagacc tttgtcaaat   3120
gcatagtttg tgaatatttt ctcccattcc ataggttgtt tactctgttg atagtttctt   3180
ttgctatgca gaagctcttt agtttagtta ggtactactt gtcaattttt gtttttgttg   3240
```

```
ctttgtccat tttaaaaaat agagtaattt gattattttg ttgttgaatt gtaggaattc   3300

tttatatatt atggatgcta acatcttatc aaatatgatt tgcaaaacat tttccctcat   3360

tctgtaggtt gccttttcac tattgtgtcc ttcaatgaac aaaagttttt atgtttgatg   3420

cagtcccatt tgtccatttt ttttggttgc ctgtgatttt ggtgtcatat ccaagaatgt   3480

ggaatgtgtc atatccacat tcaatgtcct gacgattttt ttctatgttt tcttccagaa   3540

gttttattgc tttgggtctt tggtttaagt ctttagtcca ttttgagtta atttttgtat   3600

gtggtgtaag aaacaggtcc aactgcattg ttttgcatgt aaatatccag ttttcccagc   3660

atcatttgtt gaccagactg tccttttccc atttagtgct gttggagctc ttcttggagg   3720

tcagttggcc atgtgtacac aagtttattt ctgggctctt tattctgttc tattgatttg   3780

tatatctgtc tttattccag taccacactg ttttattctt ctttttcaaa attgtttgac   3840

tcttagggcc ctttgagatt ccatatcaat tttaggatga attcttctat ttctgcaaca   3900

aatgctattg gaattttgat aaggattgaa ttgaatctgt agactgtttt gagtgatatt   3960

aacatcttaa taatattaag tctaatccat gaatgtgaga tgtttctatt tatttatctc   4020

ttctttgatt tctttcagta atgttttata gttttcatta tataagtttt tacttcctta   4080

gtcaatttct aagaattgtt ttctttttga tgccattgca acgggaatca ttttcttaat   4140

tttttcagat gctttcacta tttgtgtata gaaatgtaac tgattttttg tatgtgtgtt   4200

gattttgtat ctggtaactt tactgaattt ttaaatttgt tctaacctgt tttttttttt   4260

tggtggaatc tttaggattt tctgcatata agatcatgcc atctacaaac agaaattttt   4320

acttctttct tcccaatttg gatgcctttt attgcttttt cttgtctaat tgctttggac   4380

tggagttcca atactctgtt gaatagaagt gtccagaaca gacatttttg ccttgttctt   4440

aatcttagag gaaaagcttc cagtttttca ctgagtatgc cgttagctgt ggacttttcc   4500

taaacaacct ttattatgtg caggtaattt ccttctcttt ccacttttga gtgttttttt   4560

tcttttcttt tctttttttg tgtgtgaaag gatattgaat tttgccaaat gcttttcctg   4620

catcagtgga gatggtcatg tgggttttgt cctttattct gtaaatgtgg tgtactacat   4680

tgattttcat atgttgaacc atccttgcat cccagggata aatcccactt gatcatggtg   4740

aatgatcttt tgagtgtgct gttgaattta ttttgctagt attttttga ctacgttcat   4800

cagacatatt gggtaattat ttattttttc ttgtagtatt tttgcctagc tttgatatca   4860

cactaatgct gcccctcaaa gaatgacctt ggaagtattc ctttctcttc agtttttggg   4920

ggattgatgt aaattctttt tttttttttt ttggagacag ggtctcactg tcacccaggc   4980

tggagtgcag cggcacaatc atagctcact gcagcctcta actcctgggc tcaagcaatt   5040

ctgcttcagc ctcctgagta gctgggacta taagcatgtg ccaccatgca cagctaattt   5100

atatatatat aatataatag ataaatatat atatatatat atatatatat atatattttt   5160

tttttttttt tttttttttt tttttttttt tgcagagaca aggtaggtct tgctatgttg   5220

cccaggctgg tctcagactc ctaggctcaa gtgaacctct cacctcagtc tcccaaagtt   5280

ctgggattac aggcatgagc caccacgtct ggccagtgtt aattcttcaa tatttggtag   5340

aattcttcag tgaagtcttc tagtcctggg cttttctttg ttgggaggtt tttaattacc   5400

aactcaattt ccttactagt tattggtcta tttatatctt ctatttcttc atgattcagt   5460

cttggcaggt ttggtgtttc tagaaattta tccatttctt ataggtcatc cagtttgttg   5520

gtatagttca tagtcttctc ttataatcct ttcttatctg tagctcagta cctcctatct   5580
```

-continued

```
ggagatgcag aattaggaat tgaaactata ataggccccc cttttataat ggggtgtcct   5640
tatttttacc ttctcacctt gcaataccct tgtcttgcta gtaaagaaag aagggaaatt   5700
tgattcagga ggtaatcata cttttcaatt tgtacaagat ctaatagcca tgaactccta   5760
tgtcattcct caccatccca taattcttag cccagccatc atccttacct caatccctgc   5820
tggtgcagcc tggtttattc tgttaatgtg ctgtactgca ttgaggtaag gacttctgct   5880
cagctttctt cttgatacca ttgtaccttg attcacactt cctcttgtga aataaagttt   5940
agcatgaagc tgctttctta catattttaa gttcggctta aaggtttttc tgtacatcgt   6000
gaactgtaac aagtggaata taaccagacc gtagcttaca cttgtgccat ttaccaagtt   6060
ttggccaatc aaatgtagcc aactgtttga actgtattca aataagggaa atgctcagct   6120
gtaaccaagc caactgtttc tgtacctcac ttctgttttc tgtatgtcac tttccttttt   6180
ctgtccataa atcatcttcc atggcgtagg tgtgctggag tctcagagtc tattctggct   6240
caggaggctg cctgattttg aatcattcat ggctcaatta aacttcttta attttttttt   6300
tttttgagat tgagtttcac ccttgttgcc caagttggag tgcaatggtg cagtctctgc   6360
tcactgcagc ctctgcctcc tgggttcaag cgattctcct gcctcagcct cctgagtagc   6420
tgagattaca ggcacatgcc accatgccca gctaattttt ctatttttag tagagacagg   6480
gtttcgccat gttggccagg ctggtctcga actcctgacc tcagcctccc aaagtgctga   6540
gattacagat gtgagccact gcacctggct tcactccttc aaatttaatt cagctaaagt   6600
ttttattttt ttctctttct tttttttttt tttttttgag acagagtcac tgtcacccag   6660
gctgaagtgc agtggcacaa tctcggctca ctgcaacctc cgcctcccag actcaagcga   6720
tttctggcta atttttgtgt ttttagtaga gatgggtttt caccatattg gccaggctga   6780
tcttgaactc ctgacctcag gtgatctgcc tgccttggcc tcccaaagtg ctaggattac   6840
aggcatgagc cactgtgccc agcctcaaat ttaagaagaa acagttaaca tggacttgca   6900
tacctccagg atattgtgaa tacctctcaa tatttttcta agttctcaaa gtcaaattag   6960
actctatgac aatcactcaa ggttcccttt gtttccaata tgttgatgac ctgctacttt   7020
gcaaccaaag caaacagggt gctcttctgg actcccttac tcaccttaag gcactgactg   7080
actaaggtta taaatcttcc aggtccaaat gccaacaggt acaaaaaatt cttacctact   7140
taggccataa aatattttag ggtactcaaa aactcgtccc aaaatgcctt gaatcaattt   7200
tattcattat ctctcaaaga caaacaatta cgtgaatttt taggagcaac tggatattgc   7260
caatggattc ccaattttgc tgcccatgtc taacctttat atgctgtcct cttagataca   7320
accacagagc actttacctg gtactctgag gcaccagcct ccttggaagc attgtccaca   7380
ccccagccct tcgactaccc aactttgaca atctttttta cctatattac tgtgaaaatg   7440
atgggattgt tgtgggtatc ttaggacaat ctttttgtcc cataacatat ttctcatgtc   7500
aacctagata tgtcccacag tacctttctc atgttaagta gcatcaggca ttcctccatg   7560
cttatatgca atagacttag ctgccatcct aattgacaaa gcaagtattc ttatactgcc   7620
ccaccattca cctctctgtt ctccatgctg ttcctctaca ttggtatccc tttcaaagtg   7680
gatcttgcct caactaaccc ttaactgttt tttttttgtt tttgtttttt gtttttttgac   7740
aattctggca ctaccccaac acctgcttgt tccaatcttt caaagcctgg ccaccttaaa   7800
tagttaatct ggttactggt taggttaaca tctacataat gcagaagagt ttttgttcct   7860
accaatgtaa atatacctgg tgaacccatt ctggacaatg gatatataaa agcatatggt   7920
atccataagc aggaagacaa agtcactctg tctcctcctc tggtagatta atttggcact   7980
```

```
gggaagcctc catggaagct caaggtcagt gctttaccca agtaagacta ttggaaggaa   8040
atctctctac attgaaaata aatacagtac tggacctttt ctgggtaaca tttcaaaaat   8100
gtattgcaat caaattctgt gatttggctt cacagatggc actaaacaac cctccactgt   8160
cattgttact tggattataa ctaagtattt caatgtgagt gaatgtcaga ttacaggata   8220
atattcctgg tttgtaggaa aaagtagtgg gatatggaat agctcaagtg ttcccctagt   8280
tggcttgacc agcacccatg actatagttg gatggatgga ccttaacttg gtcaataaat   8340
aaaatacatt tctatagtaa ccaaggctaa attaaagggt ttctctgcca ggtgtttcac   8400
aacctgtttt accctcatag cctaacagaa gcacattgga agtgaagatg tgcagatgcc   8460
aacatgattg atgataaggg ttgtgaaaga cacagaattc caacttggtt gttcacaggt   8520
tccaccacta tgaccttgtc tgtaaacaac actggtctct ctctcttttt tttttttttt   8580
agaaggaatc tcactctgtt acccaggctg gagggcagtg gcacaatctc agctcactgc   8640
accctccacc ttccggttca agcgattctc ctgcctcagt ctcccgagta gctgggagta   8700
caggtgccca ccaccatgcc cggcttattt ttgtagtttt agtagagaca ggatttctcc   8760
atgttggcca ggctggtctt cacctcaagt gatccgccag cctcggcctc ccaaagtgct   8820
gggattacaa gcgtgagcca ctgtgcctgg cctggtctca tttttatgta gcaataagat   8880
atataaaagg ttcccaccta agtggtcaga gaaatgtgaa gttggatatc tggtgccttc   8940
ccttaccaga tatcccactt tgaatgctag ccacattaca actggggttc ttttatatat   9000
aaattaatgc catgtagatg cacctgatga gacatcatag acaacgcact tatgtattgc   9060
aaccctaagt tctcagtaat gagaatgctt ttccaaagcc tggcaatgta cgatgtagaa   9120
agaacaatcc taagcattcc aaagtaatga acaagcatct ggtgccacta tacagactgg   9180
gaagcctgcc atttacaagt tagcagtgta gcctctgttg cactccaaaa ttgtgtccta   9240
gatatgctga ctgcccaaca gagaggagct tgtacaatca ctggcaacaa tgctacttct   9300
atataaatta gaaaggaaaa attgtgtcta atctatatca tttaaaaaga aaggttggcc   9360
gggcacggtg gctcacgcct gtaatcacag cacttcggga ggccgaagcg ggcggatcat   9420
gaggtcaggg gatcgagacc atcctagcta acatggtgaa accctgtctc tactaaaaat   9480
acaaaaaatt agccaggcat ggtggcgggc acctgtagtc ccagctactt gggaggctga   9540
ggcaggagaa tggcgtgaac atgggaggcg gagcttgcag tgagcagaga tcacaccact   9600
gcaccccagc ctgggcgaca gaacgagact ccgtctcaaa aaaaaaaaaa aaaaaaaaaa   9660
aaaaaaaaaa gaaaggtcaa cattctacgt taggtaaata aggcatagtc caattaactg   9720
aactgaactg acctattccc acgactggga gactggttca acagaatatg gaccagtgtg   9780
ttcagatttt tctctgttgt aatctatgtt cttctttcat tttgcagatc tcttacctcc   9840
cagcacctaa tatgagtctt ttctacatag gaaataatcc aaatatttgt gaaacttcat   9900
gtgaagtttc aaatggggga agtgaaggaa cgaacaaccc acctcctaac cccaatttat   9960
acccacctgt gttagttcat ttgtattgct atgaagagat acctggaggc tgggaaattt  10020
ataaagaaaa gaggcttaat tggctcacag ttctgcaggg tgtataggca tggcatcagt  10080
atgtgctcag ctcctggtga gggcttcagg gagcttacaa tcatagctga aggtgaaggg  10140
ggagcatgca tcttacatgg tgatagaggg agcaagagag agggtcgggg ggtgccaggc  10200
tctttaaaca accagctctc atgtgaaata ccagagccag aactcactca tcaccatggg  10260
gatggcacta agccattcat gagggatctg cctcatcacc caaacacttc ccagtaggcc  10320
```

```
ccacctccaa cttggggatt gtatttcaac atgacatttt gaggggacag atatccaata  10380
ttcaaaccat atcaccacca gaaaggcata aagattactt taaactgaaa atattggaac  10440
aaacaatcgc tgcggaaagc agccttatct gaccgaaagc agacctgtcc aagagttctg  10500
ctatcatcaa ctccttctga gggactttcc agacagcgag gtgacagatg tttacaaacg  10560
tgacgttaaa aaataaagtt gtgtaaatga gtcttatcag aaccttttat actttctcac  10620
tgaagcctca gttggtatat aaacccttac cactggctgt ttgggaagtg actccttaca  10680
gagtgctccc tcaggcatgg agaataaact tttctcctgt taatgtattt tcaactaatt  10740
cgcaggccct agaccactca gatctaagtt gacagatgaa atgttttcct cccaacatga  10800
ccaagcttat agtgctttta tggtatatct gtagagattg cggtcaggca taacattgtt  10860
tgttagggtt gcagtacctt tcaggaaatg ctcaaagttt aattgattta ggggactttc  10920
actggatgag atgcctctct gagtcatcat aggttgcaaa gtattagttt tttgccactc  10980
actgtgtgtt gtgatatgac atactcataa tggggtagga caagatgtca gttttgcttc  11040
caaactttcc ttacttgttt cctttttggt tcaccactaa tgttgaagaa atgcaagatg  11100
gaaaatctca atagttgaca ctgattgatt gattgagatg gagtctcact ctgtcacctg  11160
ggctggagtg cagtggcgtg atatcggctc actgcaacct ccacctccca ggttcaagca  11220
gttctcctgc ctcagcctcc cgaacagctg ggattacagg tgcccgccac tactctcagc  11280
taatttttttg tatttttagt agagatgggg tttcaccatg ttggccagac tagtctcgaa  11340
ttcctaacct tgtgattcgc ccgcctcggc ctcccaaggt gctgggatta caggcatgag  11400
tagttgacat ttattaagtg tttatatgtg ataagcactg ttagattatc ccatgtaata  11460
catcacttga ttgatttaag agattgtcat ttgaaagatt aaagaatatt tcccagaaag  11520
gatgcttggt caagcctcat catcctggga tggatgggac cttggttttg ggcaagttta  11580
ttacaattta agactattct aggtcatgga agtgtgtgtt aggacatata agtagttttc  11640
ttgtccagaa tactttgtaa taatataccc taagtttgat cagctttttg gcattcactt  11700
aattaaaatg ttcacaagta ggtacatttt tagaattgtt aagtaatata ctatttgtag  11760
tagcaaaaca ctacaaacaa atacctaata taataagagg gagtggttga ataaactagg  11820
gcatgtcaac taaaaaacat atttgaaatg cagggaaaat gcttactcta ggcaatagtt  11880
acaacttttg tccattatag gtacataaag gaaaagagta cacaaagaat tctattaatg  11940
atgaaattag gaacaatgtt cccatcccca atttataccc aaaagaaaat atgttctggc  12000
tgggcgcggt ggctcatgcc tgtaatccta gcagtttggg aggctgagac aggtggatcg  12060
cctgagctca ggagttcaaa accagtctgg gcaacatggc aaaaccccgt ctccaccaaa  12120
aatacaaaaa attagccagg cgtgatggca catgcctgta ggtccagcta cttgggaggc  12180
cgaggtggga ggatcgcttg agctcgggat gtggaggctg cagtgagcaa agctcacacc  12240
actgcactct agcatgggtg acagagtgag accccgtctc aaataaataa ataaataaat  12300
gaaaacttat attctataac atgtattctt atgtctttgg ctaaaacaaa agagaagaaa  12360
aataagtaga gagctaagtg aagtgaagtg tcttgaaaca gataagccat aaagtgagat  12420
atatgagtaa atgagtagtt gctggcctag gaattgtttc tgatgttttc acctattgaa  12480
agaatttttt tctttttgta aatctttttt ttggtttgtt aaactgaaaa ataaaagcaa  12540
tgaagagata atattgctgt agtaatgtcc cttagtgcat ccttggagtt agttgtcttg  12600
aatttggcct gctctgattg tcatttgctg tttgctgcat tgaaaaaatt tcagatttac  12660
aaaaatatgt gtgccagggt ggaggaaatt tttaacttga tgaattctca cctttaggac  12720
```

```
actgtctgct cttatatggc acttagcaag atgctgcaac aattgtccct gctcatactg  12780
ttggaggaag agggtatttg cagggagatt gctggagtca agatgatcca aatttaaatt  12840
gcagtggtga gcagtggcca ctagagggct gtgaagtact taattctaaa atttccacat  12900
tttaatctgg agcagaggaa actctggaag gaccactggg actaagggag ctcaatccca  12960
aacatcttta tctgagccct aaatgtcttc tacgttattc tttgacaata ctttgttaca  13020
tctcagaatt tgtagttttg aggtggaggt ttaagttaga aatagtttaa tatattctat  13080
tccagaatat aattcgcttt tttccaaatg aaactggcac taaaagcttt ttacttgaaa  13140
gcaaatacac ttcatatgct ttatgtattt ttgtccctat atcattgaaa tagtagattc  13200
aaggctgttt gtaaaaataa gtgactatac tgcatatagg aatagcccca ccttaaagac  13260
tttgatttta aggacattaa gtgggagggt ctttttttgcc tttttttttt tgactatcaa  13320
aatactttca catttcttca attcaaagaa caactgttct aaatttagaa gacagacaag  13380
tgaaagagaa tatgctgcca tttccgatgg ttctttttta ctcttgatcc atcactctcc  13440
tgtctttggc tgactctttc tccaaaaagt accccttatt tttcctatgc ctttaacttc  13500
tgttttactt actctattgt agaactttga gaagttgtac accacattca ctgctacctc  13560
acattaactc tgcttactca ttgcagtctg ccttctgctc ctcaatgatt gctcctgtga  13620
aggtcatctt tggtttagca cttgtttgaa atctaatagc ctaaatgcac atcgattact  13680
gtttagaatt caaacgacat ttatttattt actttgagat ggagtttcat tcttgtcgcc  13740
cagctggagt acaatggcat gatcttggct cactgcaacc tccacctccc aggttcaagc  13800
gattctcctg cctcagcctc ctgagtagct gggattacag gcaccctcaa ccacgcctgg  13860
ctaagttttg tatttttttt agtagagatg gggtttcgcc atcttggcca ggctggtctc  13920
gaactcctga cctcaggtga tctgcctgcc tcagccccac aaagtgctgg gattacaagc  13980
gtgagccacc acgcccggcc caaatgacat ttatttttaa aagcaactaa accaggaaag  14040
accttcactc attcaatcaa aaaacatgca ttgaacacgt attcttggct agatccggtg  14100
ctgcaaagat gaaagacgcc actcctagcc tcaaggagct tgcagtttag tggtggcact  14160
ggatgtaaaa taatcataag atgtgaggtg aagactgatg aggtctattt tgttgacaca  14220
ggtaaacatt ctcagagaat atttaattag caacatgaca aaaattagtt gatttatttg  14280
aaggatattt aagtgaattt agagatgaga tttgttttta ctttttttaat ttcagagagt  14340
tatgttggtt gcaaaaatct ttgttttcta gtatctattt tataagccat ctgagaccag  14400
gatgttttct ttttaacatg taaacttgat gcagtctctt tgtaaagtaa tgaatccccc  14460
cgtgaacctc aaggagaaga aagtttagct tgaacactta atttcaagta ccttgagaag  14520
ggaacaggct gtattgctca gagaagaagg ctctattagc taaggtagaa ggacaatgta  14580
aaactcttgt gaagacacct aaatgtcatt ccactcaaag cccattatta ataatttgaa  14640
actgtctgct ctgtgaaggc aacgacctat ctttactcat ttttgactct gctaacattt  14700
ctttttatag ttgaactaga ggcaaggcaa ggaacttgac atgcttgttt tccctttaga  14760
ataaagtggc cagaagcagt ttcttctgtg tgatccaaca ctttcttatc cccagagcaa  14820
ctctgcatag tctagatgta ccagagccca gcagcctgtg aggtgatgtg atgtgatgtg  14880
atgtgaacag aaaggctcca tgttggatga tgcctatgaa tctaatcaga ttctctttct  14940
tggtcatttt gatttccaga gaaggcagta gaagcaggtt ctgtgtgtat aaccagagac  15000
tagagggagg aactgacagg gaagctgggt catgagagtg gtgtgctcag cagagtaggg  15060
```

```
agtaagagag agctggctcc agagaggatg acaaaatgcc catgtctcca gcacttcttt  15120
agcattctga gttcccatcc tatcatgaat aggaagagtt ttctagctct ccatgaagcc  15180
gaaataggtt tcagactttc ctttctttcc cacacacata ataaataccc atcaggtaac  15240
ctgggcatgg ccttttattt aggcactaac aattctaaaa ggaattaata aatgcttcac  15300
tgccatttca cagtgtaaca gcatgccagt ttaccatacc attaacattt agcctcgtgg  15360
tatttctgtg ttttttcagt cagtaatgat ggcatttttg ccaagataat atagtgttaa  15420
actgtattgg ttgaaatcct aggcttttta aatgtaaact agcactttac aaagtattac  15480
aaaggaaacg aaccagggaa acttgagaag gaactttctt atccacattg ttataggtta  15540
taaaatagtt cctatttaaa ttaaaatacc tactgttgca cttttatgtg tgtttttata  15600
tataaataac atctgggttg gcaaatatgt gattttcgtc aaataggctt tgattgaaga  15660
tgaaatattt ttgtaaaact agtccttttt taaagttaaa attttatgtt accacatgaa  15720
ttgatcagca gaaatttatt tacattatgt aaattgattt ttaagagtat ccacaaggtt  15780
ttagctatta tttttgaact tgcttcctag cccacacaat taagtaataa gagtaagaaa  15840
aaagaaagca cacatccaaa tcatctatca aaacccagct tctacccaat gacacatcat  15900
tttatttctt gatcttgtaa tgttgagcac atgccttgga catattccta tatgtgggct  15960
ctattctctg cagcacgtca ctccctcttt tatccgcccc tcttatgtgc tcccactcct  16020
atcctcttca attaaaaatg cctctttctt ttttttttaa gttaattaat taattaattt  16080
ttttttattg atcattcttg ggtgtttctc gcagaggggg atttggcagg gtcataggat  16140
aatagtggag ggaaggtcag cagataaaca agtgaacaaa ggtctctggt tttcctaggc  16200
agaggaccct gcgggcttcc acagtatttg tgtccctggg tacttgagat tagggagtgg  16260
tgatgactct taacgagtct gctgccttca agcatctgtt taacaaagca catcttgcat  16320
ggcccttaat ccatttaacc ctgagtggac acagcacatg tttcagagag cacagggttg  16380
ggggtaaggt catagatcaa cagcatccca aggcacagga atttttctta gtacagaaca  16440
aaatgaagtc tcccatgtct acttctttct acacagacac agcaacaatc tgatttctct  16500
atcctttccc cacctttccc cctttcctat tccacaaaaa ccgccatcgt catcatggcc  16560
cgttctcaat gagctgttgg gtacacctcc cagacggggt ggtggccggg cagaggggct  16620
cctcacttcc cagaaggggc ggccgggcag aggtgccccc cacctcccgg atggggcggc  16680
ggctgggtgg aggcgggccc ccacctccct cccagacggg gcggctggcc gggcgggggc  16740
tgacccccca cctgcctctg ggacggggcg gctggccggg cgggggctga ccccccacct  16800
gcctccggga cagggtggct gctgggcaga ggggctcctc acttctcaga cggggcagct  16860
gccgggcgga ggggctcctc acttctcaga cggggtggcc gggcagagac gctcctcacc  16920
tcccagacgg ggtcgcggct gggcagaggc gctcctcaca tcccagacgg ggcggcgggg  16980
cagaggcgct tcccgcatct cagacgatgg gcggccgggc agagacgctc ctcacttcct  17040
agacgtgatg gtggccggga agaggcgctc ctcacttccc agactgggca gccaggcaga  17100
ggggctcctc acatcccaga cgatgggcgg ccaggcagag acgctcctca cttcccagac  17160
ggggtggcgg ccaggcagag gctgcaatct cggcactttg ggaggccaag gcaggctgct  17220
gggaggtgga ggttgtagct agccgagatc acgccactgc actccagcct gggcaacatt  17280
gagcactgag tgaaccagac tccgtctgca atcccggcac ctcgggaggc cgaggctggc  17340
ggatcactcg cggttaggag ctggagacca gcccggccaa cacagcgaaa ccctgtctcc  17400
accaaaaaaa tacgaaaacc agtcaggcgt ggcggcgcgc acctgcaatc ccaggcactc  17460
```

```
ggcaggctga ggcaggagaa tcaggcaggg aggttgcagt gagccgcgat ggcagcagta  17520
cagtccagct ttggctcggc atcagaggga taccgtggaa agagagggag agggagactg  17580
tggggagagg gagagggaga gaaaaatgcc tctttcaata tgtaaggtaa gattgataga  17640
tgattgcctt ccgtagttcc tcccaaaatt cataggttga aatcttagcc ctcagagtgg  17700
tggtattagg aagtatggag cctttgggag ataattagct caggagggtg gagccctccc  17760
gaataaattt aatgccttta taagcaagac cccagagagc cctttcaccc ttttctaccc  17820
tatgaggaca cagcgagaag acagctgtct gtgaaccagg aagcaggccc tcactacata  17880
ccgaatctac aagcaacttg atctcagact tcccagtctc ctgaactgcg agatataaat  17940
gtttgctgtt taagtcaccc agtctaaggt atttttgtta tagcagcctg aatggactca  18000
ggcggtaggc aagaggagga cagtgcacct gagttataca ttgggcaagt catttacctt  18060
cattggagcc tcggtttact tgtgttagat atgggaataa tgatagttac actgcagggt  18120
ggttgtgaag attagagaaa gtgcatatac tctgatcagc acagtgcatg gtacttcagt  18180
acacagtgtt aactgaagac acagtgttaa ctgaagacac agttgaaaac taaagatagc  18240
tagtgaaaca catgttctct gcacatcata cagtttcttg ggcagttttc aaagtgtgac  18300
tctgcagttc ataccaccat tatcacttag tctctaacaa ataatcatat ttgacacatt  18360
tggctgggac ttaataattt tatttgggca gcagctggtt tctggaagtg ttcatgggaa  18420
gaaaatgtat attaataaag ttagcaggta atgttctttg ttgaaatgtt ggatattgtg  18480
ggacacaaaa gagtcagggt aaatgtacat ttacagaatt gagcgtcaga gtgtcatagt  18540
tctctaatga tttacaaaga aagaattcct ggaacaagtg aaatacttaa taattaattc  18600
agcctgtatt tctgcaggta atcaactgca gtgataaaaa aataaaaatg gaactgtctt  18660
ttgctcattg gaaagatatt tgctgcattc aaagtcatca aaaaggcgaa gcaatgaaac  18720
ttaagacttt tgggttttaa taattaaaaa tccatcttaa agagaacctt gggctctggc  18780
acggtggctc attcttgtaa tcctagcact ttcggaggcc caggtgggcg gatcacttga  18840
ggtcaggagt ttgagaccag cctggttaac atggtgaaac cccatctcta ctaaaaatac  18900
aaaaattagc tgggtgtggt ggtgtgcgcc tgtaatccca gctacttggg aggctgaggc  18960
acgagaatca cttgaacctg ggagatggag gttgcagtga gccaagattg tgccactgca  19020
ttccagcctg ggtgacacag tgagactctg tcttgaaaaa aaaaaaaaga gagagagacc  19080
gtttgtgaag gtgtgttaca cagagaattc ctgattccta atctccagaa tagaaaaatt  19140
caaaggctca gaatcatccc aaatcaatta tccagtggca tctgcatttt ccgatttcat  19200
tctcactagc cgtgtgaaca tgggcatgac cccaggagcc aaggaattct ctaatgccta  19260
aggacagcca tgaggtcaat gaataacatg tgtcaggttt ccctggcaca gaggagcttc  19320
ccagtaaatg ttattttcct tagctatttc ccatttaaca tgtcaattat tcttagtgag  19380
tttccattca atatgagagt ttatataatt tgtcatattg aataggaact tgctaaggaa  19440
agctgtgtag cagaggaagc agccccaagt gacaggacat aaactttaaa ttcacaagat  19500
gcttgtatgt gaattatgat ggtatctgaa ttaacagtga tatttacagt ttagtaatac  19560
atttttcttc ccttgtcttg ggctttataa aaaccctgta agtcatgtat gtcaggaatt  19620
ttatcctcat aattgagaga aaaatactcc atattttatt ggaaataaga tcagtagatt  19680
ctctgtatat catacaatgt cttgcctact taaattatca ccccccttcc tatttcaaca  19740
aagactttct ctaagtaccc ctggcctctt gccctgatcc atactgttct ccttggtaat  19800
```

```
ggagtgagtt tcctgcctgg tgggtgcagc cattggccac atttctctag tgtatggaac  19860
tcaccggata aaaggcctca gatgtaggtc tctttctgct gtcttcaccc aggtgttgtg  19920
gagtgtgtct gtccttgagc actagctttc ccctgtgtgg gctgcctcaa ggcctgcatt  19980
catcaggtag ggactgttag ctggtagacc taagccacca ctccagtact gactgtcagt  20040
aaggaaggtg acatgctgac ctccatctgc tacatcattg tgtatatgtc ttcattagtt  20100
ctgcatattg gtgagaaaat ggatgctctg attcctcttg aaccccaaga gaatgaaggt  20160
aaaaaaattg aggtcctaat gcaaattttc ttagtacacc caaatctttg gatagagtcc  20220
tgcactcttt gagatatatc acacaatctg tctcactttc ttttcgcata tgttatatat  20280
tttaaaactt ttgtttttgg ggccaccact tactggctct gtgattttag gaaagctttt  20340
cagaccctca gaaccccagt ctcttcatct ctaaagtaat aaaatatatg taaagaacct  20400
atttcagcat gtgaattctg ttttcctttt tcctctagat gtatcatatc cagttaaaaa  20460
aaaatctact tgaactttgc aggtatcttc agtgtttatt acttctcatt tttaacattt  20520
attggaaatt agcatattgt cagaattgat ataatacaat atgtaacctc tttcattaag  20580
cttatcattt ttaaaataca aataactatt ctttacttaa atttttattt ctagacacag  20640
ggtcctgctc tctcgaaccc aggctggagt gcagtggcac aatcatagct cactgcagcc  20700
tcaaactctt gggcttaagt gatcctcctg cctcacactc tggagtagct gggattatag  20760
acctgagcca tggtgtccag catgacttaa attttgaata agttgcactt actaattaca  20820
cttacactgc tgcatctgaa agagtaatac aacaatagaa gccttttata gtaattattt  20880
gtggcaggta gactcctaaa atgactccca aatgacccac acccttgtac aatcaatacc  20940
ctgtcccttg agtgacagtg acttgctcta atcagttggc tttcagttaa tcaaaagaga  21000
gattatcttg ggctgaacta aactaatccc agcaagataa cagggacttc agtcttgcaa  21060
acagatatca tataaaggga atcatatctg cacatttgat tcttggaccc tgggtaggaa  21120
tttgttagag agcaaggatg tgaataaagg tgggaaataa aggtgtatct ggtgtctctg  21180
ctcaaaagct cacatgtagc tacaaggcag agatttaggg gagtggtatc cacagtcaag  21240
aagaattaat acatagtgtt tgagtctggc ttcttccaat tagcataatg cttttgaggt  21300
tcatccatat tgttgcatta ccagtagttt ttatttattt attttatcag tagtttctaa  21360
attgttgagt agtatattac attgtgtaga tatatcctgt gtgtttatcc atacacattt  21420
atggatattt gggagttgct agtttttagc tattctatga gcattcacat acatgtcttt  21480
gtgtggaaat aggttttcat atctcttggg taaatatacg ggagtggaat tgctagatca  21540
tatggtaaat actctgtata cttaaaatga agagaaactg tcaaactatt ttccataatg  21600
gctctaccat acttgatgtt ttagaaaaga ggaaaaacac tagcaatttt gatgctgtat  21660
gtctacaacc taagagaatc taataatagc gtcctggtct gtcagtgtag gaattgccta  21720
ggtaatacat ggaaggtgtg gagggagcag gtacacagaa aatgtgcgtc agaaagtttt  21780
gcttttccta tcccacgtca tttctgagtc tgatcctccc tactcctcac aaataaattg  21840
gtagattcat ctgtttttgg acccttttct gctctagtta ctgaactatc agagacttca  21900
ggaagagctt aagctaagct attccaggga agttttggtg ttactctgta cttacggact  21960
cctgcgtgtc tgtctctgtc accccagctg ccaactcaac ttagagttta ttagcctggc  22020
attgaccagc acactgtgat attctctgag gcacactgca tgctgctagt gtgccctggt  22080
tcataaagct gggccttcag cattgatccc actccaagtt ccttgctctg tcttcccaca  22140
gctgtcccct tgggggatgt ggggggtctg acatcatttg cattattagt ctattccaag  22200
```

```
aaatgcacct gtgcactaat cagttcactt tttctgtctt agtcggcaga tctagccata  22260
gcccaatccc tcaatttcta tactaagcct tttatattag taaaactgtt atgttatcta  22320
gaaattcatc agtgggaaaa ctacttcaag ggaggtagtt agaggctgca aggtgctaaa  22380
tatttttctt tctttctttt taaatgtaac ttggatctaa agtaaggacg aatttccttt  22440
tattatttgt tcagaatata ccagctggtc ctgtgggcag aagtttgtta aggggcctgg  22500
atgtgaaata acagtgtatc tcgtgtctct gctcaagagc tcacatgtag ctacaaggca  22560
gagatttagg ggagtggcat atacggccaa ctgagaaata acaatattgt cagggactcc  22620
aaggcacttt ggaagatata aagaatttct taaattttct tgtagaattg ttgcaaaagg  22680
cagacatgct taaatgttta aataagcttc ttgaaaactc atggaacatt caatcacaac  22740
tccaacagtt ctccaaaatt tgatttattc tggccatatt atgcagcaaa gaaacacttg  22800
gctatttatc taaatctctt ctgtcttgta aatgatccta gaaaataatc tagaaataca  22860
ttttattaaa gtaatgcatg aggtacatat cgattaccag ccaatagttg aacttaaaca  22920
taatgcatgg gtgtgagggc tggcattgat gattcacaat gaacacagtt gaatatcact  22980
tccctgctga gactcgggta tcatcgcaaa accacagtga gcatcagtgg ggatctgcat  23040
gctctggtca agacagatct ccatgctgag tgtctgtttg ccatgatgaa gagaacagtc  23100
aacaggagtg tttgccatga tgtagagaac agtccgggag gagtgaatgg aggatggggg  23160
catgaggaaa gatgaggctt tctctagtta tgaccctttg tgtagaagtt aggagtaggg  23220
gataaatgtt tctgcctaat atttaacttg gaagagaaga tgtccatgtg aaaaactgct  23280
aaatactgaa acaagagagc atgtgactaa gcaataccat gtgtggcaca gaaaacaagt  23340
gcaatagcag tttagcaaag tgagttcagt gtaggctgaa ctggttagag caggtttccg  23400
ggtgaaggtg aggattggtg agggtttgga ttggtagaaa gagacgggga ggacatctca  23460
catcaagaag ttatgccagt ggatttcagg agaattgagt gtttgtgtct gaaaagcctg  23520
taagaatagg gcatgacagt gtggagaaat gcatgaaagt atgaaggatc gtgatatcca  23580
gtttgaggag tgctaactag aggctctgaa gatttgagaa gaaacataat gaaaggtgtt  23640
ctcagcctga tcttggtatg caggactggt aaaccccaaa caccttacca ttctattacc  23700
tctccctcaa ggaatgggtc ccttgataag aatttagtgt aaaaaagatt gtcaattcag  23760
tgctgctgct gagtgctagt ttctttaaac acacacagtt ttcttttgag aatttttttt  23820
ctattagata gacgaactgt tatttaaatg aaaaaggcac atagtcccat aaaacaatta  23880
cacattcggg tgataacttc aaaaggagaa attaaaatgt tcttatgttt tgagcaagca  23940
tttccacttc cagactttgc tgcataaaca tctgtggtca tctagggaat gcctgacctg  24000
gttcagaggt gtcagagcaa tgtaaagtca cggaagtgct gcagttctat tctgggctct  24060
catctttttg cagcggtcca ttctctaatt ttcaaccaca tattaccaga caatctctta  24120
agtcatacac aacaaactga ttctgtttca atgcttagaa ttagaataaa aaagcctaag  24180
caaaaatagc acaaacattt gaaaaacact cctttttttct accactccct tcttagaaca  24240
gaaataaaag ccctgtactt taagaaaatg gatggaagaa ttttctttgt acttcttatt  24300
ctccaagtta catttactac ctgatagtgt taataccttt ttgtagtacc tttctttaaa  24360
atatacaggg aaatgatctg ttccaagaaa ctgtgttttt aaatttaatt atagtgtgct  24420
atgatgattt aaaaaatggc cttttgagta aaggacacga acaagttatt taaaaagtga  24480
gcagtaagtg tggtcagtaa acacatcaaa aagttccctt cactaatatt caaagaaatg  24540
```

```
caaattagaa taataatacc cttgttgctt gtcaaattaa tactttaaca attattatgt  24600
aaattttatg gataggattg caaatcaaca cacctttcct ggccactggt gtacataata  24660
gaaattctaa aaatgttctt aggcttgacc aagcatttcc acttctagac tttgctgcac  24720
aaagatctgt ggtcatctag gagaaggctt gacctggttc agaggtatca gagcaatgca  24780
aagtcatgaa aatgctgcaa ttctatcctg gactgtcatc ttttttgtag tggtccattc  24840
tctaattttt caatgacgta gtaccagaca gtctcttaag tcaaatgtat ttgtagggct  24900
ctggatttga aattcaatct ggctttcagc cttgatgtgg ccactcccaa cttgtaaagg  24960
acctgtgaag acttagacac agaataaaac acagaagata agaaaaccaa ctttgaaaga  25020
aaatttattg tcaaaattgt actgggtcaa ttgagcaaaa acttcaaaga gcgttttcat  25080
attaaccaaa gcatccctcc tcaattgaaa catataaaga tattgttcac ccctatcctg  25140
actcagagat ccacaaatct gggcattcat catcaccata ttctgctggc aatagtttta  25200
agcagctaaa ttactgttct ctactcttga gtttcctcca tctcttcaga tacagaaagt  25260
tctagaatat attcaaataa tcaaatcttt aattcattcc atatatctgg ctcaagacag  25320
tgtcccaata accttattct agagaaagtc agatttagac ttgtgctcat catcatactc  25380
atgttcttga catcatttta agctctgagg agacatctca cataactctc attgatacgt  25440
gtatacatct gtcactctgt gtttgtgctg tgatggatgg acttggatgt agatatgcat  25500
agatgatgaa gcagatagct atatatatgg tattgatgta gattcagtac agctgtataa  25560
ttgcatctgt gtttcacata tcttgtgtac tgtatcttga ctgtatctgt gtcaatacct  25620
aattgagtta taaggcataa atatgtggag ctcttagcac aatacctggc acactgcaat  25680
cagtcgatgt atgtgtttgt gtgtgtgcgt gtgtgtgtgt gtgatacaga cagaacctgc  25740
taatatgcat aatagtcagg ttgggttgtt ataacaaaat actatagact gtgtggctta  25800
aacggcagac atttgtttct cacagttctg gagtctggga aatccaaggt caagattagt  25860
ttctggtgag agcagtcttc ctcttttgca gctccccatg gtttgcaaat cacagatttc  25920
tcgctgtatt ctcacatagt gtaggaggaa cagagggagg gaagggagga agtgcctaag  25980
gacactaatc ccatgatgag agttctatcc accatgacct aattacctcc taatgccacc  26040
atctccaaat actatcacac tgggaattag gtctttaaca tgtgaatcat ttggggtgga  26100
gaagacaaac attcagctca taacaggtaa ggtagaaaat ctcaagaatt tatattttgt  26160
atatgaaaga tcattaatga gcagaatttt aagtttaatg ccaattttaa tctattttta  26220
tcttttctac gattcttttt tactttttaa tttttaaact ttcatataca aagggataat  26280
atttggctaa atgttctctt ctttttgagc tctggatcat tgttacgatc accccataat  26340
tgtatgtgtg cagagatagt gctttataca tttttaaaac aattttatat acagtattaa  26400
attttatttt tcaataaaca atccatgaga tagaaagaac atatattttg ttttacagat  26460
aagctccagg gagagtctag ggtaccttag attgtatggg taaaacatgg tttatttaaa  26520
tcataaataa acagtcttat ttccctaaat gcacatacag gcatccacat caaatgaaat  26580
cacatcacat gaattgaaca ggcagttact gacttagaac tttgcactca caaaagacac  26640
actctcctaa atgtctccat catactatac tttttgtccc caaatgccta atcactgaag  26700
cttcagactt tgttgctttg attcccttag gaaaaattcc tggtgtttca gaaaaaaaga  26760
gccatttaac tacattagaa gttaaccctc ctttaaaaat gtg                    26803
```

<210> SEQ ID NO 20
<211> LENGTH: 26803

<212> TYPE: DNA
<213> ORGANISM: Homo sapiens

<400> SEQUENCE: 20

```
cagttaaggt ggggcaggaa taaatcacaa tggtggaatg tcatcagtta aggcaggaac     60
tggccatttt cacttctttt gtgattcttc acttgcttca ggccatctgg atgtatatgt    120
gcaggtcaca gggcatacat tggcttagct tgggctcaga ggcctgacaa ggcacagaag    180
gagctgggat agaggtgcaa agtactcatg ctgacctgac atcccatgcc cacggcagac    240
atgactactt gatcggacaa tactttcttg gaatcaaaga cacaacttca cagtcctcag    300
catcatagtt caggcagcct gtatcagtag atcagagtgg gcacatggcc tggtgctatc    360
actccatcct gtgaggggag atgggattgg aatggaggtg gaggagtcac aggtggtcct    420
gatatcacag gcctgggagt ctgaaagaag tgcagtaggt agtattatgg ccctcaaaga    480
catctgtgtc ctactgtcta gagtcaatta aagtgttacc taacatagaa aaaaggattt    540
tgcaggtggg attaaactaa ggatctcaag atagaaagac tctcctggag tatccagttg    600
tgtccaatgt aagaacaagc gttctcaaaa tagggacaca ggagattgaa ttgcaaagga    660
gatgtgctga taaacggaga ggttggagtg atgccgccat gaggcaagga atgtgggtgg    720
cctctagcag ctagcaatga ttcggaaatg gattctcccc cagagtccag aaagatcaca    780
gcagtgctga caccttgatt tgagcccagt gtcacctctg tcagacttct gccctataga    840
actgtaagag gataaatttg tgttttaagg cacaaagttt atggtaattt gttatagcag    900
caatgggaaa ctaatacaag aagggttgtg ttatcaacag aaatacagca atcagaagaa    960
agatggttgg ggagagcaga gggtggggtg ggaaggtgat ggattctgtt tgggacattc   1020
tgggtgtcat atgaatatta ttggggaact gtccatcaaa agctcagact tcaaagaaag   1080
aaaggaagga gcaacaatat tttgaaaggg agaaagtagg taatattcaa tatgtgttga   1140
gtacctacaa ggtttttagt tctttcacca agttatttta tttaattttt atggcatcaa   1200
ggggtgtttt tttttttct taaaccaaat tttctcagtt aagcatccca tgtaagtggc   1260
caggggttaa gagatgtgac taagactaga cagagtgatt ttcatcatta catggtacta   1320
tggttctact gaagcactga ggaaggaagt caagagagtt cctgagaaat gtctggagtc   1380
ttagtaacat gcaaagtgag gcagaggtat tgtcagtgtt agctggtcac tttgaaaggt   1440
tagaggtaaa taaagttcag ggcaatggta cttggagagg agtgaatctt tggtaacctg   1500
gaggagatgc ttctcagagg aaaatttctt cacagcatga agtcaccagc tctaagacta   1560
gtgggtgttc tgggggatgt tagcagtgac tcactgactg ttggcccagt gaggggaggg   1620
atgaaaggct gggtagtggg tagagaatct gactcctcct gcccccacat gtctattcct   1680
gggccttctc ttggtggggg caaaaggtat gcaaagggat ttccgcagtg tctgagtgct   1740
cccaggagac ggaaaagtaa ctgatgactt ggagttggag tcttgttggc tcaggcagct   1800
ggggcgtttt gggatttcaa cacctccctt tagtttctat gtatggtgct gagcaagtag   1860
tcaaagactt tggtcttgct ttaccccagt agcccacaag cctgagtaca tggctaacat   1920
ttattgggca cttagtgtgt gccaaagagc tttatgagac aggttctttt tgagtcccat   1980
tatactgata atgggactga taagaaacag aaggtcagaa aggcccagta acttgggcaa   2040
ggtcatgtag ctagtaagtg gtccagctga aatttaaaac caggtttatc caactccaaa   2100
tcccacatct gatttatttt gccatgaatt aaaacatagt tctgattttg agaaactccc   2160
agtcccagtg ggaaaacaga tggaatcaca aattaccata acacagtgta gtgatgtaga   2220
```

tataaaaaca aagacatggg aaccctgaaa ggaagttgta acaccaatag aggaatgcat 2280
ggaggagatc tttcagagga ggtagcctcg tagctgggct caggggtgga tgagtttctg 2340
gctagaagcg cattgtgggt agagggagaa catatataga aaggcatgaa gatggtggac 2400
atgtttggaa agagtgagta ctagactgat gaacacgatg agtcaggagc ttatgacgtc 2460
aggggctact gctagcctag ctaatgactg aagattctgt gaaaagaaaa ccctaacatt 2520
tccagctgag tactagggcc atggtgatta tatatcatct ctcatgacaa cacaaatgtt 2580
tgggcttact tatcatcctg ctcagtaatc attatgtcac tcattaaaga tgtatcaggg 2640
taaattttag gtgagaattg attagaaatg taaactctat atatgtagtt acaggcttca 2700
cagtttgcca ctcaaacaat atggtcatcc aatcatgagg cacaaccttc tgctcagaac 2760
ttttttataa ttgggagaaa gtgacatccg agttccatct cttctgagaa ctgtgcagct 2820
cagaaatctt cttccctttt ttgatccccc agttgggtga gatgacatta acagtgtgtt 2880
ataagcactt ttcatgttta ctaccccata ttcaaaatta agcatttcaa acaactgtat 2940
aattgtctat aaatgtagca ttattagtta attttccttt taacacattg aggttacctc 3000
taatgttttg ctatttttaa ctatgttgaa ataatcatgt ggtttttatt ctttgaatta 3060
ttttatattg taatgttccc tgaaatgaaa ttagttgatc aaaagatgag taatcttttc 3120
atgacttttg atacatgtca ctcaatcacc ttctggaaga gttggaacaa gagcctattg 3180
ctggcatccc atttcatagc catctcacca atgttggaaa atgggctttt cctattttct 3240
gctaattcat tagttgttaa tggcttattt taactattaa tcccttgtta ttgatgaaag 3300
ttaagcattt tctgtatttt tattttctgt ctaaattcta ctttttgcac aatttccttt 3360
gctcacttct tcactggaat ttagtatttt tctttccaat ttgtatgact ccaaaatcag 3420
tgataaaata agcaaagggt ctttcttaga ggctaaacaa gggaatgaat aaggaacaag 3480
aacagcaaag ggatagtgaa taaagataca aaataataac ttatttttat ttttgaagct 3540
ttccccaggc agtaattctt gaccttttta agattataaa ttattttgag atatgcattc 3600
ttatcctcaa aatgaattag tacataaaat ttaaatgggt tgatagatcc cctgaagtgt 3660
atccacaaaa tgctctcagg ttaagcaaca ttgttctata ataactgctt taaccaaaat 3720
gtttaattat tgcttgtgtt tacctgtcct agcaaagagc taattgttaa attttgtgtt 3780
agagggtcaa tattataaat aacttaatgt ggcctctctt tcctttcctt tttttgagag 3840
ttttgaggct atcactaagt gggctttaga gtaccaggtg ggaatctgac ctcactgctc 3900
aaactttcaa cttcaggcat gaagtggtcc cagtgatgtg ggaacctcag agtctaaaac 3960
aaaaatagta gactgaggcc ctcagaaacc agacttatca gattcagaat ttaatataac 4020
tatgtttgaa agatttaaag aaaataaatc aaattaaaaa gtgagcaaga agcaagaata 4080
acaaatgaac tggcatattt gagaaagaat tttgagcttt tagaaataat acatacactt 4140
attgaaataa aaactcaagt caataggttt aaacagcaaa atgaatatag ttaaagaaaa 4200
ctattgtgct gaaagattta aaaaactatt acacagaatg caaaatgatg aaatagggta 4260
atttaatata tggcagatat gttaagacac tatgaggata gtatgagaag acctgataga 4320
catctaatca cagcacctta aggtgaaaat agagagagtg caccaatatt gaggagttaa 4380
tgtctgagac tattccagaa ctgataaata gatgaatcta cagatctcag aaacacagct 4440
tttacaaagg ataaatgaag agaaattcac cagagataca ttgtaatgaa tctgtaaatc 4500
accaaagcta aagatattat ttcacaagtg gaatgacagc tgacttctca acaacaacga 4560
aagcaaggag acagttgaaa gacatcttga aaatggtgag agaaaaacta actgttaata 4620

```
taaaattgtg tacctatcaa aaatatcttt tggccaggcg tggtggctca cgcctataat   4680
cctagcactt tgggaagcca aggaacgtgg atcacttgag gtcaggagtt tgagaccgag   4740
accgtcctgg ccaacatggt gaaaccccat ctctactaaa aatacaaaaa aaaaaaaaaa   4800
atagccatgt gtggtggtgt gcacctgtaa tcccagctac ttgggaggct gaggcaggag   4860
aatcgcttga acccaggagg tagaggttgc agtgagctga gatcatgctg ctgcactcca   4920
gtctgggtga cagagtgaga ctgcctcaaa accaaaccaa accaaaccaa accaatcttt   4980
caagaagtac accataaaga catttccgga taaacagtga atgagattac ttcctaaacg   5040
aatatgtaag gatgtttctt tttaaaattt tttttgggtg tattcatcac ctcaagcatt   5100
tattcttttg tgttgttaca actgataaga atatctaagg atgtttcaaa aggaagaaaa   5160
atgatcccta aagtctggta tattagtttc ttattagttg ctctaagaaa ttactgcaaa   5220
cttagtggct ttaaaaaaca cgaaattatc tttcagttct gtaggtcaga aatttaacct   5280
cctgatttct ggtcagaagt cttactgggc taaaatcagg gtatcagcag ggctgctgga   5340
ggctctggag atgatgtttc tctaatttct agaggcattt gcattcctta gctagtggct   5400
tcttcccaca tcttcaaagc taacagtggc agtcgagtcc ttctcttatc tttttttttt   5460
ggggggggtt ataaattttt tttattatta ttatacttta agttttaggg tacatgtgca   5520
caacgtgcag gtttgttaca tatgtataca tgtgccacat tggtgtgctg cacccattaa   5580
ctcatcattt agcattaggt atatctccta atgctatccg tccccccctcc cccaccccac   5640
aacagtcccc agtgtgtgat gttccccttc ccttctctta tcttatcact ctgacctctt   5700
ctgcctcctt tctctacttt taaggaccct tgtgattaga ttgggtccac ctaaataatc   5760
caggataatc tctttatttt aaggttagct gattagcaac ctcaattcca tctgtaacct   5820
taatttcttt tttgccatgt aacctaacat agtcacaggc ccaagggaat aataggatgt   5880
gggaattgcg ggtggtggag taggggcatt attctgctta ccacagggga ccttggatgt   5940
cagtaaaaaa tggtgaggaa gaaaacagga aacgtagaat aatctaaaca aatctttgaa   6000
aaataagttg aaatgtgggg ttagaaaaag ggcagaacta aaatgttaag acaaattaaa   6060
atgttaagcc tataagttga gagggagatg atcaaggtta aaaatactca taaatcatat   6120
tttttgggt aggggggttag atatttatta attttagacc ctgagaagta aaatagtcat   6180
gacaaaaatt taatagtaac cactaaaaca agagaaacag agtatataac ttctaaatca   6240
atatgggaag gggaatggaa taagaaaaca atagcaacca ccaacacccc acccaaaata   6300
aataataagg tgagagagaa aaagaagcat tgaaaagggg ctaaaataaa ataaaaaatt   6360
aagtcatgcc cgtaatccca gcactttgag aggccaagat gggtggatca cctgaggtca   6420
ggagttcgag accagcctga ccaacatggg gaaaccccat ctctactaaa aattcaaaat   6480
tagctgggtg tgggggtgca tgcctgtaat cccagctact ctggaggctg aggcaggaga   6540
atcgcttgaa cccaggaggc agaggttgtg gtgagcagag attgtgccat tgcattccag   6600
cctgggcagc aagagcgaaa cgccatctaa aaaaaaaaaa aaaaaaatta agatagtaaa   6660
acaaatccaa atacattaaa gattacaaaa aatgaaaatg aactaaactt cctagttgaa   6720
agacatattg tcagattgga ttttaaaatc tggcaatgat atttccagga cacagtccta   6780
aaatattaaa cacagaaaag ttgaaagtaa agggatggaa gaacacagtc aaactaacta   6840
gaagagagct gggttcaccc ttttatatca gagcagaatt tcactgagaa aacactaaca   6900
ggaaggggga aaggcacaac atagtgatga agcacttaat tctcaacaaa tgtatgacac   6960
```

```
ttctaaacta ttatgactgc aaaaaaaaaa aaaacctcag catatataaa attttggaag   7020
agccatggct atcagctgac atgcacttac catatttgca ttgtcctact acaaacttta   7080
cccatatgac caaggtgctg tcttcatccc cattttacag atggggaaat ttccccatag   7140
agaaaaagat ttgggccatg ccttggtttc ttcttgactc tgcttcctgc tgattgatcc   7200
tcacacctca cctggagacc tacttcacat tatccatcag gatgagaact ggtgtgcctt   7260
taccaaagga ccacagtcac cttcaaaacg tgtttagata gatctggatg gagacttatg   7320
tggttgcaga tgaaaaaaaa gtccccatgg tatatctgac tccatgtcat tcactgcatg   7380
aacactcaca cacatgcaca cgtacacagg caaacacaat cctgttctgg tccggcagta   7440
gtgccaacac tcaaatccca ggtcctactc tgaagccttt gaggaaacca ttgtcattct   7500
ggggtttatg ggaatatttc ttcttggtgc cccttgttcc tcacagaagc tttttttctg   7560
tgctgtgggc ttgctatcct agctttccaa gctatcctag ttttgcaaat ttctctgatc   7620
aatcacatca ggttcttgga tcatcccaaa attaaagagg tacgttttgc tgcaagagac   7680
aaagacattc acctctcaca cagtttgaat tcctgggtag aaacagattt caatgctggc   7740
cagcctctgt agctcccagt gccccctcaa ttatgactcc cgaggcattg gagcaggatc   7800
ctcaccttgc gcaaagataa ttaggtgtgc tgaagaaagc cagacactgc tctttcttag   7860
ctctgcatcc ttaaaaagtt accactactc cttctctttg aatctttgac ttgtcaatgg   7920
taaagtgcct atgattctta aagggataaa aacgcaacct atataaagca cctggcatag   7980
tgcctggcac aggtgggtgt ttaacaaatg ttaactcctt tctatcccac tgtgggtgtc   8040
catatcctct tgggtaggct gcctctggtt tccattgtgt catcagagcc atactaaatc   8100
gatgtgttgg acatggatcc caagaactaa tttctggaat gagttatgcc taccaacttc   8160
cctgatactt acttctgtct ctccatttat caaatggaaa tgtttgcatt tggcctctgc   8220
cagttggagt aaccaaaagg cttagaggtt ttggagaggt cctacactgc catctgtttg   8280
accacatact gcctttcacg tgtaataagc attgtttctt acatttgtct aggaattagc   8340
agttcacaaa gcacattcgc atataagggc ttgttttgaa ttgatcttgg cagcaattct   8400
atgagacaag taaaaggtag gtcaagcatt ataatcctca ttttaaatct gggaaaactg   8460
aatctcaaaa aggttgaaag acttgtctag gggacagtgt gtgggtaaat gagaagttaa   8520
gatttgctga actggcattt cctgactaca tatctagtgt ttatttatgg agaaggcact   8580
acggtggcca agtggctcag agtcacacag ctctgtgcct cagtttattt gtctgtaaaa   8640
tgaagataat aatatattct gaatactgtt gtggaatttc attgagatag ttcacataat   8700
ggcatggata ctgtagtaca ccgcctagat tcacaacccc acgactatcc atgagaatgg   8760
cccatagctc aagaggtcac attctttccc caggtgaagc ccgcatccaa tgactgctca   8820
gtgtgggtat ataaaggcct ggctcccttg ccagtgccac cctacctcct ggcgaatgga   8880
ctgaggcttg cattatgact gcattgcagc tcaactgttc tttccattca gtctttcctt   8940
tacactcaca caggtgagga cccagccatt aaatgcctca catgatgacc tctattgcat   9000
gctaggcttc gtgtgcacac acaaaaacca tcctctatca gtcaggcccc ttacttgcag   9060
aggcaaagag gccagtctgg gttagatgtg caccctgttt ttacaacaga acgagacaaa   9120
caggtcctcc ttaggtgtaa gttcatggcc ttggccccac ccctgaaact cagccatctg   9180
agacagtttt aggactgagg caaccccaga ctttgggttg ttgtttgctg ggcacagcct   9240
ccttttgcca atgttgcaat cctttgtaag agaccacagg ttgatcaccc gttcctgtta   9300
ctgagcacag agaggtttgt aggccagtct ctccaggaat tctgacgcac tgcaaaatcc   9360
```

```
catggtctga atgcttctac cttccctgtg aaagcccctg gcctcagaaa aggaagctgg   9420
tttaagtgac caacatttgg ggtggagctt ccgagggccc agccaccgtg ttacatgcaa   9480
caatcaacag agatattctt tggctagagt tgtttttctg ggtataggac cctataatta   9540
aaatcagctc tccaacttcc cttcctccaa aaagtataca atgtaaggag gaaaatgcaa   9600
attgaaaagt tgctagccct tcccgccaga atgccacccc aagcctcccc tgcaggaagt   9660
tctggagtcc ccaactctgc cccaagcctg aggcccttga taaggtaaag ggatgtgagt   9720
gtggaggccg gagccccccct cgccctgtag gctgctcccc ttgcttttcc ctttgaatgt   9780
tacagtttag ttctgtgact tacttataat tgcctgaatt ccccgcccac gctttctctt   9840
actttggggc ttctcaccgt tcctcttcct ccatcttcct cctctgaccc cactcccaag   9900
cctgaatggg gtgttcctct tccgtgctcc cacaaaaccc tgtgcctctt tcatcgttgc   9960
atatattatg ctgtaatgta gttttctgga ggtgtgaaga ctatgaatcc tatgaagaca  10020
aatacacacc taccttgctg accgttgtat cctcagaatc taatactgca cttggcacac  10080
agtggttggg agtaaatatt catgaggcaa acacacagga aggactcttt tgttatggtt  10140
gtttgttgtt gttgcaagta acataacccc accttgatct agctgactga cggctctacc  10200
accttgtctt ttgcagcaca agaggaatag gaactgcacc tcttccttca gtttcagctt  10260
gaataatatc aggaagattc gtatcggtct gagttgggtc acgtacccga cgtgctatag  10320
ctgaggatgg ggtaagctga ttggagtttg caacactgtt cacatagcca agatatggaa  10380
agaacctaaa tgtcaactgg tggatgaatg gataaagaaa ttgtggtata tacatacact  10440
ggaatattat tcaaccttaa aaagaaggaa atcctaacat ttgtgacaac atggatggac  10500
ctggagggaa ttatgctgag tgaaataaga cagacacaaa aagacatttc ttgcaggagc  10560
tcacttatat gtggaatcta aaatagtcaa gcttaaagaa gagagtagac tactggttgt  10620
caggagcagg agaaaagtgg aaatgaagag gtgatagtta aagggtacaa agtttcagtt  10680
atacaagata aataagttct ggaggtttac tattaatata tcacatagta cctataagta  10740
acaatactgt attgtatact taaaattgct aagagggtat atcttatatg ttcttaccaa  10800
taataataat aatggtaata attaaggggc aggaggacac ttcaaaaggt gatggatatg  10860
tttatggcct tgatggtggt gatggtttca tgagagtata cttatcccca aactaattga  10920
gatgtaaata ttaaatatgt acagcttttt gtatgtcaat cgtacctcag taaagtagtt  10980
taaaaatggt tggactgaga aaaggaggag ctgctcagca acatgaggct gggtgctggg  11040
cagacaaaac ctcacacatg cattactgaa cccacggact catgtctgtg agctttgtgg  11100
ctgtggatgc accatgccaa tgtagtcaag gattcttcaa tgtgtacctt actggattag  11160
ttccctctgt ttatttgtat tgactcctca gttcccttat gggttgcttg ttggctcttg  11220
tggaattatt taagtaaggc tttggttgca ggagtcagac atgcttaagc tggttttggc  11280
tgtaatgggg aatttgtgag atgtgacaca gtgacaggaa gtgcagccag acgttgtgag  11340
aggcagtaac tgggaatagg aaagttatga gaagttaagg cagtagtaat tgtttctcta  11400
tcgaaggcca taatgttatc attcctgcct ctatctgttt gcttgttctt ctctctcagc  11460
agaatggtct tctctgcttc tctgtgcacc tgcagaaggt gaccacccta aggcttatgg  11520
attcaggagt cctcagtttg agagcagtta ccaaatgcct cgcccctgtg aactctagtc  11580
ccagtttctt attcctggta ctggcttagt ttgaggcagc tgcccaccgt aagtccagtg  11640
agccatggcc tggggacaag gtcaggtaca tgtgtaatca gctgggtcta tgagttgtgg  11700
```

```
tggtggcgat ggaggtagct cccagaaaaa tggattacag gttaagaaga gtctatatat 11760
cttgaccaca tttgatgtga cttggaagtt tcaatgtgtg accacttaca aagttatgat 11820
caggtgtctc atttatttat ggtgatgtat gagtccgtgt gtgagtgtgt gtgtgtctgt 11880
gtttgtgtgt gtgtgtgaga gagagagaga gaatgagaat atgagtggtg gtttcccatt 11940
tatttttcta tgggccaaat cctgggctat gagctggaga tataagagta aacaaaatag 12000
acacggtgct tgctgtgacc tgccctggga gacagatatt acacggagga tcacataaat 12060
gcagagtctg agctgaggtc ttaagggtga ggataagtaa ctagtcagtg gagcagggga 12120
gggaagggtg ttccatgcct gtgtcaaggt cctgaggtga gagaaagagg tgaatttgag 12180
gaaccaaaag gagttcaggg aacaagaggg gctgtttcac aagctgagtc tggaagctga 12240
gcaggctgag cagattctta ggaactctgc aaaaacttaa gggcttgtct atgaccgtaa 12300
acaactacgg tcgtagataa acaagttggc aaacaactca aggatttaca gtcatcagaa 12360
ttgtaaaact gatcccatgt attttcaaac ctcaaatccc ttgctctgac cttgtgtgtc 12420
taagctagaa ggaagcagga tgcacctctc ccctggctgg aatgaaggga ttcacccaag 12480
ctctcagtct tctcacggca tccagggccc ccctgcttgt gtgtggtcta gatttccatt 12540
cccatagtag gaattccttt gggagccttg gggtctctcc tgctagaggg cttcacctgt 12600
gactgtctca attcaaggga ggggttctaa taacattaaa cctcaatatc ttgctcttcc 12660
attcctgatg cctccctttc cttctaccct tcccctacct ccttctttcc tatgccacag 12720
gctggcaggt tagtgccaga gcaagtggcc agtcaccatc attggggttg tggatcctca 12780
gggttcttca gaagcccctt caccatgatc aagagtctcc agtcactcag aattccacgg 12840
ttcccaaatg ccagctctcc cactactccc agcgttctcc atctctggga tgttgggctc 12900
caggcttctc agatgcactg agtaccctag gctaagccac tgatccatca gaacttcata 12960
gcctgagagg agagggagac aggcttgcaa aggagagttc tgactagaca ctggggtgct 13020
acagatgccc gtaagttgtc cctttaccct cgatgtcccc agtgttggga ccacctggga 13080
atgcccagcc ttgtgtgctg attgacttgt agtcccctgg ccctgactgg aagcctagtt 13140
ttctctctca tgaccagcta ggcccctagc tccccaggga agaaatccaa tctatttcct 13200
ctgatagtaa tggctaatac ttaaataatg ccaaccacat gccaagcact ttacagttgt 13260
tagcccagtc ttcacaagca ccttgtgagg tgggcaagag tcttatctta ctctcatttt 13320
atagatgtgg cccaggatcc cacagctata gttcatggtg ctgggatttg aacctctggc 13380
caccagagcc caccttaatg tgtcctcctc ctgttgtcat aacagaaaag tacaacacca 13440
tgatgacaca tcaggctatc ctggcaggtt cccaggctgc cccaatgccc aactttctag 13500
gtttacaaag ttgacattta cgaagtttcc aggtttacaa atctagtttc tgattcttta 13560
gtcagcagga atttctctac aaaagctgct tcgaaaattt ccagccaaac cttacacacc 13620
ttggcattac atcttggtga gccaaggcgg aagagaacag gaagtgaagg ccccatggga 13680
agtccctgcg gtcgggagca cccaggcggg gcggggggtg gggggctttc ctgtggccgg 13740
ctccctgccc ctcccacccc cattcaggcc ctgtgagttg aatgaagaga ccctgggaat 13800
gagtccaggt ctgcagggtt agaggaaatt gaaggccctt accagatccc tgttgagaag 13860
tttatgaatt atgagccctt ctgcaaatga gagggttctt ccctgtcagg agggacagat 13920
tgtaggtggc aagattggtg gcagccagta ggctggtctg ctccttcctc tctatttcat 13980
atgtgtatga aggcattacc tgcagcaagg gcctgtgtaa atgcatgtga tttacagagc 14040
attttatgta ctgcgtgtca ttcatgcttc cggtgagccc taagtctaag atagggcaga 14100
```

```
tagcatcagg tccattttgc agctgtcaaa atgaggtctg aagggcagaa gtggtgtgcc  14160
cacacacaca caactggttg gctgcagacc tggggactag acccgggact tcgtcctgcc  14220
caggggtctc ttgccactgc tccccatcaa cttggatggc tttaagcatt tgtgagttgt  14280
ctgctccctg atggcagaat gcagagacat gaagctacaa gcaggttcgc tcccaacggc  14340
aaaaaggagg aggggtgttc agaacatcag gtgcttctag agaaagcagg gagagagtat  14400
ctggccttgt ggacaatgtc acggcagagg ccaggtatag ggcatggggg taactggaag  14460
cgggatggac cctgttattc cctaagacat ggcttccacg tagtgctcaa acaaggcctt  14520
tgcccttgct gttccctcca cctggaatat tcttcccctt ccttgacatt gctcaggtct  14580
ccactcttat gtcaccctct cagagagggc ttccctggcc actttcccta aaatagccac  14640
ccactcctag gtccctcaaa agcatatcct gctttggatt ttccctatag caatatgccc  14700
tatgaagtta ttttatttgc taacttgttt cttgtctgtt ttcctttgtt agagcgttgg  14760
ggaccttgtc tggcttgttc ccaatgcctg gaagagtgcc tggcacacag gattaagcca  14820
acacatatgt tttgaatgaa tgtgtgcaca catgcatgag ctggcggcag tcggggttgg  14880
ggtaagcacg aaggcccagc tcagttctct gcatgtgacc tcccatctta cgcagataag  14940
aaccagtttg gtttctgcta gcctgagtca ccctcctgga aactgggcct gcttggcatc  15000
aagtcagcca tcagccggcc catctcctca tgctggccaa ccctctgtga gtgtgtggga  15060
ggggaggctg ggctcctcct tgtactctct gaggtgctct ggaaggaggg gcagctccac  15120
cctgggaggg actgtggccc aggtactgcc cgggtgctac tttatgggca gcagctcagt  15180
tgagttagag tctggaagac ctcagaagac ctcctgtcct atgaggccct ccccatggct  15240
ttaggtaagc tccttccact ctcatttttt cacctgagaa atgagagagg aaaatgtcta  15300
caattggtgt ttatcaaatg ctttcaggct ctggtgagca agcgtccagg aaaatgtcaa  15360
gcgcatggag ctccaggcct gtctggggga tctgggcacg gggaggcatc catgggagac  15420
catgcaggca ctctgaggca ggggctgcaa gcctagtgcc tgctggggca gcaggtgaac  15480
agagaggtgt aactgctgtg acagaagtca tggagtcctt ggagtgtgag ggtcattttc  15540
cactgttgat agaataggga aattggtgaa atagccctgt taaatgagag aaagaacagt  15600
gtgagctcaa tgagaaatac taatagaatg tggcactgag ccacaaggtc tgaggcttga  15660
ttgataagga agggtgggga ctgtggagaa ttaagggctt ggcacaggtc agttccacca  15720
gttgtcacaa gagaatgcag gctcaggtgg ccagaacttc tcgcttttcc agaagagtcc  15780
gatattctga tttcattata tatagtattc tgattaaacc agacaataaa gcaagcagat  15840
aaaatattta aagtataagc tgccagtttg caacctccgg ttaggatttg tgtggggcaa  15900
agaaaaaaac tctcaggatc attggtatgt agactctaat tttaagtttc taatttaaaa  15960
ttggcccctg aggctgggcg tggtggctca cacctgtaat cccagcattt tgggaggcca  16020
aggtgggtgg atctcttgag gtcaagagtt caaggcctgc ctggccaaca tggtgaaacc  16080
ctgtctctat taaaaataca aaaattagct gggcatggtg gtgcatgtct gcaatcttag  16140
ctacttgggt agctaaggca ggagaattgc tggaacccgg gaggtagagg ttgcagtgaa  16200
tggagatcac accactgcac tccagtctgg gcaatagaga gagacgctct ctctaaaaaa  16260
aaatatgtaa agataaataa aatgaaataa aataggcctc taatgagcag gccattctcc  16320
tttctgggtc ttactttcct tgcactcctt tctgggtgtt aagaggaggt ctagaggaag  16380
ctggacaact cttagcttgt agtaagcaca gtggaagtat cagctcttaa tgggtcatgg  16440
```

-continued

```
acacgttaca agctaggcgc cgtgctgagc actttacatg gtttatccca ctgaaccctc  16500
tcaataaccc tatgaggaag ggctattatt gctcacattt tcagaagagg aaatggatat  16560
agagagatta gataatttgc ccatggccag acagctagta taagaggagg aggtggattg  16620
actgcagaca ttctgtcttc aaaccactac actatgctat ggaggcacag agacttaatg  16680
aaatcatgga gaggggaatt gctttgtcaa ccacaagcag ttattccggg ggcagcagat  16740
cctcccctgt cccccagtgg gtacaatggt ccctggtggg ttgtgctaca atgttagccc  16800
atggtcttat gtgtttttca aatgtgtaaa gtaggatgct ggaaccactc ttagaaccag  16860
ataccaatac attgtgaaga aataaatctc tgtgcttaaa actggttcat cccaaaatat  16920
tttgaactga cacacaatag gtgctaaata aatgtgtgtt aacttgaatt ggattgaatt  16980
cgggaaaaaa gtgcaataag cttagtgaag acaccatgtt ccctgggtag aggaaccaca  17040
ttctccatct aaggccagga gtatgggagg tatcaatgtt tgcccagcac agaacagggt  17100
gccaagaaga gaaaagttga cggggtgcat actctgactg gaaactggaa gggtgagaac  17160
agagggtaaa ggatagagat ggaaccatgt gcatacactt tgtgttacct tggacaagtc  17220
attcatttct ctggacctct gctttctctc tacacaatgg ggtcccacca cttcccttac  17280
agctgacttg tatgaagaag gaggtggagg aggaggagaa ggtgaagaca atgctgactc  17340
aaagggtaaa ttatttttag gatccaagtt tgaaaacaat tttaggctac tagatatgaa  17400
caacatcttg attatgtagt tgaaggaaat taaagatgaa tggtttaatt aaaaattaat  17460
cagaatgaaa acgattgatt actaatatat ctgcaatggt ttattttcct gagtggcaga  17520
ctcactaagg tttttgaata ctcctgtgtg attgctctat gtatgtatgt atgtatgtat  17580
gtatgcatgt atctatctat ctgttgtcta ataaaatgga tcacatctct gctaataaaa  17640
acactacact ggcagggtac aattataatc attaactgtg cctggaattt gcagcagcag  17700
ccaccagagg taccagtgcc ctttaagggt tcataattta gaataatcca attatctgag  17760
tttttcaggg actgaggggt ttggcaaggt gtagaacttt cagtaataaa gtcaagaaag  17820
tcctggacaa accaaggtag ttggtcactc tagtccataa ccaggtaaag agctttccct  17880
gtaacctgtg taaggtttta gaatcatttc tttccttatt accaaaaatc ctccccaaat  17940
tttcaagaaa ttatgaacta aatagttact ctatgagata ggagttcagc ccaaaagaaa  18000
caccataaga acaaatataa ttcttgctta tgttaaccat gcaatgaagc agagagaaaa  18060
agtcagtggc ctctttagga ggactgtagt gtgggaagaa ataactaaac tgggtttcaa  18120
tcctggcctg gccaggatct ggagcaagtg agttaatctt tctaagcctt gagtagtttc  18180
ttcttcttct tcttcttctt cctccccctt ctcctcttct tcttcctcct ccttctcctc  18240
ttcttcttct tcttcttctt cctcttcttc ttcttcctcc tcctcctcct cctcttcttc  18300
ttcttcctct tcctcttcct cttcctcttc ttcctcttcc tcttattctt cttcgtcgtc  18360
ttcgtcttct ttttattttc aaagtgaaag caagtttatt aagaaagtaa aggaataaaa  18420
gaatggccac tccatagaca gagtagcctg aaccttgagt tcttctataa agtcactatg  18480
aatttatact cattttgaaa gtgggtgtca atatgtctgt ccactttgca cagctgttat  18540
gtggacaaaa ggagatctgt gtgaaagtgt aacacagagc ctaaactata acaggtaagc  18600
aacacagttg tccccttccc catggtgtct gttcttctcc atttcctcct gtctgcaggg  18660
ggattataaa actaatcatc aaagccaaga aggcaagagc aagcatgtac cgctgaaaac  18720
acaagataac tgcataagta atgactttca gtgcagattc atagctaacc cataaactgc  18780
tggggcaaaa atcatcttgg aaggctctga acctcagaaa ggattcacag taagttaacc  18840
```

```
atgtagatct gagaggagag tagcttcttg tagataacag ttggattata taccatgtcc  18900
tgatcccctt catcatccag gagagcagag gtggtcaccc tgatagcagc aagcctgggg  18960
gctgcagctt ggtgggtaga ggtactcagg ggtacagatg tctccaaacc tgtcctgctg  19020
ccttagggag cttctaataa gttgatggat ttggttaaaa ttaacttggc tacttggcag  19080
gactgggtca gtgaggacca acaaaaagaa gacatcagat tataccctgg gggtttgtat  19140
ttcttgtgtt tctttctctt ctttgtacta aaatatttac ccatgactgg gaaagagcaa  19200
ctggagtctt tgtagcatta tcttagcaaa aatttacaaa gtttggaaaa caatattgcc  19260
catattgtgt ggtgtgtcct gtgacactca ggattcaagt gttggccgaa gccactaaat  19320
gtgagatgaa gccattacaa ggcagtgtgc acatctgtcc acccaagctg gatgccaaca  19380
tttcacaaat agtgcttgcg tgacacaaat gcagttccag gaggcccaaa tgaaaatgtt  19440
tgtactgaaa tttgttaaag cttcccgaca aactagattt atcagtaagg attgttttct  19500
gcaaggggga tgaaacttgt ggggtgagcc atttgggctg aggaggaggg aggttggagc  19560
tgagaaatgt ggagacaatt tccctttaga aggactgaat ctccctgcct ctctggggtg  19620
cggcagccag caggatccaa tggtgtatat gtctccccag ctccccattc agtgatatca  19680
tgtcagtagc ttgaaattat ccgtggtggg agtattatgt catggaaatt ggcaaatgga  19740
aacttttatt ggagattcaa ttgttaaact tttaccagca caacactgcc ctgccttcag  19800
agtcaatgac cctatccaag tttaatccat ctgtccactg tctccaacac gatctttata  19860
aaacacacct gacaacatta ccctttttatt cagtttttta aaagataagt ttccagctca  19920
tcggggtggc tttaaaggcc atttctcctc tggacctcac ccaacttttc aaatcacttt  19980
tcctacccct acctctaaat gctactcaaa ctccagccat cctgaataat aagacttttg  20040
aaaagtagat tatgggctgg gcacagtggc tcacacctgt aatcccagca ctttgggagg  20100
ccaagatggg tggatcacct gaggtcggga gttcgagacc agcctgacta acatagtgaa  20160
accctgtctc tactaaaaat acaaaattag ttgggggtgg tggcacaagc ctgtaatccc  20220
agctactcag gaggttgagg caggggaatt gcttgaacct gggaggcgga ggttgcggtg  20280
agcctagatt gctccactgc actccagcct gggcaacaag agcgaaactc catctcaaaa  20340
aaataaataa ataaataaag tagattacat cagatacctc tggcctaggt tgtttatgac  20400
caactctcct gctgagaata actagaaaag ctagacaaaa catatttcca aaagatctct  20460
ttggaggcat cagagaatgg ccaaggctgt aaggaactgc ctgagcccag agaggtggag  20520
cccagcactg gtgcccttta ctcctgggga catgtgctgg tttcaaaaac ttcagctgag  20580
cttttgagca ttcatggaac ttggtggggg agatgaaatt tgtaccttaa atcctgccta  20640
cagggagggt ccctgataat ccccacccaa tttggaaatc tgggtcagcc ttcacaggta  20700
ctgaagccct cctctgaatg atctcaagtc ctgctagggt agaggttacc tgcttttgaa  20760
aggctcctgg cctacctgtg cagcaggagc aaaagtgaac catctcaggg tacagataac  20820
aatcatccag agccttgaat gacctctact gtgcttaata tatagtattc agcagtcagt  20880
aaaaaggatt taggcacatg caagatgacc tgtgtatcag ggagaaatag gcaataaatt  20940
gagatccagc agggatttga atcatggatt tgaatcaggg gcagccttcg aaagaactat  21000
ggagaatata ctcagattta aaacataaga ttggaatttt tggcagagaa ctaacaactg  21060
tacaaaaaag gaaccaaatg gaaatcctag aactgaaaga tgcaattaac cgatgttgag  21120
aaatagccaa catctattga acacttccca tgtggacagc tgtgctaaac actttacagg  21180
```

```
catcaacata agatgtgtcc ccttacagca gtgcagtgtc cctcctaaga catggacagc  21240
ctggtttccc tatctctctg cttcatcaaa acccctttac gtggggctta gacactcctg  21300
ttgtctctag tgtctagtag cacagggctc agcacatgga agccactaga tacaatttga  21360
tgaccaggac ctccgatgaa agccatgggt gctgattggg aaggcattgt cttttatgtg  21420
ctatggtctt aaagcttcat ccaggaagca gaactcgggg ggtgctgagg acccagaacc  21480
gagaataaga ttagtcagag atttcctgtg ggcagaaatc ataaggacgc caactgtttg  21540
ggtgagataa gacgaaacca agagtggact tgtggccaga agcgtgagga agagggagag  21600
agcttccctt gtcccctttc ttcctctccc taagccacag tgattgacag cccccccccct  21660
ttggagtcag agcaggcttg agactggact gggaaaggag ggtgggtcag gatacagagc  21720
aggaaggctg ggagtgcagg gcaggagcaa ggggctgggg cattcattgt gcctgatctc  21780
tcccacttta cctggggtaa agaagcatat gcaaaagcca cggtgtgagt atttcccaag  21840
tgccagggtc agggcatgat tcatcacgtg cagcatttca ttcaatcctt atagtaaccg  21900
atgatgtggc ttctattatt agctctatca gataatgaaa ctgagaccaa gacaggctct  21960
gcacattgtg tggggtaatg acacaggggg attcagacct agactccata actcctgccc  22020
cagggaccac ccccaccctc accctgtgca tgtcgacaaa ggacagactg ggccacttct  22080
caggacacag cggggaaatg acacagagca gggaggttcc aggagccccg agcgtctttt  22140
ctccaggaga atactctctg aattcagact ggggtcagag aaacatttac ccaggagccg  22200
cagtgtgggt ggggcttttt acttgaaacg ctgtctgaag gcagtggcca ggatggaact  22260
ctccacccta ccttggcaag ccacttctct tctgcaatct gtaaggacat tgttgagaga  22320
attatggtct tccaattccg gagggttgaa gaaagacaaa taggagagaa cctatcatag  22380
tcaggtgcta gctgccttct ctttcagaga gtgtgagaat aaagtgatac acttgattat  22440
tagcaaatac tttggaaatt ttaaacgcta atattcaaca cactctggaa gaggcaaata  22500
agtagacagg ttcatataca tcatctcctt cagctagtcc tcacaaaaac aaacaaatga  22560
ataaacaaaa ttcttctttg gccctcatag gaagacactg tttcttgaac gtgtttcaaa  22620
aaggatgggt gactcactca aggtcacact gtttatgagg acagtacagg aatacagaca  22680
tgccattttg cctgaaaaaa tccatcaccc agggaggtga cacaattttg cagaaatgtt  22740
ctatttcctc tgaaggatac attctttaaa cctttgggaa attcattcat agtcttcctc  22800
ctttgaagga ttaactctct ggacacaaag tgtttgattc tgatttgttg gttggaagat  22860
gtgttggttg agagaaagat tctgatttgt tggttgaaaa tagactcatc aagatcaact  22920
gctgtagtag taaatatttt gacattttgt ctgtattcct gtgctgccct cacaagctgc  22980
atcaccttga gtgagtcatt catacttttt tgtttgtttt tgttttggag atggagtctt  23040
actctgttgc ctaggctgga gtgcggtggc gtgatcttgg ctcactgcga cctccatctc  23100
ctgggttcaa gtgatcctcc tgcctcagcc tcccgagtag ctgggattac aggcacatgc  23160
caccatccct gctaattttt gcattttcag tagagacgga gtttcaccat gttggtcagg  23220
ttggtcttga actcctgacc tcaggtgatc cgcccacctc agcctcccca agtgctggga  23280
ttacaggtgt gagccaccgt gcccagccca gccatcattt ttgaaacacg tttgagaaac  23340
agtgtcttcc tttgagggcc aaggagacat tttttttgtt tatttgtttg tttttgtgag  23400
gactagctga agggggtgat gtatattaac ctgcctactt atttgcctct tcccagagtg  23460
tgatgaatat tagggtttaa agtttctgaa gcatttgtta ataaagcccg gggctggagg  23520
tcagaagacc tggatttctc tgcatacttt tgccatcagc aagctgtgtg accttggaca  23580
```

```
gatcccttt ttgtctaaat ctttctgagt cttcttgaaa acaatgccag gttgggacag  23640
gatgattgcc aagctcccgt ccagctctaa aacactgcaa cgtatgcttc tgcaccagca  23700
ctgtccatcc tgtagatcat gcagaaattc tcttcaactt tttcctaccc ataaaatagg  23760
agcatgctta cctttttcct aatgttccag gccccgggtc tagaatattg taagtaagga  23820
agttaatgtg tatcagagcc cattatgggc cagaagttct cctcttcctt cctacacctg  23880
cttcctccct ccctccctcc ctctttccct tccttccttc catccatttg tgaagaagac  23940
atgatcaccc tcattctgag agtgaagaga cagaggctca actaatgaaa tgatttgttc  24000
aaggtcacac gggtggcaca aggcaagtgg cagaggttga atttagaccc attcctgtcc  24060
aaatgctgag tttatgtcat cgtcccgaga ccataacttt aaagatgtaa gatagtggga  24120
aaagagttga tttcaaagca cctctcagaa ggactcactt tacatcaggg gtcagcagac  24180
tcaggccaaa tccggtccat tccccgcttt tgcaaagaaa gttgtagtgg aacacagcta  24240
ggcttattga tttatggatt gccaacgtcc ttttgtgaaa cagacagctg agctgagtaa  24300
tcgtggcgca caaaacctaa aatatttact atctcgtcct ttacagaatg tttgccaatc  24360
tatggtccgg agtccaaggc tgtccatttt tcaaagaaca caaagtgaca tgagactgtc  24420
ccatgtgcag ggagccctat cattttatta tgaaaaaacg gcctttctgc tcaaatctgt  24480
tttttaaaaa gtcaacaaac agactctggg tacctgtcag gaacagtagg gagtttggtt  24540
tccattgtgc tcttcttccc aggaactcaa tgaaggggaa atagaaatct taattttggg  24600
gaaattgcac aggggaaaaa ggggagggaa tcagttacaa cactccattg cgacacttag  24660
tggggttgaa agtgacaaca gcaagggttt ctctttttgg aaatgcgagg agggtatttc  24720
cgcttctcgc agtggggcag ggtggcagac gcctagcttg ggtgagtgac tatttcttta  24780
taaaccacaa ctctgggccc gcaatggcag tccactgcct tgctgcagtc acagaatgga  24840
aatctgcaga ggcctccgca gtcacctaat cactctcctc ctcttcctgt tccattcaga  24900
gacgatctgc cgaccctctg ggagaaaatc cagcaagatg caagccttca ggtaaggcta  24960
ccccaaggag gagaaggtga gggtggatca gctggagact ggaaacatat cacagctgcc  25020
aggggctgcc aggccccaga gggcctgaga actgggtttg ggctggagag gatgtccatt  25080
attcaagaaa gaggctgtta catgcatggg cttcaggact tgtgtttcaa aatatcccag  25140
atgtggatag tgcgaccgga gggctgtctt actttcccag agactcagga acccagtgag  25200
taatagatgc atgccaagga gtgggactgc gattcaggcc tagttgaatg tgctgacaga  25260
gaagcagaga ggggcaccag gggcacagcc cgaaggccca gactgatatg ggcaaggcct  25320
gtctgtgctg acatgtcgga gggtcccact ctccagggac cttggtttcc ccgtctgtga  25380
catctgtgac atgagagtca cgataactcc ttgtgtgcct tacagggttg ttgtgaaaat  25440
taaatgcaca gataatagcg taacagtatt ccgtgcattg taaagagcct gaaaaccatt  25500
atgatttgaa aatggaatcg gctttgtgag accatcacta ttgtaaagat gtgatgctga  25560
tagaaatgac aggactgctt gtgcatgccc tctgcagtgt gacattccag cagtgaaatc  25620
atgttggggt gacttctccc ccactctgac ctttatgttt gtctgggccg aggctgcaag  25680
tcgggctctg tgggtgtatg agtgacaagt ctctcccttc cagatatggg gactgtctgc  25740
ttccctaggt tgcctctccc tgctctgatc agctagaagc tccaggagat cctcctggag  25800
gccccagcag gtgatgttta tccctccaga ctgaggctaa atctagaaac taggataatc  25860
acaaacaggc caatgctgcc atatgcaaag cactttggtt tgcctggcca cccctcgtcg  25920
```

```
agcatgtggg ctcttcagag ccacctgatg aggtgggtac agttagccac acttcacagg  25980

tgaagaggtg aggcacaggt cccaggtcag gctggccgga gctctgttta ttacgtctca  26040

cagctttgag tcctgctctc aaccagagag gccctttacc aagaagaaag gattgggacc  26100

cagaatcagg tcactggctg aggtagagag gaagccgggt tgttcccaag ggtagctgct  26160

cctgcaggac tctgagcagg tcaccagcta atggaggaaa ggctctaggg aaagaccctt  26220

ctggtctcag actcagagcg agttagctgc aaggtgttcc gtctcttgaa acttctacct  26280

aggtgctatg gtagccacta gtctcaggtg gctatttaaa tttatactta aatgaatgaa  26340

aatagaagaa aatttaaaat ccagaccctt ggtcacacta tccacattta aagaggtcaa  26400

tagccacatg tggttagtgg ccaccctatt gggcagtgca gctacagaac atttttgcat  26460

cccagaaagt tcttttggat gttgctgctc tacagcatgc tttgctgaaa cagaagtgcc  26520

ttccctggga atctcagatg ggaagcaagt aaggagggga gtcaaatgtg ggctcactgc  26580

tcaccagctg tgagggttgg gcctgcctct taaccattgt cagcctcagt cttctcatcc  26640

atgcatgccg tgggtatact aaaatactat accccctggaa gagctggatg caaatttgac  26700

aagttctggg ggacacagga aggtgccaag cacaaggctg ggcacatggt ggctgtgcac  26760

tacagctgag tccttttcct tttcagaatc tgggatgtta acc                    26803
```

```
<210> SEQ ID NO 21
<211> LENGTH: 177
<212> TYPE: PRT
<213> ORGANISM: Homo sapiens

<400> SEQUENCE: 21

Met Glu Ile Cys Arg Gly Leu Arg Ser His Leu Ile Thr Leu Leu Leu
1               5                   10                  15

Phe Leu Phe His Ser Glu Thr Ile Cys Arg Pro Ser Gly Arg Lys Ser
            20                  25                  30

Ser Lys Met Gln Ala Phe Arg Ile Trp Asp Val Asn Gln Lys Thr Phe
        35                  40                  45

Tyr Leu Arg Asn Asn Gln Leu Val Ala Gly Tyr Leu Gln Gly Pro Asn
    50                  55                  60

Val Asn Leu Glu Glu Lys Ile Asp Val Val Pro Ile Glu Pro His Ala
65                  70                  75                  80

Leu Phe Leu Gly Ile His Gly Gly Lys Met Cys Leu Ser Cys Val Lys
                85                  90                  95

Ser Gly Asp Glu Thr Arg Leu Gln Leu Glu Ala Val Asn Ile Thr Asp
            100                 105                 110

Leu Ser Glu Asn Arg Lys Gln Asp Lys Arg Phe Ala Phe Ile Arg Ser
        115                 120                 125

Asp Ser Gly Pro Thr Thr Ser Phe Glu Ser Ala Ala Cys Pro Gly Trp
    130                 135                 140

Phe Leu Cys Thr Ala Met Glu Ala Asp Gln Pro Val Ser Leu Thr Asn
145                 150                 155                 160

Met Pro Asp Glu Gly Val Met Val Thr Lys Phe Tyr Phe Gln Glu Asp
                165                 170                 175

Glu


<210> SEQ ID NO 22
<211> LENGTH: 159
<212> TYPE: PRT
<213> ORGANISM: Homo sapiens
```

<400> SEQUENCE: 22

```
Met Ala Leu Glu Thr Ile Cys Arg Pro Ser Gly Arg Lys Ser Ser Lys
1               5                   10                  15

Met Gln Ala Phe Arg Ile Trp Asp Val Asn Gln Lys Thr Phe Tyr Leu
            20                  25                  30

Arg Asn Asn Gln Leu Val Ala Gly Tyr Leu Gln Gly Pro Asn Val Asn
        35                  40                  45

Leu Glu Glu Lys Ile Asp Val Val Pro Ile Glu Pro His Ala Leu Phe
    50                  55                  60

Leu Gly Ile His Gly Gly Lys Met Cys Leu Ser Cys Val Lys Ser Gly
65                  70                  75                  80

Asp Glu Thr Arg Leu Gln Leu Glu Ala Val Asn Ile Thr Asp Leu Ser
                85                  90                  95

Glu Asn Arg Lys Gln Asp Lys Arg Phe Ala Phe Ile Arg Ser Asp Ser
            100                 105                 110

Gly Pro Thr Thr Ser Phe Glu Ser Ala Ala Cys Pro Gly Trp Phe Leu
        115                 120                 125

Cys Thr Ala Met Glu Ala Asp Gln Pro Val Ser Leu Thr Asn Met Pro
    130                 135                 140

Asp Glu Gly Val Met Val Thr Lys Phe Tyr Phe Gln Glu Asp Glu
145                 150                 155
```

<210> SEQ ID NO 23
<211> LENGTH: 180
<212> TYPE: PRT
<213> ORGANISM: Homo sapiens

<400> SEQUENCE: 23

```
Met Ala Leu Ala Asp Leu Tyr Glu Glu Gly Gly Gly Gly Gly Gly Glu
1               5                   10                  15

Gly Glu Asp Asn Ala Asp Ser Lys Glu Thr Ile Cys Arg Pro Ser Gly
            20                  25                  30

Arg Lys Ser Ser Lys Met Gln Ala Phe Arg Ile Trp Asp Val Asn Gln
        35                  40                  45

Lys Thr Phe Tyr Leu Arg Asn Asn Gln Leu Val Ala Gly Tyr Leu Gln
    50                  55                  60

Gly Pro Asn Val Asn Leu Glu Glu Lys Ile Asp Val Val Pro Ile Glu
65                  70                  75                  80

Pro His Ala Leu Phe Leu Gly Ile His Gly Gly Lys Met Cys Leu Ser
                85                  90                  95

Cys Val Lys Ser Gly Asp Glu Thr Arg Leu Gln Leu Glu Ala Val Asn
            100                 105                 110

Ile Thr Asp Leu Ser Glu Asn Arg Lys Gln Asp Lys Arg Phe Ala Phe
        115                 120                 125

Ile Arg Ser Asp Ser Gly Pro Thr Thr Ser Phe Glu Ser Ala Ala Cys
    130                 135                 140

Pro Gly Trp Phe Leu Cys Thr Ala Met Glu Ala Asp Gln Pro Val Ser
145                 150                 155                 160

Leu Thr Asn Met Pro Asp Glu Gly Val Met Val Thr Lys Phe Tyr Phe
                165                 170                 175

Gln Glu Asp Glu
            180
```

<210> SEQ ID NO 24
<211> LENGTH: 143

<212> TYPE: PRT
<213> ORGANISM: Homo sapiens

<400> SEQUENCE: 24

Met Gln Ala Phe Arg Ile Trp Asp Val Asn Gln Lys Thr Phe Tyr Leu
1               5                   10                  15

Arg Asn Asn Gln Leu Val Ala Gly Tyr Leu Gln Gly Pro Asn Val Asn
            20                  25                  30

Leu Glu Glu Lys Ile Asp Val Val Pro Ile Glu Pro His Ala Leu Phe
        35                  40                  45

Leu Gly Ile His Gly Gly Lys Met Cys Leu Ser Cys Val Lys Ser Gly
    50                  55                  60

Asp Glu Thr Arg Leu Gln Leu Glu Ala Val Asn Ile Thr Asp Leu Ser
65                  70                  75                  80

Glu Asn Arg Lys Gln Asp Lys Arg Phe Ala Phe Ile Arg Ser Asp Ser
                85                  90                  95

Gly Pro Thr Thr Ser Phe Glu Ser Ala Ala Cys Pro Gly Trp Phe Leu
            100                 105                 110

Cys Thr Ala Met Glu Ala Asp Gln Pro Val Ser Leu Thr Asn Met Pro
        115                 120                 125

Asp Glu Gly Val Met Val Thr Lys Phe Tyr Phe Gln Glu Asp Glu
    130                 135                 140

<210> SEQ ID NO 25
<211> LENGTH: 3804
<212> TYPE: DNA
<213> ORGANISM: Homo sapiens

<400> SEQUENCE: 25
taatttcagt gaaattatat aacttggtta catttaggtt acttattaca aatgaaaata 60
aatatactaa cagaagctgc ctcatatgca aatgagtaac atgttagaga ctaaaataca 120
caaaaaaatg catgtgcttt agctcatata aacaatatac aggacaactt accgggtagc 180
ataaacaacc aacaacggac tatcaaaagg aacctcgtca tctagtaact ttaaccttgt 240
tggtagatct cctttttcca tctccatata cacaggattg gaacttgcca tttctgaaat 300
ataaagcata tccttttcca aactttatct cttaggcgga aatattcaat ttatgaacat 360
gttcattcag caatcattag tcacgtacct actgtgtgga cctattatgt gcaaggccca 420
atattaagca ttacaagaga aacaaataaa agtacaagag atgtaatttc tacttttaag 480
aaccttaaaa tctaattggg aggcaaagca tattaaaagt tttaaataag acgaaggaac 540
atataattaa tacatcagtg actattactc ttaaaataat gagtatctag gcctatatat 600
agcaactgtc catataagca cacatcaaaa accaatatac atagctatca tcaatgccaa 660
gttgctcagt tttttctaga actagtattc ctactccatc ttttagaatt aaattcaatg 720
aaattaattt taaaatattt gacctttttt taaagttacc agtatagcaa atactcattc 780
tctgaagaac agaagatttg actttttgga atagccaaaa gtcacttaaa atcaagtctg 840
gtgaaaggag tgatgatcta aaactatttg tggtttaaaa aaaaaaagta tgaatctaaa 900
gtaaagtggg tttttttcca agtagttttc ttttttagtt ttttagaaac agggtctcat 960
tctgttgccc aggctggagt gcagtggtga tcactgcaac cttgaactcc tggctgtgtg 1020
tgtgtgtgtg tgtgtgtgca gcgacggggt cttcctacgt tgcctagctg cagtgcctgt 1080
gtgcacacat gcgcacatgc gtgtgtggag agacagggtc ttgctacgtt gcctagctgc 1140
aatacctggg tgtgtgcatg tgtgtgtgtg tagagacaag gtcttgaaac gttgtctagg 1200

```
ctggcatgtg tgtgtgtgtt tatatgtatg tgtgtgtaga cagggtcttg ctacattgca   1260
taggctggtg tgtgtgtttt tgtgtgtgta gagacggggt cttgctacgt tgcctaagct   1320
gggcaagtat ttttcaactg cctctgaaga caaatcccaa ataacagttc caaaagctgt   1380
ttcccataat tatcacatca ttagaagggt gaggcctact caccaggttc taagagccaa   1440
cattcatttt ctgatacatg ctttttttaaa aaagtcattt tttccccagt ctcattgttt   1500
cccatttgac tgtgtcaggc aataagtact ttaaaggaat tcagaggagg aggccattca   1560
gaggtttggg gaagcctgat gactgcgcgg gagctaaacc agacatatcc acctaaattc   1620
aagtaagcag ccatatcact caaattgccc accatgcttc ctctagccag cactggtagt   1680
aacaactatc actctggctg atggagactc ttttctgctc ttctgtgact gggtatgatc   1740
acataataga gacagataca gtaaatttcc aatgagtaat aatgtcacac atttgaactt   1800
acctgaggag aaatagcttg tttcttattt cacacaaaag acaatctacc tcaactcaga   1860
aaaaaaaaaa ttattatgct tttaactgct atatttgaat taaagcagat ctgtaactat   1920
agatccatgt ttctagaaag ctaaaatatc tttaagtaag atgacataaa aatgtatctc   1980
tattcacttt tggtaatgaa tgaaaagttg cttaaagtct aaagtattag aaatatggca   2040
tctgttattc aagtaggatt tggaattaag aaaattcact tcttcaaaaa catgggacta   2100
tggctgcaga aagggcaatg catatagttt ttagggtatg atagctggtt tctattatat   2160
gtcaggatga catatgcgac cttccgccaa ggtagatact gcgggctatg caccaaagtc   2220
tctgaggcag acatgtaagc gagctcttca cctatattca ttcttttcct cctggacagg   2280
ttacatttcc cagtttcctt tgcagttagt tgtggctata tgacagaatt ctcatcaatg   2340
gaaatgtaca cagaagagag gtaagccact accaggccag gcctataaga cagcactttc   2400
tacatgcttt ccccagacat agcaacccaa acatgaccac atcccttaag ggaagatgga   2460
gctgaaaata atggaaggaa cttggaatgc tagaatgctg aattaccacc tgggagacag   2520
ctacccactg acctggaata cctgtcctgg actgttacat gagcaagaaa tacacttcta   2580
tttatgtatg agttacttca ttatcagata tttattacag cagtttagct acctaagatc   2640
tctctctgcc tcagactgct tatctataaa atggaataac accatctact ccaaacatta   2700
ttgtaaggat gaaatgagac aatgctgaaa agtgtttacc ataatatctg ccacacaata   2760
agtaccccat atagtatttc tgtattagta agttacatga gagattttct tcttttaata   2820
catctgcatt tataaacatt ttactttaac ctcaacttcc ccagcactgc tctaccattt   2880
tctgaatgtc attatgagag aaataaaact aatttctagg gccaggcatg gtggctcaca   2940
cctataatcc cagcattttg ggaggccaag gtgggaagac tgctttgagg tcaggatttc   3000
aagaccaacc tgggcaacac agtaagaccc catctctata aaaaaatgaa gaaatcagag   3060
ggtacagtgg cacatgcctg taatcccacg actcagaaaa ctgaggcagg aggatcgctt   3120
gaacccaagg gatcaaggct acagtgagcc atgatcacac cactgcattc cagcctgggc   3180
acagagtgag accctgtctc taaaaataaa aaatagggcc aggcacagtg gttgatgcct   3240
gtgatcccaa cactttggga ggccaaggca ggtagatcac ttgaggtcag gcgtttgaga   3300
ccagcttggc cgacatggca aaaccctgtc tctactaaaa tacaaaaatt agctgggcgt   3360
ggtggtgcac gcctgcagtc ccagctactt gggaggctga ggcaagacaa tcacttgaac   3420
ccaggaggcg gaggttgcag tgagccaaga tggcgccact gcactcaaac agaatgaaac   3480
tctgtctcaa aaaaaataaa ataaataaaa atttaaaaac taatttctta taatccagtt   3540
```

```
gtgaatttaa ccaatgtctg aaagaactat taaaagttaa aatgaatgga aaacagaata   3600

aagggttgac cagaacagat gtgattttct acttaaatct ttttttaaa ccccaaaatt    3660

caaaactgct aatgtttttt aatacgaatt tctatctttg ataaggcaat ctgagtatta   3720

cctttcaatc cttcaataaa agtatcccaa acagaagggc tattactgta actaagcttg   3780

atactctcct tcgctctttt caag                                          3804


<210> SEQ ID NO 26
<211> LENGTH: 3804
<212> TYPE: DNA
<213> ORGANISM: Homo sapiens
<220> FEATURE:
<221> NAME/KEY: misc_feature
<222> LOCATION: (2122)..(2131)
<223> OTHER INFORMATION: n is a, c, g, or t

<400> SEQUENCE: 26

ggcttctggc tctgagtgag gtcctgctgc aaggtttcct agatgagcca ctgagactct     60

aataagatcc agtggaaata accaggctct cgtcggaata taagtcccaa gggaagctgt    120

gccagtcttg tgggcgactg cctgacttct cctttcattt cagcaccatg aagcttctca    180

cgggcctggt tttctgctcc ttggtcctgg gtgtcagcag ccgaagcttc ttttcgttcc    240

ttggcgaggc ttttgatggt aaggcttcag aaggtttgca ggatttctga agagaaacat    300

caccctggac ctgataaact ggggaaaatg atgctttcgg aaggctgctt ttgaaccaca    360

gagttgctag tgtctgcgtt gctgaggcct gccaggaact agggtttgct gggttgcctg    420

tctcgagtct ttcagagctg ctgggaatat cccctttccc cgtagtgcag cttctcagga    480

tgtgttaagt ggatggatca catttcagaa gccgctgcaa ggtgtatcaa aaacacatct    540

cctgagccgt aagggacggg gcatccagta acaacgcaca cggggtattt ttgggcttcc    600

ttaagatttg agccgctgcc ttaggttgtg ctgcccaatg tgcctgggga gctgctaaac    660

agattagaga gtcgaggatt gttgtcagtt actcagagaa agaacaatca tcctttccag    720

gagcacctga gctgtttgtt ttgcgtagaa gatgcaaaat aaggcctgca atgggtataa    780

aatgtccctc agcataaatc gcataggagt atgactaagg ctgttgactc ttctgtcttc    840

tttctccttc ctccttcgat ttcctagttg gataatgtac agggctcttt agcctcgctc    900

tgtcaggggc tcccttcctg gtttgttctg tttccattct tccttctcca gccttcttga    960

caagagctgg gaactaacgt gcctcaagcc cccacaagga ccacagcatt ttctcattta   1020

gtttcagaat gactctgtga cgcaatcttc ctctcttgga aggtgagaaa gctgatcttg   1080

gaaggtgaga aagctgagac ttagagcagc tgaagccaat gcccagggac ttactgccag   1140

tcagcaggtg gcagggcaga ggtttgagcc cggctgtgct tgaggtcagg gctcttgcca   1200

ggtagacgca tcactgacca cctcctagag gttgatggtt atgaatctca ggcacacctt   1260

ggcatcacct gaaataccca tgccttcaac tccccagcag agtctgcaga aactggcctg   1320

gggtgtggcc tgggcactgg gactttcagt ttctctctgg gtgattagaa agtgcagcca   1380

aggctcacgc ctgtaattcc agcactttgg gaggccaagg tggatgaatc acttgaggtc   1440

atgagttccg gagcagcctg gccaacatgg tgaaaccccg tctctactaa aaatactaaa   1500

atgtagccag gcgtggtggc aggcacctgt aatcccagct actcaggagg ctgaagcacg   1560

agaatcactt gaacccgaga agcagaggtt gcagtgacta gagatcgcac cagtgtcctc   1620

caacctgggt gacagagcga gactccatct aaaaaaaatg aaaaagaaag tgcagccaag   1680

gcagagcacc actgccctat tgcttcctca agcaacccac agcatcagta cagcctacta   1740
```

```
agaaagtatt tagggacttt tatgctccta acagtcactg gaactcacgt cacaatgacg   1800
tgtattccat ttgcaagaat atatacttta ggtcggggtg cggtggctca cgcctgtaat   1860
cccagcactt tgggaggcca aggcaggggg atcacgaggt caggagttcg agaccagcct   1920
gaccaacatg gtgaaatccc cgtctctact aaaaatacaa aaattagcca ggcgtgatgg   1980
cgcatgcctg taatctcagc tactcaggag gctgaggcag aagaatctct tgaacctggg   2040
aggtggaggt tgcgatgagc tgagatagca ccactgcact ccagcctggg cgacagagca   2100
agactctgtc taaaaaaaaa annnnnnnnn naaaaaaaaa aaaaaaaaaa aaaaaaaaaa   2160
aaagaatata aactttagta gtcagggcag aagtactctg tgtctgccac ctttctcagc   2220
atcagtattc catgtcacta cctcattcat acacactcct ggatcttatc ataggcagct   2280
tcattctata gcagtggctc ttcaccaggg cacttgaaga agccaactag gataaaggaa   2340
tgtgcttctc aacccatggt atccaaggct gctatgatca caggctgaaa gcttgaagtc   2400
agtggaagat ttgtccttcc tcattcccct ctaaggtgtt gttggagtct ttatgttctc   2460
ctgatgtccc ttctgccttt cctttccttt ccaggggctc gggacatgtg gagagcctac   2520
tctgacatga gagaagccaa ttacatcggc tcagacaaat acttccatgc tcgggggaac   2580
tatgatgctg ccaaaagggg acctgggggt gcctgggctg cagaagtgat caggtaactg   2640
gagctcctgg gacgttaggg ctgggtgagc agagcttgcc tgccttggac agtcaggagg   2700
gagacgagct ccttgtggag aagttagagg ctgcggcccc tcctcctctt gccctctctc   2760
tgcctctgtg ctcagtgtga ggtctgagtg gatggtagga gtgagtgatt cctcatcctc   2820
cctctctggg tgctgttcat ccagcctagg ggtgcccagc ctggctgaat ggggtggtgc   2880
ccagtgtttt catccctcct tccttggcct ttctgggctc ctctctgagc cctcccttgg   2940
aacagggaga atgggagggt gggctattgc tcactggcct gattattaat ctccttcttg   3000
cctgccttga ttacagcgat gccagagaga atatccagag attctttggc catggtgcgg   3060
aggactcgct ggctgatcag gctgccaatg aatggggcag gagtggcaaa gaccccaatc   3120
acttccgacc tgctggcctg cctgagaaat actgagcttc ctcttcactc tgctctcagg   3180
agatctggct gtgaggccct cagggcaggg atacaaagcg gggagagggt acacaatggg   3240
tatctaataa atacttaaga ggtggaattt gtggaaactg ggtgttatac tttgtggtat   3300
agactgcctg tttagtatga aggggcgatc catgcacatc taagtgaacg tggaggctgg   3360
gtgggtggga gacgactcct gggcacacag ggcatcctgg gcatccctga ggcaaggaca   3420
tgatgagttc agtggccacc cccacaggat cccaggggct tcagcagatc ccacccctta   3480
ccccatgtga gcagctgccc agtgagtctg taggaacccg agccacattc ccagtgagtt   3540
caactgcacc ccggcacgtt ttgctagcac ctcaatggag agctccttgc ttgcagcttt   3600
ggcttgtggc acccagcaaa agcttcctgc cacccagtgg ctacagccac acactctcca   3660
gcaagattta atctcagcct tgtgaggagc cctttcccaa atttatttct ttctgtgttt   3720
tttatccctt agtagctaat ctcatgttag ccattaataa ctctctatgt taaacccttc   3780
cttttgtatc tgcggctaca ttga                                          3804
```

<210> SEQ ID NO 27
<211> LENGTH: 3804
<212> TYPE: DNA
<213> ORGANISM: Homo sapiens

<400> SEQUENCE: 27

```
gtataaatgc agaggtgcag taactgggct tttcaggata tccagatgga gttgtggtgt     60
tgttttgctt gtggttttta acgttaactt ttttttcccc tttattttaa gagaagcaca    120
aaatgaacaa actagtgagc ccagcaacat ggatggaaat tccggagatg cagactgctt    180
tcagccagca gtcaaaaggg tatgggcaaa aaaatatgaa ccatttgggg ctcaagtttc    240
tccaaatact ttatgtgact gcaagtactg tatacgctta tttcctgtga ctcagttctt    300
ctaactaaga tgttaagcat ttggcttaaa gtgtatagca ttacaaagag tatttcccca    360
gctttggctt gccagccaac tttccattga ctctagcctg ttagccattt ttattgtttt    420
ttgtttgttt gtttgtttgt tttcctcaca tgtacacata catacagatt gttcttatat    480
gtgattttgt tctctgggaa taaaatcttc attcaacaga ggcaatatga cagaaaaacc    540
gaagtttcat gtatatgatt tttcaaagaa agtgaattgg ccctcatgtt aaacctagca    600
tttcagagct gaaagtgtct tctcattaaa tattgaagaa atcatttgag ggtgtggaga    660
aggatggaca gaattagctg cttgtgtatt tattcttctc ctgcaacttt gccacgctat    720
tttgtacctc ccttcctaat tatgataaag ctttcttaga gagcagtcag gcaatgtgta    780
ttaaatgttt aaagctttac acccttagtt ctacttgtgg acatttattt cttaagaaag    840
atgtatacta agatttagat agaaatattc attacagtat cataataaag acagtagcaa    900
ggattctgtt atctgtgttg cattaataca atagagattg atgcaactgt tcattatttt    960
gaaagcatta atgataatat tgcatcaaag agttcactga acagattgta cagtacagtt   1020
ttacacacaa aaaaaatagt ttgtgagctt taaaagggcc ttcaaatgaa tatgctaaac   1080
ggttatcttt caataaagag agtatgggta agtcttaatt tctttcattt atttcagtaa   1140
tttaatgttt ttgttgttgt tattgtttgt ttttttgaga cagagtcttg ctctgtcacc   1200
caggctggag tgcagtggtg caatctcagc tcactgcaat ctcggctcac tgcaacgtct   1260
gcctcctgga ttcaagcaat tcttctgcct cagcctccgg agtagctggg attacaggcg   1320
tgcaccacca tacctagcta atttttgtat ttttagtaga gacggagttt tgccatattg   1380
gccaggctgg tgttgaactc ctggcctcat gtgatccgcc catctcagcc tcccaaagtg   1440
ctggggttac aggcatgagc cactgtgcca gcctatttca gtaacttaat gtttttacag   1500
gcatgtatta cctataaaat taataaagcc agtgaggtat ttcttttttg aactaaagca   1560
aagctaataa taagttatag agaagttaga gaagaaatct attaagtgat actttctttg   1620
tatactgttg ggctgagtac ccttgattct tggtggtgaa caagttatca gaaatttctt   1680
ggccaggagc cgtggctcac acctgtagtc ccagcacttt gggagtccaa ggtgggtgga   1740
tcacttgagg tcagaatttc tagatcagcc tggccagcat ggtgaaaccc tgtctctatt   1800
aaaaatacag aaattagcca ggcatggtga cgtgcgcctg taattccagc tacctgggag   1860
gctgaggcag caaaatcact tgaacctggc aggcggagtt cgcagtgagc tgggatcgcg   1920
tcgctgcact ccagcctgga tgacagagca agactccatc tcaaagaaaa aataaaaaag   1980
aaatttattt acttgtgtga atttttacaa tacagatgct tctcgactta aatggggcta   2040
catcccaata aactcataag ttgcaaatac tgtaaatcaa aaatgcattg aatacaccta   2100
atgtatggaa caccatagtt tagcctatcc tactttaaat gtgttccgaa cacttagatt   2160
agcctgtagt tgggcagcat tacctactat aaagtgtatt ttctaataaa atgttgaata   2220
tctcatgtaa ctcattgaat actgaaagtg aaaaacaatg tatgggtact caaaatatgg   2280
```

```
tttctctact gaatgtgaat cactttgaca ccatcataaa gttgaaaaat tccaagtcaa   2340

accattgtaa gtcaggggct atcagtattc agtggtaaat gctggctcta actattcttc   2400

caagtcagtg gttgactgct gtttattcta taaagggtta caatttatag attctctcac   2460

ttgtagaatg agagattcag aattaatagc agacagagtc cctaccttga tggagctttc   2520

atttaagtgt gaaagtcagg tgacctaaca aggccttggc ataagtttag gatttggatt   2580

gttatgggag cttgggtagg gacatgtcat aggtaaggca acagcagggg tagagataag   2640

cttgacatat gtcaaaaatc atgaagacat cagtaatcct tgaagttggc tgaaaggtat   2700

agagttgaga aagtagttaa aaaaaaaaaa gtcaggctga gtctaggtaa ggatgtgttt   2760

ctctgaggtc agatttgttc ctgtaccata aagggactat ttagaatctt aaagctggag   2820

caatttaaaa cgttaagttt tcagattgag gtcagatttg tgacttcatg tgaggtcaga   2880

tttgttcctg taccataaag ggactattta gaatcttaaa gctggagcaa tttaaaacgt   2940

taagttttca gattgacgtt ttttgaggta tagttaataa cctgaatgtt ctgattctag   3000

tcttggtagt caataagagt tgaccagatg aatttcatag ctttgtagag gatgaaatat   3060

ttcaaggctg atttgcacaa atgtttacat agatcatgta tctttcataa gtaatatgtt   3120

tgtattatta caaggctgta aaaatttaag caggttgtta atagcacagg gggtaacaga   3180

ttaataaaat taatgaataa aattactaaa agagtccaga agtaaaccca aatacgtgga   3240

ggaattaagc atatgtatga tacacatgac attttaaaaa tcagtgggaa aaggtaaatt   3300

attttacaaa tggtgttaga agcactgatt gataattttg ttaaaagaaa cttagattcc   3360

ctattttact cctaatccaa aataaattct gagtggatct aagattaagc aaaaattaag   3420

ccggaagctg agcatggtag catgtgtctg taatctccgc aatttaggag actgagtttg   3480

gctggggagg tggtgatatg cgcctagaaa aaaaaaattt tttaagccac agatgtataa   3540

gcaaaaagcg ggcaaagagg cggaattttt tttttttttt ttgatgaagt ctcacttgtc   3600

gcccaggctg gaacgcagtg gcgtgatctc agctcactgc aacctctgcc tcccgggttc   3660

aagcgattct cctgcctcag cctcccaagt agctgggatt acaggcacct gccgaggaga   3720

ggattttttt ataattaaaa caaaacaaaa caaaaaaaca ccaaactgga agataaagta   3780

tttacaacat gtaaaagact gttt                                          3804
```

<210> SEQ ID NO 28
<211> LENGTH: 662
<212> TYPE: PRT
<213> ORGANISM: Homo sapiens

<400> SEQUENCE: 28

```
Met Val Val Ser Glu Val Asp Ile Ala Lys Ala Asp Pro Ala Ala Ala
1               5                   10                  15

Ser His Pro Leu Leu Leu Asn Gly Asp Ala Thr Val Ala Gln Lys Asn
            20                  25                  30

Pro Gly Ser Val Ala Glu Asn Asn Leu Cys Ser Gln Tyr Glu Glu Lys
        35                  40                  45

Val Arg Pro Cys Ile Asp Leu Ile Asp Ser Leu Arg Ala Leu Gly Val
    50                  55                  60

Glu Gln Asp Leu Ala Leu Pro Ala Ile Ala Val Ile Gly Asp Gln Ser
65                  70                  75                  80

Ser Gly Lys Ser Ser Val Leu Glu Ala Leu Ser Gly Val Ala Leu Pro
                85                  90                  95
```

-continued

```
Arg Gly Ser Gly Ile Val Thr Arg Cys Pro Leu Val Leu Lys Leu Lys
            100                 105                 110

Lys Leu Val Asn Glu Asp Lys Trp Arg Gly Lys Val Ser Tyr Gln Asp
        115                 120                 125

Tyr Glu Ile Glu Ile Ser Asp Ala Ser Glu Val Glu Lys Glu Ile Asn
    130                 135                 140

Lys Ala Gln Asn Ala Ile Ala Gly Glu Gly Met Gly Ile Ser His Glu
145                 150                 155                 160

Leu Ile Thr Leu Glu Ile Ser Ser Arg Asp Val Pro Asp Leu Thr Leu
                165                 170                 175

Ile Asp Leu Pro Gly Ile Thr Arg Val Ala Val Gly Asn Gln Pro Ala
            180                 185                 190

Asp Ile Gly Tyr Lys Ile Lys Thr Leu Ile Lys Lys Tyr Ile Gln Arg
        195                 200                 205

Gln Glu Thr Ile Ser Leu Val Val Val Pro Ser Asn Val Asp Ile Ala
    210                 215                 220

Thr Thr Glu Ala Leu Ser Met Ala Gln Glu Val Asp Pro Glu Gly Asp
225                 230                 235                 240

Arg Thr Ile Gly Ile Leu Thr Lys Pro Asp Leu Val Asp Lys Gly Thr
                245                 250                 255

Glu Asp Lys Val Val Asp Val Val Arg Asn Leu Val Phe His Leu Lys
            260                 265                 270

Lys Gly Tyr Met Ile Val Lys Cys Arg Gly Gln Gln Glu Ile Gln Asp
        275                 280                 285

Gln Leu Ser Leu Ser Glu Ala Leu Gln Arg Glu Lys Ile Phe Phe Glu
    290                 295                 300

Asn His Pro Tyr Phe Arg Asp Leu Leu Glu Glu Gly Lys Ala Thr Val
305                 310                 315                 320

Pro Cys Leu Ala Glu Lys Leu Thr Ser Glu Leu Ile Thr His Ile Cys
                325                 330                 335

Lys Ser Leu Pro Leu Leu Glu Asn Gln Ile Lys Glu Thr His Gln Arg
            340                 345                 350

Ile Thr Glu Glu Leu Gln Lys Tyr Gly Val Asp Ile Pro Glu Asp Glu
        355                 360                 365

Asn Glu Lys Met Phe Phe Leu Ile Asp Lys Val Asn Ala Phe Asn Gln
    370                 375                 380

Asp Ile Thr Ala Leu Met Gln Gly Glu Glu Thr Val Gly Glu Glu Asp
385                 390                 395                 400

Ile Arg Leu Phe Thr Arg Leu Arg His Glu Phe His Lys Trp Ser Thr
                405                 410                 415

Ile Ile Glu Asn Asn Phe Gln Glu Gly His Lys Ile Leu Ser Arg Lys
            420                 425                 430

Ile Gln Lys Phe Glu Asn Gln Tyr Arg Gly Arg Glu Leu Pro Gly Phe
        435                 440                 445

Val Asn Tyr Arg Thr Phe Glu Thr Ile Val Lys Gln Gln Ile Lys Ala
    450                 455                 460

Leu Glu Glu Pro Ala Val Asp Met Leu His Thr Val Thr Asp Met Val
465                 470                 475                 480

Arg Leu Ala Phe Thr Asp Val Ser Ile Lys Asn Phe Glu Glu Phe Phe
                485                 490                 495

Asn Leu His Arg Thr Ala Lys Ser Lys Ile Glu Asp Ile Arg Ala Glu
            500                 505                 510
```

```
Gln Glu Arg Glu Gly Glu Lys Leu Ile Arg Leu His Phe Gln Met Glu
        515                 520                 525

Gln Ile Val Tyr Cys Gln Asp Gln Val Tyr Arg Gly Ala Leu Gln Lys
    530                 535                 540

Val Arg Glu Lys Glu Leu Glu Glu Glu Lys Lys Lys Lys Ser Trp Asp
545                 550                 555                 560

Phe Gly Ala Phe Gln Ser Ser Ser Ala Thr Asp Ser Ser Met Glu Glu
                565                 570                 575

Ile Phe Gln His Leu Met Ala Tyr His Gln Glu Ala Ser Lys Arg Ile
            580                 585                 590

Ser Ser His Ile Pro Leu Ile Ile Gln Phe Phe Met Leu Gln Thr Tyr
        595                 600                 605

Gly Gln Gln Leu Gln Lys Ala Met Leu Gln Leu Leu Gln Asp Lys Asp
    610                 615                 620

Thr Tyr Ser Trp Leu Leu Lys Glu Arg Ser Asp Thr Ser Asp Lys Arg
625                 630                 635                 640

Lys Phe Leu Lys Glu Arg Leu Ala Arg Leu Thr Gln Ala Arg Arg Arg
                645                 650                 655

Leu Ala Gln Phe Pro Gly
            660
```

<210> SEQ ID NO 29
<211> LENGTH: 662
<212> TYPE: PRT
<213> ORGANISM: Homo sapiens

<400> SEQUENCE: 29

```
Met Val Val Ser Glu Val Asp Ile Ala Lys Ala Asp Pro Ala Ala Ala
1               5                   10                  15

Ser His Pro Leu Leu Leu Asn Gly Asp Ala Thr Val Ala Gln Lys Asn
            20                  25                  30

Pro Gly Ser Val Ala Glu Asn Asn Leu Cys Ser Gln Tyr Glu Glu Lys
        35                  40                  45

Val Arg Pro Cys Ile Asp Leu Ile Asp Ser Leu Arg Ala Leu Gly Val
    50                  55                  60

Glu Gln Asp Leu Ala Leu Pro Ala Ile Ala Val Ile Gly Asp Gln Ser
65                  70                  75                  80

Ser Gly Lys Ser Ser Val Leu Glu Ala Leu Ser Gly Val Ala Leu Pro
                85                  90                  95

Arg Gly Ser Gly Ile Val Thr Arg Cys Pro Leu Val Leu Lys Leu Lys
            100                 105                 110

Lys Leu Val Asn Glu Asp Lys Trp Arg Gly Lys Val Ser Tyr Gln Asp
        115                 120                 125

Tyr Glu Ile Glu Ile Ser Asp Ala Ser Glu Val Glu Lys Glu Ile Asn
    130                 135                 140

Lys Ala Gln Asn Ala Ile Ala Gly Glu Gly Met Gly Ile Ser His Glu
145                 150                 155                 160

Leu Ile Thr Leu Glu Ile Ser Ser Arg Asp Val Pro Asp Leu Thr Leu
                165                 170                 175

Ile Asp Leu Pro Gly Ile Thr Arg Val Ala Val Gly Asn Gln Pro Ala
            180                 185                 190

Asp Ile Gly Tyr Lys Ile Lys Thr Leu Ile Lys Lys Tyr Ile Gln Arg
        195                 200                 205

Gln Glu Thr Ile Ser Leu Val Val Val Pro Ser Asn Val Asp Ile Ala
    210                 215                 220
```

```
Thr Thr Glu Ala Leu Ser Met Ala Gln Glu Val Asp Pro Glu Gly Asp
225                 230                 235                 240

Arg Thr Ile Gly Ile Leu Thr Lys Pro Asp Leu Val Asp Lys Gly Thr
                245                 250                 255

Glu Asp Lys Val Val Asp Val Val Arg Asn Leu Val Phe His Leu Lys
            260                 265                 270

Lys Gly Tyr Met Ile Val Lys Cys Arg Gly Gln Gln Glu Ile Gln Asp
        275                 280                 285

Gln Leu Ser Leu Ser Glu Ala Leu Gln Arg Glu Lys Ile Phe Phe Glu
    290                 295                 300

Asn His Pro Tyr Phe Arg Asp Leu Leu Glu Glu Gly Lys Ala Thr Val
305                 310                 315                 320

Pro Cys Leu Ala Glu Lys Leu Thr Ser Glu Leu Ile Thr His Ile Cys
                325                 330                 335

Lys Ser Leu Pro Leu Leu Glu Asn Gln Ile Lys Glu Thr His Gln Arg
            340                 345                 350

Ile Thr Glu Glu Leu Gln Lys Tyr Gly Val Asp Ile Pro Glu Asp Glu
        355                 360                 365

Asn Glu Lys Met Phe Phe Leu Ile Asp Lys Val Asn Ala Phe Asn Gln
    370                 375                 380

Asp Ile Thr Ala Leu Met Gln Gly Glu Glu Thr Val Gly Glu Glu Asp
385                 390                 395                 400

Ile Arg Leu Phe Thr Arg Leu Arg His Glu Phe His Lys Trp Ser Thr
                405                 410                 415

Ile Ile Glu Asn Asn Phe Gln Glu Gly His Lys Ile Leu Ser Arg Lys
            420                 425                 430

Ile Gln Lys Phe Glu Asn Gln Tyr Arg Gly Arg Glu Leu Pro Gly Phe
        435                 440                 445

Val Asn Tyr Arg Thr Phe Glu Thr Ile Val Lys Gln Gln Ile Lys Ala
    450                 455                 460

Leu Glu Glu Pro Ala Val Asp Met Leu His Thr Val Thr Asp Met Val
465                 470                 475                 480

Arg Leu Ala Phe Thr Asp Val Ser Ile Lys Asn Phe Glu Glu Phe Phe
                485                 490                 495

Asn Leu His Arg Thr Ala Lys Ser Lys Ile Glu Asp Ile Arg Ala Glu
            500                 505                 510

Gln Glu Arg Glu Gly Glu Lys Leu Ile Arg Leu His Phe Gln Met Glu
        515                 520                 525

Gln Ile Val Tyr Cys Gln Asp Gln Val Tyr Arg Gly Ala Leu Gln Lys
    530                 535                 540

Val Arg Glu Lys Glu Leu Glu Glu Glu Lys Lys Lys Lys Ser Trp Asp
545                 550                 555                 560

Phe Gly Ala Phe Gln Ser Ser Ser Ala Thr Asp Ser Ser Met Glu Glu
                565                 570                 575

Ile Phe Gln His Leu Met Ala Tyr His Gln Glu Ala Ser Lys Arg Ile
            580                 585                 590

Ser Ser His Ile Pro Leu Ile Ile Gln Phe Phe Met Leu Gln Thr Tyr
        595                 600                 605

Gly Gln Gln Leu Gln Lys Ala Met Leu Gln Leu Leu Gln Asp Lys Asp
    610                 615                 620

Thr Tyr Ser Trp Leu Leu Lys Glu Arg Ser Asp Thr Ser Asp Lys Arg
625                 630                 635                 640
```

```
Lys Phe Leu Lys Glu Arg Leu Ala Arg Leu Thr Gln Ala Arg Arg Arg
                645                 650                 655

Leu Ala Gln Phe Pro Gly
            660


<210> SEQ ID NO 30
<211> LENGTH: 508
<212> TYPE: PRT
<213> ORGANISM: Homo sapiens

<400> SEQUENCE: 30

Met Val Val Ser Glu Val Asp Ile Ala Lys Ala Asp Pro Ala Ala Ala
1               5                   10                  15

Ser His Pro Leu Leu Leu Asn Gly Asp Ala Thr Val Ala Gln Lys Asn
            20                  25                  30

Pro Gly Ser Val Ala Glu Asn Asn Leu Cys Ser Gln Tyr Glu Glu Lys
        35                  40                  45

Val Arg Pro Cys Ile Asp Leu Ile Asp Ser Leu Arg Ala Leu Gly Val
    50                  55                  60

Glu Gln Asp Leu Ala Leu Pro Ala Ile Ala Val Ile Gly Asp Gln Ser
65                  70                  75                  80

Ser Gly Lys Ser Ser Val Leu Glu Ala Leu Ser Gly Val Ala Leu Pro
                85                  90                  95

Arg Gly Ser Gly Ile Val Thr Arg Cys Pro Leu Val Leu Lys Leu Lys
            100                 105                 110

Lys Leu Val Asn Glu Asp Lys Trp Arg Gly Lys Val Ser Tyr Gln Asp
        115                 120                 125

Tyr Glu Ile Glu Ile Ser Asp Ala Ser Glu Val Glu Lys Glu Ile Asn
    130                 135                 140

Lys Ala Gln Asn Ala Ile Ala Gly Glu Gly Met Gly Ile Ser His Glu
145                 150                 155                 160

Leu Ile Thr Leu Glu Ile Ser Ser Arg Asp Val Pro Asp Leu Thr Leu
                165                 170                 175

Ile Asp Leu Pro Gly Ile Thr Arg Val Ala Val Gly Asn Gln Pro Ala
            180                 185                 190

Asp Ile Gly Tyr Lys Ile Lys Thr Leu Ile Lys Lys Tyr Ile Gln Arg
        195                 200                 205

Gln Glu Thr Ile Ser Leu Val Val Val Pro Ser Asn Val Asp Ile Ala
    210                 215                 220

Thr Thr Glu Ala Leu Ser Met Ala Gln Glu Val Asp Pro Glu Gly Asp
225                 230                 235                 240

Arg Thr Ile Gly Ile Leu Thr Lys Pro Asp Leu Val Asp Lys Gly Thr
                245                 250                 255

Glu Asp Lys Val Val Asp Val Val Arg Asn Leu Val Phe His Leu Lys
            260                 265                 270

Lys Gly Tyr Met Ile Val Lys Cys Arg Gly Gln Gln Glu Ile Gln Asp
        275                 280                 285

Gln Leu Ser Leu Ser Glu Ala Leu Gln Arg Glu Lys Ile Phe Phe Glu
    290                 295                 300

Asn His Pro Tyr Phe Arg Asp Leu Leu Glu Glu Gly Lys Ala Thr Val
305                 310                 315                 320

Pro Cys Leu Ala Glu Lys Leu Thr Ser Glu Leu Ile Thr His Ile Cys
                325                 330                 335

Lys Ser Leu Pro Leu Leu Glu Asn Gln Ile Lys Glu Thr His Gln Arg
            340                 345                 350
```

```
Ile Thr Glu Glu Leu Gln Lys Tyr Gly Val Asp Ile Pro Glu Asp Glu
        355                 360                 365

Asn Glu Lys Met Phe Phe Leu Ile Asp Lys Val Asn Ala Phe Asn Gln
    370                 375                 380

Asp Ile Thr Ala Leu Met Gln Gly Glu Glu Thr Val Gly Glu Glu Asp
385                 390                 395                 400

Ile Arg Leu Phe Thr Arg Leu Arg His Glu Phe His Lys Trp Ser Thr
                405                 410                 415

Ile Ile Glu Asn Asn Phe Gln Glu Gly Gly Gln Gln Ala His Leu Gln
            420                 425                 430

Pro His Pro Phe Asp His Pro Val Leu His Ala Pro Asp Val Arg Pro
        435                 440                 445

Ala Ala Ser Glu Gly His Ala Ala Ala Pro Ala Gly Gln Gly His Leu
    450                 455                 460

Gln Leu Ala Pro Glu Gly Ala Glu Arg His Gln Arg Gln Ala Glu Val
465                 470                 475                 480

Pro Glu Gly Ala Ala Cys Thr Ala Asp Ala Gly Ser Ala Pro Ala Cys
                485                 490                 495

Pro Val Pro Arg Leu Thr Thr Leu Cys Pro Ala Pro
            500                 505
```

<210> SEQ ID NO 31
<211> LENGTH: 5687
<212> TYPE: DNA
<213> ORGANISM: Homo sapiens

<400> SEQUENCE: 31

```
ctctctggtt gcccttaaca ttttttcctt catttcaact ttggtgggtc tgatgattat     60

gtgtcttggg gttgctcttc tcgaggagta tcttagtagt attctctgta tttcctgaat    120

ttgaatgttg gcctgtcttt ctaggttggg gaagttctcc tggataatat cctgaagagt    180

atttttcaac ttggttctat tctccttgtt actttcaggt acaccaatca aacgtagatt    240

tggtcttgtc acatagtccc atatttcttg gaggttttat tcgttccttt ttattctttt    300

ttctctagtt ttgtcttctc gctttatttc actaagttga tcttcaatct ctgatatcct    360

tgcttctgct tgattgattc agctatcccc cgctcgatat tacaaaccat gtcacgaggc    420

gtggacaccc cccatgatat ggggagtatt atcacccccc tcttccccca ctggatatta    480

caaaccatgt catagggagg tggacatccc ccacaatatg aggagtaata tcacacccct    540

ttccccgcag tggatattat gaaccatgtc acaggcggtt aaacaccccc aacgatatgg    600

ggagtaatat cacactcctc tccccccctgg atattacgaa ccatgtcatg gggggtggac    660

acccctttgca atatggggag taaaatcacc cccctctccc ccaactggat attatgaacc    720

atgtcacagt gggggaaaaa tcctctgtga tatgcagagt aatatcaccc cactctcacc    780

acctggatat tacgaaccat gtcacagggg ggtggacacc ccccaagatg gggagtaat    840

atcacctcac tctctgccac cagatattac aaactgtgtc acaggggggt gaacaacccc    900

cacaatatgg ggagcactat caccccccctc ccccagggta ttatgatcca tgtcacaggg    960

gggtggatac cacccactat atggggagta atatcacctt tctctcccgc cctggttttt   1020

atgaaccgtg tcacaggggg gtggacaccc cttgcgatat ggggagtaat atcacccccc   1080

tctccaccat ctggatatta cgaaccatgt cacagggggg tggacacccc tgcgatatgg   1140

ggaggaatat gcccctctcc ccacctggat attacaaatc atgtcacggg ggacggacat   1200
```

```
cccccacaat atggggagta atatcaccac actctcccct gctggatatt acgaaccata   1260
tcacaggcgg ctggagacac aaggcattaa caatatttcg agtaatatta tctttccctt   1320
tgaacattat gaacaatatg acagaggggt gtacacctcc tgcgatattg ggagtaatgt   1380
catcccctcc cccactggat attaggaacc atattactgg gggatgtatt cccccttcta   1440
gattgggagg aagatcatac ttgccctccc tgaatatttg aaacaatatc atagggggttt  1500
gtacactttt acgatattgg gagtaatatc atcctttctc cccctggaaa ttaggaacaa   1560
tatcacaggg gtggtgtaca cccctgcaat atttagggta atattattgt cttctcccct   1620
cgatattagg aacaatatta caaggacggt gtaaagtacc tgccaaattg ggaaaaatac   1680
tatcctctcc ctcttgtata ttagaaacaa taacacaggg ggaatgtaca cccactgcca   1740
tattgggagt aatatcatac tcgccccatc ccccagatat taggaacaat atcacagcag   1800
gggtgtacac ttttacgata ttgggagtaa tatcatactc tctccccctg gaaattagga   1860
ataatatcac agagatggtg tagaccctct gcaatactta ggataatatt atcatctccc   1920
ccctcgatat taggaacaat attacgggga gtgtaaatta cctgccaaat tggaggtaat   1980
cctctcctct ctctccctgt attttagaaa atataacaca caggaaatgt acaacactgc   2040
gatattcgga gtaatatctt cttctcccca cctggatatt aggaacaata acacggacgg   2100
ggcgtacacc cctcgcgata ttgaatgtaa tgtcatcctc tccctccctt tatattacga   2160
acaatatcac agggggggtgt acaacccctg caatattgga agtagtatca tccattctcc  2220
catgaatatt aggaacaata tcacaggggt agagtacacc ctctgcaatt tcgggagtaa   2280
catcatcctc tcgttccctg gatattataa acaacaccac gggggggtgg gggtgtacac   2340
acccttcgat attgggagta atataatcct ttccctccct atatattaga agcaatatca   2400
caggggttgg tgtaaacttc ttgcgatatg gggattaata tcacccccct ctcctgccct   2460
ggatattatg aaccatatca cagggaggtg gacacacttt gcgatatggg gagtaatatc   2520
acgcccctct cccccccgat attacgaacc atatcacaag ggagtggacc ccccccacga   2580
tatggggagt aatatcaccc ccctctcccg ccctggatat tacgaaccat atcacagggg   2640
gatggacacc ccccgcgatg cggggagtaa tgtcaccccc ttctgccccc taggatatta   2700
cgaaccatat catggacacc ctccacgata ttggaaataa tatcatcctc tcccccttgg   2760
atattaggaa caatatcaca gggggttgta cacctcctat gatattggaa gtaatatcat   2820
cctctccctc ctggatatta gcaacaatat cacagggagt gtgtacaacc ccagcgatat   2880
ttggagtaat atcaccctct caccccatgg atatgagaaa caatatcaca ggggaggtgt   2940
acatcccacg tgatattgtg tgtaatatca ttcttcccca acccctgcaa tattgtggtg   3000
taatataatt ctctcccttc ctggacatta tgaacaatat cactactagg tgatacatta   3060
ggagtaatgt atccatagga tattatgagg aatatcacag ggtgtacacc cactgtgata   3120
ttagaggtaa tatctcccta aaatattaag aagaatatct tacacccact gtgactttag   3180
aagtaatatc tccctaaaac gttacaaata acatcgcagg gtgtacactc acagtgatat   3240
taggagtaat atctccctag aatattacaa atacacatgg tgtaaaccca ctgtgacttt   3300
agaagaacta tctccctaaa ataatacaaa aatatcgcag tgtataccat aatatcccct   3360
agaatatcat aaataatatc acagggtgta cacccactgt gataatagga ataataccac   3420
cccaggatat tatgaataat gtcacaggct gtacacccac tatgacatta ggagtaatat   3480
ctccctagga cactatgaat aacatcacag attttacacc catggtgtgc acccactatg   3540
atattaggag taatatctgc acaggatata acaaataata gtacagggtg tacacatatg   3600
```

```
atatacaccc actgtgatat taggagaaat atatccctag gatattatga ataacctctc   3660

agagtacaca cacatggtat acaccctctg tggcattagg aacaataact ttctaaaaca   3720

ttacgaataa catcacagaa tgtacacaca tggtttacac ccactgtgac aggtgcaata   3780

tctcccttgg atattatgaa taacaacaaa ctatcactgt catattagga gtaatttctc   3840

cctagaatat tacaaataac atcacagggt gttcatttat ggtgcacacc cactgtgata   3900

ttaggagtaa tatctcccta ggatattact tttcatataa aagtgtgtac atccactgtg   3960

atattgggaa aaatatttct ctaggatatt atgaataata tcacagagcg tacacccact   4020

gtgatattag gagtaataat tccctgggtt attatgaata atatcacagg atgtacaacc   4080

actgtgatat taggagcaat atcttcctag gatattacaa ataatatcac agggtgtaca   4140

cccactgtga tattaaagta atttttaggt tattgtgaat aatatcacca agtgtacaaa   4200

catggtgtac actcactgtg atatcaggag taatatctca gtaaaatatt atgaataata   4260

tcacagggta tacacccact gtgatattag cagtagtatc tttgtaggat attacaaata   4320

atatcacagg gtgtatgccc actatgacat tagaagcaat atctccctag gatatcaaaa   4380

ataatatcac agggtgtaca acttctacat cccaggttct aagggattct cctgcttcag   4440

cctcctgagt ggctgggatt acagatgccc accaccacac ctggctaatt tcgtattttc   4500

agtagagatg gggtatcacc atgctggtca ggctggtctg gaacttctga cctcaggtga   4560

tccaccagcc tcggccttcc aaagtgctgg gaatacaggt gtgagccaac gtgcttggca   4620

gagagttata tattaaataa atctggaaac atagctccca tgtttgagtg tgcatttact   4680

tttatgaaga aattatgtca gaaaacctaa ggatgataat aaatatgaaa agtaactggc   4740

atgtaaaaag gtcttttgat taagaactat aaggttcgat ttcattttta gataacgtga   4800

tcctagctct tgtatagtgc ttataaatat tctacatcaa aggaatttgt tgcacagtgt   4860

cagaataaaa taaagtgtat ttcactgctt cttaattttt aaattagact gagtttgttt   4920

tcctagagag agaagaacat tttttatttt ttctgaaaag agtaggccat attttactga   4980

gatcttagat ttgttatata ttaggttttg gtcttctaac attctccagt ggattttctc   5040

taaagtaggt atgcacagaa agagttgaat agcaaaaaag taaatcatgt aataattctg   5100

agatttttgg gtttgtcaca actgagaaat attgctgagg gtgtatggtc ctcaagtgtg   5160

aaaatgttcc ttgtgaattg cttgtatccg aaatatacac acaacattaa gtcctggttt   5220

ttatctttta ttttttccaa tcctttttc ttctcaaggt gtccaagtca cacagagcca   5280

cagaatctca caggtgtctc agaattcctc ctcctgggac tctcagagga tccagaactg   5340

cagccactcc ttgctgggct gttcctatcc atgtgcctgg tcacgatgct ggggaacctg   5400

ctcatcatcc tggccgtcag ccctgactcc cacctccaca tccccatgta cttcttcctc   5460

tccaacctgt ccttgcctga cattggtttc accttggcca cggtccccaa gatgattgta   5520

gacatgcaat cacatagcag agtcatctcc catgcaggct gtctgacaca gataccttc   5580

tttgtccttt ttgtatgtat agatgacatg ctcctgactg tgatggccta tgactgattt   5640

gtggccatct gtcacccct gcactaccca gtcatcatga atcctca                5687
```

<210> SEQ ID NO 32
<211> LENGTH: 5687
<212> TYPE: DNA
<213> ORGANISM: Homo sapiens

<400> SEQUENCE: 32

```
attgaatttt atctcagagc ccacatgaag caggatcaaa gtcagtacac atgaaaacta      60
gagcccaaag actataaagc atgaaataag gatttaagct aaccctatct tgtaaggggt     120
ttgtaaagcc cagcttgcat ctgagctaca ctagcaccag gacagccact cagtaatggg     180
gtttctcaag gttattgctt ttcattcagt tgaaatgaga gtcatttctt acccttatgc     240
cctgtgagat ttcactggag gttgttcact gaaacatttt catatcattg catcaaccct     300
cttgaactca ctgtgcctgc ccccagttca gtctgtgact cacaagtacc ctgcagcaaa     360
agaaatccaa tagagggcaa atccctcacc ttaccttcct ttctaagacc tttgatgttc     420
tcatgtgtca tttcataatt gggattgtca attagtcgcc tcatctctgg tcctcacttt     480
cctctctccc agccaaactc aaccttcagc ccacacaatg gaattcaaca aaatgaggta     540
acagttttct gtgtgagtca ctctgggcaa ctctgttcac agagcactgt gaggtgagca     600
gccagaaccc aggcaagtgt ttcagccatc caagaactgg caggcagccc aagagacact     660
ctcacctgat gacagactag caggatgagt cctggaggaa atggttccca acagctgcag     720
aaggagtctc ttggctcatg cacagcaatg ctcttctcaa ttaaaaacgt tgtcattatt     780
gacactgcag tgtaaaatcc ttttacactg tgctcacatt tctacaggcc ttcacctgct     840
ctgcccatta aagacaagac ccttccatga gatgatgaca tctctaagtt actgttccac     900
ccaaacagtc ctatataatg aagagaaaaa ttttgctggc cctcaaaagg caaacacaag     960
gagaaagatt tccacaagct gtttctcttt gctgagcact tagaggaaaa ctgtaagtgg    1020
ttggaagaag gctttgtttt ctacaagact tttagttatt cctcagaaat tttcctgctt    1080
attcccagag gaggtcatct cttagatgct gtcagtcaga tagggattgg cagccaagca    1140
gaggtgctca gagaggtttc caactaatgt ggccagcgga aaactgccaa agaagcaggg    1200
atccttagga caaataaact ggaagatatt ttggggataa aaataaatcc ttttgaaaat    1260
gaaagatgga gagatgctgt atatacaaat tgccctgttc tgaacaatgt tgtcactagg    1320
actggccctg gagaccaatg atacaaacca aaatgttctc agacatgctt tgatggtctt    1380
tttctccaaa gttatctatt ctgtttccat ttcattctca caggacttgc catggggttc    1440
tcataagatt tcacattggt cataatccag gtggccctgg actgcaacct ctgagttggc    1500
aacatcagaa taggaattac gaaaaaccaa tttaaagtta aatacagaca caggcaaaag    1560
agagatgggt tgtcgaagct agtgcctagg tggacactgc ctcacatttt taattccaga    1620
agccatcagt actgagtgtc agatctcatt agtcaaacac agtgatcagg aatcctgttt    1680
tcctggagga tttccttgag ggagggacca ctcaagagtc tgaaatattt cacgtcatag    1740
agtatggatc tcaccccaac acccaatcag aaaataggga gaactggaaa ccaaaattcc    1800
ccctcccgct gtggaaggat gaaaaccaga gtgttggagt tctgtcctga taatggagca    1860
gacagctagg cagcaatcaa tgagggccag tacaggaatt cagtgctaag tattgggtca    1920
taacagaagt agggaaggta ttaatccagt gctatatgag gatcctggga cactggctcc    1980
tagtaatcta gttataacta ttagcaaaaa agaaaaaaaa aatcagtgat gtgaagagat    2040
ggcctaaagg agctccagca atatagctaa gcagctggca agtggtctga ggagcattgc    2100
aattccaggc ctcctaaggt ggcagtacgg gcactggtaa gacattctgc tgtggtgaaa    2160
ctagtttacc atagaggatt cacaattaaa ataggcaaac aggaaatgca agacagaggc    2220
taacaaaggg ttttttttt ggtggggggg agttgtttgt ttgtttgttt gttttctgag    2280
```

-continued

```
acggagtctt cctctgttgc ccaggctgga atgcagtggc acgatctcag ctcactacaa   2340
cctctgcctc ccaggttcaa gcagttcttc tgcctcagcc tcccaggttc aagcagttct   2400
tctgcctcag cctcccaagt acctgggact atagctgtgt gccaccacat tgactaattt   2460
ttgtactttt agtacagact gggtttcacc atgttggcca ggctggtgtc gaactcctga   2520
cctcaagtaa tccccccgcc ttggcctccc aaagtgctgg aattacaggc atgagccacc   2580
acacctggcc agtttttggt aattcttaaa gaactcaatg agcaacactc aaacaaccat   2640
aaagactata gagctcatgg ttgaatttta gatagctaaa cagacaggag tttttgtaag   2700
ttttgtaagt cttgctcatc cttccctctt ccatcctcta tctcaactat tctgtctacc   2760
attaaagcac cttagacctt gagtttggca atgcaacaag tgtgtgctca acacgaaata   2820
ggtaattcaa tagcaaagcc ctaaaacagc ctggcttgat tatttctcag ggcatgcagt   2880
tcctttgaag caggatcatt ttaataataa taataataga aataataata gaaattgaag   2940
acaattattt cacaatttcc atacacctaa gagctataca tatgaatgat aatgcataat   3000
tgtaaagcat gcatattaca ggtaataaat atgttagcta attataaaca atgcccattt   3060
tcatatagtt tatccttgcc aaataaaact gtaaaaaaaa gacacctttc aaatgctgct   3120
aaggagtaat acctgaatga ggttgattta atggagtctt agttcctgca tgtgttctaa   3180
ttgaatagac tatgtagtaa ttcccttaca tacccatcca tgtccaagaa cagtgaagat   3240
ctttatttaa tatgaattat tgcagatgat tagcacagtc tagccaaacc attccagtaa   3300
ttgtttttac ttgttatatt aatatataaa ttctcaaagg atataacagt gatgttgggt   3360
gaatttcact gaatgatagc tcaaacacct gaaatattga ctaagaaaac taatttatca   3420
atactgataa tcaattttaa tatgttaatt gattgtaata caggattctg tggttcaaaa   3480
aaaaagaaca agcaaaaaaa ctttcttcca tttccaaata ccaattaata gatctctact   3540
tccccttgga tttcttctta ccacctacca cctccaatct tcattctttc ctcacaaact   3600
aaacataaaa gttacctaca aagcatagaa tctgtgttaa aggatattct tgcttgtttt   3660
aagtccaaaa ttaaacagct ctgaattatt aaaaagcaca tgaattcaaa tgtcctattc   3720
taataagaaa atggtttaca tttctctatg ttcaaggaaa aaaatagtca agggtgtaca   3780
agtggggtaa aaattatttc cagtaggtta tgtgatttaa gttatagaaa cgaaccaggc   3840
aattcaatta aatgtcatgg aaagtaggtt ttttcttttc ctcttttttt ctaatatgta   3900
cactttgtga gaagataaat ccatagtgtg ataatttgtc cactgggtcc atcagacact   3960
ggagacagct tcctaagaat tataaggctt ctaaaggctt ctaaagccta aattgcctag   4020
agcattttgt gtgccaggca ctttgctagg tgccctaggg atgcaagaag tataaatgtt   4080
ttatgagaat acaggctgga aatgtattct tgattattcc tgtggaattt ctaggcagaa   4140
aagagtctaa tggggtatag gtatattttc tcaacacaat tttctgagcc tttaccagat   4200
gcagttctat ggtttgaatg tgtccctcag agtttgtgtg ttggaaactt aatccccaat   4260
gcaataatgt tggtgaggcc taatgaaagc ctaataatgt aggtgaggcc taatgagagc   4320
tgtttagacc atgaaggctc ttccctcatg gatggattaa tgctgttatg gtgggaatgg   4380
gttcattatt actggggtgg gttcataata aaaagatgag tttggcctgc tattctctct   4440
ctttctcatc ctctcttcca ccatgggatg acacagcaag aaggcccctg caagatgccc   4500
tcccctcagt attggacttc acagcctcca ggaccataag ccaataaatt tttgttcatt   4560
ataaatttcc cagtctgtgg tattctgtta tagcaacact caatttatgc attacttcca   4620
gattcttatg gctataccta cttctcacag tttgtattca cccctccttc aaccaagtac   4680
```

```
ccttaacaca gttcccatag tcacaaagcc aggtcactga agctgccctc tctccaacca   4740

cacacatata gatcaaatga ccccagacat agagctgatt gagaaggagg gaccagtacg   4800

agctctgctt ccccagcagc ttcctggaaa gaagaggcaa tacaacccaa cccaaaagtg   4860

caagagaagt aacacctcat gggatgagct taattaatca atgggagagg acactagaag   4920

acactagagg atctcccttc ctccctttct ttcccacttc accccctcca gtctctgaac   4980

catgagctat ttcaaaggtg cagtaatgct atatttggct tctctgaaga tatcctatga   5040

ggccaagtca tcagctttgt tcattatcta agagtggtgg ccagctcacc agcacttccc   5100

atcatgtttg ccctccctct ttcccttgtg ttacttccca ttttccctta cttctgcttt   5160

cttggcatta aattctactc tgcaatgtta ggatataagt ttttgcctca gattctgttt   5220

tctaggaaac ccatgctaag acaacactgg cagtggccct ggaaaagtaa acctcatgat   5280

ggatttggag ttggattgtt cactgatctg aaggacagag gactccactt aagtggtaag   5340

cagtgtagct atgaactctg ccacgcaggc ctcacaatta ctgaggcttc ttttacctgt   5400

ggttaactgg gacacagaac agcaggaaat tgagtgtaga ggttatcaag tagctgcttc   5460

acttaattgg tataatttta tggagttaac ctggtttaga gtccagagaa cattccacat   5520

agcctagaaa gggtagttat ttgtccttac cataatcaag tcatactttg aatatgagtt   5580

ttccttccct gttcagcacc acttctctta gacttaagaa tgcctgatct gttgatatta   5640

tgtcccatgt aacattgcct gagacaaaga tatccatgta ccttaaa                 5687
```

<210> SEQ ID NO 33
<211> LENGTH: 140
<212> TYPE: PRT
<213> ORGANISM: Homo sapiens

<400> SEQUENCE: 33

```
Met Gly Phe Gln Lys Phe Ser Pro Phe Leu Ala Leu Ser Ile Leu Val
1               5                   10                  15

Leu Leu Gln Ala Gly Ser Leu His Ala Ala Pro Phe Arg Ser Ala Leu
            20                  25                  30

Glu Ser Ser Pro Ala Asp Pro Ala Thr Leu Ser Glu Asp Glu Ala Arg
        35                  40                  45

Leu Leu Leu Ala Ala Leu Val Gln Asp Tyr Val Gln Met Lys Ala Ser
    50                  55                  60

Glu Leu Glu Gln Glu Gln Glu Arg Glu Gly Ser Ser Leu Asp Ser Pro
65                  70                  75                  80

Arg Ser Lys Arg Cys Gly Asn Leu Ser Thr Cys Met Leu Gly Thr Tyr
                85                  90                  95

Thr Gln Asp Phe Asn Lys Phe His Thr Phe Pro Gln Thr Ala Ile Gly
            100                 105                 110

Val Gly Ala Pro Gly Lys Lys Arg Asp Met Ser Ser Asp Leu Glu Arg
        115                 120                 125

Asp His Arg Pro His Val Ser Met Pro Gln Asn Ala
    130                 135                 140
```

<210> SEQ ID NO 34
<211> LENGTH: 128
<212> TYPE: PRT
<213> ORGANISM: Homo sapiens

<400> SEQUENCE: 34

```
Met Gly Phe Gln Lys Phe Ser Pro Phe Leu Ala Leu Ser Ile Leu Val
1               5                   10                  15

Leu Leu Gln Ala Gly Ser Leu His Ala Ala Pro Phe Arg Ser Ala Leu
            20                  25                  30

Glu Ser Ser Pro Ala Asp Pro Ala Thr Leu Ser Glu Asp Glu Ala Arg
        35                  40                  45

Leu Leu Leu Ala Ala Leu Val Gln Asp Tyr Val Gln Met Lys Ala Ser
    50                  55                  60

Glu Leu Glu Gln Glu Gln Glu Arg Glu Gly Ser Arg Ile Ile Ala Gln
65                  70                  75                  80

Lys Arg Ala Cys Asp Thr Ala Thr Cys Val Thr His Arg Leu Ala Gly
                85                  90                  95

Leu Leu Ser Arg Ser Gly Gly Val Val Lys Asn Asn Phe Val Pro Thr
            100                 105                 110

Asn Val Gly Ser Lys Ala Phe Gly Arg Arg Arg Arg Asp Leu Gln Ala
        115                 120                 125
```

<210> SEQ ID NO 35
<211> LENGTH: 141
<212> TYPE: PRT
<213> ORGANISM: Homo sapiens

<400> SEQUENCE: 35

```
Met Gly Phe Gln Lys Phe Ser Pro Phe Leu Ala Leu Ser Ile Leu Val
1               5                   10                  15

Leu Leu Gln Ala Gly Ser Leu His Ala Ala Pro Phe Arg Ser Ala Leu
            20                  25                  30

Glu Ser Ser Pro Ala Asp Pro Ala Thr Leu Ser Glu Asp Glu Ala Arg
        35                  40                  45

Leu Leu Leu Ala Ala Leu Val Gln Asp Tyr Val Gln Met Lys Ala Ser
    50                  55                  60

Glu Leu Glu Gln Glu Gln Glu Arg Glu Gly Ser Ser Leu Asp Ser Pro
65                  70                  75                  80

Arg Ser Lys Arg Cys Gly Asn Leu Ser Thr Cys Met Leu Gly Thr Tyr
                85                  90                  95

Thr Gln Asp Phe Asn Lys Phe His Thr Phe Pro Gln Thr Ala Ile Gly
            100                 105                 110

Val Gly Ala Pro Gly Lys Lys Arg Asp Met Ser Ser Asp Leu Glu Arg
        115                 120                 125

Asp His Arg Pro His Val Ser Met Pro Gln Asn Ala Asn
    130                 135                 140
```

<210> SEQ ID NO 36
<211> LENGTH: 116
<212> TYPE: PRT
<213> ORGANISM: Homo sapiens

<400> SEQUENCE: 36

```
Ala Pro Phe Arg Ser Ala Leu Glu Ser Ser Pro Ala Asp Pro Ala Thr
1               5                   10                  15

Leu Ser Glu Asp Glu Ala Arg Leu Leu Leu Ala Ala Leu Val Gln Asp
            20                  25                  30

Tyr Val Gln Met Lys Ala Ser Glu Leu Glu Gln Glu Gln Glu Arg Glu
        35                  40                  45
```

```
Gly Ser Ser Leu Asp Ser Pro Arg Ser Lys Arg Cys Gly Asn Leu Ser
    50                  55                  60

Thr Cys Met Leu Gly Thr Tyr Thr Gln Asp Phe Asn Lys Phe His Thr
65                  70                  75                  80

Phe Pro Gln Thr Ala Ile Gly Val Gly Ala Pro Gly Lys Lys Arg Asp
                85                  90                  95

Met Ser Ser Asp Leu Glu Arg Asp His Arg Pro His Val Ser Met Pro
            100                 105                 110

Gln Asn Ala Asn
        115


<210> SEQ ID NO 37
<211> LENGTH: 187
<212> TYPE: PRT
<213> ORGANISM: Homo sapiens

<400> SEQUENCE: 37

Thr Ser Glu Glu Thr Ile Ser Thr Val Gln Glu Lys Gln Gln Asn Ile
1               5                   10                  15

Ser Pro Leu Val Arg Glu Arg Gly Pro Gln Arg Val Ala Ala His Ile
            20                  25                  30

Thr Gly Thr Arg Gly Arg Ser Asn Thr Leu Ser Ser Pro Asn Ser Lys
        35                  40                  45

Asn Glu Lys Ala Leu Gly Arg Lys Ile Asn Ser Trp Glu Ser Ser Arg
    50                  55                  60

Ser Gly His Ser Phe Leu Ser Asn Leu His Leu Arg Asn Gly Glu Leu
65                  70                  75                  80

Val Ile His Glu Lys Gly Phe Tyr Tyr Ile Tyr Ser Gln Thr Tyr Phe
                85                  90                  95

Arg Phe Gln Glu Glu Ile Lys Glu Asn Thr Lys Asn Asp Lys Gln Met
            100                 105                 110

Val Gln Tyr Ile Tyr Lys Tyr Thr Ser Tyr Pro Asp Pro Ile Leu Leu
        115                 120                 125

Met Lys Ser Ala Arg Asn Ser Cys Trp Ser Lys Asp Ala Glu Tyr Gly
    130                 135                 140

Leu Tyr Ser Ile Tyr Gln Gly Gly Ile Phe Glu Leu Lys Glu Asn Asp
145                 150                 155                 160

Arg Ile Phe Val Ser Val Thr Asn Glu His Leu Ile Asp Met Asp His
                165                 170                 175

Glu Ala Ser Phe Phe Gly Ala Phe Leu Val Gly
            180                 185


<210> SEQ ID NO 38
<211> LENGTH: 168
<212> TYPE: PRT
<213> ORGANISM: Homo sapiens

<400> SEQUENCE: 38

Val Arg Glu Arg Gly Pro Gln Arg Val Ala Ala His Ile Thr Gly Thr
1               5                   10                  15

Arg Gly Arg Ser Asn Thr Leu Ser Ser Pro Asn Ser Lys Asn Glu Lys
            20                  25                  30

Ala Leu Gly Arg Lys Ile Asn Ser Trp Glu Ser Ser Arg Ser Gly His
        35                  40                  45

Ser Phe Leu Ser Asn Leu His Leu Arg Asn Gly Glu Leu Val Ile His
    50                  55                  60
```

```
Glu Lys Gly Phe Tyr Tyr Ile Tyr Ser Gln Thr Tyr Phe Arg Phe Gln
65                  70                  75                  80

Glu Glu Ile Lys Glu Asn Thr Lys Asn Asp Lys Gln Met Val Gln Tyr
                85                  90                  95

Ile Tyr Lys Tyr Thr Ser Tyr Pro Asp Pro Ile Leu Leu Met Lys Ser
            100                 105                 110

Ala Arg Asn Ser Cys Trp Ser Lys Asp Ala Glu Tyr Gly Leu Tyr Ser
        115                 120                 125

Ile Tyr Gln Gly Gly Ile Phe Glu Leu Lys Glu Asn Asp Arg Ile Phe
    130                 135                 140

Val Ser Val Thr Asn Glu His Leu Ile Asp Met Asp His Glu Ala Ser
145                 150                 155                 160

Phe Phe Gly Ala Phe Leu Val Gly
                165


<210> SEQ ID NO 39
<211> LENGTH: 662
<212> TYPE: PRT
<213> ORGANISM: Homo sapiens

<400> SEQUENCE: 39

Met Val Val Ser Glu Val Asp Ile Ala Lys Ala Asp Pro Ala Ala Ala
1               5                   10                  15

Ser His Pro Leu Leu Leu Asn Gly Asp Ala Thr Val Ala Gln Lys Asn
            20                  25                  30

Pro Gly Ser Val Ala Glu Asn Asn Leu Cys Ser Gln Tyr Glu Glu Lys
        35                  40                  45

Val Arg Pro Cys Ile Asp Leu Ile Asp Ser Leu Arg Ala Leu Gly Val
    50                  55                  60

Glu Gln Asp Leu Ala Leu Pro Ala Ile Ala Val Ile Gly Asp Gln Ser
65                  70                  75                  80

Ser Gly Lys Ser Ser Val Leu Glu Ala Leu Ser Gly Val Ala Leu Pro
                85                  90                  95

Arg Gly Ser Gly Ile Val Thr Arg Cys Pro Leu Val Leu Lys Leu Lys
            100                 105                 110

Lys Leu Val Asn Glu Asp Lys Trp Arg Gly Lys Val Ser Tyr Gln Asp
        115                 120                 125

Tyr Glu Ile Glu Ile Ser Asp Ala Ser Glu Val Glu Lys Glu Ile Asn
    130                 135                 140

Lys Ala Gln Asn Ala Ile Ala Gly Glu Gly Met Gly Ile Ser His Glu
145                 150                 155                 160

Leu Ile Thr Leu Glu Ile Ser Ser Arg Asp Val Pro Asp Leu Thr Leu
                165                 170                 175

Ile Asp Leu Pro Gly Ile Thr Arg Val Ala Val Gly Asn Gln Pro Ala
            180                 185                 190

Asp Ile Gly Tyr Lys Ile Lys Thr Leu Ile Lys Lys Tyr Ile Gln Arg
        195                 200                 205

Gln Glu Thr Ile Ser Leu Val Val Val Pro Ser Asn Val Asp Ile Ala
    210                 215                 220

Thr Thr Glu Ala Leu Ser Met Ala Gln Glu Val Asp Pro Glu Gly Asp
225                 230                 235                 240

Arg Thr Ile Gly Ile Leu Thr Lys Pro Asp Leu Val Asp Lys Gly Thr
                245                 250                 255

Glu Asp Lys Val Val Asp Val Val Arg Asn Leu Val Phe His Leu Lys
            260                 265                 270
```

```
Lys Gly Tyr Met Ile Val Lys Cys Arg Gly Gln Gln Glu Ile Gln Asp
        275                 280                 285

Gln Leu Ser Leu Ser Glu Ala Leu Gln Arg Glu Lys Ile Phe Phe Glu
    290                 295                 300

Asn His Pro Tyr Phe Arg Asp Leu Leu Glu Glu Gly Lys Ala Thr Val
305                 310                 315                 320

Pro Cys Leu Ala Glu Lys Leu Thr Ser Glu Leu Ile Thr His Ile Cys
                325                 330                 335

Lys Ser Leu Pro Leu Leu Glu Asn Gln Ile Lys Glu Thr His Gln Arg
            340                 345                 350

Ile Thr Glu Glu Leu Gln Lys Tyr Gly Val Asp Ile Pro Glu Asp Glu
        355                 360                 365

Asn Glu Lys Met Phe Phe Leu Ile Asp Lys Val Asn Ala Phe Asn Gln
    370                 375                 380

Asp Ile Thr Ala Leu Met Gln Gly Glu Glu Thr Val Gly Glu Glu Asp
385                 390                 395                 400

Ile Arg Leu Phe Thr Arg Leu Arg His Glu Phe His Lys Trp Ser Thr
                405                 410                 415

Ile Ile Glu Asn Asn Phe Gln Glu Gly His Lys Ile Leu Ser Arg Lys
            420                 425                 430

Ile Gln Lys Phe Glu Asn Gln Tyr Arg Gly Arg Glu Leu Pro Gly Phe
        435                 440                 445

Val Asn Tyr Arg Thr Phe Glu Thr Ile Val Lys Gln Gln Ile Lys Ala
    450                 455                 460

Leu Glu Glu Pro Ala Val Asp Met Leu His Thr Val Thr Asp Met Val
465                 470                 475                 480

Arg Leu Ala Phe Thr Asp Val Ser Ile Lys Asn Phe Glu Glu Phe Phe
                485                 490                 495

Asn Leu His Arg Thr Ala Lys Ser Lys Ile Glu Asp Ile Arg Ala Glu
            500                 505                 510

Gln Glu Arg Glu Gly Glu Lys Leu Ile Arg Leu His Phe Gln Met Glu
        515                 520                 525

Gln Ile Val Tyr Cys Gln Asp Gln Val Tyr Arg Gly Ala Leu Gln Lys
    530                 535                 540

Val Arg Glu Lys Glu Leu Glu Glu Glu Lys Lys Lys Lys Ser Trp Asp
545                 550                 555                 560

Phe Gly Ala Phe Gln Ser Ser Ser Ala Thr Asp Ser Ser Met Glu Glu
                565                 570                 575

Ile Phe Gln His Leu Met Ala Tyr His Gln Glu Ala Ser Lys Arg Ile
            580                 585                 590

Ser Ser His Ile Pro Leu Ile Ile Gln Phe Phe Met Leu Gln Thr Tyr
        595                 600                 605

Gly Gln Gln Leu Gln Lys Ala Met Leu Gln Leu Leu Gln Asp Lys Asp
    610                 615                 620

Thr Tyr Ser Trp Leu Leu Lys Glu Arg Ser Asp Thr Ser Asp Lys Arg
625                 630                 635                 640

Lys Phe Leu Lys Glu Arg Leu Ala Arg Leu Thr Gln Ala Arg Arg Arg
                645                 650                 655

Leu Ala Gln Phe Pro Gly
            660
```

<210> SEQ ID NO 40
<211> LENGTH: 3444

<212> TYPE: DNA
<213> ORGANISM: Artificial Sequence
<220> FEATURE:
<223> OTHER INFORMATION: An exemplary cDNA sequence of human MX1

<400> SEQUENCE: 40

```
cgagcagaaa tgaaaccgaa actgaattgt ccgggaaatt cgcggtgggg gcggagagcg      60
cagggagaag taagcccagt gcaggatcct gaggcccgtg tttgcaggac cagggccggc     120
cttccgattc cccattcatt ccagaagcac cgaaccacgc tgtgcccgga tcccaagtgc     180
agcggcaccc agcgtgggcc tggggttgcc ggttgacccg gtcctcagcc tggtagcaga     240
ggccaggcca gtgccacaag gcacctaagt ccacctgggc ctggagcagg acaggttgca     300
aaagaaaata tctcgggacc cccaaactcc ttatgctaag ggaaacatcg agcctgggaa     360
ctgagccatc aacgctgcca ttctttttcc caaacagaac cctgttgtca gaggtacacc     420
cagagcaact ccacaccggg tgcatgccac agcaactcca tcttaaatag gagctggtaa     480
aacgaggctg atacctactg ggctgcattc ccagacggca tagcgaggag gtgctgaaga     540
gcgcaggttt ggagaatgat cacctggatt ggaaccatag ctctaccaat atggaaccca     600
gctccttagg cctcggtctt ctcatggaga acatggtgtg ataatcctac tcctctggga     660
gggtggctgt taagccttgg accgcagttg ccggccagga atcccagtgt cacggtggac     720
acgcctccct cgcgcccttg ccgcccacct gctcacccag ctcaggggct ttggaattct     780
gtggccacac tgcgaggaga tcggttctgg gtcggaggct acaggaagac tcccactccc     840
tgaaatctgg agtgaagaac gccgccatcc agccaccatt ccaaggaggt gcaggagaac     900
agctctgtga taccatttaa cttgttgaca ttacttttat ttgaaggaac gtatattaga     960
gcttactttg caaagaagga agatggttgt ttccgaagtg gacatcgcaa aagctgatcc    1020
agctgctgca tcccaccctc tattactgaa tggagatgct actgtggccc agaaaaatcc    1080
aggctcggtg gctgagaaca acctgtgcag ccagtatgag gagaaggtgc gcccctgcat    1140
cgacctcatt gactccctgc gggctctagg tgtggagcag gacctggccc tgccagccat    1200
cgccgtcatc ggggaccaga gctcgggcaa gagctccgtg ttggaggcac tgtcaggagt    1260
tgcccttccc agaggcagcg ggatcgtgac cagatgcccg ctggtgctga aactgaagaa    1320
acttgtgaac gaagataagt ggagaggcaa ggtcagttac caggactacg agattgagat    1380
ttcggatgct tcagaggtag aaaaggaaat taataaagcc cagaatgcca tcgccgggga    1440
aggaatggga atcagtcatg agctaatcac cctggagatc agctcccgag atgtcccgga    1500
tctgactcta atagaccttc ctggcataac cagagtggct gtgggcaatc agcctgctga    1560
cattgggtat aagatcaaga cactcatcaa gaagtacatc cagaggcagg agacaatcag    1620
cctggtggtg gtccccagta atgtggacat cgccaccaca gaggctctca gcatggccca    1680
ggaggtggac cccgagggag acaggaccat cggaatcttg acgaagcctg atctggtgga    1740
caaaggaact gaagacaagg ttgtggacgt ggtgcggaac ctcgtgttcc acctgaagaa    1800
gggttacatg attgtcaagt gccggggcca gcaggagatc caggaccagc tgagcctgtc    1860
cgaagccctg cagagagaga agatcttctt tgagaaccac ccatatttca gggatctgct    1920
ggaggaagga aaggccacgg ttccctgcct ggcagaaaaa cttaccagcg agctcatcac    1980
acatatctgt aaatctctgc ccctgttaga aaatcaaatc aaggagactc accagagaat    2040
aacagaggag ctacaaaagt atggtgtcga cataccggaa gacgaaaatg aaaaaatgtt    2100
cttcctgata gataaagtta atgcctttaa tcaggacatc actgctctca tgcaaggaga    2160
```

```
ggaaactgta ggggaggaag acattcggct gtttaccaga ctccgacacg agttccacaa   2220

atggagtaca ataattgaaa acaattttca agaaggccat aaaattttga gtagaaaaat   2280

ccagaaattt gaaaatcagt atcgtggtag agagctgcca ggctttgtga attacaggac   2340

atttgagaca atcgtgaaac agcaaatcaa ggcactggaa gagccggctg tggatatgct   2400

acacaccgtg acggatatgg tccggcttgc tttcacagat gtttcgataa aaaattttga   2460

agagtttttt aacctccaca gaaccgccaa gtccaaaatt gaagacatta gagcagaaca   2520

agagagagaa ggtgagaagc tgatccgcct ccacttccag atggaacaga ttgtctactg   2580

ccaggaccag gtatacaggg gtgcattgca gaaggtcaga gagaaggagc tggaagaaga   2640

aaagaagaag aaatcctggg attttggggc tttccagtcc agctcggcaa cagactcttc   2700

catggaggag atctttcagc acctgatggc ctatcaccag gaggccagca agcgcatctc   2760

cagccacatc cctttgatca tccagttctt catgctccag acgtacggcc agcagcttca   2820

gaaggccatg ctgcagctcc tgcaggacaa ggacacctac agctggctcc tgaaggagcg   2880

gagcgacacc agcgacaagc ggaagttcct gaaggagcgg cttgcacggc tgacgcaggc   2940

tcggcgccgg cttgcccagt tccccggtta accacactct gtccagcccc gtagacgtgc   3000

acgcacactg tctgccccg ttcccgggta gccactggac tgacgacttg agtgctcagt   3060

agtcagactg gatagtccgt ctctgcttat ccgttagccg tggtgattta gcaggaagct   3120

gtgagagcag tttggtttct agcatgaaga cagagcccca ccctcagatg cacatgagct   3180

ggcgggattg aaggatgctg tcttcgtact gggaaaggga ttttcagccc tcagaatcgc   3240

tccaccttgc agctctcccc ttctctgtat tcctagaaac tgacacatgc tgaacatcac   3300

agcttatttc ctcattttta taatgtccct tcacaaaccc agtgttttag gagcatgagt   3360

gccgtgtgtg tgcgtcctgt cggagccctg tctcctctct ctgtaataaa ctcatttcta   3420

gcagacaaaa aaaaaaaaaa aaaa                                          3444
```

<210> SEQ ID NO 41
<211> LENGTH: 715
<212> TYPE: PRT
<213> ORGANISM: Artificial Sequence
<220> FEATURE:
<223> OTHER INFORMATION: An exemplary amino acid sequences of human MX2

<400> SEQUENCE: 41

```
Met Ser Lys Ala His Lys Pro Trp Pro Tyr Arg Arg Arg Ser Gln Phe
1               5                   10                  15

Ser Ser Arg Lys Tyr Leu Lys Lys Glu Met Asn Ser Phe Gln Gln Gln
            20                  25                  30

Pro Pro Pro Phe Gly Thr Val Pro Pro Gln Met Met Phe Pro Pro Asn
        35                  40                  45

Trp Gln Gly Ala Glu Lys Asp Ala Ala Phe Leu Ala Lys Asp Phe Asn
    50                  55                  60

Phe Leu Thr Leu Asn Asn Gln Pro Pro Pro Gly Asn Arg Ser Gln Pro
65                  70                  75                  80

Arg Ala Met Gly Pro Glu Asn Asn Leu Tyr Ser Gln Tyr Glu Gln Lys
                85                  90                  95

Val Arg Pro Cys Ile Asp Leu Ile Asp Ser Leu Arg Ala Leu Gly Val
            100                 105                 110

Glu Gln Asp Leu Ala Leu Pro Ala Ile Ala Val Ile Gly Asp Gln Ser
        115                 120                 125
```

```
Ser Gly Lys Ser Ser Val Leu Glu Ala Leu Ser Gly Val Ala Leu Pro
    130                 135                 140

Arg Gly Ser Gly Ile Val Thr Arg Cys Pro Leu Val Leu Lys Leu Lys
145                 150                 155                 160

Lys Gln Pro Cys Glu Ala Trp Ala Gly Arg Ile Ser Tyr Arg Asn Thr
                165                 170                 175

Glu Leu Glu Leu Gln Asp Pro Gly Gln Val Glu Lys Glu Ile His Lys
            180                 185                 190

Ala Gln Asn Val Met Ala Gly Asn Gly Arg Gly Ile Ser His Glu Leu
        195                 200                 205

Ile Ser Leu Glu Ile Thr Ser Pro Glu Val Pro Asp Leu Thr Ile Ile
    210                 215                 220

Asp Leu Pro Gly Ile Thr Arg Val Ala Val Asp Asn Gln Pro Arg Asp
225                 230                 235                 240

Ile Gly Leu Gln Ile Lys Ala Leu Ile Lys Lys Tyr Ile Gln Arg Gln
                245                 250                 255

Gln Thr Ile Asn Leu Val Val Val Pro Cys Asn Val Asp Ile Ala Thr
            260                 265                 270

Thr Glu Ala Leu Ser Met Ala His Glu Val Asp Pro Glu Gly Asp Arg
        275                 280                 285

Thr Ile Gly Ile Leu Thr Lys Pro Asp Leu Met Asp Arg Gly Thr Glu
    290                 295                 300

Lys Ser Val Met Asn Val Val Arg Asn Leu Thr Tyr Pro Leu Lys Lys
305                 310                 315                 320

Gly Tyr Met Ile Val Lys Cys Arg Gly Gln Gln Glu Ile Thr Asn Arg
                325                 330                 335

Leu Ser Leu Ala Glu Ala Thr Lys Lys Glu Ile Thr Phe Phe Gln Thr
            340                 345                 350

His Pro Tyr Phe Arg Val Leu Leu Glu Glu Gly Ser Ala Thr Val Pro
        355                 360                 365

Arg Leu Ala Glu Arg Leu Thr Thr Glu Leu Ile Met His Ile Gln Lys
    370                 375                 380

Ser Leu Pro Leu Leu Glu Gly Gln Ile Arg Glu Ser His Gln Lys Ala
385                 390                 395                 400

Thr Glu Glu Leu Arg Arg Cys Gly Ala Asp Ile Pro Ser Gln Glu Ala
                405                 410                 415

Asp Lys Met Phe Phe Leu Ile Glu Lys Ile Lys Met Phe Asn Gln Asp
            420                 425                 430

Ile Glu Lys Leu Val Glu Gly Glu Glu Val Val Arg Glu Asn Glu Thr
        435                 440                 445

Arg Leu Tyr Asn Lys Ile Arg Glu Asp Phe Lys Asn Trp Val Gly Ile
    450                 455                 460

Leu Ala Thr Asn Thr Gln Lys Val Lys Asn Ile Ile His Glu Glu Val
465                 470                 475                 480

Glu Lys Tyr Glu Lys Gln Tyr Arg Gly Lys Glu Leu Leu Gly Phe Val
                485                 490                 495

Asn Tyr Lys Thr Phe Glu Ile Ile Val His Gln Tyr Ile Gln Gln Leu
            500                 505                 510

Val Glu Pro Ala Leu Ser Met Leu Gln Lys Ala Met Glu Ile Ile Gln
        515                 520                 525

Gln Ala Phe Ile Asn Val Ala Lys Lys His Phe Gly Glu Phe Phe Asn
    530                 535                 540
```

-continued

```
Leu Asn Gln Thr Val Gln Ser Thr Ile Glu Asp Ile Lys Val Lys His
545                 550                 555                 560

Thr Ala Lys Ala Glu Asn Met Ile Gln Leu Gln Phe Arg Met Glu Gln
                565                 570                 575

Met Val Phe Cys Gln Asp Gln Ile Tyr Ser Val Val Leu Lys Lys Val
            580                 585                 590

Arg Glu Glu Ile Phe Asn Pro Leu Gly Thr Pro Ser Gln Asn Met Lys
        595                 600                 605

Leu Asn Ser His Phe Pro Ser Asn Glu Ser Ser Val Ser Ser Phe Thr
    610                 615                 620

Glu Ile Gly Ile His Leu Asn Ala Tyr Phe Leu Glu Thr Ser Lys Arg
625                 630                 635                 640

Leu Ala Asn Gln Ile Pro Phe Ile Ile Gln Tyr Phe Met Leu Arg Glu
                645                 650                 655

Asn Gly Asp Ser Leu Gln Lys Ala Met Met Gln Ile Leu Gln Glu Lys
            660                 665                 670

Asn Arg Tyr Ser Trp Leu Leu Gln Glu Gln Ser Glu Thr Ala Thr Lys
        675                 680                 685

Arg Arg Ile Leu Lys Glu Arg Ile Tyr Arg Leu Thr Gln Ala Arg His
    690                 695                 700

Ala Leu Cys Gln Phe Ser Ser Lys Glu Ile His
705                 710                 715


<210> SEQ ID NO 42
<211> LENGTH: 2961
<212> TYPE: DNA
<213> ORGANISM: Artificial Sequence
<220> FEATURE:
<223> OTHER INFORMATION: An exemplary cDNA sequence of human MX2

<400> SEQUENCE: 42

aagagatgat ttctccatcc tgaacgtgca gcgagcttgt caggaagatc ggaggtgcca      60

agtagcagag aaagcatccc ccagctctga cagggagaca gcacatgtct aaggcccaca     120

agccttggcc ctaccggagg agaagtcaat tttcttctcg aaaatacctg aaaaaagaaa     180

tgaattcctt ccagcaacag ccaccgccat tcggcacagt gccaccacaa atgatgtttc     240

ctccaaactg gcaggggca gagaaggacg ctgctttcct cgccaaggac ttcaactttc      300

tcactttgaa caatcagcca ccaccaggaa acaggagcca accaagggca atggggcccg     360

agaacaacct gtacagccag tacgagcaga aggtgcgccc ctgcattgac ctcatcgact     420

ccctgcgggc tctgggtgtg gagcaggacc tggccctgcc agccatcgcc gtcatcgggg     480

accagagctc gggcaagagc tctgtgctgg aggcactgtc aggagtcgcg cttcccagag     540

gcagcggaat cgtaaccagg tgtccgctgg tgctgaaact gaaaaagcag ccctgtgagg     600

catgggccgg aaggatcagc taccggaaca ccgagctaga gcttcaggac cctggccagg     660

tggagaaaga gatacacaaa gcccagaacg tcatggccgg gaatggccgg ggcatcagcc     720

atgagctcat cagcctggag atcacctccc ctgaggttcc agacctgacc atcattgacc     780

ttcccggcat caccagggtg gctgtggaca accagccccg agacatcgga ctgcagatca     840

aggctctcat caagaagtac atccagaggc agcagacgat caacttggtg gtggttccct     900

gtaacgtgga cattgccacc acggaggcgc tgagcatggc ccatgaggtg gacccggaag     960

gggacaggac catcggtatc ctgaccaaac cagatctaat ggacaggggc actgagaaaa    1020

gcgtcatgaa tgtggtgcgg aacctcacgt acccccctcaa gaagggctac atgattgtga   1080
```

-continued

```
agtgccgggg ccagcaggag atcacaaaca ggctgagctt ggcagaggca accaagaaag   1140
aaattacatt ctttcaaaca catccatatt tcagagttct cctggaggag gggtcagcca   1200
cggttccccg actggcagaa agacttacca ctgaactcat catgcatatc caaaaatcgc   1260
tcccgttgtt agaaggacaa ataagggaga gccaccagaa ggcgaccgag gagctgcggc   1320
gttgcggggc tgacatcccc agccaggagg ccgacaagat gttctttcta attgagaaaa   1380
tcaagatgtt taatcaggac atcgaaaagt tagtagaagg agaagaagtt gtaagggaga   1440
atgagacccg tttatacaac aaaatcagag aggattttaa aaactgggta ggcatacttg   1500
caactaatac ccaaaaagtt aaaaatatta tccacgaaga agttgaaaaa tatgaaaagc   1560
agtatcgagg caaggagctt ctgggatttg tcaactacaa gacatttgag atcatcgtgc   1620
atcagtacat ccagcagctg gtggagcccg cccttagcat gctccagaaa gccatggaaa   1680
ttatccagca agctttcatt aacgtggcca aaaaacattt tggcgaattt ttcaacctta   1740
accaaactgt tcagagcacg attgaagaca taaaagtgaa acacacagca aaggcagaaa   1800
acatgatcca acttcagttc agaatggagc agatggtttt ttgtcaagat cagatttaca   1860
gtgttgttct gaagaaagtc cgagaagaga tttttaaccc tctggggacg ccttcacaga   1920
atatgaagtt gaactctcat tttcccagta atgagtcttc ggtttcctcc tttactgaaa   1980
taggcatcca cctgaatgcc tacttcttgg aaaccagcaa acgtctcgcc aaccagatcc   2040
catttataat tcagtatttt atgctccgag agaatggtga ctccttgcag aaagccatga   2100
tgcagatact acaggaaaaa aatcgctatt cctggctgct tcaagagcag agtgagaccg   2160
ctaccaagag aagaatcctt aaggagagaa tttaccggct cactcaggcg cgacacgcac   2220
tctgtcaatt ctccagcaaa gagatccact gaagggcggc gatgcctgtg gttgttttct   2280
tgtgcgtact cattcattct aaggggagtc ggtgcaggat gccgcttctg ctttggggcc   2340
aaactcttct gtcactatca gtgtccatct ctactgtact ccctcagcat cagagcatgc   2400
atcaggggtc cacacaggct cagctctctc caccacccag ctcttccctg accttcacga   2460
agggatggct ctccagtcct tgggtcccgt agcacacagt tacagtgtcc taagatactg   2520
ctatcattct tcgctaattt gtatttgtat tcccttcccc ctacaagatt atgagacccc   2580
agagggggaa ggtctgggtc aaattcttct tttgtatgtc cagtctcctg cacagcacct   2640
gcagcattgt aactgcttaa taaatgacat ctcactgaac gaatgagtgc tgtgtaagtg   2700
atggagatac ctgaggctat tgctcaagcc caggccttgg acatttagtg actgttagcc   2760
ggtccctttc agatccagtg gccatgcccc ctgcttccca tggttcactg tcattgtgtt   2820
tcccagcctc tccactcccc cgccagaaag gagcctgagt gattctcttt tcttcttgtt   2880
tccctgatta tgatgagctt ccattgttct gttaagtctt gaagaggaat ttaataaagc   2940
aaagaaactt tttaaaaacg t                                              2961
```

SYSTEM AND METHOD FOR ANALYSIS OF BIOLOGICAL DATA

RELATED APPLICATIONS

This application is a National Phase of PCT Patent Application No. PCT/IL2017/050886 having International filing date of Aug. 10, 2017, which claims the benefit of priority under 35 USC § 119 (e) of U.S. Provisional Patent Application No. 62/372,820 filed on Aug. 10, 2016. The contents of the above applications are all incorporated by reference as if fully set forth herein in their entirety

SEQUENCE LISTING STATEMENT

The ASCII file, entitled 76015SequenceListing.txt, created on Feb. 10, 2019, comprising 223,597 bytes, submitted concurrently with the filing of this application is incorporated herein by reference. The sequence listing submitted herewith is identical to the sequence listing forming part of the international application.

FIELD AND BACKGROUND OF THE INVENTION

The present invention, in some embodiments thereof, relates to computational analysis, and, more particularly, but not exclusively, to computational analysis of biological data, e.g., for the purpose of distinguishing between bacterial infection and non-bacterial disease, and/or between a bacterial infection and viral infection, and/or between an infectious and non-infectious disease.

Antibiotics (Abx) are the world's most prescribed class of drugs with a 25-30 billion $US global market. Abx are also the world's most misused drug with a significant fraction of all drugs (40-70%) being wrongly prescribed (Linder, J. A. and R. S. Stafford 2001; Scott, J. G. and D. Cohen, et al. 2001; Davey, P. and E. Brown, et al. 2006; Cadieux, G. and R. Tamblyn, et al. 2007; Pulcini, C. and E. Cua, et al. 2007), ("CDC—Get Smart: Fast Facts About Antibiotic Resistance" 2011).

One type of Abx misuse is when the drug is administered in case of a non-bacterial disease, such as a viral infection, for which Abx is ineffective. For example, according to the USA center for disease control and prevention CDC, over 60 Million wrong Abx prescriptions are given annually to treat flu in the US. The health-care and economic consequences of the Abx over-prescription include: (i) the cost of antibiotics that are unnecessarily prescribed globally, estimated at >$10 billion annually; (ii) side effects resulting from unnecessary Abx treatment are reducing quality of healthcare, causing complications and prolonged hospitalization (e.g. allergic reactions, Abx associated diarrhea, intestinal yeast etc.) and (iii) the emergence of resistant strains of bacteria as a result of the overuse (the CDC has declared the rise in antibiotic resistance of bacteria as "one of the world's most pressing health problems in the 21$^{st}$ century" (Arias, C. A. and B. E. Murray 2009; "CDC—About Antimicrobial Resistance" 2011).

Antibiotics under-prescription is not uncommon either. For example up to 15% of adult bacterial pneumonia hospitalized patients in the US receive delayed or no Abx treatment, even though in these instances early treatment can save lives and reduce complications (Houck, P. M. and D. W. Bratzler, et al. 2002).

Technologies for infectious disease diagnosis have the potential to reduce the associated health and financial burden associated with Abx misuse. Ideally, such a technology should: (i) accurately differentiate between a bacterial and viral infections; (ii) be rapid (within minutes); (iii) be able to differentiate between pathogenic and non-pathogenic bacteria that are part of the body's natural flora; (iv) differentiate between mixed co-infections and pure viral infections and (v) be applicable in cases where the pathogen is inaccessible (e.g. sinusitis, pneumonia, otitis-media, bronchitis, etc).

WO 2013/117746 teaches signatures and determinants for distinguishing between a bacterial and viral infection.

WO2016/024278 teaches a method of analyzing biological data containing expression values of polypeptides in the blood of a subject. The method is based on the calculation of a distance between a segment of a curved line and an axis. The distance is calculated at a point over the curved line defined by a coordinate. The distance is correlated to the presence of, absence of, or likelihood that the subject has a bacterial infection.

SUMMARY OF THE INVENTION

According to some embodiments of the invention the present invention there is provided a method of analyzing biological data. The method comprises: obtaining biological data containing at least an expression level of MX dynamin-like GTPase 1 (MX1) and an expression level of C-reactive protein (CRP) in the blood of a subject; and calculating a distance between a segment of a curved line and an axis defined by a direction, wherein the distance is calculated at a point over the curved line defined by a coordinate δ along the direction. The method also comprises correlating the distance to the presence of, absence of, or likelihood that the subject has, a bacterial infection. In some embodiments, at least 90% of the segment is between a lower bound line $f(\delta)-\varepsilon_0$ and an upper bound line $f(\delta)+\varepsilon_1$, wherein $f(\delta)$ equals $1/(1+\exp(-\delta))$, wherein the coordinate δ, once calculated, equals $a_0+a_1X+a_2Z_{MX1}$, wherein X is a value of the CRP in μg/ml, and $Z_{MX1}$ is a z-score of the MX1 relative to a group of subjects previously diagnosed with a bacterial infection, wherein each of $\varepsilon_0$ and $\varepsilon_1$ is less than 0.5, and wherein $a_0$ is from about −2.4 to about −1.9, $a_1$ is from about 0.04 to about 0.05, and $a_2$ is from about −0.39 to about −0.43.

According to an aspect of some embodiments of the present invention there is provided a method of analyzing biological data. The method comprises: obtaining biological data containing at least an expression level of MX dynamin-like GTPase 1 (MX1) and an expression level of C-reactive protein (CRP) in the blood of a subject; and calculating a distance between a segment of a curved line and an axis defined by a direction, wherein the distance is calculated at a point over the curved line defined by a coordinate δ along the direction. The method also comprises correlating the distance to the presence of, absence of, or likelihood that the subject has, a bacterial infection. In some embodiments, at least 90% of the segment is between a lower bound line $f(\delta)-\varepsilon_0$ and an upper bound line $f(\delta)+\varepsilon_1$, wherein $f(\delta)$ equals $1/(1+\exp(-\delta))$, wherein the coordinate δ, once calculated, equals $a_0+a_1X+a_2Y$, wherein the X is a value of the CRP in μg/ml, and the Y is a value of the MX1 in ng/ml, wherein each of $\varepsilon_0$ and $\varepsilon_1$ is less than 0.5, and wherein $a_0$ is from about 0.4 to about 0.5, $a_1$ is from about 0.015 to about 0.02, and $a_2$ is from about −0.0025 to about −0.0018.

According to an aspect of some embodiments of the present invention there is provided a method of analyzing biological data. The method comprises: obtaining biological data containing at least an expression level of MX dynamin-like GTPase 1 (MX1) and an expression level of C-reactive protein (CRP) in the blood of a subject; and calculating a distance between a segment of a curved line and an axis defined by a direction, wherein the distance is calculated at a point over the curved line defined by a coordinate $\delta$ along the direction. The method also comprises correlating the distance to the presence of, absence of, or likelihood that the subject has, a bacterial infection. In some embodiments, at least 90% of the segment is between a lower bound line $f(\delta)-\varepsilon_0$ and an upper bound line $f(\delta)+\varepsilon_1$, wherein $f(\delta)$ equals $1/(1+\exp(-\delta))$, wherein the coordinate $\delta$, once calculated, equals $a_0+a_1X+a_2Y$, wherein the X is a value of the CRP in μg/ml, and the Y is a value of the MX1 when measured by flow cytometery, wherein each of $\varepsilon_0$ and $\varepsilon_1$ is less than 0.5, and wherein $a_0$ is from about −1.7 to about −1.4, $a_1$ is from about 0.03 to about 0.05, and $a_2$ is from about −5.8E-05 to about −4.7E-05.

According to some embodiments of the invention at least one of the MX1 and the CRP is measured by an immunoassay.

According to some embodiments of the invention at least one of the MX1 and CRP is measured by flow cytometry.

According to some embodiments of the invention at least one of the MX1 and CRP is measured by lateral flow immunoassay (LFIA).

According to some embodiments of the invention at least one of the MX1 and CRP is measured by automated immunoassay.

According to some embodiments of the invention at least one of the MX1 and CRP is measured by enzyme-linked immunosorbent assay (ELISA).

According to some embodiments of the invention the method is executed for distinguishing between a viral infection and a co-infection including both bacterial and viral infections.

According to some embodiments of the invention the subject has a lower respiratory tract infection.

According to some embodiments of the invention the subject has an upper respiratory tract infection.

According to some embodiments of the invention the subject has a fever without identifiable source.

According to some embodiments of the invention the subject has a serious bacterial infection.

According to some embodiments of the invention the subject is suspected as having Adenovirus.

According to some embodiments of the invention the subject is suspected as having Coronavirus.

According to some embodiments of the invention the subject is suspected as having Parainfluenza virus.

According to some embodiments of the invention the subject is suspected as having Influenza A.

According to some embodiments of the invention the subject is suspected as having Influenza B.

According to some embodiments of the invention the subject is suspected as having respiratory syncytial virus A or B.

According to some embodiments of the invention the subject is suspected as having Bocavirus.

According to some embodiments of the invention the subject is suspected as having Enterovirus.

According to some embodiments of the invention the subject is suspected as having CMV/EBV.

According to some embodiments of the invention the subject is suspected as having *Mycoplasma pneumoniae.*

According to some embodiments of the invention the subject is suspected as having *E. coli.*

According to some embodiments of the invention the subject is suspected as having Group A Strep.

According to some embodiments of the invention the subject is suspected as having GI virus selected from the group consisting of Rota Virus, Astrovirus, Enteric Adenovirus, Norovirus G I and G II.

According to some embodiments of the invention the subject is suspected as having *Streptococcus pneumoniae.*

According to some embodiments of the invention the subject is suspected as having *Staphylococcus aureus.*

According to some embodiments of the invention the subject is suspected as having a lung disease.

According to an aspect of some embodiments of the present invention there is provided a method of analyzing biological data. The method comprises: obtaining biological data containing at least an expression level of MX dynamin-like GTPase 1 (MX1) and an expression level of C-reactive protein (CRP) in the blood of a subject; obtaining a background condition of the subject; and calculating a distance between a segment of a curved line and an axis defined by a direction, wherein the distance is calculated at a point over the curved line defined by a coordinate $\delta$ along the direction. The method also comprises correlating the distance to the presence of, absence of, or likelihood that the subject has, a bacterial infection. In some embodiments, at least 90% of the segment is between a lower bound line $f(\delta)-\varepsilon_0$ and an upper bound line $f(\delta)+\varepsilon_1$, wherein $f(\delta)$ equals $1/(1+\exp(-\delta))$, wherein the coordinate $\delta$, once calculated, equals $a_0+a_1X+a_2Y$, wherein the X is a value of the CRP in μg/ml, and the Y is a value of the MX1 when measured by flow cytometery, wherein each of $\varepsilon_0$ and $\varepsilon_1$ is less than 0.5, and wherein: when the background condition is low respiratory tract infection, then $a_0$ is from about −4.235 to about −3.500, $a_1$ is from about 0.091 to about 0.110, and $a_2$ is from about −2.04E-05 to about −1.68E-05; when the background condition is upper respiratory tract infection, then $a_0$ is from about −1.166 to about −0.964, $a_1$ is from about 0.036 to about 0.044, and $a_2$ is from about −1.45E-04 to about −1.20E-04; when the background condition is Fever Without Source, then $a_0$ is from about −5.819 to about −4.809, $a_1$ is from about 0.055 to about 0.066, and $a_2$ is from about −1.53E-07 to about −1.26E-07; when the background condition is serious bacterial infection, then $a_0$ is from about −1.144 to about −0.945, $a_1$ is from about 0.045 to about 0.055, and $a_2$ is from about −7.67E-05 to about −6.34E-05; when the background condition is Adenovirus, then $a_0$ is from about −0.011 to about −0.009, $a_1$ is from about 0.027 to about 0.033, and $a_2$ is from about −5.83E-05 to about −4.82E-05; when the background condition is Coronavirus, then $a_0$ is from about 1.727 to about 2.090, $a_1$ is from about 0.036 to about 0.044, and $a_2$ is from about −1.04E-04 to about −8.55E-05; when the background condition is Parainfluenza virus, then $a_0$ is from about −0.704 to about −0.582, $a_1$ is from about 0.064 to about 0.077, and $a_2$ is from about −7.33E-05 to about −6.05E-05; when the background condition is Influenza A, then $a_0$ is from about −3.586 to about −2.964, $a_1$ is from about 0.145 to about 0.176, and $a_2$ is from about −5.12E-05 to about −4.23E-05; when the background condition is Influenza B, then $a_0$ is from about 56.618 to about 68.508, $a_1$ is from about 4.255 to about 5.148, and $a_2$ is from about −8.75E-03 to about −7.23E-03; when the background condition is Respiratory syncytial virus A or B, then $a_0$ is from about −1.958 to about −1.618, $a_1$ is from about 0.118 to about 0.143, and $a_2$ is from about −1.20E-04 to about −9.93E-05; when the background condition is Bocavirus 1, 2, 3 or 4, then $a_0$ is from about −2.299 to about −1.900, $a_1$ is from about 0.073 to about 0.088, and $a_2$ is from about 5.50E-05 to about 6.66E-05; when the background condition is Enterovirus, then $a_0$ is from about 1.382 to about 1.672, $a_1$ is from about 0.064 to about 0.077, and $a_2$ is from about −1.59E-04 to about −1.31E-04; when the background condition is CMV/EBV, then $a_0$ is from about 0.609 to about 0.737, $a_1$ is from about 0.036 to about 0.044, and $a_2$ is from about −6.82E-06 to about −5.64E-06; when the background condition is Atypical bacteria selected from the group consisting of *Chlamydophila pneumoniae, Mycoplasma pneumoniae* and *Legionella pneumophila*, then $a_0$ is from about −2.970 to about −2.455, $a_1$ is from about 0.027 to about 0.033, and $a_2$ is from about −8.99E-05 to about −7.43E-05; when the background condition is *E. coli*, then $a_0$ is from about −0.385 to about −0.318, $a_1$ is from about 0.082 to about 0.099, and $a_2$ is from about −6.52E-04 to about −5.39E-04; when the background condition is Group A Strep, then $a_0$ is from about −3.080 to about −2.545, $a_1$ is from about 0.036 to about 0.044, and $a_2$ is from about −1.93E-04 to about −1.60E-04; when the background condition is GI virus selected from the group consisting of Rota Virus, Astrovirus, Enteric Adenovirus, Norovirus G I and G II, then $a_0$ is from about −0.924 to about −0.764, $a_1$ is from about 0.045 to about 0.055, and $a_2$ is from about 3.20E-05 to about 3.87E-05; when the background condition is diabetes, then $a_0$ is from about −1.628 to about −1.345, $a_1$ is from about 0.055 to about 0.066, and $a_2$ is from about −3.11E-05 to about −2.57E-05; when the background condition is a lung disease, then $a_0$ is from about −68.750 to about −56.818, $a_1$ is from about 5.445 to about 6.589, and $a_2$ is from about −1.30E-02 to about −1.07E-02.

According to an aspect of some embodiments of the present invention there is provided a method of analyzing biological data. The method comprises: obtaining biological data containing at least an expression level of MX dynamin-like GTPase 1 (MX1) and an expression level of C-reactive protein (CRP) in the blood of a subject; and calculating a distance between a segment of a curved line and an axis defined by a direction, wherein the distance is calculated at a point over the curved line defined by a coordinate δ along the direction. The method also comprises correlating the distance to the presence of, absence of, or likelihood that the subject has, an infection. In some embodiments, at least 90% of the segment is between a lower bound line $f(\delta)-\varepsilon_0$ and an upper bound line $f(\delta)+\varepsilon_1$, wherein $f(\delta)$ equals $1/(1+\exp(-\delta))$, wherein the coordinate δ, once calculated, equals $a_0+a_1X+a_2Y$, wherein the X is a value of the CRP in μg/ml, and the Y is a value of the MX1 when measured by flow cytometery, wherein each of $\varepsilon_0$ and $\varepsilon_1$ is less than 0.5, and wherein $a_0$ is from about −3 to about −2.4, $a_1$ is from about 0.16 to about 0.2, and $a_2$ is from about 0.0002 to about 0.0003.

According to an aspect of some embodiments of the present invention there is provided a method of analyzing biological data. The method comprises: obtaining biological data containing at least an expression level of MX dynamin-like GTPase 1 (MX1) and an expression level of Radical S-adenosyl methionine domain containing 2 (RSAD2) in the blood of a subject; and calculating a distance between a segment of a curved line and an axis defined by a direction, wherein the distance is calculated at a point over the curved line defined by a coordinate δ along the direction. The method also comprises correlating the distance to the presence of, absence of, or likelihood that the subject has, a bacterial infection. In some embodiments, at least 90% of the segment is between a lower bound line $f(\delta)-\varepsilon_0$ and an upper bound line $f(\delta)+\varepsilon_1$, wherein $f(\delta)$ equals $1/(1+\exp(-\delta))$, wherein the coordinate δ, once calculated, equals $a_0+a_1X+a_2Y$, wherein the X is a value of the RSAD2, when measured by flow cytometry, and the Y is a value of the MX1 when measured by flow cytometery, wherein each of $\varepsilon_0$ and $\varepsilon_1$ is less than 0.5, and wherein $a_0$ is from about 0.6 to about 0.75, $a_1$ is from about −0.00015 to about −0.00009, and $a_2$ is from about 5.2E-06 to about 6E-06.

According to an aspect of some embodiments of the present invention there is provided a method of analyzing biological data. The method comprises: obtaining biological data containing at least an expression level of MX dynamin-like GTPase 1 (MX1) and an expression level of TNF Related Apoptosis Inducing Ligand (TRAIL) in the blood of a subject; and calculating a distance between a segment of a curved line and an axis defined by a direction, wherein the distance is calculated at a point over the curved line defined by a coordinate δ along the direction. The method also comprises correlating the distance to the presence of, absence of, or likelihood that the subject has, a bacterial infection. In some embodiments, at least 90% of the segment is between a lower bound line $f(\delta)-\varepsilon_0$ and an upper bound line $f(\delta)+\varepsilon_1$, wherein $f(\delta)$ equals $1/(1+\exp(-\delta))$, wherein the coordinate δ, once calculated, equals $a_0+a_1X+a_2Y$, wherein the X is a value of the TRAIL in pg/ml, and the Y is a value of the MX1 when measured by flow cytometery, wherein each of $\varepsilon_0$ and $\varepsilon_1$ is less than 0.5, and wherein $a_0$ is from about 2.4 to about 3, $a_1$ is from about −0.055 to about −0.045, and $a_2$ is from about 2.4E-05 to about 2.5E-05.

According to some embodiments of the invention the method comprises obtaining an expression level of Neutrophil gelatinase-associated lipocalin (NGAL), wherein the likelihood is based also on the expression level of the NGAL.

According to some embodiments of the invention the method comprises obtaining an expression level of procalcitonin (PCT), wherein the likelihood is based also on the expression level of the PCT.

According to an aspect of some embodiments of the present invention there is provided a method of analyzing biological data. The method comprises: obtaining biological data containing at least an expression level of MX dynamin-like GTPase 1 (MX1) and an expression level of Neutrophil gelatinase-associated lipocalin (NGAL) in the blood of a subject; and calculating a distance between a segment of a curved line and an axis defined by a direction, wherein the distance is calculated at a point over the curved line defined by a coordinate δ along the direction. The method also comprises correlating the distance to the presence of, absence of, or likelihood that the subject has, a bacterial infection. In some embodiments, at least 90% of the segment is between a lower bound line $f(\delta)-\varepsilon_0$ and an upper bound line $f(\delta)+\varepsilon_1$, wherein $f(\delta)$ equals $1/(1+\exp(-\delta))$, wherein the coordinate δ, once calculated, equals $a_0+a_1X+a_2 Z_{MX1}$, wherein the X is a value of the NGAL, and the $Z_{MX1}$ is a z-score of the MX1 relative to a group of subjects previously diagnosed with a bacterial infection, wherein each of the $\varepsilon_0$ and the $\varepsilon_1$ is less than 0.5.

According to an aspect of some embodiments of the present invention there is provided a method of analyzing biological data. The method comprises: obtaining biological data containing at least an expression level of MX dynamin-like GTPase 1 (MX1) and an expression level of procalcitonin (PCT) in the blood of a subject; and calculating a distance between a segment of a curved line and an axis defined by a direction, wherein the distance is calculated at a point over the curved line defined by a coordinate δ along the direction. The method also comprises correlating the distance to the presence of, absence of, or likelihood that the subject has, a bacterial infection. In some embodiments, at least 90% of the segment is between a lower bound line $f(\delta)-\varepsilon_0$ and an upper bound line $f(\delta)+\varepsilon_1$, wherein $f(\delta)$ equals $1/(1+\exp(-\delta))$, wherein the coordinate $\delta$, once calculated, equals $a_0+a_1X+a_2 Z_{MX1}$, wherein the X is a value of the PCT, and the $Z_{MX1}$ is a z-score of the MX1 relative to a group of subjects previously diagnosed with a bacterial infection, wherein each of the $\varepsilon_0$ and the $\varepsilon_1$ is less than 0.5.

According to some embodiments of the invention the method further comprises determining whether said subject has Sepsis based on said expression levels.

According to some embodiments of the invention the subject has Chronic Obstructive Pulmonary Disease (COPD) and the method comprises determining whether said subject is in an infectious exacerbation state or a non-infectious exacerbation state.

According to some embodiments of the invention the method comprises obtaining an age of the subject, and correcting the likelihood based on the age.

According to some embodiments of the invention the expression level is a protein expression level.

According to some embodiments of the invention the expression level is an RNA expression level.

According to an aspect of some embodiments of the present invention there is provided a method of analyzing biological data. The method comprises: obtaining biological data containing at least an expression level of MX dynamin-like GTPase 2 (MX2) and an expression level of C-reactive protein (CRP) in the blood of a subject; and calculating a distance between a segment of a curved line and an axis defined by a direction, wherein the distance is calculated at a point over the curved line defined by a coordinate $\delta$ along the direction. The method also comprises correlating the distance to the presence of, absence of, or likelihood that the subject has, a bacterial infection. In some embodiments, at least 90% of the segment is between a lower bound line $f(\delta)-\varepsilon_0$ and an upper bound line $f(\delta)+\varepsilon_1$, wherein $f(\delta)$ equals $1/(1+\exp(-\delta))$, wherein the coordinate $\delta$, once calculated, equals $a_0+a_1X+a_2Z_{MX2}$, wherein the X is a value of the CRP in µg/ml, and the $Z_{MX2}$ is a z-score of the MX2 relative to a group of subjects previously diagnosed with a bacterial infection, wherein each of $\varepsilon_0$ and $\varepsilon_1$ is less than 0.5, and wherein $a_0$ is from about −2.4 to about −1.9, $a_1$ is from about 0.04 to about 0.05, and $a_2$ is from about −0.39 to about −0.43.

According to some embodiments of the invention the method comprises obtaining the likelihood based on the distance, comparing the likelihood to a predetermined threshold, and prescribing treatment to the subject based on the comparison.

According to some embodiments of the invention the method comprises obtaining the likelihood based on the distance, comparing the likelihood to a predetermined threshold, and, treating the subject for the bacterial infection when the likelihood is above the predetermined threshold.

According to some embodiments of the invention the method comprises generating an output of the likelihood, the output is presented as text.

According to some embodiments of the invention the method comprises generating an output of the likelihood, the output is presented graphically.

According to some embodiments of the invention the method comprises generating an output of the likelihood, the output is presented using a color index.

According to some embodiments of the invention the blood sample is whole blood.

According to some embodiments of the invention the blood sample is a fraction of whole blood.

According to some embodiments of the invention the blood fraction comprises serum or plasma.

According to some embodiments of the invention the calculating and the correlating is executed by a computer remote from the subject.

According to some embodiments of the invention the calculating and the correlating is executed by a computer near the subject.

According to some embodiments of the invention the calculating and the correlating is executed by a cloud computing resource of a cloud computing facility.

According to an aspect of some embodiments of the present invention the obtaining biological data comprises loading a blood sample of the subject onto a cartridge containing reagents for detecting CRP and MX1 in the blood sample, loading the cartridge to a system configured for measuring the expression levels from the cartridge, and receiving the expression levels from the system.

According to an aspect of some embodiments of the present invention there is provided a computer software product, comprising a computer-readable medium in which program instructions are stored, which instructions, when read by a hardware processor, cause the hardware processor to receive expression levels of a plurality of polypeptides in the blood of a subject who has an unknown disease, and to execute the method as delineated above optionally and preferably as further exemplified below.

According to an aspect of some embodiments of the present invention there is provided a system for analyzing a blood sample. The system comprises a cartridge holder configured to receive a cartridge containing the blood sample and reagents for detecting CRP and MX1 in the blood sample, a measuring system configured to automatically measure protein expression levels from the cartridge, once loaded, and a computer system configured to automatically receive the measured expression values from the measuring system and execute the method as delineated above optionally and preferably as further exemplified below.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 12A-D are schematic illustrations of a procedure for obtaining a smooth version of a segment of a curved object, according to some embodiments of the present invention;

DETAILED DESCRIPTION OF SPECIFIC EMBODIMENTS OF THE INVENTION

Figure 1:
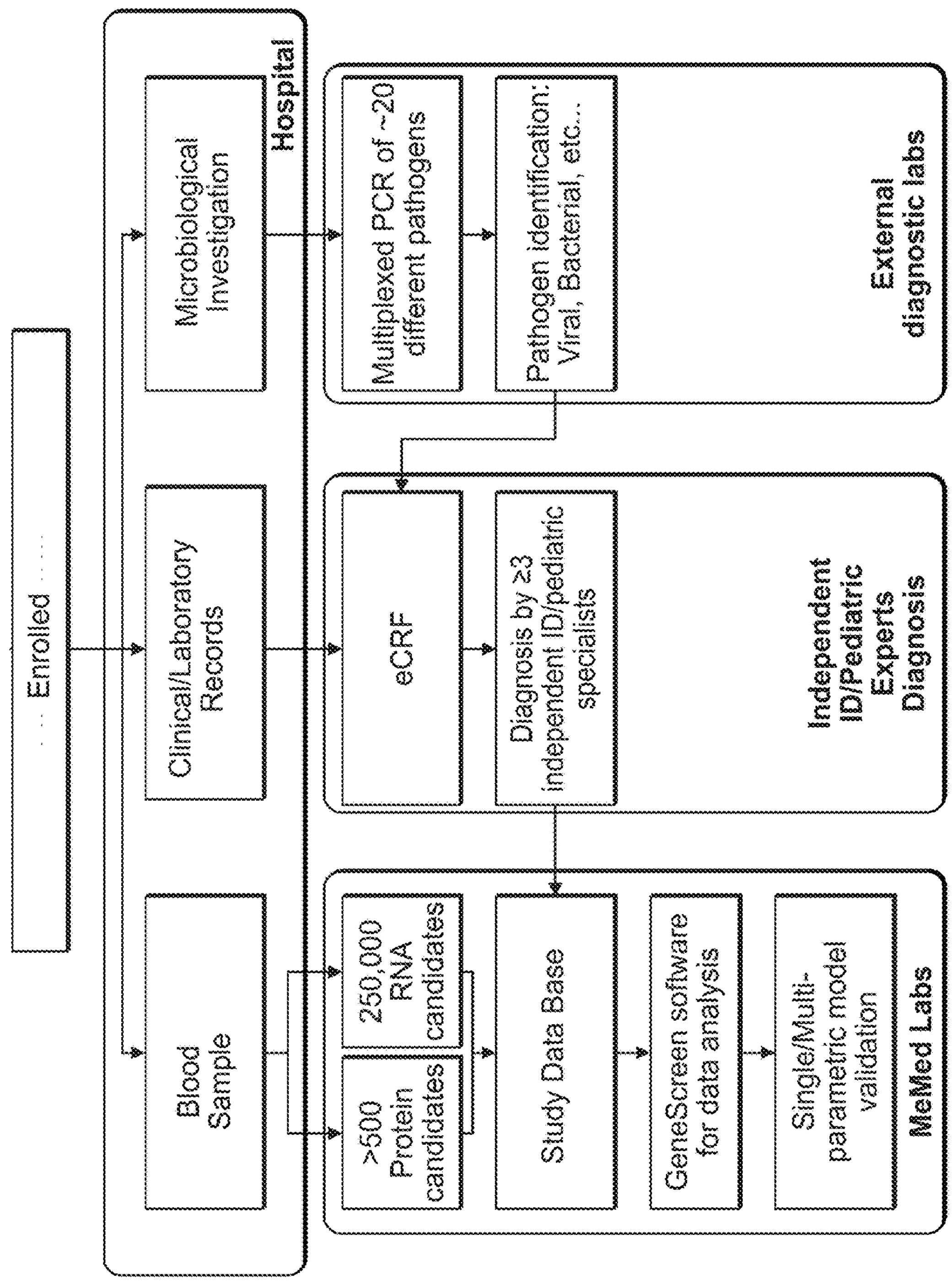
FIG. 1 is a diagram describing a workflow of a clinical study performed according to some embodiments of the present invention.
Figures 2A, 2B:
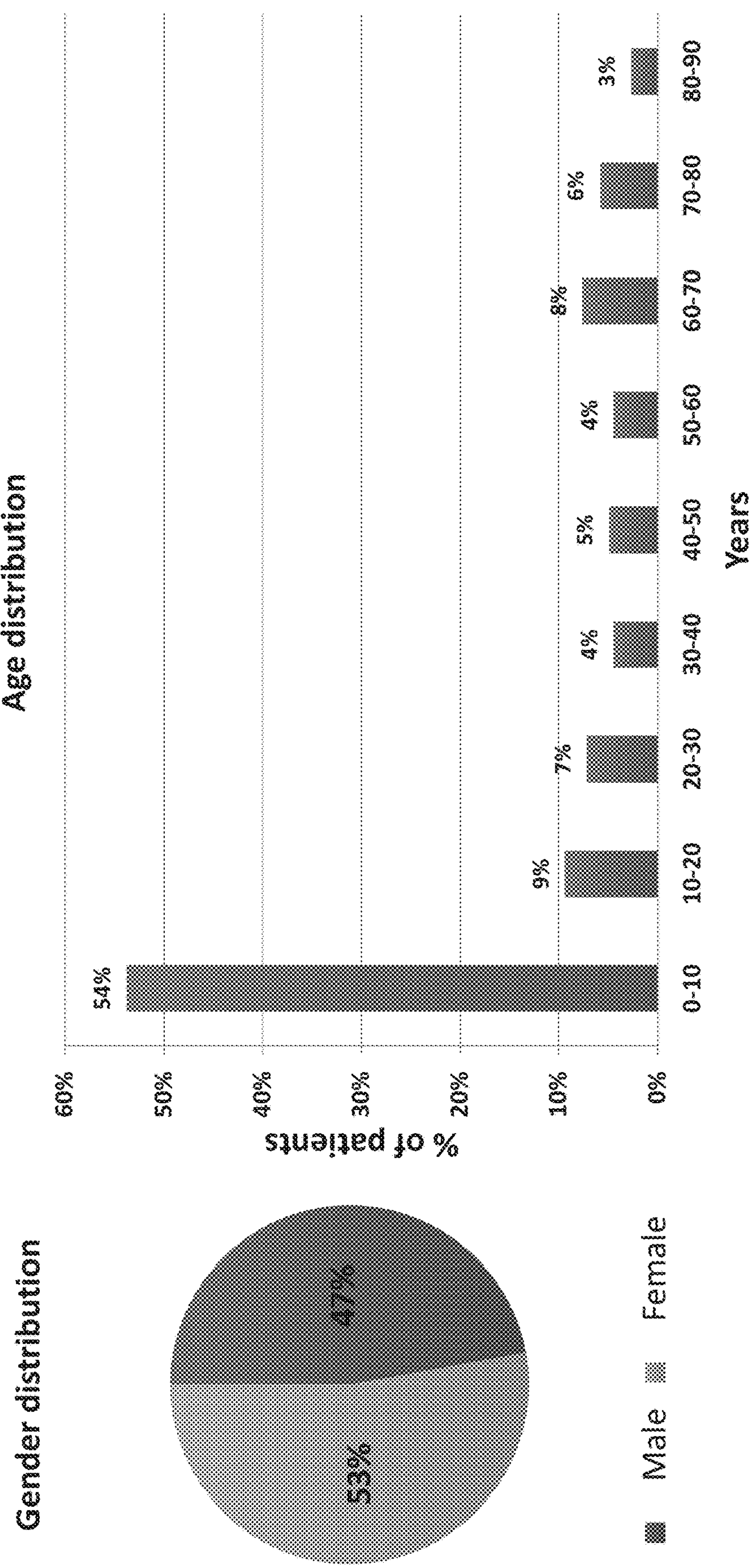
FIGS. 2A and 2B show distribution of gender (FIG. 2A) and age (FIG. 2B) of infectious disease patients enrolled in the clinical study (N=224)
Figure 3:
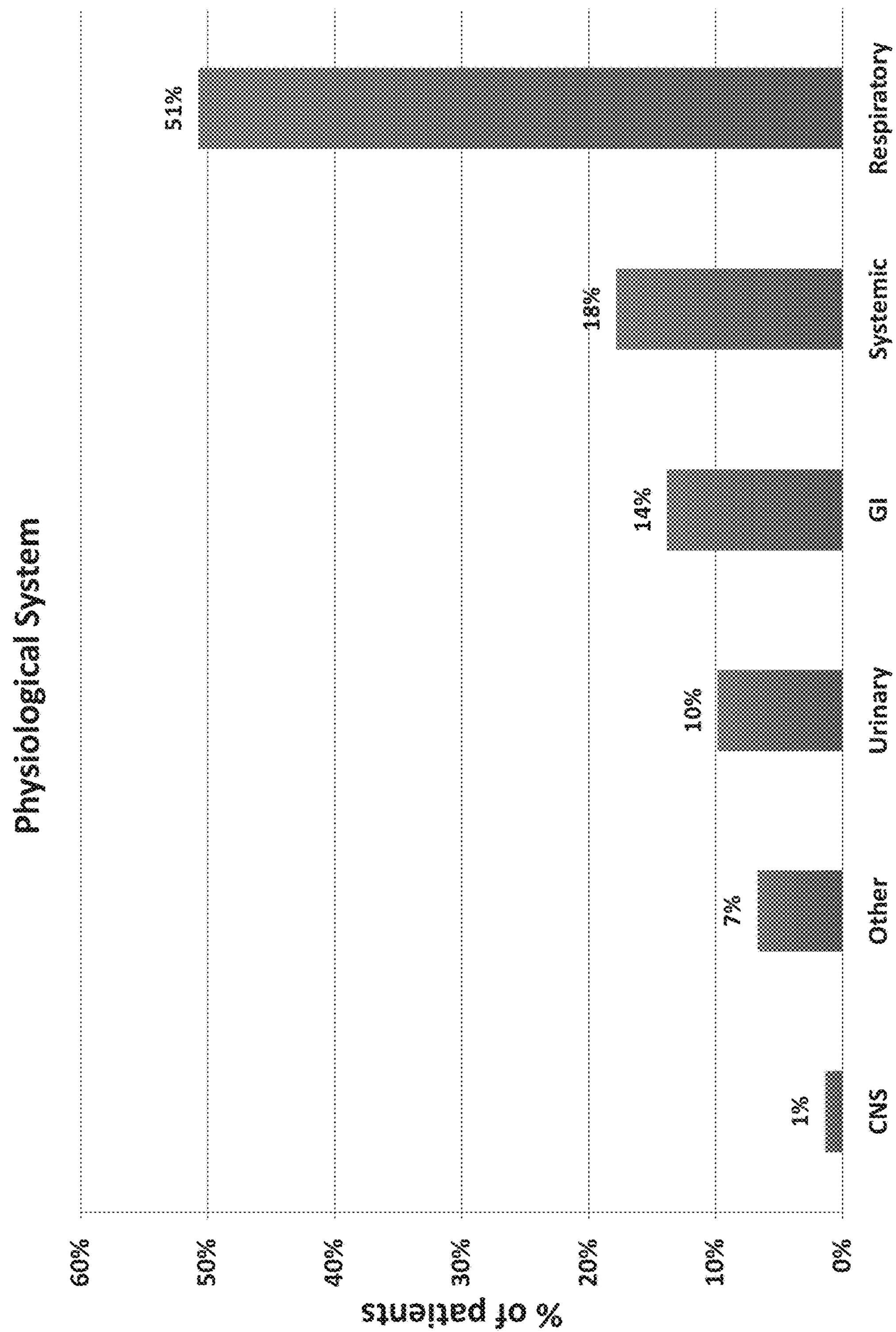
FIG. 3 shows distribution of physiological systems of the infectious disease patients enrolled in the clinical study.
Figure 4:
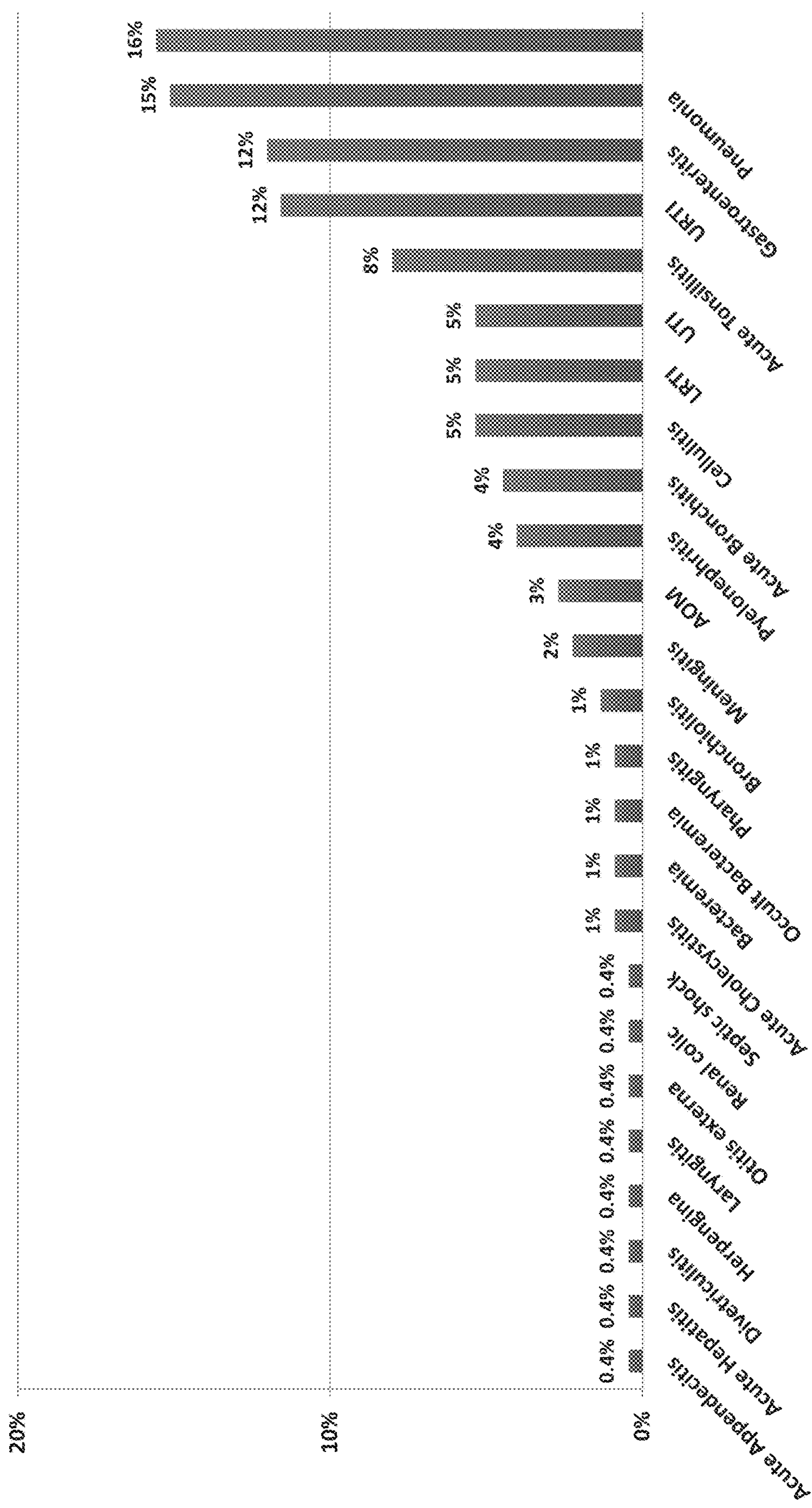
FIG. 4 shows distribution of major clinical syndromes of the infectious disease patients enrolled in the clinical study.
Figure 5:
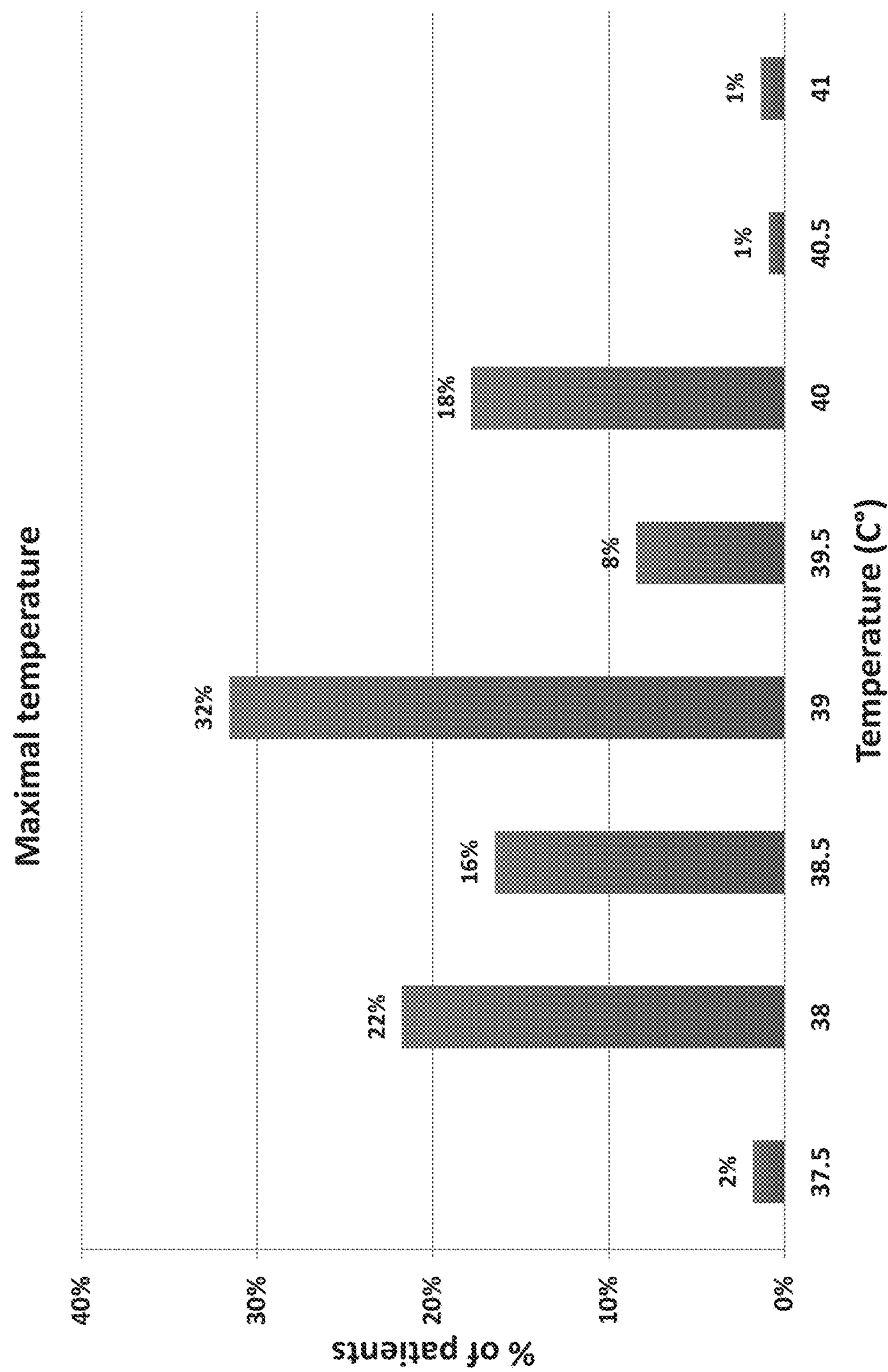
FIG. 5 shows distribution of maximal body temperature of the infectious disease patients enrolled in the clinical study.
Figure 6:
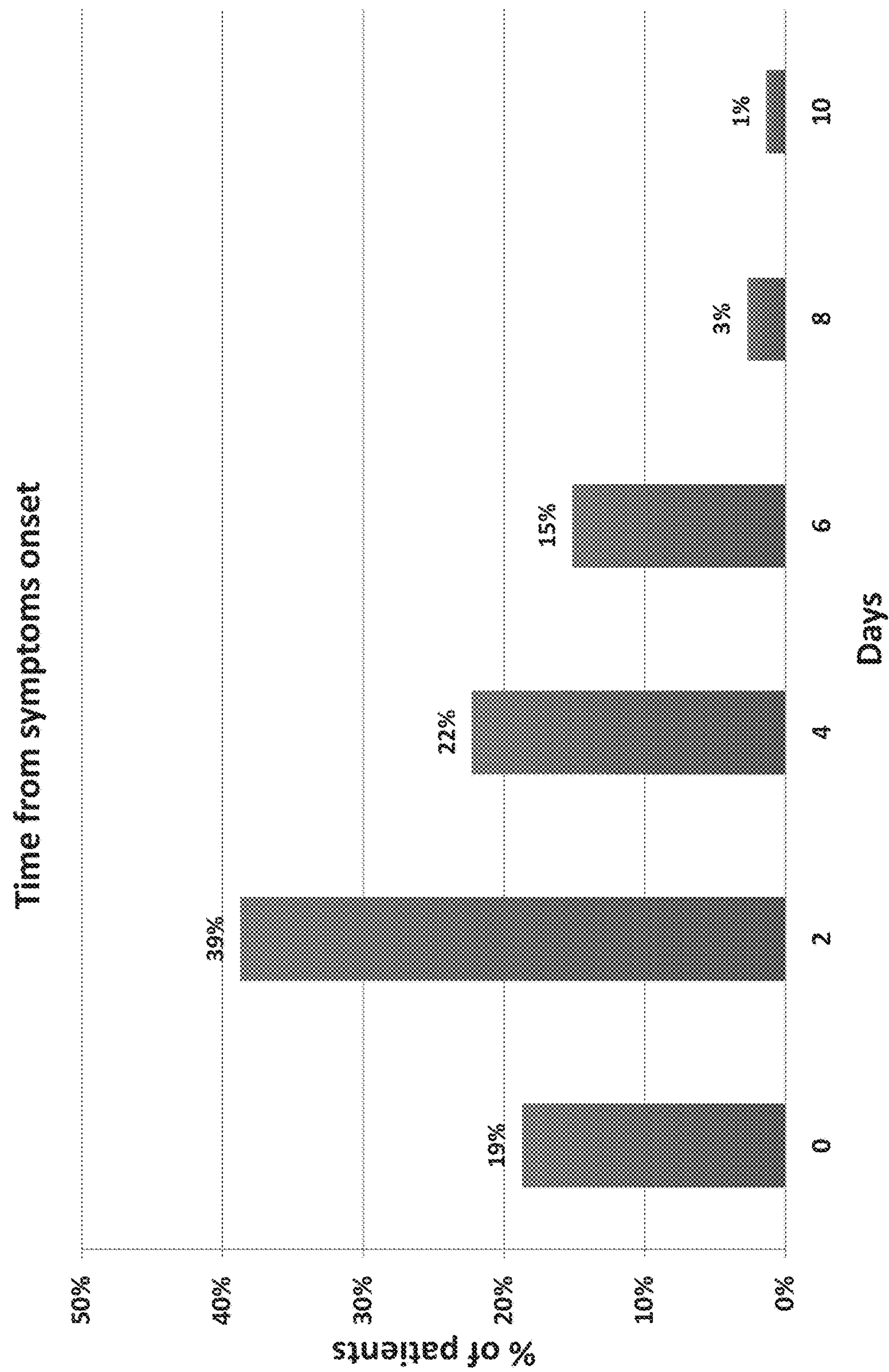
FIG. 6 shows distribution of time from initiation of symptoms of the infectious disease patients enrolled in the clinical study.
Figure 7:
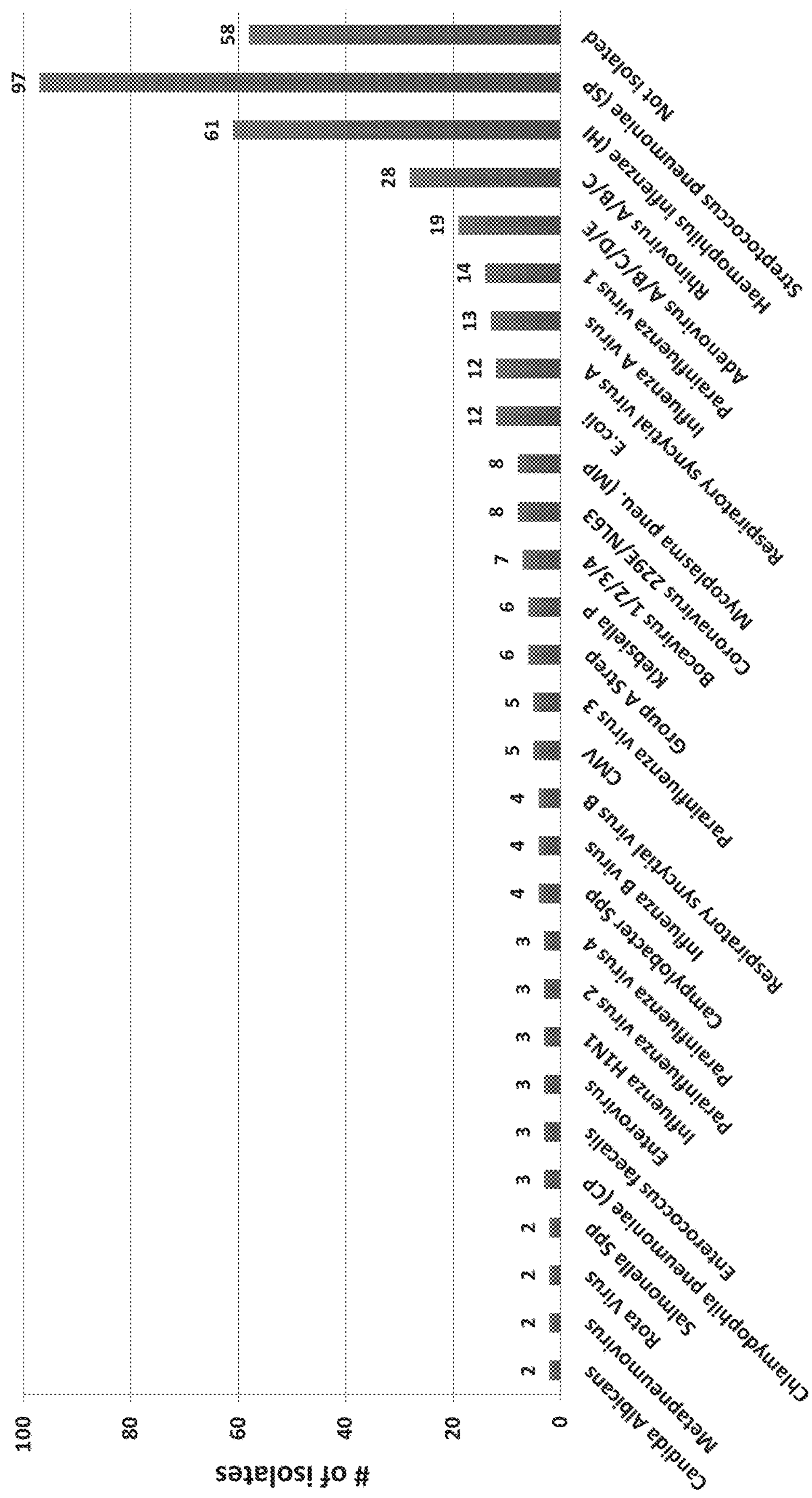
FIG. 7 shows pathogen isolated from infectious disease patients enrolled in the clinical study.

The present invention, in some embodiments thereof, relates to computational analysis, and, more particularly, but not exclusively, to computational analysis of biological data, e.g., for the purpose of distinguishing between bacterial infection and non-bacterial disease, and/or between a bacterial infection and viral infection, and/or between an infectious and non-infectious disease.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Different infectious agents have unique molecular patterns that can be identified and targeted by the immune system. Pathogen-associated molecular patterns (PAMPs) are an example of such molecules that are associated with different groups of pathogens and may be recognized by cells of the innate immune system using Toll-like receptors (TLRs) and other pattern recognition receptors (e.g. NOD proteins).

These patterns may vary considerably between different classes of pathogens and thus elicit different immune responses. For example, TLR-4 can recognize lipopolysaccharide, a constituent of gram negative bacteria, as well as lipoteichoic acids, constituent of gram positive bacteria, hence promoting an anti-microbial response of the immune system. TLR-3 can recognize single stranded RNA (often indicative of a viral infection) and thus prompt the appropriate anti-viral response. By distinguishing between different classes of pathogens (e.g bacterial versus viral) the immune system can mount the appropriate defense.

Correct identification of bacterial patients is of high importance as these patients require antibiotic treatment and in some cases more aggressive management (hospitalization, additional diagnostic tests etc). Misclassification of bacterial patients increases the chance of morbidity and mortality. The clinical challenge is to distinguish between these patients from patients with viral infection that have similar symptoms but do not require antibiotic treatment. Circulating host-proteins, such as C-reactive protein (CRP), are routinely used to support diagnosis of infection. The blood levels of these biomarkers are moderately elevated in response to viral infections and to higher extent in response to bacterial infections, with some degree of overlapping. Moreover, some virus type (e.g., adenovirus and influenza), can cause a significant increase in CRP levels, similar to various bacterial infections.

The present inventors previously identified novel sets of biomarkers whose pattern of expression significantly correlates with infection type—as documented in International Patent Applications WO2011132086, WO2013/117746, WO 2016/024278 and WO 2016/092554, all of which are incorporated herein by reference.

The present embodiments provide a method and a system suitable for analyzing biological data obtained from a subject. In some embodiments of the present invention the subject has been previously treated with an antibiotic, and in some embodiments of the present invention the subject has not been previously treated with an antibiotic.

Some embodiments are based on the use of signature of polypeptides for the diagnosis of bacterial infections, viral infections and non-bacterial, non-viral diseases. The method and/or system of the present embodiments identifies the type of infection a subject is suffering from, which in turn allows for the selection of an appropriate treatment regimen. Various embodiments of the invention address limitations of current diagnostic solutions by: (i) allowing accurate diagnostics on a broad range of pathogens; (ii) enabling rapid diagnosis (within minutes); (iii) insensitivity to the presence of non-pathogenic bacteria and viruses (thus reducing the problem of false-positive); and (iv) eliminating the need for direct sampling of the pathogen, thus enabling diagnosis of inaccessible infections. Thus, some methods of the invention allow for the selection of subjects for whom antibiotic treatment is desired and prevent unnecessary antibiotic treatment of subjects having only a viral infection or a non-infectious disease. Some methods of the invention also allow for the selection of subjects for whom anti-viral treatment is advantageous.

In the context of the present invention, the following abbreviations may be used: ANC=Absolute neutrophil count; ANN=Artificial neural networks; AUC=Area under the receiver operating curve; BP=*Bordetella pertussis*; CHF=Congestive heart failure; CI=Confidence interval; CID=Congenital immune deficiency; CLL=Chronic lymphocytic leukemia; CMV=Cytomegalovirus; CNS=Central nervous system; COPD=Chronic obstructive pulmonary disease; CP=*Chlamydophila* pneumonia; CRP=C-reactive protein; MX1=MX dynamin-like GTPase 1; CSF=Cerebrospinal fluid; CV=Coefficient of variation; DOR=Diagnostic odds ratio; EBV=Epstein bar virus; eCRF=Electronic case report form; ED=Emergency department, ELISA=Enzyme-linked immunosorbent assay; FDR=False discovery rate; FMF=Familial Mediterranean fever; G-CSF=Granulocyte colony-stimulating factor; GM-CSF=Granulocyte-macrophage colony-stimulating factor; HBV=Hepatitis B virus; HCV=Hepatitis C virus; HI=*Haemophilus* influenza; HIV=Human immunodeficiency virus; IDE=Infectious disease experts; IL=Interleukin; IRB=institutional review board; IVIG=Intravenous immunoglobulin; KNN=K-nearest neighbors; LP=*Legionella pneumophila*; LR+=Positive likelihood ratio; LR-=Negative likelihood ratio; LRTI=Lower respiratory tract infections; mAb=Monoclonal antibodies; MDD=Minimum detectable dose; MDS=Myelodysplastic syndrome; MP=*Mycoplasma* pneumonia; MPD=Myeloproliferative disease; NPV=Negative predictive value; PCT=Procalcitonin; PED=Pediatric emergency department; PPV=Positive predictive value; QA=Quality assurance; RSV=Respiratory syncytial virus; RV=Rhinovirus; SIRS=systemic inflammatory syndrome; SP=*Streptococcus pneumonia*; STARD=Standards for Reporting of Diagnostic Accuracy; SVM=Support vector machine; TNF=Tumor necrosis factor; URTI=Upper respiratory tract infection; UTI=Urinary tract infection; WBC=White blood cell; WS=Wilcoxon rank-sum.

In the context of the present invention, the following statistical terms may be used:

"TP" is true positive, means positive test result that accurately reflects the tested-for activity. For example in the context of the present invention a TP, is for example but not limited to, truly classifying a bacterial infection as such.

"TN" is true negative, means negative test result that accurately reflects the tested-for activity. For example in the context of the present invention a TN, is for example but not limited to, truly classifying a viral infection as such.

"FN" is false negative, means a result that appears negative but fails to reveal a situation. For example in the context of the present invention a FN, is for example but not limited to, falsely classifying a bacterial infection as a viral infection.

"FP" is false positive, means test result that is erroneously classified in a positive category. For example in the context of the present invention a FP, is for example but not limited to, falsely classifying a viral infection as a bacterial infection.

"Sensitivity" is calculated by TP/(TP+FN) or the true positive fraction of disease subjects.

"Specificity" is calculated by TN/(TN+FP) or the true negative fraction of non-disease or normal subjects.

"Total accuracy" is calculated by (TN+TP)/(TN+FP+TP+FN).

"Positive predictive value" or "PPV" is calculated by TP/(TP+FP) or the true positive fraction of all positive test results. It is inherently impacted by the prevalence of the disease and pre-test probability of the population intended to be tested.

"Negative predictive value" or "NPV" is calculated by TN/(TN+FN) or the true negative fraction of all negative test results. It also is inherently impacted by the prevalence of the disease and pre-test probability of the population intended to be tested. See, e.g., O'Marcaigh A S, Jacobson R M, "Estimating The Predictive Value Of A Diagnostic Test, How To Prevent Misleading Or Confusing Results," Clin. Ped. 1993, 32(8): 485-491, which discusses specificity, sensitivity, and positive and negative predictive values of a test, e.g., a clinical diagnostic test.

"MCC" (Mathews Correlation coefficient) is calculated as follows: MCC=(TP*TN−FP*FN)/{(TP+FN)*(TP+FP)*(TN+FP)*(TN+FN)}^0.5 where TP, FP, TN, FN are true-positives, false-positives, true-negatives, and false-negatives, respectively. Note that MCC values range between −1 to +1, indicating completely wrong and perfect classification, respectively. An MCC of 0 indicates random classification. MCC has been shown to be a useful for combining sensitivity and specificity into a single metric (Baldi, Brunak et al. 2000). It is also useful for measuring and optimizing classification accuracy in cases of unbalanced class sizes (Baldi, Brunak et al. 2000).

"Accuracy" refers to the degree of conformity of a measured or calculated quantity (a test reported value) to its actual (or true) value. Clinical accuracy relates to the proportion of true outcomes (true positives (TP) or true negatives (TN) versus misclassified outcomes (false positives (FP) or false negatives (FN)), and may be stated as a sensitivity, specificity, positive predictive values (PPV) or negative predictive values (NPV), Mathews correlation coefficient (MCC), or as a likelihood, odds ratio, Receiver Operating Characteristic (ROC) curve, Area Under the Curve (AUC) among other measures.

"Analytical accuracy" refers to the reproducibility and predictability of the measurement process itself, and may be summarized in such measurements as coefficients of variation (CV), Pearson correlation, and tests of concordance and calibration of the same samples or controls with different times, users, equipment and/or reagents. These and other considerations in evaluating new biomarkers are also summarized in Vasan, 2006.

"Performance" is a term that relates to the overall usefulness and quality of a diagnostic or prognostic test, including, among others, clinical and analytical accuracy, other analytical and process characteristics, such as use characteristics (e.g., stability, ease of use), health economic value, and relative costs of components of the test. Any of these factors may be the source of superior performance and thus usefulness of the test, and may be measured by appropriate "performance metrics," such as AUC and MCC, time to result, shelf life, etc. as relevant.

By "statistically significant", it is meant that the alteration is greater than what might be expected to happen by chance alone (which could be a "false positive"). Statistical significance can be determined by any method known in the art. Commonly used measures of significance include the p-value, which presents the probability of obtaining a result at least as extreme as a given data point, assuming the data point was the result of chance alone. A result is often considered highly significant at a p-value of 0.05 or less.

The performance and thus absolute and relative clinical usefulness of the invention may be assessed in multiple ways as noted above. Amongst the various assessments of performance, some embodiments of the invention are intended to provide accuracy in clinical diagnosis and prognosis. The accuracy of a diagnostic or prognostic test, assay, or method concerns the ability of the test, assay, or method to distinguish between subjects having an infection is based on whether the subjects have, a "significant alteration" (e.g., clinically significant and diagnostically significant) in the levels of a determinant. By "effective amount" it is meant that the measurement of an appropriate number of determinants (which may be one or more) to produce a "significant alteration" (e.g. level of expression or activity of a determinant) that is different than the predetermined cut-off point (or threshold value) for that determinant (s) and therefore indicates that the subject has an infection for which the determinant (s) is an indication. The difference in the level of determinant is preferably statistically significant. As noted below, and without any limitation of the invention, achieving statistical significance, and thus the preferred analytical, diagnostic, and clinical accuracy, may require that combinations of several determinants be used together in panels and combined with mathematical algorithms in order to achieve a statistically significant determinant index.

In the categorical diagnosis of a disease state, changing the cut point or threshold value of a test (or assay) usually changes the sensitivity and specificity, but in a qualitatively inverse relationship. Therefore, in assessing the accuracy and usefulness of a proposed medical test, assay, or method for assessing a subject's condition, one should optionally and preferably take both sensitivity and specificity into account and be mindful of what the cut point is at which the sensitivity and specificity are being reported because sensitivity and specificity may vary significantly over the range of cut points. One way to achieve this is by using the Matthews correlation coefficient (MCC) metric, which depends upon both sensitivity and specificity. Use of statistics such as area under the ROC curve (AUC), encompassing all potential cut point values, is preferred for most categorical risk measures when using some aspects of the invention, while for continuous risk measures, statistics of goodness-of-fit and calibration to observed results or other gold standards, are preferred.

By predetermined level of predictability it is meant that the method provides an acceptable level of clinical or diagnostic accuracy. Using such statistics, an "acceptable degree of diagnostic accuracy", is herein defined as a test or assay (such as the test used in some aspects of the invention for determining the clinically significant presence of determinants, which thereby indicates the presence an infection type) in which the AUC (area under the ROC curve for the test or assay) is at least 0.60, desirably at least 0.65, more desirably at least 0.70, preferably at least 0.75, more preferably at least 0.80, and most preferably at least 0.85.

By a "very high degree of diagnostic accuracy", it is meant a test or assay in which the AUC (area under the ROC curve for the test or assay) is at least 0.75, 0.80, desirably at least 0.85, more desirably at least 0.875, preferably at least 0.90, more preferably at least 0.925, and most preferably at least 0.95.

Alternatively, the methods predict the presence or absence of an infection or response to therapy with at least 75% total accuracy, more preferably 80%, 85%, 90%, 95%, 97%, 98%, 99% or greater total accuracy.

Alternatively, the methods predict the presence of a bacterial infection or response to therapy with at least 75% sensitivity, more preferably 80%, 85%, 90%, 95%, 97%, 98%, 99% or greater sensitivity.

Alternatively, the methods predict the presence of a viral infection or response to viral therapy with at least 75% specificity, more preferably 80%, 85%, 90%, 95%, 97%, 98%, 99% or greater specificity.

Alternatively, the methods rule out the presence of a bacterial infection or rule in a viral infection with at least 75% NPV, more preferably 80%, 85%, 90%, 95%, 97%, 98%, 99% or greater NPV. Alternatively, the methods rule in the presence of a bacterial infection or rule out a viral infection with at least 75% PPV, more preferably 80%, 85%, 90%, 95%, 97%, 98%, 99% or greater PPV.

Alternatively, the methods predict the presence of a viral infection or response to therapy with at least 75% specificity, more preferably 80%, 85%, 90%, 95%, 97%, 98%, 99% or greater specificity. Alternatively, the methods predict the presence or absence of an infection or response to therapy with an MCC larger than 0.2, 0.3, 0.4, 0.5, 0.6, 0.7, 0.8, 0.9 or 1.0.

Any of the methods described herein can be embodied in many forms. For example, it can be embodied in on a tangible medium such as a computer for performing the method operations. It can be embodied on a computer readable medium, comprising computer readable instructions for carrying out the method operations. It can also be embodied in electronic device having digital computer capabilities arranged to run the computer program on the tangible medium or execute the instruction on a computer readable medium.

Computer programs implementing the method of the present embodiments can commonly be distributed to users on a distribution medium such as, but not limited to, CD-ROMs or flash memory media. From the distribution medium, the computer programs can be copied to a hard disk or a similar intermediate storage medium. In some embodiments of the present invention, computer programs implementing the method of the present embodiments can be distributed to users by allowing the user to download the programs from a remote location, via a communication network, e.g., the internet. The computer programs can be run by loading the computer instructions either from their distribution medium or their intermediate storage medium into the execution memory of the computer, configuring the computer to act in accordance with the method of the present embodiments. All these operations are well-known to those skilled in the art of computer systems.

The computational operations of the method of the present embodiments can be executed by a computer, either remote from the subject or near the subject. When the computer is remote from the subject, it can receive the data over a network, such as a telephone network or the Internet. To this end, a local computer can be used to transmit the data to the remote computer. This configuration allows performing the analysis while the subject is at a different location (e.g., at home), and also allows performing simultaneous analyses for multiple subjects in multiple different locations.

The computational operations of the method can also be executed by a cloud computing resource of a cloud computing facility. The cloud computing resource can include a computing server and optionally also a storage server, and can be operated by a cloud computing client as known in the art.

The method and/or system according to some embodiments may be used to "rule in" a bacterial infection. Alternatively, the method and/or system may be used to rule out a non-bacterial infection. The method and/or system according to some embodiments can be used to "rule out" a bacterial infection and "rule in" a non-bacterial disease.

The method and/or system according to some embodiments may be used to "rule in" a viral infection. Alternatively, the method and/or system may be used to rule out a non-viral infection.

The method and/or system according to some embodiments can be used to "rule out" a viral infection and "rule in" a non-viral disease.

The method and/or system according to some embodiments may be used to "rule in" an infectious disease. Alternatively, the method and/or system may be used to rule out a non-infectious disease. The method and/or system according to some embodiments can be used to "rule out" an infectious disease and "rule in" a non-infectious disease.

The method and/or system according to some embodiments may be used to "rule in" a mixed infection defined as a combination of a bacterial infection and viral infection. Alternatively, the method and/or system may be used to rule out such a mixed infection. The method and/or system according to some embodiments can be used to "rule out" a viral infectious disease and "rule in" a mixed infectious disease.

According to a particular embodiment, the method of this aspect of the present invention is used to identify an infection (e.g. a bacterial infection) in patients with Systemic inflammatory response syndrome (SIRS).

Thus, it can distinguish between patients with sepsis and patients with non-infectious SIRS, which in turn allows for the selection of an appropriate treatment regimen.

SIRS is a serious condition related to systemic inflammation, organ dysfunction, and organ failure. It is defined as 2 or more of the following variables: fever of more than 38° C. (100.4° F.) or less than 36° C. (96.8° F.); heart rate of more than 90 beats per minute; respiratory rate of more than 20 breaths per minute or arterial carbon dioxide tension ($PaCO_2$) of less than 32 mm Hg; abnormal white blood cell count (>12,000/μL or <4,000/μL or >10% immature [band] forms). SIRS is nonspecific and can be caused by ischemia, inflammation, trauma, infection, or several insults combined. Thus, SIRS is not always related to infection.

Sepsis is a life-threatening condition that is caused by inflammatory response to an infection. The early diagnosis of sepsis is essential for clinical intervention before the disease rapidly progresses beyond initial stages to the more severe stages, such as severe sepsis or septic shock, which are associated with high mortality. Current diagnostics are limited in their ability to distinguish between non-infective SIRS and sepsis. Therefore, there is a need for new biomarkers or combinations of biomarkers that can provide added value in the accurate and timely diagnosis of sepsis.

According to this aspect the subject that is tested has been diagnosed with SIRS. The method that is carried out is used to determine if the SIRS is infective (i.e. sepsis) or non-infective.

In another embodiment, sepsis is diagnosed in a subject suspected of having an infection and which fulfils each of the three criteria:

Respiratory rate greater or equal to 22/min;

Altered mentation (e.g. a Glasgow coma score of less than 15);

Systolic blood pressure lower than or equal to 10 mmHg.

Further criteria for diagnosing sepsis are disclosed in Singer et al. 2016, 31.5(8):801-810 JAMA.

Thus, according to another aspect of the present invention there is provided a method of ruling in sepsis in a subject suspected of having in infection comprising:

(a) measuring the expression level of MX dynamin-like GTPase 1 (MX1) and an expression level of C-reactive protein (CRP) in a sample derived from the subject;

(b) calculating a distance between a segment of a curved line and an axis defined by a direction, said distance being calculated at a point over said curved line defined by a coordinate δ along said direction; and (c) correlating said distance to the presence of, absence of, or likelihood that the subject has, a bacterial infection;

wherein at least 90% of said segment is between a lower bound line $f(\delta)-\varepsilon_0$ and an upper bound line $f(\delta)+\varepsilon_1$, wherein said $f(\delta)$ equals $1/(1+\exp(-\delta))$, wherein said coordinate δ, once calculated, equals $a_0+a_1X+a_2Z_{MX1}$, wherein said X is a value of said CRP in μg/ml, and said $Z_{MX1}$ is a z-score of said MX1 relative to a group of subjects previously diagnosed with a bacterial infection, wherein each of said $\varepsilon_0$ and said $\varepsilon_1$ is less than 0.5, and wherein $a_0$ is from about −2.4 to about −1.9, $a_1$ is from about 0.04 to about 0.05, and $a_2$ is from about −0.39 to about −0.43.

(d) measuring the respiratory rate of the subject;

(e) analyzing the mental state of the subject; and (f) measuring the blood pressure of the subject;

wherein when step (c) is indicative of a bacterial infection and steps (d)-(f) are indicative of sepsis, sepsis is ruled in.

It will be appreciated that steps (d), (e) and (f) may be carried out as part of determining the SOFA score (originally the Sepsis-related Organ Failure Assessment; Vincent J. L et $a_1$ Intensive Care Med. 1996; 22(7):707-710) of a subject.

In one embodiment, steps (a)-(c) are carried out in order to confirm the subject has an infection (e.g. bacterial infection). Only when subjects have a confirmed infection are steps (d), (e) and (f) are carried out to confirm sepsis.

In another embodiment, the subject, has a suspected infection, steps (d)-(f) are carried out to rule in sepsis (or if the subject has a SOFA score above 2); and steps (a-c) are carried out to corroborate the diagnosis.

In still another embodiment, the method is used to distinguish between an infective exacerbation state (e.g. due to a bacterial infection) and a non-infective exacerbation state of chronic obstructive pulmonary disease (COPD) in a subject.

Chronic obstructive pulmonary disease (COPD) is an obstructive, inflammatory lung disease characterized by long-term poor airflow. The main symptoms include shortness of breath and cough with sputum production. COPD is a progressive disease, worsening over time.

An exacerbation of COPD may be defined as an event in the natural course of the disease characterized by a change in the patient's baseline dyspnea, cough, and/or sputum that is beyond normal day-to-day variations. The exacerbation is typically acute. It may present with signs of increased work of breathing such as fast breathing, a fast heart rate, sweating, active use of muscles in the neck, a bluish tinge to the skin, and confusion or combative behavior in very severe exacerbations. Crackles may also be heard over the lungs on examination with a stethoscope.

The CRP-MX1 classifiers were proven accurate in distinguishing between bacterial and viral infections in patients presenting with a variety of clinical syndromes (see Example 1, herein below). Thus, the present invention, in some embodiments thereof, is based on the identification of signatures and determinants associated with bacterial, viral or mixed infection in patients with specific clinical syndromes. In one embodiment, the present invention is based on the identification of signatures and determinants associated with bacterial, viral or mixed infection in patients presenting with low respiratory tract infection (LRTI). In another embodiment, the signatures and determinants are associated with bacterial, viral or mixed infection in patients with upper respiratory tract infection (URTI). In another embodiment, the signatures and determinants are associated with bacterial, viral or mixed infection in patients with serious bacterial infection (SBI). In another embodiment, the signatures and determinants are associated with bacterial, viral or mixed infection in patients with fever without an identifiable source.

The biological data analyzed by the method and/or system optionally and preferably contain expression values of a plurality of polypeptides in the blood of a subject. The expression values are typically stored in a memory location within computer-readable medium, from which the data processor reads the data and performs the analysis as further detailed herein below. The biological data can optionally include additional information, including, without limitation, preliminary diagnosis, observed clinical syndrome, suspected pathogen, age of the subject, gender of the subject, ethnicity of the subject and the like. The additional information can be stored in another memory location within the same or different computer-readable medium, from which the data processor can read the additional information or a portion thereof and optionally perform the analysis based also on this information. The results of the analysis can be stored in another memory location within the same or different computer-readable medium, from which it can optionally and preferably conveyed to a remote or local display, in the form of a textual or graphical output.

In some embodiments the biological data comprises expression values of only two determinants, in some embodiments the biological data comprises expression values of at least three determinants, in some embodiments biological data comprises expression values of only three determinants, in some embodiments biological data comprises expression values of at least four determinants, in some embodiments biological data comprises expression values of only four determinants, in some embodiments biological data comprises expression values of at least five determinants, and in some embodiments biological data comprises expression values of only five determinants.

It will be appreciated that the determinants of this aspect of the present invention may relate to polypeptide determinants and/or RNA determinants.

According to the method of this aspect of the present invention at least two determinants are measured—MX1 and CRP.

The present inventors contemplate measuring the expression of many additional determinants. Representative examples include, without limitation, IP-10, TRAIL, IL1ra, PCT, NGAL and SAA. In some embodiments the additional determinants comprise at least TRAIL and IP-10.

It will be appreciated that the determinant names presented herein are given by way of example. Many alternative names, aliases, modifications, isoforms and variations will be apparent to those skilled in the art. Accordingly, it is intended to embrace all the alternative protein names, aliases, modifications isoforms and variations.

Gene products, are identified based on the official letter abbreviation or gene symbol assigned by the international Human Genome Organization Naming Committee (HGNC) and listed at the date of this filing at the US National Center for Biotechnology Information (NCBI) web site also known as Entrez Gene.

Further information about the determinants which may be measured in combination with MX1 and CRP is set forth in Table 1, below.

TABLE 1

| Protein symbol | Full Gene Name | RefSeq DNA sequence | RefSeq proteins |
|---|---|---|---|
| CRP | C-reactive protein, pentraxin-related | NC_000001.11<br>NT_004487.20<br>NC_018912.2 | NP_000558.2 |
| TRAIL | Tumor necrosis factor super-family member 10 | NC_000003.12<br>NC_018914.2<br>NT_005612.17 | NP_001177871.1<br>NP_001177872.1<br>NP_003801.1 |
| IP-10 | Chemokine (C-X-C motif) ligand 10 | NC_000004.12<br>NC_018915.2<br>NT_016354.20 | NP_001556.2 |
| IL1R/IL1R1/ IL1RA | Interleukin 1 receptor, type I | NC_000002.12<br>NT_005403.18<br>NC_018913.2 | NP_000868.1<br>NP_001275635.1 |
| Procalcitonin (PCT) | Calcitonin-related polypeptide alpha | NC_000011.10<br>NC_018922.2<br>NT_009237.19 | NP_001029124.1<br>NP_001029125.1<br>NP_001732.1 |
| SAA/SAA1 | Serum amyloid A1 | NC_000011.10<br>NC_018922.2<br>NT_009237.19 | NP_000322.2<br>NP_001171477.1<br>NP_954630.1 |
| TREM1 | Triggering receptor expressed on myeloid cells 1 | NC_000006.12<br>NT_007592.16<br>NC_018917.2 | NP_001229518.1<br>NP_001229519.1<br>NP_061113.1 |
| TREM2 | Triggering receptor expressed on myeloid cells 2 | NC_000006.12<br>NT_007592.16<br>NC_018917.2 | NP_001258750.1<br>NP_061838.1 |
| RSAD2 | Radical S-adenosyl methionine domain containing 2 | NC_000002.12<br>NT_005334.17<br>NC_018913.2 | NP_542388.2 |
| NGAL | Lipocalin 2 | NC_000009.12<br>NC_018920.2<br>NT_008470.20 | NP_005555.2 |
| MMP8 | Matrix metallopeptidase 8 | NC_000011.10<br>NT_033899.9<br>NC_018922.2 | NP_001291370.1<br>NP_001291371.1<br>NP_002415.1 |
| MX1 | MX Dynamin-Like GTPase 1 | NC_000021.9<br>NT_011512.12<br>NC_018932.2 | NP_001138397.1<br>NP_001171517.1<br>NP_001269849.1<br>NP_002453.2 |
| MX2 | MX dynamin like GTPase 2 | NC_000021.9,<br>NT_011512.12<br>NC_018932.2 | NP_002454.1 |
| Neopterin | 2-amino-6-(1,2,3-trihydroxypropyl)-1H-pteridin-4-one IUPAC name | N/A | N/A |

Exemplary cDNA sequences of human TRAIL are set forth in SEQ ID NOs: 1-3.

Exemplary amino acid sequences of human TRAIL are set forth in SEQ ID NOs: 4-8 and 37 and 38.

Exemplary cDNA sequences of human IP10 are set forth in SEQ ID NOs: 9-12.

An exemplary amino acid sequence of human IP10 is set forth in SEQ ID NO: 13.

Exemplary cDNA sequences of human CRP are set forth in SEQ ID NOs: 14-16.

An exemplary amino acid sequence of human CRP is set forth in SEQ ID NO: 17.

Exemplary cDNA sequences of human IL1RA are set forth in SEQ ID NOs: 18, 19 and 20.

Exemplary amino acid sequences of human IL1RA are set forth in SEQ ID NOs:21-24.

Exemplary cDNA sequences of human PCT are set forth in SEQ ID NOs: 31-32.

Exemplary amino acid sequences of human PCT are set forth in SEQ ID NOs:33-36.

Exemplary cDNA sequences of human SAA are set forth in SEQ ID NOs: 25-27.

Exemplary amino acid sequences of human MX1 are set forth in SEQ ID NO:28-30 and 39.

An exemplary cDNA sequence of human MX1 is set forth in SEQ ID NO: 40. Other exemplary cDNA sequences are set forth in RefSeq Nos. NM_001144925.2, NM_001178046.2, NM_001282920.1, NM_002462.4, XM_005260978.3, XM_005260979.1, XM_005260980.1, XM_005260981.1, XM_005260982.1, XM_011529568.1, XM_011529569.1 and XM_011529570.1.

An exemplary amino acid sequences of human MX2 is set forth in SEQ ID NO:41.

An exemplary cDNA sequence of human MX2 is set forth in SEQ ID NO: 42. Other exemplary cDNA sequences are set forth in RefSeq Nos. NM_002463.1, XM_005260983.3, XM_005260984.1, XM_011529571.1, XM_011529572.1, XM_011529573.1 and XM_011529574.1.

It will be appreciated that since patient to patient DNA variations may give rise to SNPs which can cause differences in the amino acid sequence of the proteins, the present inventors also contemplate proteins having amino acid sequences at least 90%, 95% or 99% homologous to the sequences provided herein above.

Particular combinations of determinants which may be measured include the following:

MX1+NGAL; MX1+PCT, MX1+CRP+TRAIL; MX1+CRP+PCT; MX1+CRP+IL-6; MX1+CRP+IP-10; MX1+CRP+NGAL; MX1+CRP+Neopterin; MX1+CRP+MMP8; MX1+CRP+TRAIL+PCT; MX1+CRP+TRAIL+IL-6; MX1+CRP+TRAIL+IP-10; MX1+CRP+TRAIL+NGAL; MX1+CRP+TRAIL+Neopterin; MX1+CRP+TRAIL+MMP8; MX1+CRP+PCT+IL-6; MX1+CRP+PCT+IP-10; MX1+CRP+PCT+NGAL; MX1+CRP+PCT+Neopterin; MX1+CRP+PCT+MMP8; MX1+CRP+IP-10+IL-6; MX1+CRP+IP-10+NGAL; MX1+CRP+IP-10+Neopterin; MX1+CRP+IP-10+MMP8; MX1+CRP+IL-6+NGAL; MX1+CRP+IL-6+Neopterin; MX1+CRP+IL-6+MMP8; MX1+CRP+NGAL+Neopterin; MX1+CRP+NGAL+MMP8; MX1+CRP+Neopterin+MMP8; MX1+CRP+TRAIL+PCT+IP-10; MX1+CRP+TRAIL+PCT+IL-6; MX1+CRP+TRAIL+PCT+NGAL; MX1+CRP+TRAIL+PCT+Neopterin; MX1+CRP+TRAIL+PCT+MMP8; MX1+CRP+TRAIL+IP-10+IL-6; MX1+CRP+TRAIL+IP-10+NGAL; MX1+CRP+TRAIL+IP-10+Neopterin; MX1+CRP+TRAIL+IP-10+MMP8; MX1+CRP+TRAIL+IL-6+NGAL; MX1+CRP+TRAIL+IL-6+Neopterin; MX1+CRP+TRAIL+IL-6+MMP8; MX1+CRP+TRAIL+NGAL+Neopterin; MX1+CRP+TRAIL+NGAL+MMP8; MX1+CRP+TRAIL+Neopterin+MMP8; MX1+CRP+PCT+IP-10+IL-6; MX1+CRP+PCT+IP-10+NGAL; MX1+CRP+PCT+IP-10+Neopterin; MX1+CRP+PCT+IP-10+MMP8; MX1+CRP+PCT+IL-6+NGAL; MX1+CRP+PCT+IL-6+Neopterin; MX1+CRP+PCT+IL-6+MMP8; MX1+CRP+PCT+NGAL+Neopterin; MX1+CRP+PCT+NGAL+MMP8; MX1+CRP+PCT+Neopterin+MMP8; MX1+CRP+IP-10+IL-6+NGAL; MX1+CRP+IP-10+IL-6+Neopterin; MX1+CRP+IP-10+IL-6+MMP8; MX1+CRP+IP-10+NGAL+Neopterin; MX1+CRP+IP-10+NGAL+MMP8; MX1+CRP+IP-10+Neopterin+MMP8; MX1+CRP+IL-6+NGAL+Neopterin; MX1+CRP+IL-6+NGAL+MMP8; MX1+CRP+IL-6+Neopterin+MMP8; MX1+CRP+NGAL+Neopterin+MMP8.

A "sample" in the context of the present invention is a biological sample isolated from a subject and can include, by way of example and not limitation, whole blood, serum, plasma, saliva, mucus, breath, urine, CSF, sputum, sweat, stool, hair, seminal fluid, biopsy, rhinorrhea, tissue biopsy, cytological sample, platelets, reticulocytes, leukocytes, epithelial cells, or whole blood cells.

In a particular embodiment, the sample is a blood sample—e.g. serum or a sample comprising blood cells. In a particular embodiment, the sample is depleted of red blood cells.

According to this aspect of the present invention, the sample is derived from the subject no more than 72 hours, no more than 60 hours, no more than 48 hours, no more than 36 hours, no more than one 24 hours or even no more than 12 hours following symptom onset.

The sample may be fresh or frozen.

Preferably, the level of the determinants (e.g. polypeptides) is measured within about 24 hours after the sample is obtained. Alternatively, the concentration of the determinants is measured in a sample that was stored at 12° C. or lower, when storage begins less than 24 hours after the sample is obtained.

It will be appreciated that for measuring polypeptide determinants a protein sample is prepared.

An RNA sample may be prepared for measuring RNA. The sample may comprise RNA from a heterogeneous population of cells or from a single population of cells. The RNA may comprise total RNA, mRNA, mitochondrial RNA, chloroplast RNA, DNA-RNA hybrids, viral RNA, cell free RNA, and mixtures thereof. In one embodiment, the RNA sample is devoid of DNA.

Isolation, extraction or derivation of RNA may be carried out by any suitable method. Isolating RNA from a biological sample generally includes treating a biological sample in such a manner that the RNA present in the sample is extracted and made available for analysis. Any isolation method that results in extracted RNA may be used in the practice of the present invention. It will be understood that the particular method used to extract RNA will depend on the nature of the source.

In some embodiments of the present invention, the biological data is provided in the form of a subject-specific dataset, as further detailed herein.

The term "subject" as used herein is preferably a mammal e.g. human. Other exemplary mammals that may be diagnosed according to this aspect of the present invention include dogs, cats, horses, cows, sheep, pigs and goats. According to another embodiment, the subject is a bird (e.g. chicken, turkey, duck or goose. A subject can be male or female.

The subject may be an adult (e.g. older than 18, 21, or 22 years or a child (e.g. younger than 18, 21 or 22 years). In another embodiment, the subject is an adolescent (between 12 and 21 years), an infant (29 days to less than 2 years of age) or a neonate (birth through the first 28 days of life).

A subject can be one who has been previously diagnosed or identified as having an infection, and optionally has already undergone, or is undergoing, a therapeutic intervention for the infection. Alternatively, a subject can also be one who has not been previously diagnosed as having an infection. For example, a subject can be one who exhibits one or more symptoms of having an infection. A subject may also have an infection but show no symptoms of infection.

Exemplary symptoms which the subject may present include but are not limited to fever, nausea, headache, sore throat, runny nose, rash and/or muscle soreness.

According to a particular embodiment, the subject does not show signs of having had a heart attack (e.g. has a normal level of creatine kinase, troponin or serum myoglobin, and/or has a normal ECG or EKG).

The subjects of this aspect of the present invention may present with a variety of pathogens including, but not limited to Adenovirus, Coronavirus, Parainfluenza virus, Influenza A virus, Influenza B virus, Respiratory syncytial virus A/B, *Chlamydophila pneumoniae, Mycoplasma pneumoniae, Legionella pneumophila*, Rota Virus, *Staphylococcus aureus, Streptococcus pneumoniae*, Astrovirus, Enteric Adenovirus, Norovirus G I and G II, Bocavirus 1/2/3/4, Enterovirus, CMV virus, EBV virus, Group A Strep, or *Escherichia coli.*

The subjects (e.g. children) may present with a particular clinical syndrome—for example, low respiratory tract infection (LRTI) infection, upper respiratory tract infection (URTI), fever without identifiable source (FWS), or a serious bacterial infection (SBI) such as UTI (urinary tract infections), septic shock, bacteremia, pneumonia or meningitis.

The subject whose disease is being diagnosed according to some embodiments of the present invention is referred to below as the "test subject". The present Inventors have collected knowledge regarding the expression pattern of polypeptides, of a plurality of subjects whose disease has already been diagnosed, and have devised the analysis technique of the present embodiments based on the collected knowledge. This plurality of subjects is referred to below as "pre-diagnosed subjects" or "other subjects".

As used herein, the phrase "bacterial infection" refers to a condition in which a subject is infected with a bacterium. The infection may be symptomatic or asymptomatic. In the context of this invention, the bacterial infection may also comprise a viral component (i.e. be a mixed infection being the result of both a bacteria and a virus).

The bacterial infection may be acute or chronic.

An acute infection is characterized by rapid onset of disease, a relatively brief period of symptoms, and resolution within days. A chronic infection is an infection that develops slowly and lasts a long time. One difference between acute and chronic infection is that during acute infection the immune system often produces IgM+antibodies against the infectious agent, whereas the chronic phase of the infection is usually characteristic of IgM−/IgG+antibodies. In addition, acute infections cause immune mediated necrotic processes while chronic infections often cause inflammatory mediated fibrotic processes and scaring. Thus, acute and chronic infections may elicit different underlying immunological mechanisms.

The bacterial infection may be the result of gram-positive, gram-negative bacteria or atypical bacteria.

The term "Gram-positive bacteria" as used herein refers to bacteria characterized by having as part of their cell wall structure peptidoglycan as well as polysaccharides and/or teichoic acids and are characterized by their blue-violet color reaction in the Gram-staining procedure. Representative Gram-positive bacteria include: *Actinomyces* spp., *Bacillus anthracis, Bifidobacterium* spp., *Clostridium botulinum, Clostridium perfringens, Clostridium* spp., *Clostridium tetani, Corynebacterium diphtheriae, Corynebacterium jeikeium, Enterococcus faecalis, Enterococcus faecium, Erysipelothrix rhusiopathiae, Eubacterium* spp., *Gardnerella vaginalis, Gemella morbillorum, Leuconostoc* spp., *Mycobacterium abcessus, Mycobacterium avium* complex, *Mycobacterium chelonae, Mycobacterium fortuitum, Mycobacterium haemophilium, Mycobacterium kansasii, Mycobacterium leprae, Mycobacterium marinum, Mycobacterium scrofulaceum, Mycobacterium smegmatis, Mycobacterium terrae, Mycobacterium tuberculosis, Mycobacterium ulcerans, Nocardia* spp., *Peptococcus niger, Peptostreptococcus* spp., *Proprionibacterium* spp., *Staphylococcus aureus, Staphylococcus auricularis, Staphylococcus capitis, Staphylococcus cohnii, Staphylococcus epidermidis, Staphylococcus haemolyticus, Staphylococcus hominis, Staphylococcus lugdanensis, Staphylococcus saccharolyticus, Staphylococcus saprophyticus, Staphylococcus schleiferi, Staphylococcus similans, Staphylococcus warneri, Staphylococcus xylosus, Streptococcus agalactiae* (group B *streptococcus*), *Streptococcus anginosus, Streptococcus bovis, Streptococcus canis, Streptococcus equi, Streptococcus milleri, Streptococcus mitior, Streptococcus mutans, Streptococcus pneumoniae, Streptococcus pyogenes* (group A *streptococcus*), *Streptococcus salivarius, Streptococcus sanguis.*

The term "Gram-negative bacteria" as used herein refer to bacteria characterized by the presence of a double membrane surrounding each bacterial cell.

Representative Gram-negative bacteria include *Acinetobacter calcoaceticus, Actinobacillus actinomycetemcomitans, Aeromonas hydrophila, Alcaligenes xylosoxidans, Bacteroides, Bacteroides fragilis, Bartonella bacilliformis, Bordetella* spp., *Borrelia burgdorferi, Branhamella catarrhalis, Brucella* spp., *Campylobacter* spp., *Chalmydia pneumoniae, Chlamydia psittaci, Chlamydia trachomatis, Chromobacterium violaceum, Citrobacter* spp., *Eikenella corrodens, Enterobacter aerogenes, Escherichia coli, Flavobacterium meningosepticum, Fusobacterium* spp., *Haemophilus influenzae, Haemophilus* spp., *Helicobacter pylori, Klebsiella* spp., *Legionella* spp., *Leptospira* spp., *Moraxella catarrhalis, Morganella morganii, Mycoplasma pneumoniae, Neisseria gonorrhoeae, Neisseria meningitidis, Pasteurella multocida, Plesiomonas shigelloides, Prevotella* spp., *Proteus* spp., *Providencia rettgeri, Pseudomonas aeruginosa, Pseudomonas* spp., *Rickettsia prowazekii, Rickettsia rickettsii, Rochalimaea* spp., *Salmonella* spp., *Salmonella typhi, Serratia marcescens, Shigella* spp., *Treponema carateum, Treponema pallidum, Treponema pallidum endemicum, Treponema pertenue, Veillonella* spp., *Vibrio cholerae, Vibrio vulnificus, Yersinia enterocolitica* and *Yersinia pestis.*

The term "Atypical bacteria" refers to bacteria that do not fall into one of the classical "Gram" groups. Typically they are intracellular bacterial pathogens. They include, without limitations, Mycoplasmas spp., *Legionella* spp. *Rickettsiae* spp., and *Chlamydiae* spp.

The term "non-bacterial disease" as used herein, refers to any disease or condition that is not caused by infectious bacteria.

Some embodiments of the present invention analyze the biological data by calculating a value of a likelihood function using the expression levels. When the value of a likelihood function, as calculated using the expression levels obtained from the subject, is between a lower bound $S_{LB}$ and an upper bound $S_{UB}$, wherein each of the lower and upper bounds is calculated using a combination $\delta$ (e.g., a linear combination) of the expression levels, the value of the likelihood function can be used to provide information pertaining an infection the subject is suffering from.

Figure 10:
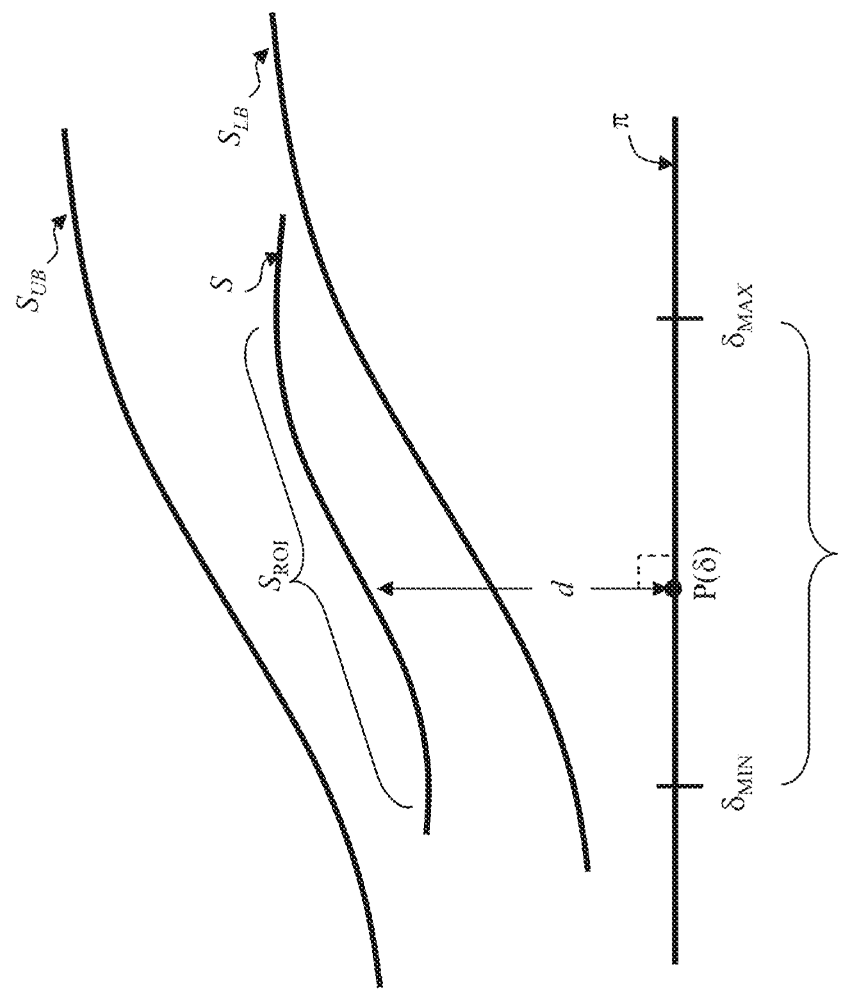
FIG. 10 is a schematic illustration of geometrical objects that can be used for determining a likelihood, according to some embodiments of the present invention.

The lower bound $S_{LB}$ and upper bound $S_{UB}$ can be viewed geometrically as two curved objects, and the combination $\delta$ of the expression levels, can be can be viewed geometrically as a non-curved object, as illustrated schematically in FIG. 10. In this geometrical representation, the value of the likelihood function is represented by a distance d between the non-curved object $\pi$ and a curved object S, where at least a segment $S_{ROI}$ of the curved object S is between the lower bound $S_{LB}$ and the upper bound $S_{UB}$.

Generally, each of the curved objects S, $S_{LB}$ and $S_{UB}$ is a manifold in n dimensions, where n is a positive integer, and the non-curved object π is a hyperplane in an n+1 dimensional space.

The concept of n-dimensional manifolds and hyperplanes in n+1 dimensions are well known to those skilled in the art of geometry. For example, when n=1 the first curved object is a curved line, and the non-curved object π is a hyperplane in 2 dimensions, namely a straight line defining an axis. When n=2, the first curved object is a curved surface, and the non-curved object π is a hyperplane in 3 dimensions, namely a flat plane, referred to below as "a plane".

In the simplest case each of S, $S_{LB}$ and $S_{UB}$ is a curved line and π is a straight axis defined by a direction.

Thus, the present embodiments provide information pertaining to the infection by calculating distances between curved and non-curved geometrical objects.

Figure 11:
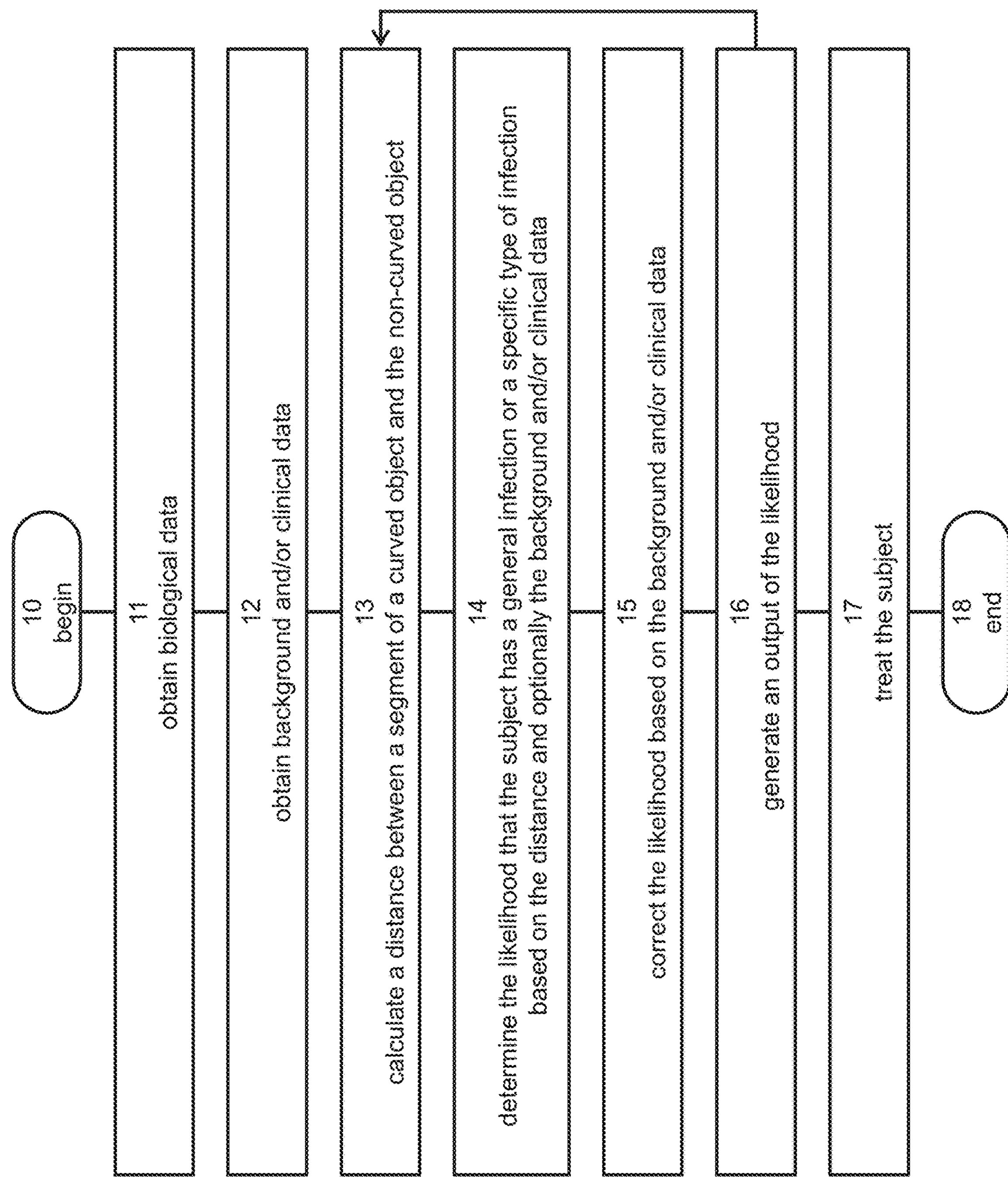
FIG. 11 is a flowchart diagram of a method suitable for analyzing biological data obtained from a subject, according to some embodiments of the present invention.

FIG. 11 is a flowchart diagram of a method suitable for analyzing biological data obtained from a subject, according to various exemplary embodiments of the present invention. It is to be understood that, unless otherwise defined, the operations described hereinbelow can be executed either contemporaneously or sequentially in many combinations or orders of execution. Specifically, the ordering of the flowchart diagrams is not to be considered as limiting. For example, two or more operations, appearing in the following description or in the flowchart diagrams in a particular order, can be executed in a different order (e.g., a reverse order) or substantially contemporaneously. Additionally, several operations described below are optional and may not be executed.

The method begins at 10 and optionally and preferably continuous to 11 at which biological data containing, e.g., expression values of two or more determinants in the blood of a subject are obtained. In some embodiments of the present invention the biological data includes at least an expression value of MX1 and an expression value of CRP, and in some embodiments of the present invention the biological data includes at least an expression value of MX2 and an expression value of CRP. Other types of determinants are also contemplated as disclosed herein.

The method optionally and preferably continues to 12 at which background and/or clinical data that relate to the subject are obtained. In some embodiments of the present invention the background data includes the age of the subject, in some embodiments of the present invention the background data includes the ethnicity of the subject, in some embodiments of the present invention the background data includes the gender of the subject, in some embodiments of the present invention the clinical data includes a syndrome that the subject is experiencing, in some embodiments of the present invention the clinical data includes a pathogen suspected as being present in the subject.

The method proceeds to 13 at which the distance d between a segment of the curved object S (e.g., a curved line) and a non-curved object π (e.g., an axis defined by a direction) is calculated. The distance d is calculated at a point P(δ) over the curved line S defined by a coordinate δ along the direction. The direction is denoted herein using the same Greek letters as the coordinate, except that the direction is denoted by underlined Greek letters to indicate that these are vectors. Thus, when the coordinate is denoted δ, the direction is denoted $\underline{\delta}$.

The distance d is measured from S to the point P, perpendicularly to π. The segment $S_{ROI}$ of S is above a region-of-interest $\pi_{ROI}$ defined in the non-curved object π. For example, when π is an axis, $\pi_{ROI}$ is a linear segment along the axis. Thus, $\pi_{ROI}$ is the projection of $S_{ROI}$ on π. For n=1, $S_{ROI}$ is preferably a curved segment of (the curve) S. The coordinate δ is optionally and preferably defined by a combination of expression values of the determinants. For example, δ can be a combination of the determinants, according to the following equation:

$$\delta=a_0+a_1D_1+a_2D_2+\ldots+\phi$$

where $a_0$, $a_1$, . . . are constant and predetermined coefficients, where each of the variables $D_1$, $D_2$, . . . is an expression levels of one of the determinants, and where φ is a function that is nonlinear with respect to at least one of the expression levels.

The function φ is optional and may, independently, be set to zero (or, equivalently, not included in the calculation of the respective coordinate). When φ=0 the coordinate δ is a linear combination of the determinants.

The nonlinear function φ can optionally and preferably be expressed as a sum of powers of expression levels, for example, according to the following equations:

$$\phi=\sum_i q_i X_i^{\gamma i}$$

where i is a summation index, $q_i$ and $r_i$ are sets of coefficients, $X_i \in \{D_1, D_2, \ldots\}$, and γi is a numerical exponent. Note that the number of terms in the nonlinear function φ does not necessarily equals the number of the determinants, and that two or more terms in the sum may correspond to the same determinant, albeit with a different numerical exponent.

One or more of the predetermined coefficients ($a_i$, $q_i$, $r_i$) typically depends on the respective type of the determinant, but can also depend on the background and/or clinical data obtained at 12. Thus, the calculation of the distance d can optionally and preferably be based on the background and/or clinical data, because the location of the coordinate δ on π can depend on such data. For example, the coefficient $a_i$ for a particular determinant $D_i$ can be different when the subject has a particular syndrome or pathogen, than when the subject does not have this particular syndrome or pathogen. In this case, the location of the point P(δ) on π is different for subjects with the particular syndrome or pathogen, than for subjects without the particular syndrome or pathogen. Since the location is different, the distance d can also be different. Similarly, the coefficient $a_i$ (hence also the location of the point P(δ) on π) for a particular determinant $D_i$ can be different when the subject is of a particular age, gender and/or ethnicity, than when the subject is of a different age, gender and/or ethnicity.

The patient background and/or clinical data can be used for determining the coefficients, in more than one way. In some embodiments of the present invention, a lookup table is used. Such a lookup table can include a plurality of entries wherein each entry includes a determinant, information pertaining to the background and/or clinical data, and a coefficient that is specific to the determinant and the background and/or clinical data of the respective entry. Relevant clinical data includes but is not limited to absolute neutrophil count (abbreviated ANC), absolute lymphocyte count (abbreviated ALC), white blood count (abbreviated WBC), neutrophil % (defined as the fraction of white blood cells that are neutrophils and abbreviated Neu (%)), lymphocyte % (defined as the fraction of white blood cells that are lymphocytes and abbreviated Lym (%)), monocyte % (defined as the fraction of white blood cells that are monocytes and abbreviated Mon (%)), Sodium (abbreviated Na), Potassium (abbreviated K), Bilirubin (abbreviated Bili). Other clinical parameters are described herein below.

As used herein the term "patient background" refers to the history of diseases or conditions of the patient, or which the patient is prone to. For example, the patient medical background may include conditions such as chronic lung diseases and diabetes that affect its immune response to infection (see Example 1, herein below).

In some embodiments of the present invention, the coefficients are initially selected based on the particular determinants, (without taking into account the background and/or clinical data), and thereafter corrected, e.g., by normalization, based on the background and/or clinical data. For example, the coefficients can be normalized according to the age of the subject. In these embodiments, the subject is optionally and preferably stratified according to the subject's age, and the coefficient for the particular determinant is normalized by an age-dependent normalization procedure. In some embodiments, there are different coefficients, normalizations or stratification when the subject is an adult (e.g., older than 18, 21, or 22 years), than when the subject is a child (e.g., younger than 18, 21 or 22 years). In some embodiments, there are different coefficients, normalizations or stratifications when the subject is an adult (e.g., older than 18, 21, or 22 years), an adolescent (e.g., between 12 and 21 years), a child (e.g., between 2 and 12 years), an infant (e.g., 29 days to less than 2 years of age), and a neonates (e.g., birth through the first 28 days of life). In some embodiments, there are different coefficients, normalizations or stratification when the subject is older than 70, 65, 60, 55, 50, 40, 30, 22, 21, 18, 12, 2, 1 years than when the subject is older than 3, 2 and/or 1 month. In some embodiments, there are different coefficients, normalizations or stratification when the subject is younger than 70, 65, 60, 55, 50, 40, 30, 22, 21, 18, 12, 2, 1 year, than when the subject is older than 3, 2 and/or 1 month.

Representative examples of coefficients suitable for the present embodiments are provided below and also in Example 1 of the Examples section that follows (see, for example, Tables 1.1, 1.2, 1.3, 1.7 and 1.8).

In embodiments in which $\phi=0$ and the determinants include MX1 and CRP or MX2 and CRP, $\delta$ can be a linear combination of MX1 and CRP, according to the following equation:

$$\delta=a_0+a_1C+a_2M$$

where C is the expression level of CRP, and M is the expression level of MX1 or MX2.

In embodiments in which $\phi\neq0$ and the determinants include MX1 and CRP or MX2 and CRP, $\delta$ can be a combination of MX1 and CRP or MX2 and CRP, according to the following equations:

$$\delta=a_0+a_1C+a_2M+\phi$$

where $\phi$ is a nonlinear function of at least one of C and M. As representative example, $\phi$ can be expressed as:

$$\phi=q_1C^{r^1}+q_2M^{r^2}.$$

The boundaries of $\pi_{ROI}$ are denoted herein $\delta_{MIN}$ and $\delta_{MAX}$. These boundaries preferably correspond to the physiologically possible ranges of the expression values of the determinants. The range of the expression values can be set by the protocol used for obtaining the respective determinants. Alternatively, the expression values of one or more of the determinants that are used in the calculation of $\delta$ can be score values, for example, z-scored values, relative to a group of subjects previously diagnosed with a bacterial infection. These embodiments are particularly useful when the distance d is used for distinguishing between bacterial and viral infections. Still alternatively, the expression values of one or more of the determinants that are used in the calculation of $\delta$ can be score values, for example, z-scored values, relative to a group of subjects previously diagnosed with an infection. These embodiments are particularly useful when the distance d is used for distinguishing between infectious and non-infectious subjects. Still alternatively, the expression values of one or more of the determinants that are used in the calculation of $\delta$ can be score values, for example, z-scored values, relative to a group of subjects previously diagnosed with a mixed infection. These embodiments are particularly useful when the distance d is used for distinguishing between mixed infection and viral infection. Typically, but not necessarily score values are useful for determinants for which the obtained value varies significantly across different assays, such as, but not limited to, MX1 and MX2. Representative examples of coefficients suitable for the embodiments in which z-scored expression levels are employed are provided below and also in Example 1 of in the Examples section that follows (see, for example, Table 1.3).

At least a major part of the segment $S_{ROI}$ of curved object S is between two curved objects referred to below as a lower bound curved object $S_{LB}$ and an upper bound curved object $S_{UB}$.

As used herein "major part of the segment $S_{ROI}$" refers to a part of a smoothed version $S_{ROI}$ whose length (when n=1), surface area (when n=2) or volume (when n≥3) is 60% or 70% or 80% or 90% or 95% or 99% of a smoothed version of the length, surface area or volume of $S_{ROI}$, respectively.

As used herein, "a smooth version of the segment $S_{ROI}$" refers to the segment $S_{ROI}$, excluding regions of $S_{ROI}$ at the vicinity of points at which the Gaussian curvature is above a curvature threshold, which is X times the median curvature of $S_{ROI}$, where X is 1.5 or 2 or 4 or 8.

The following procedure can be employed for the purpose of determining whether the major part of the segment $S_{ROI}$ is between $S_{LB}$ and $S_{UB}$. Firstly, a smoothed version of the segment $S_{ROI}$ is obtained. Secondly, the length (when n=1), surface area (when n=2) or volume (when n≥3) $A_1$ of the smoothed version of the segment $S_{ROI}$ is calculated. Thirdly, the length (when n=1) surface area (when n=2) or volume (when n≥3) $A_2$ of the part of the smoothed version of the segment $S_{ROI}$ that is between $S_{LB}$ and $S_{UB}$ is calculated. Fourthly, the percentage of $A_2$ relative to $A_1$ is calculated.

FIGS. 12A-D illustrate a procedure for obtaining the smooth version of $S_{ROI}$.

For clarity of presentation, $S_{ROI}$ is illustrated as a one dimensional segment, but the skilled person would understand that $S_{ROI}$ is generally an n-dimensional mathematical object. The Gaussian curvature is calculated for a sufficient number of sampled points on $S_{ROI}$. For example, when the manifold is represented as point cloud, the Gaussian curvature can be calculated for the points in the point cloud. The median of the Gaussian curvature is then obtained, and the curvature threshold is calculated by multiplying the obtained median by the factor X. FIG. 12A illustrates $S_{ROI}$ before the smoothing operation. Marked is a region 320 having one or more points 322 at which the Gaussian curvature is above the curvature threshold. The point or points at which with the Gaussian curvature is maximal within region 320 is removed and region 320 is smoothly interpolated, e.g., via polynomial interpolation, (FIG. 12B). The removal and interpolation is repeated iteratively (FIG. 12C) until the segment $S_{ROI}$ does not contain regions at which the Gaussian curvature is above the curvature threshold (FIG. 12D).

When n=1 (namely when S is a curved line), $S_{LB}$ is a lower bound curved line, and $S_{UB}$ an upper bound curved line. In these embodiments, $S_{LB}$ and $S_{UB}$ can be written in the form:

$$S_{LB}=f(\delta)-\varepsilon_0,$$

$$S_{UB}=f(\delta)+\varepsilon_1$$

where f(δ) is a probabilistic classification function of the coordinate δ (along the direction $\underline{\delta}$) which represents the likelihood that the test subject has an infection of a predetermined type (e.g., a bacterial infection, or a viral infection or a mixed infection). Also contemplated, are embodiments in which f(δ) is a probabilistic classification function which represents the likelihood that the test subject has an infection. In some embodiments of the invention $f(\delta)=1/(1+\exp(-\delta))$. In some embodiments of the invention both $S_{LB}$ and $S_{UB}$ are positive for any value of δ within $\pi_{ROI}$.

In any of the above embodiments each of the parameters $\varepsilon_0$ and $\varepsilon_1$ is less than 0.5 or less than 0.4 or less than 0.3 or less than 0.2 or less than 0.1 or less than 0.05.

The method preferably proceeds to 14 at which the calculated distance d is correlated to the presence of, absence of, or likelihood that the subject has, a disease or condition corresponding to the type of the probabilistic function f. For example, when the probabilistic function f represents the likelihood that the test subject has a bacterial infection, the calculated distance d is correlated to the presence of, absence of, or likelihood that the subject has, a bacterial infection, when the probabilistic function f represents the likelihood that the test subject has a viral infection, the calculated distance d is correlated to the presence of, absence of, or likelihood that the subject has, a viral infection, and when the probabilistic function f represents the likelihood that the test subject has a mixed infection, the calculated distance d is correlated to the presence of, absence of, or likelihood that the subject has, a mixed infection.

In various exemplary embodiments of the invention the correlation includes determining that the distance d is the likelihood that the subject has the respective infection (bacterial, viral, mixed). The likelihood is optionally and preferably compared to a predetermined threshold $\omega_B$, wherein the method can determine that it is likely that the subject has a bacterial infection when the likelihood is above $\omega_B$, and that it is unlikely that the subject has a bacterial infection otherwise. Typical values for $\omega_B$ include, without limitation, about 0.2, about 0.3, about 0.4, about 0.5, about 0.6 and about 0.7. Other likelihood thresholds are also contemplated.

In some embodiments of the present invention the method proceeds to 15 at which the likelihood is corrected based on the background and/or clinical data. Such a correction can be executed in more than one way. For example, the method can employ different predetermined thresholds $\omega_B$ for different ages, ethnicities, genders, syndromes, and/or suspected pathogens. The method can alternatively or additionally employ different values for one or both the parameters $\varepsilon_0$ and $\varepsilon_1$ for different ages, ethnicities, genders, syndromes, and/or suspected pathogens. The method can alternatively or additionally normalize the value of the probabilistic classification function δ, based on the age, ethnicity, gender, syndrome, and/or suspected pathogen.

The method optionally and preferably continues to 16 at which an output of the likelihood(s) is generated. The output can be presented as text, and/or graphically and/or using a color index. The output can optionally include the results of the comparison to the threshold $\omega_B$. From 16 the method can optionally and preferably loops back to 13 for repeating the analysis using a different set of coefficients for the calculation of the coordinate δ and/or a different probabilistic classification function f. For example, the analysis can be initially executed using a set of coefficients and probabilistic classification function f that are selected for determining the presence of, absence of, or likelihood that the subject has, a bacterial infection or a mixed infection, and then, in a subsequent execution, the analysis can use a set of coefficients and probabilistic classification function f that are selected for determining the presence of, absence of, or likelihood that the subject has, a viral infection.

In some embodiments of the present invention, when the method determines that it is likely that the subject has a bacterial infection, the subject is treated (17) for the bacterial infection, as further detailed herein. In some embodiments of the present invention, when the method determines that it is likely that the subject has a viral infection, the subject is treated (17) for the viral infection, as further detailed herein.

The method ends at 18.

Following are representative examples of coefficients that can be used for defining the coordinate δ according to some embodiments of the present invention.

When the probabilistic classification function f represents the likelihood the subject has a bacterial infection, and the coordinate δ is defined as $\delta=a_0+a_1X+a_2Y$, where X is an expression level of CRP in μg/ml, and Y is a z-score of MX1 expression level relative to a group of subjects previously diagnosed with a bacterial infection, $a_0$ is preferably from about −2.4 to about −1.9, more preferably from about −2.2 to about −1.9, more preferably from about −2.2 to about −2.0, e.g., about −2.15; $a_1$ is preferably from about 0.04 to about 0.05, more preferably from about 0.041 to about 0.045, more preferably from about 0.042 to about 0.045, e.g., about 0.044; and $a_2$ is preferably from about −0.39 to about −0.43, more preferably from about −0.40 to about −0.42, more preferably from about −0.41 to about −0.42, e.g., about −0.418. In these embodiments, $\delta_{MIN}$ is from about −4 to about −3 or from about −3.6 to about −3.2, e.g., about −3.4, and $\delta_{MAX}$ is from about 23 to about 30 or from about 24 to about 27, e.g., about 25.5.

When the probabilistic classification function f represents the likelihood the subject has a bacterial infection, and the coordinate δ is defined as $\delta=a_0+a_1X+a_2Y$, where X is an expression level of CRP in μg/ml, and Y is an expression level of MX1 in ng/ml, $a_0$ is preferably from about 0.4 to about 0.5, more preferably from about 0.42 to about 0.48, more preferably from about 0.44 to about 0.47, e.g., about 0.46; $a_1$ is preferably from about 0.016 to about 0.02, more preferably from about 0.017 to about 0.019, e.g., about 0.018; and $a_2$ is preferably from about −0.0025 to about −0.0018, more preferably from about −0.0022 to about −0.0018, more preferably from about −0.0020 to about −0.0019, e.g., about −0.00195. In these embodiments, $\delta_{MIN}$ is from about −15 to about −12 or from about −14 to about −13, e.g., about −13.2, and $\delta_{MAX}$ is from about 10 to about 13 or from about 11 to about 12, e.g., about 11.4.

When the probabilistic classification function f represents the likelihood the subject has a bacterial infection, and the coordinate δ is defined as $\delta=a_0+a_1X+a_2Y$, where X is an expression level of CRP in μg/ml, and Y is an expression level of MX1 when measured by flow cytometry, $a_0$ is preferably from about −1.7 to about −1.4, more preferably from about −1.6 to about −1.45, more preferably from about −1.6 to about −1.5, e.g., about −1.54; $a_1$ is preferably from about 0.03 to about 0.05, more preferably from about 0.035 to about 0.045, more preferably from about 0.038 to about 0.042, e.g., about 0.04; and $a_2$ is preferably from about −5.8E-05 to about −4.7E-05, more preferably from about −5.4E-05 to about −5.0E-05, more preferably from about −5.3E-05 to about −5.2E-05, e.g., about −5.25E-05. In these embodiments, $\delta_{MIN}$ is from about −60 to about −50 or from about −55 to about −52, e.g., about −54, and $\delta_{MAX}$ is from about 18 to about 28 or from about 20 to about 24, e.g., about 22.5.

When the probabilistic classification function f represents the likelihood the subject has an infection, and the coordinate δ is defined as $\delta=a_0+a_1X+a_2Y$, where X is an expression level of CRP in μg/ml, and Y is an expression level of MX1 when measured by flow cytometry, $a_0$ is preferably from about −3 to about −2.4, more preferably from about −3 to about −2.4, more preferably from about −2.9 to about −2.5, more preferably from about −2.8 to about −2.6, e.g., about −2.7; $a_1$ is preferably from about 0.16 to about 0.2, more preferably from about 0.17 to about 0.19, more preferably from about 0.175 to about 0.185, e.g., about 0.18; and $a_2$ is preferably from about 0.0002 to about 0.0003, more preferably from about 0.0002 to about 0.00026, more preferably from about 0.00021 to about 0.00024, e.g., about 0.00023. In these embodiments, $\delta_{MIN}$ is from about −3 to about −2.4 or from about −2.8 to about −2.6, e.g., about −2.7, and $\delta_{MAX}$ is from 300 to about 370 or from about 325 to about 350, e.g., about 338.3.

When the probabilistic classification function f represents the likelihood the subject has a bacterial infection, and the coordinate δ is defined as $\delta=a_0+a_1X+a_2Y$, where X is an expression level of RSAD2, when measured by flow cytometry, and Y is an expression level of MX1 when measured by flow cytometry, $a_0$ is preferably from about 0.6 to about 0.75, more preferably from about 0.63 to about 0.7, more preferably from about 0.65 to about 0.7, e.g., about 0.68; $a_1$ is preferably from about −0.00015 to about −0.00009, more preferably from about −0.00017 to about −0.00009, more preferably from about −0.00018 to about −0.00009, e.g., about −0.0001; and $a_2$ is preferably from about 5.2E-06 to about 6E-06, more preferably from about 5.4E-06 to about 5.8E-06, more preferably from about 5.5E-06 to about 5.7E-06, e.g., about 5.63E-06. In these embodiments, $\delta_{MIN}$ is from about −9 to about −5 or from about −7.5 to about −6, e.g., about −6.8, and $\delta_{MAX}$ is from about 5 to about 7 or from about 6 to about 6.6, e.g., about 6.3.

When the probabilistic classification function f represents the likelihood the subject has a bacterial infection, and the coordinate δ is defined as $\delta=a_0+a_1X+a_2Y$, where X is an expression level of TRAIL in pg/ml, and Y is an expression level of MX1 when measured by flow cytometry, $a_0$ is preferably from about 2.4 to about 3, more preferably from about 2.5 to about 2.9, more preferably from about 2.6 to about 2.8, e.g., about 2.7; $a_1$ is preferably from about −0.055 to about −0.045, more preferably from about −0.054 to about −0.046, more preferably from about −0.053 to about −0.047, e.g., about −0.05; and $a_2$ is preferably from about 2.4E-05 to about 2.5E-05, more preferably from about 2.42E-05 to about 2.48E-05, more preferably from about 2.43E-05 to about 2.46E-05, e.g., about 2.44E-05. In these embodiments, $\delta_{MIN}$ is from about −80 to about −65 or from about −75 to about −71, e.g., about −73.1, and $\delta_{MAX}$ is from about 24 to about 30 or from about 26 to about 28, e.g., about 27.1.

In some embodiments, the method can be carried out using a system 330, which optionally and preferably, but not necessarily, comprises a hand-held device. The system can comprise two or more compartments, wherein the levels of determinants in the blood is measured in one of the compartments (e.g. using an immunohistochemical method), and wherein an analysis of the obtained levels is executed in the other compartment to provide an output relating to the diagnosis.

Figure 13:
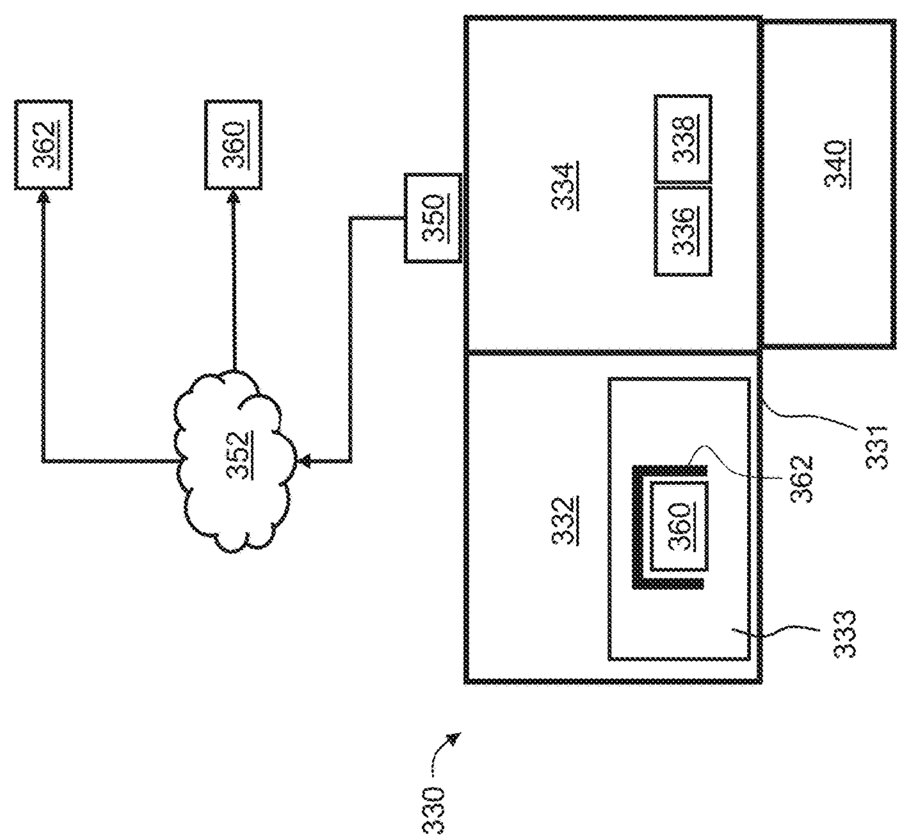
FIG. 13 is a schematic illustration of a block diagram of a system for analyzing biological data, according to some embodiments of the present invention.

A block diagram of representative example of system 330 is illustrated in FIG. 13. System 330 measures the expression value of the determinants in the blood of a subject and optionally and preferably also analyzes the measured expression values, according to the analysis technique described herein. System 330 can comprise a first compartment 332 in which the measurement is performed, and may optionally and preferably also comprise a second compartment 334 in which the analysis is performed. In some embodiments of the present invention, first compartment 332, and optionally and preferably also second compartment 334, is/are housed in a device 331 which is preferably, but not necessarily a hand-held device.

First compartment 332 can include a measuring system 333 configured to measure the expression value of the determinants in the blood of a subject. For example, the blood of a subject can be loaded onto a cartridge 360 containing reagents for detecting the determinants (e.g., CRP and MX1), and the cartridge 360 can then be loaded to compartment 332, e.g., into a cartridge holder or socket 362 being sized and shaped to receive cartridge 360.

Measuring system 333 can perform at least one assay selected from the group consisting of an immunoassay such as ELISA or LFIA, and a functional assay. In some embodiments of the present invention measuring system 333 uses chemiluminescence or florescence for measuring the expression value of the determinants.

System 330 can also comprise a second compartment 334 comprising a hardware processor 336 having a computer-readable medium 338 for storing computer program instructions for executing the operations described herein (e.g., computer program instructions for defining the first and/or second coordinates, computer program instructions for defining the curved line and/or plane, computer program instructions for calculating the first and/or distances, computer program instructions for correlating the calculated distance(s) to the presence of, absence of, or likelihood that the subject has, a bacterial and/or viral infection). Hardware processor 336 is configured to receive expression value measurements from first compartment 332 and execute the program instructions responsively to the measurements and output the processed data to a display device 340.

Figure 14A:
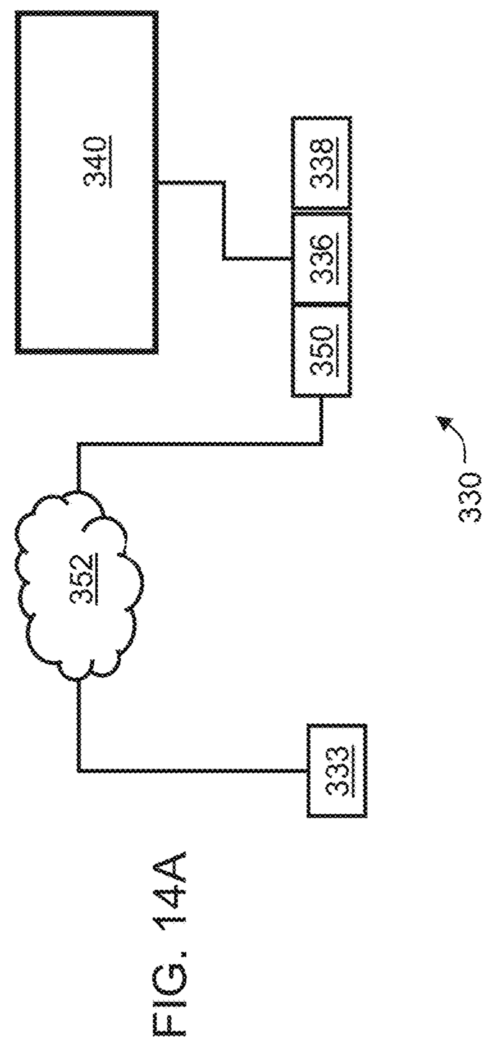
FIGS. 14A and 14B are schematic illustrations of a block diagram of a system for analyzing biological data, in embodiments of the invention in which the system comprises a network interface (FIG. 14A) and a user interface (FIG. 14B).

In some embodiments of the present invention system 330 communicates with a communication network, as schematically illustrated in the block diagram of FIG. 14A. In these embodiments, system 330 can comprise computer-readable medium 338, as further detailed hereinabove, and a hardware processor, such as, but not limited to, processor 336. Hardware processor 336 comprises a network interface 350 that communicates with a communication network 352. Via interface 350, hardware processor 336 receives expression value measurements from a measuring system, such as, but not limited to, measuring system 333, and executes the computer program instructions in computer-readable medium 338, responsively to the received measurements. Hardware processor 336 can then output the processed data to display device 340.

Figure 14B:
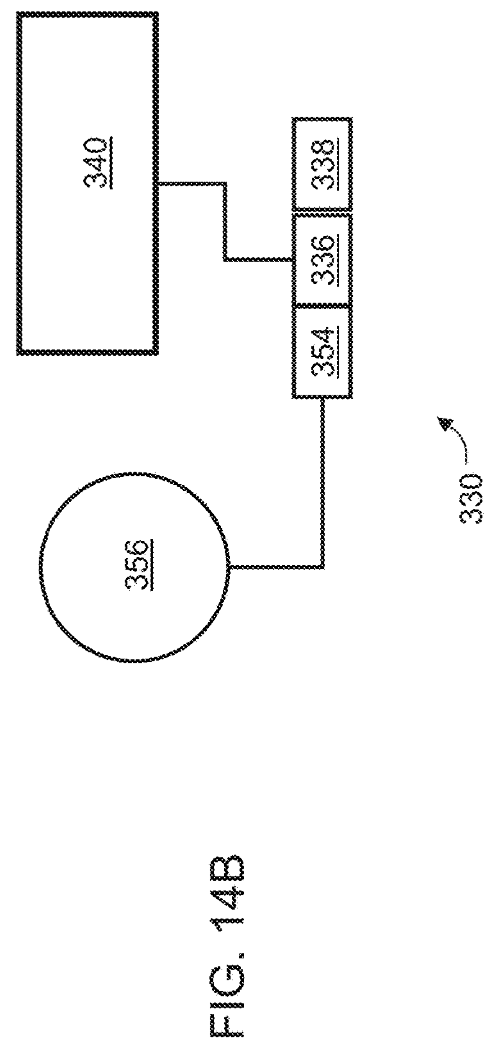

In some embodiments of the present invention system 330 communicates with a user, as schematically illustrated in the block diagram of FIG. 14B. In these embodiments, system 330 can comprise computer-readable medium 338, as further detailed hereinabove, and a hardware processor, such as, but not limited to, processor 336. Hardware processor 336 comprises a user interface 354 that communicates with a user 356. Via interface 350, hardware processor 336 receives expression value measurements from user 356. User 356 can obtain the expression value from an external source, or by executing at least one assay selected from the group consisting of an immunoassay and a functional assay, or by operating system 333 (not shown, see FIGS. 13 and 14A). Hardware processor 336 executes the computer program instructions in computer-readable medium 338, responsively to the received measurements. Hardware processor 336 can then output the processed data to display device 340.

Measuring the determinant (for example, MX1 and CRP) levels is typically affected at the protein level as further described herein below.

Methods of Detecting Expression and/or Activity of Proteins

Expression and/or activity level of proteins expressed in the cells of the cultures of some embodiments of the invention can be determined using methods known in the arts and typically involve the use of antibodies. Such methods may be referred to an immunoassays. Immunoassays may be run in multiple steps with reagents being added and washed away or separated at different points in the assay. Multi-step assays are often called separation immunoassays or heterogeneous immunoassays. Some immunoassays can be carried out simply by mixing the reagents and sample and making a physical measurement. Such assays are called homogenous immunoassays or less frequently non-separation immunoassays. The use of a calibrator is often employed in immunoassays. Calibrators are solutions that are known to contain the analyte in question, and the concentration of that analyte is generally known. Comparison of an assay's response to a real sample against the assay's response produced by the calibrators makes it possible to interpret the signal strength in terms of the presence or concentration of analyte in the sample.

The antibody may be monoclonal, polyclonal, chimeric, or a fragment of the foregoing, and the step of detecting the reaction product may be carried out with any suitable immunoassay.

Suitable sources for antibodies for the detection of the polypeptides include commercially available sources such as, for example, Abazyme, Abnova, AssayPro, Affinity Biologicals, AntibodyShop, Aviva bioscience, Biogenesis, Biosense Laboratories, Calbiochem, Cell Sciences, Chemicon International, Chemokine, Clontech, Cytolab, DAKO, Diagnostic BioSystems, eBioscience, Endocrine Technologies, Enzo Biochem, Eurogentec, Fusion Antibodies, Genesis Biotech, GloboZymes, Haematologic Technologies, Immunodetect, Immunodiagnostik, Immunometrics, Immunostar, Immunovision, Biogenex, Invitrogen, Jackson ImmunoResearch Laboratory, KMI Diagnostics, Koma Biotech, LabFrontier Life Science Institute, Lee Laboratories, Lifescreen, Maine Biotechnology Services, Mediclone, MicroPharm Ltd., ModiQuest, Molecular Innovations, Molecular Probes, Neoclone, Neuromics, New England Biolabs, Novocastra, Novus Biologicals, Oncogene Research Products, Orbigen, Oxford Biotechnology, Panvera, PerkinElmer Life Sciences, Pharmingen, Phoenix Pharmaceuticals, Pierce Chemical Company, Polymun Scientific, Polysiences, Inc., Promega Corporation, Proteogenix, Protos Immunoresearch, QED Biosciences, Inc., R&D Systems, Repligen, Research Diagnostics, Roboscreen, Santa Cruz Biotechnology, Seikagaku America, Serological Corporation, Serotec, SigmaAldrich, StemCell Technologies, Synaptic Systems GmbH, Technopharm, Terra Nova Biotechnology, TiterMax, Trillium Diagnostics, Upstate Biotechnology, US Biological, Vector Laboratories, Wako Pure Chemical Industries, and Zeptometrix. However, the skilled artisan can routinely make antibodies, against any of the polypeptides described herein.

Polyclonal antibodies for measuring polypeptides include without limitation antibodies that were produced from sera by active immunization of one or more of the following: Rabbit, Goat, Sheep, Chicken, Duck, Guinea Pig, Mouse, Donkey, Camel, Rat and Horse.

Examples of additional detection agents, include without limitation: scFv, dsFv, Fab, sVH, $F(ab')_2$, Cyclic peptides, Haptamers, A single-domain antibody, Fab fragments, Single-chain variable fragments, Affibody molecules, Affilins, Nanofitins, Anticalins, Avimers, DARPins, Kunitz domains, Fynomers and Monobody.

The detection agents may be labeled with a label and detected by inspection, or a detector which monitors a particular probe or probe combination is used to detect the detection reagent label. Typical detectors include spectrophotometers, phototubes and photodiodes, microscopes, scintillation counters, cameras, film and the like, as well as combinations thereof. Those skilled in the art will be familiar with numerous suitable detectors that widely available from a variety of commercial sources and may be useful for carrying out the method disclosed herein. Commonly, an optical image of a substrate comprising bound labeling moieties is digitized for subsequent computer analysis. See generally The Immunoassay Handbook (Wild 2005).

Enzyme Linked Immunosorbent Assay (ELISA):

Performing an ELISA involves at least one antibody with specificity for a particular antigen. The sample with an unknown amount of antigen is immobilized on a solid support (usually a polystyrene microtiter plate) either non-specifically (via adsorption to the surface) or specifically (via capture by another antibody specific to the same antigen, in a "sandwich" ELISA). After the antigen is immobilized, the detection antibody is added, forming a complex with the antigen. The detection antibody can be covalently linked to an enzyme, or can itself be detected by a secondary antibody that is linked to an enzyme through bioconjugation. Between each step, the plate is typically washed with a mild detergent solution to remove any proteins or antibodies that are a specifically bound. After the final wash step, the plate is developed by adding an enzymatic substrate to produce a visible signal, which indicates the quantity of antigen in the sample.

Enzymes commonly employed in this method include horseradish peroxidase and alkaline phosphatase. If well calibrated and within the linear range of response, the amount of substrate present in the sample is proportional to the amount of color produced. A substrate standard is generally employed to improve quantitative accuracy.

Western Blot:

This method involves separation of a substrate from other protein by means of an acrylamide gel followed by transfer of the substrate to a membrane (e.g., nylon or PVDF). Presence of the substrate is then detected by antibodies specific to the substrate, which are in turn detected by antibody binding reagents. Antibody binding reagents may be, for example, protein A, or other antibodies. Antibody binding reagents may be radiolabeled or enzyme linked as described hereinabove. Detection may be by autoradiography, colorimetric reaction or chemiluminescence. This method allows both quantitation of an amount of substrate and determination of its identity by a relative position on the membrane which is indicative of a migration distance in the acrylamide gel during electrophoresis.

Fluorescence Activated Cell Sorting (FACS):

This method involves detection of a substrate in situ in cells by substrate specific antibodies. The substrate specific antibodies are linked to fluorophores. Detection is by means of a cell sorting machine which reads the wavelength of light emitted from each cell as it passes through a light beam. This method may employ two or more antibodies simultaneously.

Automated Immunoassay:

An automated analyzer applied to an immunoassay (often called "Automated Immunoassay") is a medical laboratory instrument designed to measure different chemicals and other characteristics in a number of biological samples quickly, with minimal human assistance. These measured properties of blood and other fluids may be useful in the diagnosis of disease. Many methods of introducing samples into the analyzer have been invented. This can involve placing test tubes of sample into racks, which can be moved along a track, or inserting tubes into circular carousels that rotate to make the sample available. Some analyzers require samples to be transferred to sample cups. However, the effort to protect the health and safety of laboratory staff has prompted many manufacturers to develop analyzers that feature closed tube sampling, preventing workers from direct exposure to samples. Samples can be processed singly, in batches, or continuously. Examples of automated immunoassay machines include, without limitation, ARCHITECT ci4100, ci8200 (2003), ci16200 (2007), ARCHITECT i1000SR, ARCHITECT i2000, i2000SR, i4000SR, AxSYM/AxSYM Plus, 1994 U.S., DS2, AIMS, AtheNA, DSX, ChemWell, UniCel DxI 860i Synchron Access Clinical System, UniCel DxC 680i Synchron Access Clinical System, Access/Access 2 Immunoassay System, UniCel DxI 600 Access Immunoassay System, UniCel DxC 600i Synchron Access Clinical System, UniCel DxI 800 Access Immunoassay System, UniCel DxC 880i Synchron Access Clinical System, UniCel DxI 660i Synchron Access Clinical System, SPA PLUS (Specialist Protein Analyzer), VIDAS Immunoassay Analyzer, BioPlex 2200, PhD System EVOLIS PR 3100TSC Photometer, MAGO 4S/2011 Mago Plus Automated EIA Processor, LIAISON XL/2010 LIAISON, ETI-MAX 3000 Agility, Triturus, HYTEC 288 PLUSDSX, VITROS ECi Immunodiagnostic System, VITROS 3600 Immunodiagnostic System, Phadia Laboratory System 100E, Phadia Laboratory System 250, Phadia Laboratory System 1000, Phadia Laboratory System 2500, Phadia Laboratory System 5000, cobas e 602/2010, cobas e411, cobas e601, MODULAR ANALYTICS E170, Elecsys 2010, Dimension EXL 200/2011, Dimension Xpand Plus Integrated Chemistry System, Dimension RxL Max/Max Suite Integrated Chemistry System; Dimension RxL Integrated Chemistry System, Dimension EXL with LM Integrated Chemistry System, Stratus CS Acute Care Diagnostic System, IMMULITE 2000 XPi Immunoassay System, ADVIA Centaur CP Immunoassay System, IMMULITE 2000, IMMULITE 1000, Dimension Vista 500 Intelligent Lab System, Dimension Vista 1500 Intelligent Lab System, ADVIA Centaur XP, AIA-900, AIA-360, AIA-2000, AIA-600 II, AIA-1800. Measurements of CRP, IP-10 and TRAIL can also be performed on a Luminex machine.

Lateral Flow Immunoassays (LFIA):

This is a technology which allows rapid measurement of analytes at the point of care (POC) and its underlying principles are described below. According to one embodiment, LFIA is used in the context of a hand-held device.

The technology is based on a series of capillary beds, such as pieces of porous paper or sintered polymer. Each of these elements has the capacity to transport fluid (e.g., urine) spontaneously. The first element (the sample pad) acts as a sponge and holds an excess of sample fluid. Once soaked, the fluid migrates to the second element (conjugate pad) in which the manufacturer has stored the so-called conjugate, a dried format of bio-active particles (see below) in a salt-sugar matrix that contains everything to guarantee an optimized chemical reaction between the target molecule (e.g., an antigen) and its chemical partner (e.g., antibody) that has been immobilized on the particle's surface. While the sample fluid dissolves the salt-sugar matrix, it also dissolves the particles and in one combined transport action the sample and conjugate mix while flowing through the porous structure. In this way, the analyte binds to the particles while migrating further through the third capillary bed. This material has one or more areas (often called stripes) where a third molecule has been immobilized by the manufacturer. By the time the sample-conjugate mix reaches these strips, analyte has been bound on the particle and the third 'capture' molecule binds the complex.

After a while, when more and more fluid has passed the stripes, particles accumulate and the stripe-area changes color. Typically there are at least two stripes: one (the control) that captures any particle and thereby shows that reaction conditions and technology worked fine, the second contains a specific capture molecule and only captures those particles onto which an analyte molecule has been immobilized. After passing these reaction zones the fluid enters the final porous material, the wick, that simply acts as a waste container. Lateral Flow Tests can operate as either competitive or sandwich assays.

Thus, the method of analyzing MX1 and CRP using a LFIA device can be effected as follows:

(a) contacting the fluid sample with a lateral flow test strip which comprises a conjugate pad, the conjugate pad comprising a labeled antibody against MX1 polypeptide and a labeled antibody against CRP polypeptide, wherein the contacting is effected under conditions that allow for the formation of an immunocomplex between the labeled antibody and the MX1 polypeptide of the sample; and an immunocomplex between the labeled antibody and the CRP polypeptide of the sample (b) flowing the unbound labeled antibody or immunocomplex through a test band; and (c) determining the amount of the MX1 and CRP polypeptide by analyzing the amount of either the unbound labeled antibody or the immunocomplex at the test band.

Further descriptions of LFIA devices may be found in PCT Application IL2017/050697, the contents of which are incorporated herein by reference.

Different formats may be adopted in LFIA. Strips used for LFIA contain four main components. A brief description of each is given before describing format types.

Sample Application Pad:

It is made of cellulose and/or glass fiber and sample is applied on this pad to start assay. Its function is to transport the sample to other components of lateral flow test strip (LFTS). Sample pad should be capable of transportation of the sample in a smooth, continuous and homogenous manner. Sample application pads are sometimes designed to pretreat the sample before its transportation. This pretreatment may include separation of sample components, removal of interferences, adjustment of pH, etc.

Conjugate Pad:

It is the place where labeled biorecognition molecules are dispensed. Material of conjugate pad should immediately release labeled conjugate upon contact with moving liquid sample. Labeled conjugate should stay stable over entire life span of lateral flow strip. Any variations in dispensing, drying or release of conjugate can change results of assay significantly. Poor preparation of labeled conjugate can adversely affect sensitivity of assay. Glass fiber, cellulose, polyesters and some other materials are used to make conjugate pad for LFIA. Nature of conjugate pad material has an effect on release of labeled conjugate and sensitivity of assay.

Nitrocellulose Membrane:

It is highly critical in determining sensitivity of LFIA. Nitrocellulose membranes are available in different grades. Test and control lines are drawn over this piece of membrane. So an ideal membrane should provide support and good binding to capture probes (antibodies, aptamers etc.). Nonspecific adsorption over test and control lines may affect results of assay significantly, thus a good membrane will be characterized by lesser non-specific adsorption in the regions of test and control lines. Wicking rate of nitrocellulose membrane can influence assay sensitivity. These membranes are easy to use, inexpensive, and offer high affinity for proteins and other biomolecules. Proper dispensing of bioreagents, drying and blocking play a role in improving sensitivity of assay.

Adsorbent Pad:

It works as sink at the end of the strip. It also helps in maintaining flow rate of the liquid over the membrane and stops back flow of the sample. Adsorbent capacity to hold liquid can play an important role in results of assay.

All these components are fixed or mounted over a backing card. Materials for backing card are highly flexible because they have nothing to do with LFIA except providing a platform for proper assembling of all the components. Thus backing card serves as a support and it makes easy to handle the strip.

Major steps in LFIA are (i) preparation of antibody against target analyte (ii) preparation of label (iii) labeling of biorecognition molecules (iv) assembling of all components onto a backing card after dispensing of reagents at their proper pads (v) application of sample and obtaining results.

Sandwich Format:

In a typical format, label (Enzymes or nanoparticles or fluorescence dyes) coated antibody or aptamer is immobilized at conjugate pad. This is a temporary adsorption which can be flushed away by flow of any buffer solution. A primary antibody or aptamer against target analyte is immobilized over test line. A secondary antibody or probe against labeled conjugate antibody/aptamer is immobilized at control zone.

Sample containing the analyte is applied to the sample application pad and it subsequently migrates to the other parts of strip. At conjugate pad, target analyte is captured by the immobilized labeled antibody or aptamer conjugate and results in the formation of labeled antibody conjugate/analyte complex. This complex now reaches at nitrocellulose membrane and moves under capillary action. At test line, label antibody conjugate/analyte complex is captured by another antibody which is primary to the analyte. Analyte becomes sandwiched between labeled and primary antibodies forming labeled antibody conjugate/analyte/primary antibody complex. Excess labeled antibody conjugate will be captured at control zone by secondary antibody. Buffer or excess solution goes to absorption pad. Intensity of color at test line corresponds to the amount of target analyte and is measured with an optical strip reader or visually inspected. Appearance of color at control line ensures that a strip is functioning properly.

Competitive Format:

Such a format suits best for low molecular weight compounds which cannot bind two antibodies simultaneously. Absence of color at test line is an indication for the presence of analyte while appearance of color both at test and control lines indicates a negative result. Competitive format has two layouts. In the first layout, solution containing target analyte is applied onto the sample application pad and prefixed labeled biomolecule (antibody/aptamer) conjugate gets hydrated and starts flowing with moving liquid. Test line contains pre-immobilized antigen (same analyte to be detected) which binds specifically to label conjugate. Control line contains pre-immobilized secondary antibody which has the ability to bind with labeled antibody conjugate. When liquid sample reaches at the test line, pre-immobilized antigen will bind to the labeled conjugate in case target analyte in sample solution is absent or present in such a low quantity that some sites of labeled antibody conjugate were vacant. Antigen in the sample solution and the one which is immobilized at test line of strip compete to bind with labeled conjugate. In another layout, labeled analyte conjugate is dispensed at conjugate pad while a primary antibody to analyte is dispensed at test line. After application of analyte solution a competition takes place between analyte and labeled analyte to bind with primary antibody at test line.

Multiplex Detection Format:

Multiplex detection format is used for detection of more than one target species and assay is performed over the strip containing test lines equal to number of target species to be analyzed. It is highly desirable to analyze multiple analytes simultaneously under same set of conditions. Multiplex detection format is very useful in clinical diagnosis where multiple analytes which are inter-dependent in deciding about the stage of a disease are to be detected. Lateral flow strips for this purpose can be built in various ways i.e. by increasing length and test lines on conventional strip, making other structures like stars or T-shapes. Shape of strip for LFIA will be dictated by number of target analytes. Miniaturized versions of LFIA based on microarrays for multiplex detection of DNA sequences have been reported to have several advantages such as less consumption of test reagents, requirement of lesser sample volume and better sensitivity.

Labels:

Any material that is used as a label should be detectable at very low concentrations and it should retain its properties upon conjugation with biorecognition molecules. This conjugation is also expected not to change features of biorecognition probes. Ease in conjugation with biomolecules and stability over longer period of time are desirable features for a good label. Concentrations of labels down to $10^{-9}$ M are optically detectable. After the completion of assay, some labels generate direct signal (as color from gold colloidal) while others require additional steps to produce analytical signal (as enzymes produce detectable product upon reaction with suitable substrate). Hence the labels which give direct signal are preferable in LFA because of less time consumption and reduced procedure.

Gold Nanoparticles:

Colloidal gold nanoparticles are the most commonly used labels in LFA. Colloidal gold is inert and gives very perfect spherical particles. These particles have very high affinity toward biomolecules and can be easily functionalized. Optical properties of gold nanoparticles are dependent on size and shape. Size of particles can be tuned by use of suitable chemical additives. Their unique features include environment friendly preparation, high affinity toward proteins and biomolecules, enhanced stability, exceptionally higher values for charge transfer and good optical signaling. Optical signal of gold nanoparticles in colorimetric LFA can be amplified by deposition of silver, gold nanoparticles and enzymes.

Magnetic Particles and Aggregates:

Colored magnetic particles produce color at the test line which is measured by an optical strip reader but magnetic signals coming from magnetic particles can also be used as detection signals and recorded by a magnetic assay reader. Magnetic signals are stable for longer time compared to optical signals and they enhance sensitivity of LFA by 10 to 1000 folds.

Fluorescent and Luminescent Materials:

Fluorescent molecules are widely used in LFA as labels and the amount of fluorescence is used to quantitate the concentration of analyte in the sample. Detection of proteins is accomplished by using organic fluorophores such as rhodamine as labels in LFA.

Current developments in nanomaterial have headed to manufacture of quantum dots which display very unique electrical and optical properties. These semiconducting particles are not only water soluble but can also be easily combined with biomolecules because of closeness in dimensions. Owing to their unique optical properties, quantum dots have come up as a substitute to organic fluorescent dyes. Like gold nanoparticles QDs show size dependent optical properties and a broad spectrum of wavelengths can be monitored. Single light source is sufficient to excite quantum dots of all different sizes. QDs have high photo stability and absorption coefficients.

Upconverting phosphors (UCP) are characterized by their excitation in infra-red region and emission in high energy visible region. Compared to other fluorescent materials, they have a unique advantage of not showing any auto fluorescence. Because of their excitation in IR regions, they do not photo degrade biomolecules. A major advantage lies in their production from easily available bulk materials. Although difference in batch to batch preparation of UCP reporters can affect sensitivity of analysis in LFA, it was observed that they can enhance sensitivity of analytical signal by 10 to 100 folds compared to gold nanoparticles or colored latex beads, when analysis is carried out under same set of biological conditions.

Enzymes:

Enzymes are also employed as labels in LFA. But they increase one step in LFA which is application of suitable substrate after complete assay. This substrate will produce color at test and control lines as a result of enzymatic reaction. In case of enzymes, selection of suitable enzyme substrate combination is one necessary requirement in order to get a colored product for strip reader or electroactive product for electrochemical detection. In other words, sensitivity of detection is dependent on enzyme substrate combination.

Colloidal Carbon:

Colloidal carbon is comparatively inexpensive label and its production can be easily scaled up. Because of their black color, carbon NPs can be easily detected with high sensitivity. Colloidal carbon can be functionalized with a large variety of biomolecules for detection of low and high molecular weight analytes.

Detection Systems:

In case of gold nanoparticles or other color producing labels, qualitative or semi-quantitative analysis can be done by visual inspection of colors at test and control lines. The major advantage of visual inspection is rapid qualitative answer in "Yes" or "NO". Such quick replies about presence of an analyte in clinical analysis have very high importance. Such tests help doctors to make an immediate decision near the patients in hospitals in situations where test results from central labs cannot be waited for because of huge time consumption. But for quantification, optical strip readers are employed for measurement of the intensity of colors produced at test and control lines of strip. This is achieved by inserting the strips into a strip reader and intensities are recorded simultaneously by imaging softwares. Optical images of the strips can also be recorded with a camera and then processed by using a suitable software. Procedure includes proper placement of strip under the camera and a controlled amount of light is thrown on the areas to be observed. Such systems use monochromatic light and wavelength of light can be adjusted to get a good contrast among test and control lines and background. In order to provide good quantitative and reproducible results, detection system should be sensitive to different intensities of colors. Optical standards can be used to calibrate an optical reader device. Automated systems have advantages over manual imaging and processing in terms of time consumption, interpretation of results and adjustment of variables.

In case of fluorescent labels, a fluorescence strip reader is used to record fluorescence intensity of test and control lines. Fluorescence brightness of test line increased with an increase in nitrated seruloplasmin concentration in human serum when it was detected with a fluorescence strip reader. A photoelectric sensor was also used for detection in LFIA where colloidal gold is exposed to light emitting diode and resulting photoelectrons are recorded. Chemiluminescence which results from reaction of enzyme and substrate is measured as a response to amount of target analyte. Magnetic strip readers and electrochemical detectors are also reported as detection systems in LFTS but they are not very common. Selection of detector is mainly determined by the label employed in analysis.

Immunohistochemical Analysis:

Immunoassays carried out in accordance with some embodiments of the present invention may be homogeneous assays or heterogeneous assays. In a homogeneous assay the immunological reaction usually involves the specific antibody (e.g., anti-MX1 and CRP antibody), a labeled analyte, and the sample of interest. The signal arising from the label is modified, directly or indirectly, upon the binding of the antibody to the labeled analyte. Both the immunological reaction and detection of the extent thereof can be carried out in a homogeneous solution. Immunochemical labels, which may be employed, include free radicals, radioisotopes, fluorescent dyes, enzymes, bacteriophages, or coenzymes.

In a heterogeneous assay approach, the reagents are usually the sample, the antibody, and means for producing a detectable signal. Samples as described above may be used. The antibody can be immobilized on a support, such as a bead (such as protein A and protein G agarose beads), plate or slide, and contacted with the specimen suspected of containing the antigen in a liquid phase.

According to a particular embodiment, the antibody is immobilized to a porous strip to form a detection site. The measurement or detection region of the porous strip may include a plurality of sites, one for MX1 and one for CRP. A test strip may also contain sites for negative and/or positive controls.

Alternatively, control sites can be located on a separate strip from the test strip. Optionally, the different detection sites may contain different amounts of antibodies, e.g., a higher amount in the first detection site and lesser amounts in subsequent sites. Upon the addition of test sample, the number of sites displaying a detectable signal provides a quantitative indication of the amount of polypeptides present in the sample. The detection sites may be configured in any suitably detectable shape and are typically in the shape of a bar or dot spanning the width of a test strip.

The support is then separated from the liquid phase and either the support phase or the liquid phase is examined for a detectable signal employing means for producing such signal. The signal is related to the presence of the analyte in the sample. Means for producing a detectable signal include the use of radioactive labels, fluorescent labels, or enzyme labels. For example, if the antigen to be detected contains a second binding site, an antibody which binds to that site can be conjugated to a detectable group and added to the liquid phase reaction solution before the separation step. The presence of the detectable group on the solid support indicates the presence of the antigen in the test sample. Examples of suitable immunoassays are oligonucleotides, immunoblotting, immunofluorescence methods, immunoprecipitation, chemiluminescence methods, electrochemiluminescence (ECL) or enzyme-linked immunoassays.

Those skilled in the art will be familiar with numerous specific immunoassay formats and variations thereof which may be useful for carrying out the method disclosed herein. See generally E. Maggio, Enzyme-Immunoassay, (1980) (CRC Press, Inc., Boca Raton, Fla.); see also U.S. Pat. No. 4,727,022 to Skold et al. titled "Methods for Modulating Ligand-Receptor Interactions and their Application," U.S. Pat. No. 4,659,678 to Forrest et al. titled "Immunoassay of Antigens," U.S. Pat. No. 4,376,110 to David et al., titled "Immunometric Assays Using Monoclonal Antibodies," U.S. Pat. No. 4,275,149 to Litman et al., titled "Macromolecular Environment Control in Specific Receptor Assays," U.S. Pat. No. 4,233,402 to Maggio et al., titled "Reagents and Method Employing Channeling," and U.S. Pat. No. 4,230,767 to Boguslaski et al., titled "Heterogenous Specific Binding Assay Employing a Coenzyme as Label."

Antibodies can be conjugated to a solid support suitable for a diagnostic assay (e.g., beads such as protein A or protein G agarose, microspheres, plates, slides or wells formed from materials such as latex or polystyrene) in accordance with known techniques, such as passive binding. Antibodies as described herein may likewise be conjugated to detectable labels or groups such as radiolabels (e.g., $^{35}S$, $^{125}I$, $^{131}I$) enzyme labels (e.g., horseradish peroxidase, alkaline phosphatase), and fluorescent labels (e.g., fluorescein, Alexa, green fluorescent protein, rhodamine) in accordance with known techniques.

Examples of monoclonal antibodies for measuring CRP include without limitation: Mouse, Monoclonal (108-2A2); Mouse, Monoclonal (108-7G41D2); Mouse, Monoclonal (12D-2C-36), IgG1; Mouse, Monoclonal (1G1), IgG1; Mouse, Monoclonal (5A9), IgG2a kappa; Mouse, Monoclonal (63F4), IgG1; Mouse, Monoclonal (67A1), IgG1; Mouse, Monoclonal (8B-5E), IgG1; Mouse, Monoclonal (B893M), IgG2b, lambda; Mouse, Monoclonal (C1), IgG2b; Mouse, Monoclonal (C11F2), IgG; Mouse, Monoclonal (C2), IgG1; Mouse, Monoclonal (C3), IgG1; Mouse, Monoclonal (C4), IgG1; Mouse, Monoclonal (C5), IgG2a; Mouse, Monoclonal (C6), IgG2a; Mouse, Monoclonal (C7), IgG1; Mouse, Monoclonal (CRP103), IgG2b; Mouse, Monoclonal (CRP11), IgG1; Mouse, Monoclonal (CRP135), IgG1; Mouse, Monoclonal (CRP169), IgG2a; Mouse, Monoclonal (CRP30), IgG1; Mouse, Monoclonal (CRP36), IgG2a; Rabbit, Monoclonal (EPR283Y), IgG; Mouse, Monoclonal (KT39), IgG2b; Mouse, Monoclonal (N-a), IgG1; Mouse, Monoclonal (N1G1), IgG1; Monoclonal (P5A9AT); Mouse, Monoclonal (S5G1), IgG1; Mouse, Monoclonal (SB78c), IgG1; Mouse, Monoclonal (SB78d), IgG1 and Rabbit, Monoclonal (Y284), IgG, Human C-Reactive Protein/CRP Biot MAb (Cl 232024), Mouse IgG2B, Human C-Reactive Protein/CRP MAb (Clone 232007), Mouse IgG2B, Human/Mouse/Porcine C-Reactive Protein/CRP MAb (Cl 232026), Mouse IgG2A.

Antibodies for measuring CRP include monoclonal antibodies for measuring CRP and polyclonal antibodies for measuring CRP.

Antibodies for measuring CRP also include antibodies that were developed to target epitopes from the list comprising of: Human plasma derived CRP, Human serum derived CRP, Mouse myeloma cell line NSO-derived recombinant human C-Reactive Protein/CRP (Phe17-Pro224 Accession #P02741).

As mentioned, the present invention also contemplates measuring determinants at the RNA level.

Methods of analyzing the amount of RNA are known in the art and are summarized infra:

Northern Blot Analysis:

This method involves the detection of a particular RNA in a mixture of RNAs. An RNA sample is denatured by treatment with an agent (e.g., formaldehyde) that prevents hydrogen bonding between base pairs, ensuring that all the RNA molecules have an unfolded, linear conformation. The individual RNA molecules are then separated according to size by gel electrophoresis and transferred to a nitrocellulose or a nylon-based membrane to which the denatured RNAs adhere. The membrane is then exposed to labeled DNA probes. Probes may be labeled using radio-isotopes or enzyme linked nucleotides. Detection may be using autoradiography, colorimetric reaction or chemiluminescence. This method allows both quantitation of an amount of particular RNA molecules and determination of its identity by a relative position on the membrane which is indicative of a migration distance in the gel during electrophoresis.

RT-PCR Analysis:

This method uses PCR amplification of relatively rare RNAs molecules. First, RNA molecules are purified from the cells and converted into complementary DNA (cDNA) using a reverse transcriptase enzyme (such as an MMLV-RT) and primers such as, oligo dT, random hexamers or gene specific primers. Then by applying gene specific primers and Taq DNA polymerase, a PCR amplification reaction is carried out in a PCR machine. Those of skills in the art are capable of selecting the length and sequence of the gene specific primers and the PCR conditions (i.e., annealing temperatures, number of cycles and the like) which are suitable for detecting specific RNA molecules. It will be appreciated that a semi-quantitative RT-PCR reaction can be employed by adjusting the number of PCR cycles and comparing the amplification product to known controls.

RNA In Situ Hybridization Stain:

In this method DNA or RNA probes are attached to the RNA molecules present in the cells. Generally, the cells are first fixed to microscopic slides to preserve the cellular structure and to prevent the RNA molecules from being degraded and then are subjected to hybridization buffer containing the labeled probe. The hybridization buffer includes reagents such as formamide and salts (e.g., sodium chloride and sodium citrate) which enable specific hybridization of the DNA or RNA probes with their target mRNA molecules in situ while avoiding non-specific binding of probe. Those of skills in the art are capable of adjusting the hybridization conditions (i.e., temperature, concentration of salts and formamide and the like) to specific probes and types of cells.

Following hybridization, any unbound probe is washed off and the bound probe is detected using known methods. For example, if a radio-labeled probe is used, then the slide is subjected to a photographic emulsion which reveals signals generated using radio-labeled probes; if the probe was labeled with an enzyme then the enzyme-specific substrate is added for the formation of a colorimetric reaction; if the probe is labeled using a fluorescent label, then the bound probe is revealed using a fluorescent microscope; if the probe is labeled using a tag (e.g., digoxigenin, biotin, and the like) then the bound probe can be detected following interaction with a tag-specific antibody which can be detected using known methods.

In Situ RT-PCR Stain:

This method is described in Nuovo G J, et al. [Intracellular localization of polymerase chain reaction (PCR)-amplified hepatitis C cDNA. Am J Surg Pathol. 1993, 17: 683-90] and Komminoth P, et al. [Evaluation of methods for hepatitis C virus detection in archival liver biopsies. Comparison of histology, immunohistochemistry, in situ hybridization, reverse transcriptase polymerase chain reaction (RT-PCR) and in situ RT-PCR. Pathol Res Pract. 1994, 190: 1017-25]. Briefly, the RT-PCR reaction is performed on fixed cells by incorporating labeled nucleotides to the PCR reaction. The reaction is carried on using a specific in situ RT-PCR apparatus such as the laser-capture microdissection PixCell I LCM system available from Arcturus Engineering (Mountainview, CA).

DNA Microarrays/DNA Chips:

The expression of thousands of genes may be analyzed simultaneously using DNA microarrays, allowing analysis of the complete transcriptional program of an organism during specific developmental processes or physiological responses. DNA microarrays consist of thousands of individual gene sequences attached to closely packed areas on the surface of a support such as a glass microscope slide. Various methods have been developed for preparing DNA microarrays. In one method, an approximately 1 kilobase segment of the coding region of each gene for analysis is individually PCR amplified. A robotic apparatus is employed to apply each amplified DNA sample to closely spaced zones on the surface of a glass microscope slide, which is subsequently processed by thermal and chemical treatment to bind the DNA sequences to the surface of the support and denature them.

Typically, such arrays are about 2×2 cm and contain about individual nucleic acids 6000 spots. In a variant of the technique, multiple DNA oligonucleotides, usually 20 nucleotides in length, are synthesized from an initial nucleotide that is covalently bound to the surface of a support, such that tens of thousands of identical oligonucleotides are synthesized in a small square zone on the surface of the support. Multiple oligonucleotide sequences from a single gene are synthesized in neighboring regions of the slide for analysis of expression of that gene. Hence, thousands of genes can be represented on one glass slide. Such arrays of synthetic oligonucleotides may be referred to in the art as “DNA chips”, as opposed to “DNA microarrays”, as described above [Lodish et al. (eds.). Chapter 7.8: DNA Microarrays: Analyzing Genome-Wide Expression. In: Molecular Cell Biology, 4th ed., W. H. Freeman, New York. (2000)].

Oligonucleotide Microarray—

In this method oligonucleotide probes capable of specifically hybridizing with the polynucleotides of some embodiments of the invention are attached to a solid surface (e.g., a glass wafer). Each oligonucleotide probe is of approximately 20-25 nucleic acids in length. To detect the expression pattern of the polynucleotides of some embodiments of the invention in a specific cell sample (e.g., blood cells), RNA is extracted from the cell sample using methods known in the art (using e.g., a TRIZOL solution, Gibco BRL, USA). Hybridization can take place using either labeled oligonucleotide probes (e.g., 5'-biotinylated probes) or labeled fragments of complementary DNA (cDNA) or RNA (cRNA). Briefly, double stranded cDNA is prepared from the RNA using reverse transcriptase (RT) (e.g., Superscript II RT), DNA ligase and DNA polymerase I, all according to manufacturer's instructions (Invitrogen Life Technologies, Frederick, Maryland., USA). To prepare labeled cRNA, the double stranded cDNA is subjected to an in vitro transcription reaction in the presence of biotinylated nucleotides using e.g., the BioArray High Yield RNA Transcript Labeling Kit (Enzo, Diagnostics, Affymetix Santa Clara CA). For efficient hybridization the labeled cRNA can be fragmented by incubating the RNA in 40 mM Tris Acetate (pH 8.1), 100 mM potassium acetate and 30 mM magnesium acetate for 35 minutes at 94° C. Following hybridization, the microarray is washed and the hybridization signal is scanned using a confocal laser fluorescence scanner which measures fluorescence intensity emitted by the labeled cRNA bound to the probe arrays.

For example, in the Affymetrix microarray (Affymetrix®, Santa Clara, CA) each gene on the array is represented by a series of different oligonucleotide probes, of which, each probe pair consists of a perfect match oligonucleotide and a mismatch oligonucleotide. While the perfect match probe has a sequence exactly complimentary to the particular gene, thus enabling the measurement of the level of expression of the particular gene, the mismatch probe differs from the perfect match probe by a single base substitution at the center base position. The hybridization signal is scanned using the Agilent scanner, and the Microarray Suite software subtracts the non-specific signal resulting from the mismatch probe from the signal resulting from the perfect match probe.

RNA Sequencing:

Methods for RNA sequence determination are generally known to the person skilled in the art. Preferred sequencing methods are next generation sequencing methods or parallel high throughput sequencing methods. An example of an envisaged sequence method is pyrosequencing, in particular 454 pyrosequencing, e.g. based on the Roche 454 Genome Sequencer. This method amplifies DNA inside water droplets in an oil solution with each droplet containing a single DNA template attached to a single primer-coated bead that then forms a clonal colony. Pyrosequencing uses luciferase to generate light for detection of the individual nucleotides added to the nascent DNA, and the combined data are used to generate sequence read-outs. Yet another envisaged example is Illumina or Solexa sequencing, e.g. by using the Illumina Genome Analyzer technology, which is based on reversible dye-terminators. DNA molecules are typically attached to primers on a slide and amplified so that local clonal colonies are formed. Subsequently one type of nucleotide at a time may be added, and non-incorporated nucleotides are washed away.

Subsequently, images of the fluorescently labeled nucleotides may be taken and the dye is chemically removed from the DNA, allowing a next cycle. Yet another example is the use of Applied Biosystems' SOLiD technology, which employs sequencing by ligation. This method is based on the use of a pool of all possible oligonucleotides of a fixed length, which are labeled according to the sequenced position. Such oligonucleotides are annealed and ligated. Subsequently, the preferential ligation by DNA ligase for matching sequences typically results in a signal informative of the nucleotide at that position. Since the DNA is typically amplified by emulsion PCR, the resulting bead, each containing only copies of the same DNA molecule, can be deposited on a glass slide resulting in sequences of quantities and lengths comparable to Illumina sequencing. A further method is based on Helicos' Heliscope technology, wherein fragments are captured by polyT oligomers tethered to an array. At each sequencing cycle, polymerase and single fluorescently labeled nucleotides are added and the array is imaged. The fluorescent tag is subsequently removed and the cycle is repeated. Further examples of sequencing techniques encompassed within the methods of the present invention are sequencing by hybridization, sequencing by use of nanopores, microscopy-based sequencing techniques, microfluidic Sanger sequencing, or microchip-based sequencing methods. The present invention also envisages further developments of these techniques, e.g. further improvements of the accuracy of the sequence determination, or the time needed for the determination of the genomic sequence of an organism etc.

According to one embodiment, the sequencing method comprises deep sequencing.

As used herein, the term "deep sequencing" refers to a sequencing method wherein the target sequence is read multiple times in the single test. A single deep sequencing run is composed of a multitude of sequencing reactions run on the same target sequence and each, generating independent sequence readout.

It will be appreciated that the expression level of the determinants described herein can be an absolute expression level, a normalized expression and/or a relative expression level.

In general scientific context, normalization is a process by which a measurement raw data is converted into data that may be directly compared with other so normalized data. In the context of the present invention, measurements of expression levels are prone to errors caused by, for example, unequal degradation of measured samples, different loaded quantities per assay, and other various errors. More specifically, any assayed sample may contain more or less biological material than is intended, due to human error and equipment failures. Thus, the same error or deviation applies to both the polypeptide of the invention and to the control reference, whose expression is essentially constant. Thus, division of MX1 or CRP raw expression value by the control reference raw expression value yields a quotient which is essentially free from any technical failures or inaccuracies (except for major errors which destroy the sample for testing purposes) and constitutes a normalized expression value of the polypeptide. Since control reference expression values are equal in different samples, they constitute a common reference point that is valid for such normalization.

According to a particular embodiment, each of the polypeptide expression values are normalized using the same control reference.

Once the tests are carried out to determine the level of the determinants, a subject specific dataset is optionally generated which contains the results of the measurements.

The subject-specific dataset may be stored in a computer readable format on a non-volatile computer readable medium, and is optionally and preferably accessed by a hardware processor, such as a general purpose computer or dedicated circuitry.

As mentioned, the levels of the determinants (e.g. polypeptides) in the test subjects blood are compared to the levels of the identical polypeptides in a plurality of subjects' blood, when the subjects have already been verified as having a bacterial infection, viral infection or non-bacterial/non-viral disease on the basis of parameters other than the blood level of the polypeptides. The levels of the polypeptides of the plurality of subjects together with their verified diagnosis can be stored in a second dataset, also referred to herein as the "group dataset" or "prediagnosed dataset", as further described herein below.

The phrase "non-bacterial/non-viral disease" refers to disease that is not caused by a bacteria or virus. This includes diseases such as acute myocardial infarction, physical injury, epileptic attack, inflammatory disorders etc, fungal diseases, parasitic diseases etc.

The phrase "viral infection" as used herein refers to a disease that is caused by a virus and does not comprise a bacterial component.

Methods of analyzing a dataset, for example, for the purpose of calculating one or more probabilistic classification function representing the likelihood that a particular subject has a bacterial infection, or the likelihood that a particular subject has a viral infection or the likelihood that a particular subject has a non-bacterial non-viral disease, may be performed as described in the Examples section below.

For example, diagnosis may be supported using PCR diagnostic assays such as (i) Seeplex® RV15 for detection of parainfluenza virus 1, 2, 3, and 4, coronavirus 229E/NL63, adenovirus A/B/C/D/E, bocavirus 1/2/3/4, influenza virus A and B, metapneumovirus, coronavirus OC43, rhinovirus A/B/C, respiratory syncytial virus A and B, and Enterovirus, or (ii) Seeplex® PB6 for detection of *Streptococcus pneumoniae, Haemophilus influenzae, Chlamydophila pneumoniae, Legionella pneumophila, Bordetella pertussis*, and *Mycoplasma pneumoniae.*

Blood cultures, urine cultures and stool cultures may be analyzed for *Shigella* spp., *Campylobacter* spp. and *Salmonella* spp.; serological testing (IgM and/or IgG) for cytomegalovirus (CMV), Epstein-Barr virus (EBV), *Mycoplasma* Pneumonia, and *Coxiella burnetii* (Q-Fever).

Radiological tests (e.g. chest X-ray for suspected lower respiratory tract infection [LRTI]) may be used to confirm chest infections.

Alternatively, or additionally at least one trained physician may be used to establish the diagnosis.

Methods of determining the expression level of the polypeptides in the pre-diagnosed subjects have been described herein above.

Preferably, the same method which is used for determining the expression level of the polypeptides in the pre-diagnosed subjects is used for determining the level of the polypeptides in the test subject. Thus, for example if an immunoassay type method is used for determining the expression level of the polypeptides in the pre-diagnosed subjects, then an immunoassay type method should be used for determining the level of the polypeptides in the test subject.

It will be appreciated that, the type of blood sample need not be identical in the test subject and the pre-diagnosed subjects. Thus, for example, if a serum sample is used for determining the expression level of the polypeptides in the pre-diagnosed subjects, then a plasma sample may be used for determining the level of the polypeptides in the test subject.

The additional dimensions of the datasets provides additional information pertaining to the subject under analysis, to the other subjects and/or to levels of polypeptides other than CRP and MX1.

"Traditional laboratory risk factors" also referred to as "clinical data" encompass biomarkers isolated or derived from subject samples and which are currently evaluated in the clinical laboratory and used in traditional global risk assessment algorithms. Examples of same are provided herein above.

Preferably, at least one of the traditional laboratory risk factors of the subject under analysis is included in the subject specific dataset, and at least one of the traditional laboratory risk factors of one or more (more preferably all) of the other subjects is included in the group dataset. When the subject specific dataset includes at least one of the traditional laboratory risk factors, the risk factors can be included as a separate entry. When the group dataset includes the risk factors, the risk factors is optionally and preferably included per subject. Thus, for example, a group dataset entry can be described by the tuple (S, G, D, L {R}), where S, G, D and L have been introduced before and {R} is the at least one risk factor of subject S.

"Clinical parameters" encompass all non-sample or non-analyte biomarkers of subject health status or other characteristics, such as, without limitation, age (Age), ethnicity (RACE), gender (Sex), core body temperature (abbreviated "temperature"), maximal core body temperature since initial appearance of symptoms (abbreviated "maximal temperature"), time from initial appearance of symptoms (abbreviated "time from symptoms"), pregnancy, or family history (abbreviated FamHX).

Preferably, at least one of the clinical parameters of the subject under analysis is included in the subject specific dataset, and at least one of the clinical parameters of one or more (more preferably all) of the other subjects is included in the group dataset. When the subject specific dataset includes at least one of the clinical parameters, the clinical parameters can be included as a separate entry. When the group dataset includes the clinical parameters, the clinical parameters is optionally and preferably included per subject. Thus, for example, a group dataset entry can be described by the tuple (S, G, D, L {C}), where S, G, D and L have been introduced before and {C} is the clinical parameter of subject S.

As used herein "blood chemistry" refers to the concentration, or concentrations, of any and all substances dissolved in, or comprising, the blood. Representative examples of such substances, include, without limitation, albumin, amylase, alkaline phosphatase, bicarbonate, total bilirubin, BUN, C-reactive protein, calcium, chloride, LDL, HDL, total cholesterol, creatinine, CPK, γ-GT, glucose, LDH, inorganic phosphorus, lipase, potassium, total protein, AST, ALT, sodium, triglycerides, uric acid and VLDL.

Once the diagnosis has been made, it will be appreciated that a number of actions may be taken.

Thus, for example, if a bacterial infection is ruled in, then the subject may be treated with an antibiotic agent.

Examples of antibiotic agents include, but are not limited to Daptomycin; Gemifloxacin; Telavancin; Ceftaroline; Fidaxomicin; Amoxicillin; Ampicillin; Bacampicillin; Carbenicillin; Cloxacillin; Dicloxacillin; Flucloxacillin; Mezlocillin; Nafcillin; Oxacillin; Penicillin G; Penicillin V; Piperacillin; Pivampicillin; Pivmecillinam; Ticarcillin; Aztreonam; Imipenem; Doripenem; Meropenem; Ertapenem; Clindamycin; Lincomycin; Pristinamycin; Quinupristin; Cefacetrile (cephacetrile); Cefadroxil (cefadroxyl); Cefalexin (cephalexin); Cefaloglycin (cephaloglycin); Cefalonium (cephalonium); Cefaloridine (cephaloradine); Cefalotin (cephalothin); Cefapirin (cephapirin); Cefatrizine; Cefazaflur; Cefazedone; Cefazolin (cephazolin); Cefradine (cephradine); Cefroxadine; Ceftezole; Cefaclor; Cefamandole; Cefmetazole; Cefonicid; Cefotetan; Cefoxitin; Cefprozil (cefproxil); Cefuroxime; Cefuzonam; Cefcapene; Cefdaloxime; Cefdinir; Cefditoren; Cefetamet; Cefixime; Cefmenoxime; Cefodizime; Cefotaxime; Cefpimizole; Cefpodoxime; Cefteram; Ceftibuten; Ceftiofur; Ceftiolene; Ceftizoxime; Ceftriaxone; Cefoperazone; Ceftazidime; Cefclidine; Cefepime; Cefluprenam; Cefoselis; Cefozopran; Cefpirome; Cefquinome; Fifth Generation; Ceftobiprole; Ceftaroline; Not Classified; Cefaclomezine; Cefaloram; Cefaparole; Cefcanel; Cefedrolor; Cefempidone; Cefetrizole; Cefivitril; Cefmatilen; Cefmepidium; Cefovecin; Cefoxazole; Cefrotil; Cefsumide; Cefuracetime; Ceftioxide; Azithromycin; Erythromycin; Clarithromycin; Dirithromycin; Roxithromycin; Telithromycin; Amikacin; Gentamicin; Kanamycin; Neomycin; Netilmicin; Paromomycin; Streptomycin; Tobramycin; Flumequine; Nalidixic acid; Oxolinic acid; Piromidic acid; Pipemidic acid; Rosoxacin; Ciprofloxacin; Enoxacin; Lomefloxacin; Nadifloxacin; Norfloxacin; Ofloxacin; Pefloxacin; Rufloxacin; Balofloxacin; Gatifloxacin; Grepafloxacin; Levofloxacin; Moxifloxacin; Pazufloxacin; Sparfloxacin; Temafloxacin; Tosufloxacin; Besifloxacin; Clinafloxacin; Gemifloxacin; Sitafloxacin; Troyafloxacin; Prulifloxacin; Sulfamethizole; Sulfamethoxazole; Sulfisoxazole; Trimethoprim-Sulfamethoxazole; Demeclocycline; Doxycycline; Minocycline; Oxytetracycline; Tetracycline; Tigecycline; Chloramphenicol; Metronidazole; Tinidazole; Nitrofurantoin; Vancomycin; Teicoplanin; Telavancin; Linezolid; Cycloserine 2; Rifampin; Rifabutin; Rifapentine; Bacitracin; Polymyxin B; Viomycin; Capreomycin.

If a viral infection is ruled in, the subject may be treated with an antiviral agent. Examples of antiviral agents include, but are not limited to Abacavir; Aciclovir; Acyclovir; Adefovir; Amantadine; Amprenavir; Ampligen; Arbidol; Atazanavir; Atripla; Balavir; Boceprevirertet; Cidofovir; Combivir; Dolutegravir; Darunavir; Delavirdine; Didanosine; Docosanol; Edoxudine; Efavirenz; Emtricitabine; Enfuvirtide; Entecavir; Ecoliever; Famciclovir; Fomivirsen; Fosamprenavir; Foscarnet; Fosfonet; Fusion inhibitor; Ganciclovir; Ibacitabine; Imunovir; Idoxuridine; Imiquimod; Indinavir; Inosine; Integrase inhibitor; Interferon type III; Interferon type II; Interferon type I; Interferon; Lamivudine; Lopinavir; Loviride; Maraviroc; Moroxydine; Methisazone; Nelfinavir; Nevirapine; Nexavir; Oseltamivir; Peginterferon alfa-2a; Penciclovir; Peramivir; Pleconaril; Podophyllotoxin; Raltegravir; Reverse transcriptase inhibitor; Ribavirin; Rimantadine; Ritonavir; Pyramidine; Saquinavir; Sofosbuvir; StavudineTelaprevir; Tenofovir; Tenofovir disoproxil; Tipranavir; Trifluridine; Trizivir; Tromantadine; Truvada; traporved; Valaciclovir; Valganciclovir; Vicriviroc; Vidarabine; Viramidine; Zalcitabine; Zanamivir; Zidovudine; RNAi antivirals; inhaled rhibovirons; monoclonal antibody respigams; neuriminidase blocking agents.

The information gleaned using the methods described herein may aid in additional patient management options.

For example, the information may be used for determining whether a patient should or should not be admitted to hospital. It may also affect whether or not to prolong hospitalization duration. It may also affect the decision whether additional tests need to be performed or may save performing unnecessary tests such as CT and/or X-rays and/or MRI and/or culture and/or serology and/or PCR assay for specific bacteria and/or PCR assays for viruses and/or perform procedures such as lumbar puncture.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, MD (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, CT (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, CA (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Host-Response Proteins can Distinguish Between Acute Bacterial and Viral Infections Patients were recruited as part of a multi-center, observational, prospective clinical study with the aim to develop and test a host proteins-signature for the purpose of rapid and accurate diagnosis of patients with viral and bacterial diseases.

Methods

Patient Recruitment

A total of 253 patients were recruited of whom 224 had a suspected infectious disease and 29 had a non-infectious disease (control group). Informed consent was obtained from each participant or legal guardian, as applicable. Inclusion criteria for the infectious disease cohort included:

clinical suspicion of an acute infectious disease, peak fever >37.5° C. since symptoms onset, and duration of symptoms ≤12 days. Inclusion criteria for the control group included: clinical impression of a non-infectious disease (e.g. trauma, stroke and myocardial infarction), or healthy subjects. Exclusion criteria included: evidence of any episode of acute infectious disease in the two weeks preceding enrollment; diagnosed congenital immune deficiency; current treatment with immunosuppressive or immunomodulatory therapy; active malignancy, proven or suspected human immunodeficiency virus (HIV)-1, hepatitis B virus (HBV), or hepatitis C virus (HCV) infection. In order to enable broad generalization, antibiotic treatment at enrollment did not cause exclusion from the study. An overview of study workflow is depicted in FIG. 1.

Enrollment Process and Data Collection

For each patient, the following baseline variables were recorded: demographics, physical examination, medical history (e.g. main complaints, underlying diseases, chronically-administered medications, comorbidities, time of symptom onset, and peak temperature), complete blood count (CBC) obtained at enrollment, and chemistry panel (e.g. creatinine, urea, electrolytes, and liver enzymes). A nasal swab was obtained from each patient for further microbiological investigation, and a blood sample was obtained for protein screening and validation. Additional samples were obtained as deemed appropriate by the physician (e.g. urine and stool samples in cases of suspected urinary tract infection [UTI], and gastroenteritis [GI] respectively). Radiological tests were obtained at the discretion of the physician (e.g. chest X-ray for suspected lower respiratory tract infection [LRTI]). All information was recorded in a custom electronic case report form (eCRF).

Establishing the Reference Standard

Currently, no single reference standard exists for determining bacterial and viral infections in a wide range of clinical syndromes. Therefore, a rigorous reference standard was created following recommendations of the Standards for Reporting of Diagnostic Accuracy (STARD) (Bossuyt et al. 2003). First, a thorough clinical and microbiological investigation was performed for each patient as described above. Then, all the data collected throughout the disease course was reviewed by a panel of up to three physicians that assigned one of the following diagnostic labels to each patient: (i) bacterial; (ii) viral; (iii) no apparent infectious disease or healthy (controls); and (iv) indeterminate. The panel members were blinded to the labeling of their peers to prevent group pressure or influential personality bias as recommended by NHS-HTA (Rutjes et al. 2007), and to the results of the host-proteins measurements.

Samples, Procedures and Sample Processing

Whole blood was fractionated to cellular and serum fractions and subsequently treated with red blood cell lysing buffer (BD Bioscience). White blood cells were subsequently washed three times with phosphate buffered saline pH 7.3. CRP was measured from serum using either Cobas-6000, Cobas-Integra-400/800, or Modular-Analytics-P800 (Roche). For measuring MX1, cells were first fixed and permeabilized with fixation and permeabilization buffer kit (eBioscience). Following fixation and permeabilization cells were incubated with primary antibodies for 40 minutes, washed twice and incubated with PE conjugated secondary antibody for additional 20 minutes. IgG Isotype controls were used for each mode of staining as negative control background. Following the staining procedure, cells were analyzed by using an LSRII flow cytometer. Granulocytes, monocytes and lymphocytes were distinguished from each other by using an SSC/FSC dot plot. Background and specific staining were determined for lymphocytes, monocytes and granulocytes for each specific antigen. Total leukocytes mean levels was computed by summing the DETERMINANT polypeptides levels of all the cell types and dividing by the white blood count. Nasal swabs and stool samples were stored at 4° C. for up to 72 hours and subsequently transported to a certified service laboratory for multiplex PCRs.

Statistical Analysis

Primary analysis was based on area under the receiver operating curve (AUC), Matthews correlation coefficient (MCC), sensitivity, specificity, total accuracy. positive predictive value (PPV), and negative predictive value (NPV). These measures are defined as follows:

$$\text{Sensitivity} = \frac{TP}{TP + FN}$$

$$\text{Specificity} = \frac{TN}{TN + FP}$$

$$\text{total accuracy} = \frac{TP + TN}{TP + FN + TN + FP}$$

$$PPV = \frac{TP}{TP + FP} = \frac{\text{sensitivity} \cdot \text{prevalence}}{\text{sensitivity} \cdot \text{prevalence} + (1 - \text{specificity}) \cdot (1 - \text{prevalence})}$$

$$NPV = \frac{TN}{TN + FN} = \frac{\text{specificity} \cdot (1 - \text{prevalence})}{\text{specificity} \cdot (1 - \text{prevalence}) + (1 - \text{sensitivity}) \cdot (\text{prevalence})}$$

$$MCC = \frac{TP \times TN - FP \times FN}{\sqrt{(TP + FP)(TP + FN)(TN + FP)(TN + FN)}}$$

P, N, TP, FP, TN, FN are positives, negatives, true-positives, false-positives, true-negatives, and false-negatives, respectively. Unless mentioned otherwise, positives and negatives refer to patients with bacterial and viral infections, respectively.

Results

Patients Characteristics

The studied group of acute infection patients included 119 females (53%) and 105 males (47%) aged 3 months to 79 years. The patients presented with a variety of clinical syndromes affecting different physiological systems (e.g., respiratory, urinal, central nervous system, systemic). Detailed characterization of studied patients is depicted in FIGS. 2A-7.

Using Statistical Classification for Combining CRP and MX1 for Diagnosis of Acute Infection Patients C-reactive protein (CRP) is an acute-phase protein with normal serum concentrations of less than 3 mg/L that increases during inflammation or response to infection. It is routinely used to support diagnosis of patients with suspicion of acute infection. However, CRP is sensitive to inter-patient variability, including time from symptom onset, clinical syndrome, and pathogen species (Oved et al. 2015). For example, elevated CRP levels are suggestive of a bacterial infection (Woodhead et al. 2011), but similar levels may be observed in patients with some viral strains (e.g., adenovirus and influenza) (Kunze, Beier, and Groeger 2010), and inflammatory diseases. MX1 (MX Dynamin-Like GTPase 1) is a protein coding gene that participates in the cellular antiviral response, and therefore might prove useful in distinguishing between bacterial and viral patients. As CRP is mostly bacterially induced and MX1 is mostly virally induced, their combination might be superior compared to the individual proteins. However, there are various ways (and formulations) to combine CRP and MX1 and not all provide significant added value. For example, FIG. 8A is a graph demonstrating separation between two variables, using defined biomarker cutoff (one for CRP and one for MX1). As shown, this generates a quadrary separation pattern that is less preferred for separating between closely related data sets (FIG. 8A).

Figure 8B:
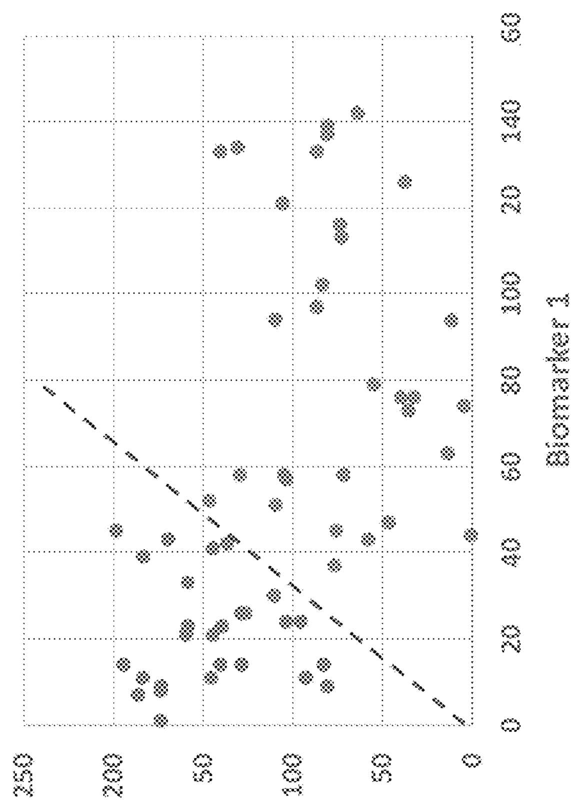
FIGS. 8A and 8B are graphs demonstrating separation between two variables, using defined biomarker cutoff (FIG. 8A), and using a cutoff independent model (FIG. 8B)
Figure 8A:
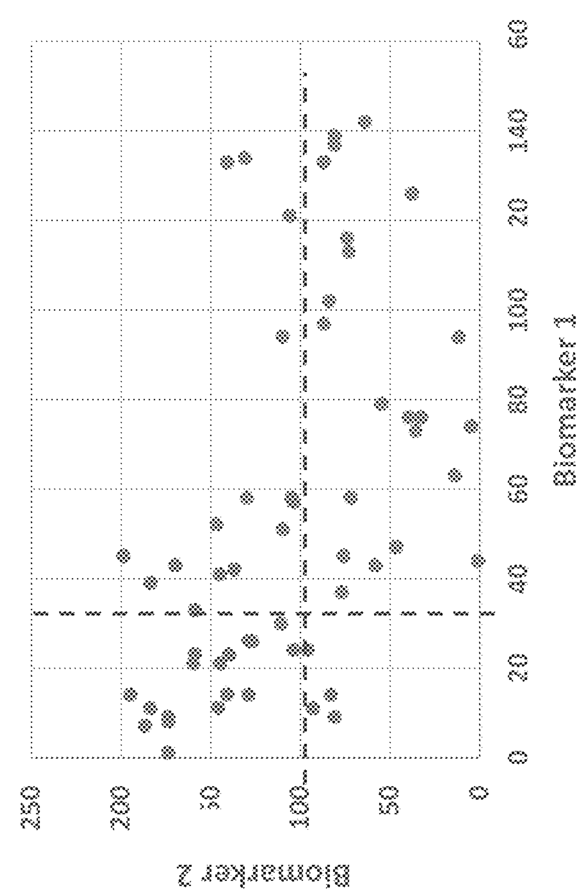

FIG. 8B is a graph demonstrating separation between two variables using a cutoff independent model. The graph demonstrates that the use of statistical classification techniques can generate various unique separation hyperplanes that distinguish between two groups of patients with higher levels of accuracy.

The present inventors discovered that cutoff independent models (generated for example using statistical classification techniques) can provide a likelihood score (e.g., 90% chance for bacterial infection) compared to a binary result (bacterial or viral result only) obtained using defined cutoffs and a quadrary separation pattern. Thus, it can provide additional clinical information that can guide correct patient management. To this end, the present inventors have developed statistical classification techniques that combine MX1 and CRP in order to distinguish between bacterial and viral and between infectious and non-infectious patients. To integrate the two protein levels into a single predictive score, multiple computational models including Artificial Neural Networks (ANN), Support Vector Machines (SVM), Bayesian Networks (BN), K-Nearest Neighbor (KNN) and Logistic Regression were examined. While any of these models (or similar) can be used, the results presented herein as an example were generated using Logistic Regression. The inventors further evaluated the performance (accuracy levels) of the developed models using real world infectious disease clinical samples in different indications and subgroups as described below. For each of the developed models, the inventors provide a set of quantitative parameters (model coefficients) that specifically define the hyperplane separating between two patient groups. Finally, they compare the logistic regression models to models based on CRP routinely used cutoffs (20 μg/ml, 65 μg/ml, 80 μg/ml).

Distinguishing Between Bacterial (or Mixed) and Viral Patients

CRP and MX1 were measured in serum samples obtained from 117 bacterial patients and 107 viral patients described above.

Figure 9A:
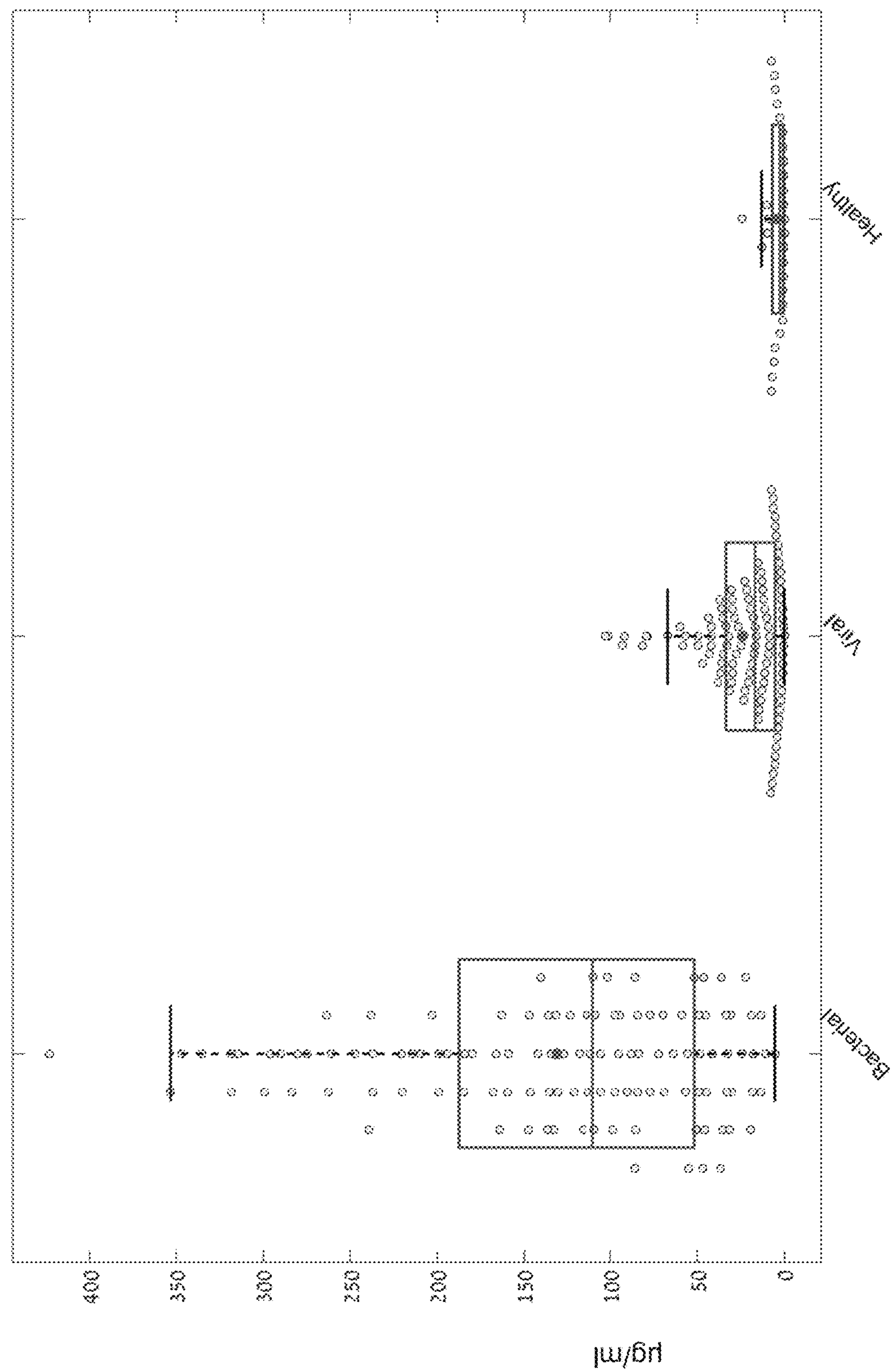
FIG. 9A shows CRP serum levels of patients with bacterial infection (n=117), viral infection (n=107), and non-infectious controls (n=29)
Figure 9B:
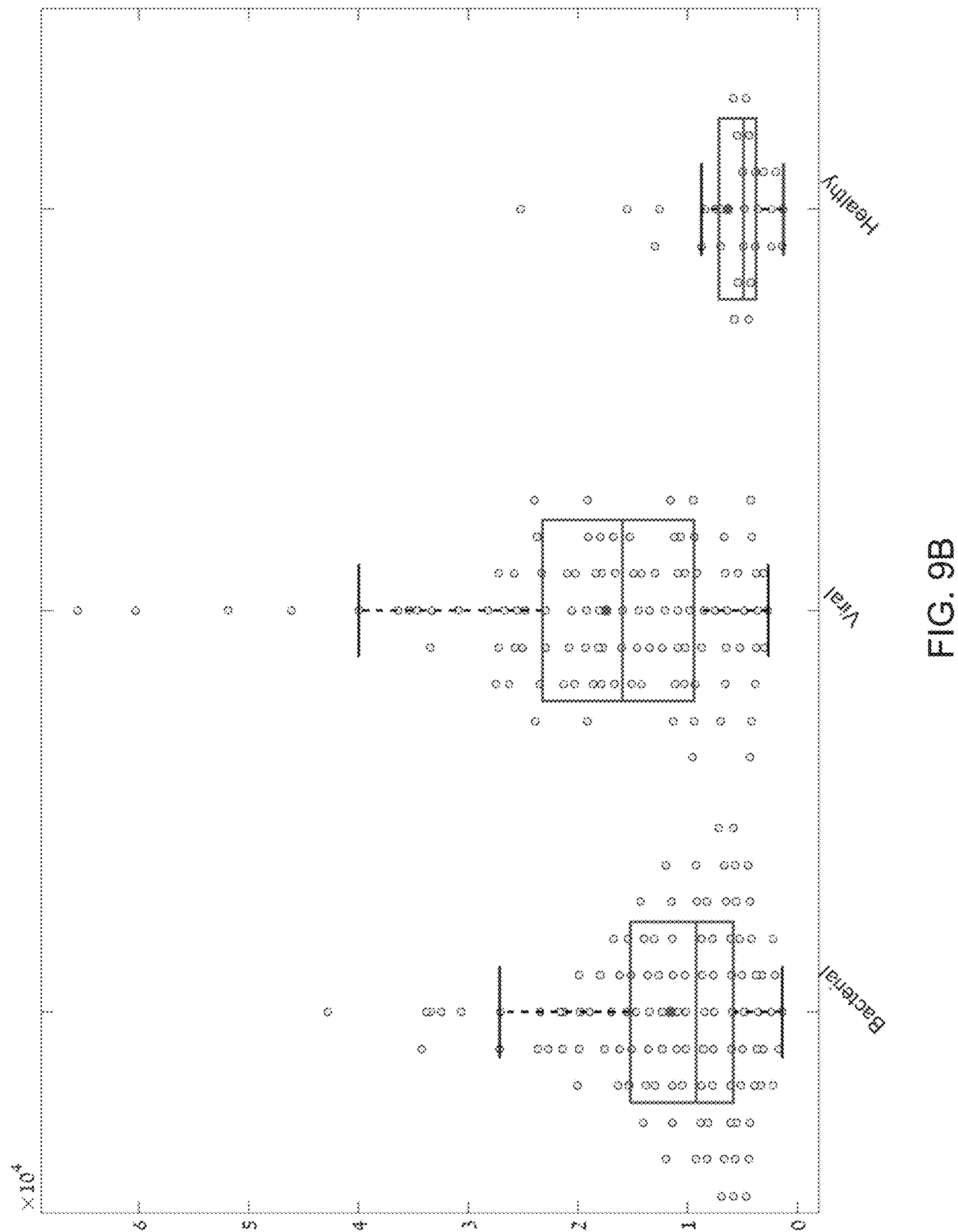
FIG. 9B shows MX1 levels (measured using flow cytometry) of patients with bacterial infection (n=117), viral infection (n=107), and non-infectious controls (n=29)
Figure 9C:
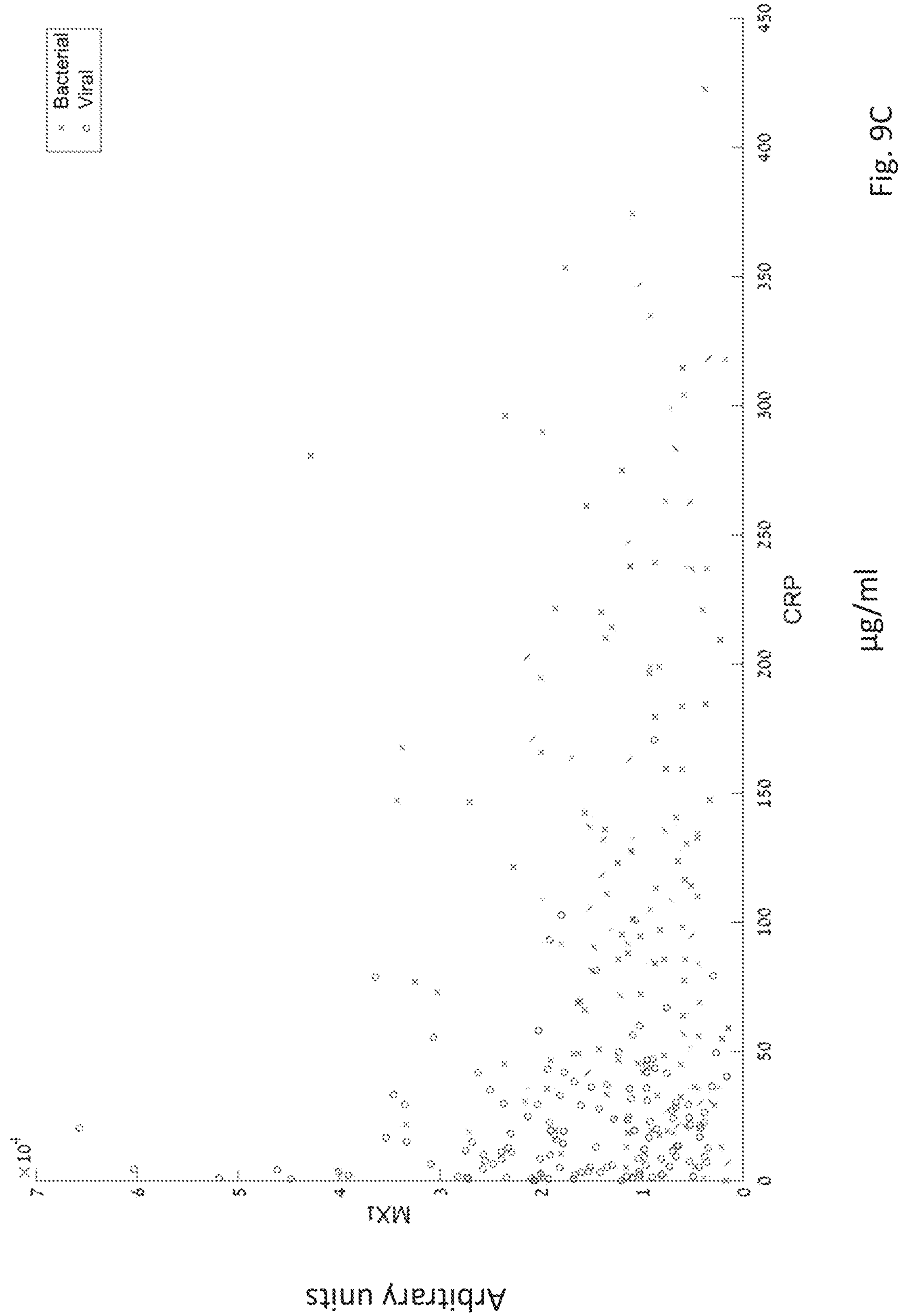
FIG. 9C shows MX1 levels (measured using flow cytometry) and CRP serum levels of patients with bacterial infection (n=117), viral infection (n=107), and non-infectious controls (n=29)

FIGS. 9A-C demonstrate that combination of CRP and MX1 can assist in correct diagnosis of acute infection patients (MX1 measured using flow cytometry). FIG. 9A shows CRP levels in bacterial patients (n=117), viral patients (n=107), and non-infectious controls (n=29). For bacterial patients, the median of bacterial and viral infected patients (hereinafter "Med") is 110, the mean value (hereinafter "Mean") is 131.3085±93.4679, and the Wilcoxon ranksum P-value (hereinafter "RS p") is 2.5925e-32; for viral patients Med=16.7, Mean=23.5486±23.6717 and RS p-4.4137e-13; and for non-infectious controls Med-2.6, Mean-4.3655±5.3591, and RS p=3.1099e-13. FIG. 9B shows MX1 levels (in arbitrary units as measured using flow cytometry) in bacterial patients (n=117), viral patients (n=107), and non-infectious controls (n=29). For bacterial patients, Med=9195.3642, Mean=11583.0953±7965.0999, and RS p=0.027717; for viral patients, Med=15913.898, Mean=17379.1886±11551.3714, and RS p=3.2165e-08 (Viral); and for non-infectious controls, Med=4933, Mean=6338.5428±4958.4454, and RS p=2.9285e-7. FIG. 9C shows CRP and MX1 levels in bacterial (crosses; n=117) and viral patients (open circles; n=107).

Based on these measurements, a classifier was developed for distinguishing between bacterial (or mixed) and viral patients using logistic regression (logistic regression coefficients are: constant=−1.54, CRP=0.04 μg/ml, MX1=−5.25E-05). It was further calculated for these determinants the measures of accuracy in distinguishing between bacterial and viral patients including AUC, MCC, total accuracy, sensitivity, specificity, PPV and NPV (Tables 1.1A-C). The MX1 and CRP combination was very accurate with AUC of 0.92 and sensitivity and specificity of 0.85 and 0.84 respectively.

Distinguishing Between Infectious and Non-Infectious Patients

CRP and MX1 were measured in serum samples obtained from 224 infectious patients (bacterial and viral) and 29 non-infectious controls patients described above (FIGS. 9A-B). Based on these measurements, a classifier was developed for distinguishing between infectious and non-infectious patients using logistic regression (logistic regression coefficients are: constant=−2.70, CRP=0.18 μg/ml, MX1=0.00023). It was further calculated for these determinants the measures of accuracy in distinguishing between bacterial and viral patients including AUC, MCC, total accuracy, sensitivity, specificity, PPV and NPV (Tables 1.1A-B). The MX1 and CRP combination was very accurate with AUC of 0.96 and sensitivity and specificity of 0.9.

Distinguishing Between Bacterial (or Mixed) and Viral Patients Presenting with Specific Clinical Syndromes Patients were stratified according to their clinical syndromes and a classifier was developed for distinguishing between bacterial (or mixed) and viral patients for each of the underlying syndromes using logistic regression. It was further calculated for these determinants the measures of accuracy in distinguishing between bacterial and viral patients including AUC, MCC, total accuracy, sensitivity, specificity, PPV and NPV (Tables 1.1A-C). Although the AUC was high across syndromes (0.91-0.98), the sensitivity and specificity of the combined CRP-MX1 classifiers varied between clinical syndromes (0.71-0.89 and 0.79-0.97 respectively; Tables 1.1A-C). Thus, information regarding the underlying clinical syndrome of the patient can be integrated with CRP-MX1 classifiers predicted outcome in order to improve patient diagnosis.

Distinguishing Between Bacterial (or Mixed) and Viral Patients Presenting with Specific Pathogens Patients were stratified according to the bacteria or virus isolated during patient characterization and a classifier was developed for distinguishing between bacterial (or mixed) and viral patients for each of the underlying pathogens using logistic regression. It was further calculated for these determinants the measures of accuracy in distinguishing between bacterial and viral patients including AUC, MCC, total accuracy, sensitivity, specificity, PPV and NPV (Tables 1.1A-B). Although the AUC was high across syndromes (0.84-1.0), the sensitivity and specificity of the combined CRP-MX1 classifiers varied between clinical syndromes (0.7-1.0 and 0.67-1.0 respectively; Tables 1.1A-C). Thus, information regarding the underlying pathogen or updated epidemiological data can be integrated with CRP-MX1 classifiers predicted outcome in order to improve interpretation of microbiological results and patient diagnosis.

Distinguishing Between Bacterial (or Mixed) and Viral Patients Presenting with Different Background Conditions (Comorbidities)

Patients were stratified according to their background conditions (diabetes and chronic lung disease) and a classifier was developed for distinguishing between bacterial (or mixed) and viral patients for each of the underlying syndromes using logistic regression. It was further calculated for these determinants the measures of accuracy in distinguishing between bacterial and viral patients including AUC, MCC, total accuracy, sensitivity, specificity, PPV and NPV (Tables 1.1A-C). The models presented higher sensitivity but lower specificity in patients with chronic lung diseases compared to patients with diabetes (sensitivity: 0.93 compared to 0.7; specificity: 0.83 compared to 1.00 respectively; Tables 1.1A-C, below). Thus, information regarding the patient background clinical conditions could potentially be integrated with CRP-MX1 classifiers predicted outcome in order to improve patient diagnosis.

Tables 1.1A-C detail logistic regression models combining MX1 and CRP in cutoff independent manner and their measures of accuracy in various indications and sub-groups. In the tables, B stands for bacterial patients; V stands for viral patients; LRTI stands for low respiratory tract infection; URTI stands for upper respiratory tract infection; SBI stands for serious bacterial infection; RSV stands for Respiratory syncytial virus. Atypical bacteria include *Chlamydophila pneumoniae, Mycoplasma pneumoniae* and *Legionella pneumophila*; GI (gastrointestinal) viruses include Rota Virus, Astrovirus, Enteric Adenovirus, Norovirus G I and G II.

TABLE 1.1A

| | AUC | MCC | Total accuracy | Sensitivity | Specificity |
|---|---|---|---|---|---|
| Bacterial vs Viral | 0.92 | 0.65 | 0.84 | 0.85 | 0.84 |
| Infectious vs Non-infectious | 0.96 | 0.59 | 0.90 | 0.90 | 0.90 |
| Syndrome | | | | | |
| LRTI | 0.97 | 0.70 | 0.88 | 0.87 | 0.91 |
| URTI | 0.91 | 0.56 | 0.83 | 0.89 | 0.79 |
| Fever Without Source | 0.98 | 0.58 | 0.92 | 0.71 | 0.97 |
| SBI | 0.94 | 0.63 | 0.86 | 0.84 | 0.92 |
| Pathogen | | | | | |
| Adenovirus | 0.84 | 0.41 | 0.74 | 0.73 | 0.80 |
| Coronavirus | 0.90 | 0.21 | 0.86 | 0.87 | 0.67 |
| Parainfluenza virus | 0.95 | 0.51 | 0.92 | 0.93 | 0.83 |
| Influenza A | 0.99 | 0.77 | 0.93 | 0.91 | 1.00 |
| Influenza B | 1.00 | 1.00 | 1.00 | 1.00 | 1.00 |
| RSV A/B | 0.98 | 0.66 | 0.89 | 0.87 | 1.00 |
| Bocavirus 1/2/3/4 | 0.95 | 0.38 | 0.92 | 0.93 | 0.83 |
| Enterovirus | 0.96 | 0.43 | 0.90 | 0.90 | 1.00 |
| CMV/EBV | 0.85 | 0.18 | 0.93 | 0.94 | 0.67 |
| Atypical bacteria | 0.87 | 0.38 | 0.85 | 0.70 | 0.86 |
| *E. coli* | 0.97 | 0.77 | 0.93 | 0.91 | 0.93 |
| Group A Strep | 0.91 | 0.24 | 0.80 | 0.75 | 0.80 |
| GI viruses | 0.89 | 0.24 | 0.92 | 0.96 | 0.67 |
| Chronic disease | | | | | |
| Diabetes | 0.87 | 0.19 | 0.74 | 0.70 | 1.00 |
| Lung disease | 1.00 | 0.67 | 0.91 | 0.93 | 0.83 |

TABLE 1.1B

| | | | | | Logistic regression coefficients | | |
|---|---|---|---|---|---|---|---|
| | PPV | NPV | B | V | Constant | CRP (μg/ml) | MX1 |
| Bacterial vs Viral | 0.85 | 0.83 | 117 | 107 | −1.54 | 0.04 | −5.25E−05 |
| Infectious vs Non-infectious | 0.99 | 0.53 | 224 | 29 | −2.70 | 0.18 | 0.00023304 |
| Syndrome | | | | | | | |
| LRTI | 0.94 | 0.79 | 39 | 21 | −3.85 | 0.10 | −1.85E−05 |
| URTI | 0.73 | 0.92 | 18 | 28 | −1.06 | 0.04 | −0.00013202 |
| Fever Without Source | 0.83 | 0.93 | 7 | 29 | −5.29 | 0.06 | −1.39E−07 |
| SBI | 0.97 | 0.61 | 44 | 12 | −1.04 | 0.05 | −6.97E−05 |
| Pathogen | | | | | | | |
| Adenovirus | 0.94 | 0.39 | 70 | 15 | −0.01 | 0.03 | −5.30E−05 |
| Coronavirus | 0.98 | 0.18 | 70 | 3 | 1.90 | 0.04 | −9.41E−05 |
| Parainfluenza virus | 0.97 | 0.67 | 70 | 12 | −0.64 | 0.07 | −6.66E−05 |
| Influenza A | 1.00 | 0.65 | 70 | 11 | −3.26 | 0.16 | −4.65E−05 |
| Influenza B | 1.00 | 1.00 | 70 | 4 | 62.28 | 4.68 | −0.00795356 |
| RSV A/B | 1.00 | 0.53 | 70 | 10 | −1.78 | 0.13 | −0.00010922 |
| Bocavirus 1/2/3/4 | 0.99 | 0.50 | 70 | 6 | −2.09 | 0.08 | 6.05E−05 |
| Enterovirus | 1.00 | 0.30 | 70 | 3 | 1.52 | 0.07 | −0.00014421 |
| CMV/EBV | 0.99 | 0.33 | 70 | 3 | 0.67 | 0.04 | −6.20E−06 |
| Atypical bacteria | 0.37 | 0.96 | 10 | 87 | −2.70 | 0.03 | −8.17E−05 |
| *E. coli* | 0.83 | 0.97 | 11 | 30 | −0.35 | 0.09 | −0.00059305 |

TABLE 1.1B-continued

| | PPV | NPV | B | V | Logistic regression coefficients Constant | CRP (μg/ml) | MX1 |
|---|---|---|---|---|---|---|---|
| Group A Strep | 0.15 | 0.99 | 4 | 86 | −2.80 | 0.04 | −0.00017567 |
| GI viruses | 0.96 | 0.67 | 22 | 3 | −0.84 | 0.05 | 3.52E−05 |
| Chronic disease | | | | | | | |
| Diabetes | 1.00 | 0.36 | 23 | 4 | −1.48 | 0.06 | −2.83E−05 |
| Lung disease | 0.93 | 0.83 | 15 | 6 | −62.50 | 5.99 | −1.18E−02 |

TABLE 1.1C

| | Min δ | Max δ |
|---|---|---|
| Bacterial vs Viral | −54.0 | 22.5 |
| Infectious vs Non-infectious | −2.7 | 338.3 |
| Syndrome | | |
| LRTI | −22.4 | 56.2 |
| URTI | −133.1 | 22.9 |
| Fever Without Source | −5.4 | 30.7 |
| SBI | −70.7 | 29.0 |
| Pathogen | | |
| Adenovirus | −53.0 | 18.0 |
| Coronavirus | −92.2 | 25.9 |
| Parainfluenza virus | −67.2 | 41.4 |
| Influenza A | −49.8 | 92.7 |
| Influenza B | −7,891.3 | 2,870.3 |
| RSV A/B | −111.0 | 76.2 |
| Bocavirus 1/2/3/4 | −2.1 | 106.4 |
| Enterovirus | −142.7 | 43.5 |
| CMV/EBV | −5.5 | 24.7 |
| Atypical bacteria | −84.4 | 15.3 |
| *E. coli* | −593.4 | 53.7 |
| Group A Strep | −178.5 | 21.2 |
| GI viruses | −0.8 | 64.4 |
| Chronic disease | | |
| Diabetes | −29.8 | 34.5 |
| Lung disease | −11,862.5 | 3,531.5 |

Comparison of MX1 Measurements Using Different Patient Samples and Measurement Techniques Measuring MX1 in different techniques can affect the coefficients defining the hyperplane that separates between bacterial and viral patients. Therefore, the present inventors performed a rigorous analysis of CRP and MX1 combination using an external dataset generated from a cohort of 33 patients with confirmed bacterial infection and 47 patients with confirmed viral infection, in which MX1 was measured in a sandwich-type immunoassay.

Figure 9D:
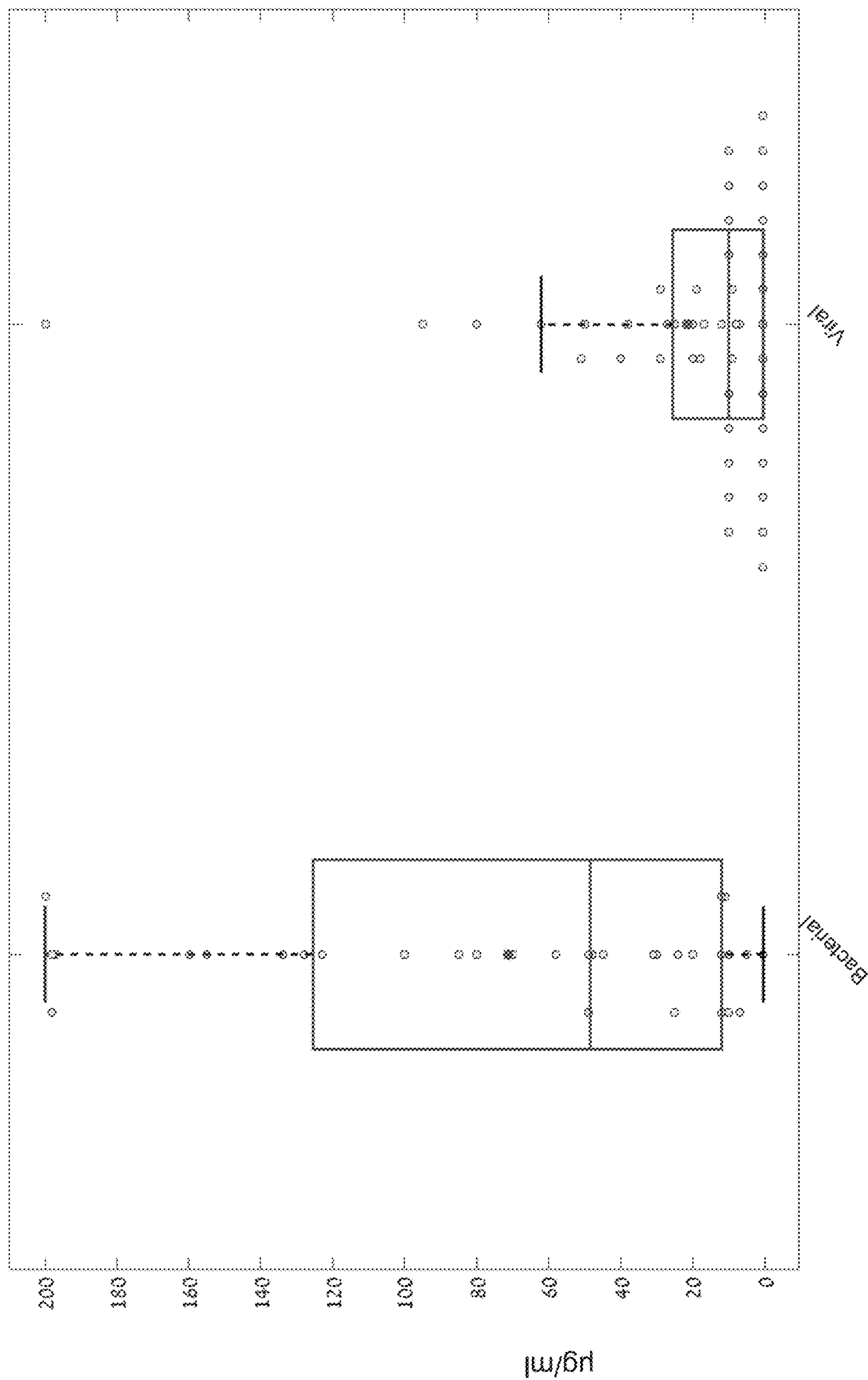
FIG. 9D shows CRP serum levels of patients with bacterial infection (n=33), and viral infection (n=47)
Figure 9E:
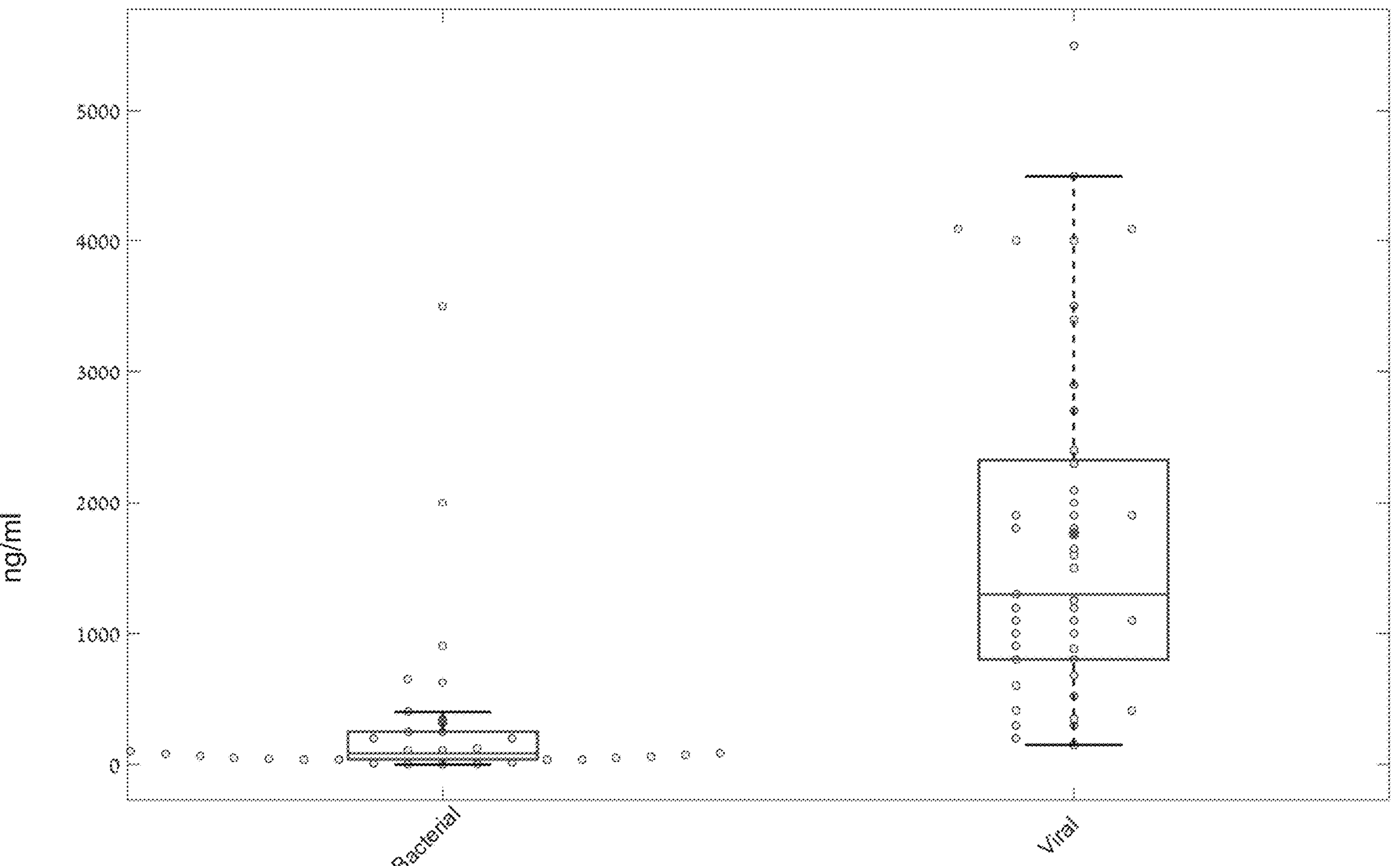
FIG. 9E shows MX1 levels (measured using immunoassay) of patients with bacterial infection (n=33), and viral infection (n=47)
Figure 9F:
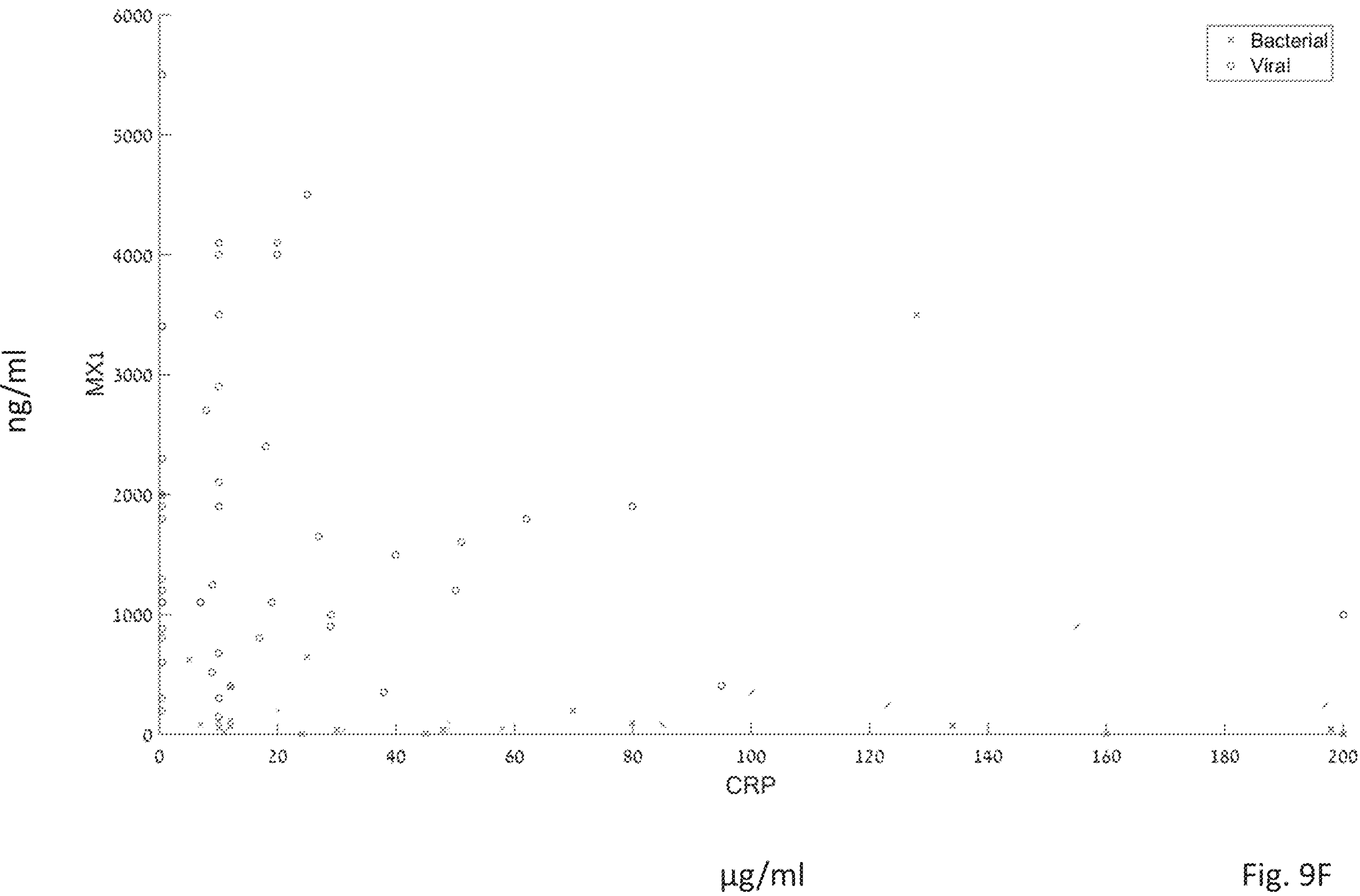
FIG. 9F shows MX1 levels (measured using immunoassay) and CRP serum levels of patients with bacterial infection (n=33), and viral infection (n=47)

FIGS. 9D-F demonstrate that combination of CRP and MX1 can assist in correct diagnosis of acute infection patients (MX1 measured using immunoassay) (Engelmann et al. 2015). FIG. 9D shows CRP levels in bacterial patients (n=33) and viral patients (n=47). For bacterial patients Med=48.5, Mean=71.4531±66.779, and RS p=2.3453e-05; and for viral patients, Med=10, Mean=21.3778±34.7004 and RS p=2.3453e-05. FIG. 9E shows MX1 levels measured using a sandwich-type immunoassay in bacterial patients (n=33) and viral patients (n=47). For bacterial patients, Med=84.5, Mean=326.2594±696.4417, and RS p=5.0217e-10; and for viral patients, Med=1300, Mean=1757.7778±1325.5632, and RS p=5.0217e-10. FIG. 9F shows levels of CRP and MX1 (measured using a sandwich-type immunoassay) in bacterial patients (crosses; n=33) and viral patients (open circles; n=47).

Based on these measurements, a classifier was developed for distinguishing between bacterial and viral patients using logistic regression. It was further calculated for this classifier the measures of accuracy in distinguishing between bacterial and viral patients including AUC, MCC, total accuracy, sensitivity, specificity, PPV, and NPV.

Table 1.2 details a set of coefficients for a logistic regression model distinguishing between bacterial (or mixed) and viral patients, combining MX1 (measured using a sandwich-type immunoassay) and CRP in cutoff independent manner for distinguishing between bacterial (n=33) and viral (n=47) patients. The accuracy measures AUC, MCC, Total accuracy, Sensitivity, Specificity, PPV and NPV are, respectively, 0.91, 0.69, 0.90, 0.84, 0.93, 0.90 and 0.89, respectively.

TABLE 1.2

| Logistic regression coefficients Constant | CRP (μg/ml) | MX1 (ng/ml) | Min δ | Max δ |
|---|---|---|---|---|
| 0.4561 | 0.018283 | −0.00195 | −13.2 | 11.4 |

Measuring MX1 using flow cytometry or immunoassay did not significantly alter the model accuracy (AUC of 0.92 and 0.91 respectively; Tables 1.1A, 1.1B and 1.2). However, the different measuring methods produce different units (arbitrary units vs concentration) therefore altering the coefficients used to define the hyperplane that separates between bacterial and viral patients. To overcome this and to further generalize their findings, the present inventors performed standard score transformation for the MX1 measurements and developed a classifier for distinguishing between bacterial and viral patients using logistic regression. The classifier is based on CRP levels in μg/ml, and on Z-score values of MX1, obtained from CRP and MX1 measurements applied to 117 bacterial patients and 107 viral patients described above. The Z-score values of MX1 were calculated based on the mean and standard deviation of the MX1 levels as measured from the bacterial patients.

This analysis specifies the model coefficients allowing to define a manifold and a hyperplane for distinguishing between bacterial and viral patients based on the expression levels of CRP and MX1 (regardless of the method used to quantify MX1).

Table 1.3 details a set of coefficients for a logistic regression model distinguishing between bacterial (or mixed) and viral patients, combining CRP levels in μg/ml, and Z-score values of MX1 following standard score transformation. The corresponding AUC, MCC, Total accuracy, Sensitivity, Specificity, PPV and NPV are 0.92, 0.65, 0.84, 0.85, 0.84, 0.85 and 0.83, respectively.

TABLE 1.3

| Logistic regression coefficients | | | | |
|---|---|---|---|---|
| Constant | CRP (μg/ml) | MX1 (Z-Score) | Min δ | Max δ |
| −2.1526 | 0.043963 | −0.41794 | −3.4 | 25.5 |

Cutoff independent models are superior to cutoff dependent schemes CRP is routinely used in the clinical setting to assist in the diagnosis of acute infection patients based on several standard cutoffs. Thus, logistic regression was used to develop different classifiers for distinguishing between bacterial (or mixed) and viral patients, which combine CRP applying routinely used cutoffs (20 μg/ml, 65 μg/ml and 80 μg/ml) together with MX1 measurements, in various indications and sub-groups. For these determinants, the measures of accuracy in distinguishing between bacterial and viral patients including AUC, MCC, total accuracy, sensitivity, specificity, PPV and NPV were calculated (Tables 1.4A(i)-C(ii)). The difference between the measures of accuracy of the cutoff independent models and the CRP cutoff dependent models were also calculated (Tables 1.5A-C).

The cutoff independent models were superior to the models which combine MX1 with a specific CRP cutoff. For example, the sensitivity of the cutoff independent model in distinguishing between bacterial and viral patients was significantly higher than each of the CRP cutoff models tested (0.85 compared to 0.78, 0.74, and 0.73 for the 20 μg/ml, 65 μg/ml and 80 μg/ml cutoffs respectively). Measures of accuracy of different combinations of CRP and MX1 cutoffs were evaluated (Tables 1.6A-B). The sensitivity of the cutoff independent models was significantly superior to the various cutoffs tested (Tables 1.6A-B). The improved sensitivity is of high clinical importance as it means identifying more patients with bacterial infection which require antibiotic treatment.

Tables 1.4A(i) and 1.4A(ii) detail logistic regression models combining CRP at a fixed cutoff of 20 μg/ml and MX1 and their measures of accuracy in various indications and sub-groups. The columns of the tables are as defined for Table 1.1A-C above. Atypical bacteria include the bacteria listed above with respect to Tables 1.1A-C.

For fixed cutoffs, binary values were used for the expression values. For example, when the measured CRP level was below the threshold, the CRP value was assigned with the value 1, and when the measured CRP level was above or equal to the threshold, the CRP value was assigned with the value 0.

TABLE 1.4A(i)

| | AUC | MCC | Total accuracy | Sensitivity | Specificity |
|---|---|---|---|---|---|
| Bacterial vs Viral | 0.79 | 0.49 | 0.75 | 0.78 | 0.71 |
| Infectious vs Non-infectious | 0.94 | 0.57 | 0.89 | 0.89 | 0.90 |
| Syndrome | | | | | |
| LRTI | 0.79 | 0.46 | 0.75 | 0.80 | 0.67 |
| URTI | 0.79 | 0.34 | 0.72 | 0.61 | 0.79 |
| Fever Without Source | 0.83 | 0.49 | 0.78 | 0.71 | 0.79 |
| SBI | 0.74 | 0.30 | 0.75 | 0.77 | 0.67 |
| Pathogen | | | | | |
| Adenovirus | 0.65 | 0.12 | 0.69 | 0.73 | 0.53 |
| Coronavirus | 0.76 | 0.08 | 0.64 | 0.64 | 0.67 |
| Parainfluenza virus | 0.81 | 0.49 | 0.84 | 0.86 | 0.75 |
| Influenza A | 0.85 | 0.68 | 0.94 | 0.97 | 0.73 |
| Influenza B | 1.00 | 0.65 | 0.97 | 0.97 | 1.00 |
| RSV A/B | 0.85 | 0.45 | 0.93 | 0.97 | 0.60 |
| Bocavirus 1/2/3/4 | 0.67 | 0.24 | 0.92 | 0.97 | 0.33 |
| Enterovirus | 0.81 | −0.09 | 0.97 | 1.00 | 0.33 |
| CMV/EBV | 0.91 | 0.49 | 0.96 | 0.97 | 0.67 |
| Atypical bacteria | 0.81 | 0.24 | 0.67 | 0.80 | 0.66 |
| *E. coli* | 0.88 | 0.57 | 0.83 | 0.91 | 0.80 |
| Group A Strep | 0.88 | 0.19 | 0.83 | 0.75 | 0.84 |
| GI viruses | 0.70 | 0.51 | 0.88 | 0.91 | 0.67 |
| Chronic disease | | | | | |
| Diabetes | 0.73 | 0.47 | 0.82 | 0.83 | 0.75 |
| Lung disease | 0.84 | 0.39 | 0.76 | 0.73 | 0.83 |

TABLE 1.4A(ii)

| | | | | | Logistic regression coefficients | | |
|---|---|---|---|---|---|---|---|
| | PPV | NPV | B | V | Constant | CRP (μg/ml) | MX1 |
| Bacterial vs Viral | 0.75 | 0.75 | 117 | 107 | −1.23 | 2.67 | −4.73E−05 |
| Infectious vs Non-infectious | 0.99 | 0.51 | 224 | 29 | −1.49 | 4.70 | 2.24E−04 |
| Syndrome | | | | | | | |
| LRTI | 0.82 | 0.64 | 39 | 21 | −1.59 | 3.46 | −4.37E−05 |
| URTI | 0.65 | 0.76 | 18 | 28 | −0.86 | 2.04 | −9.30E−05 |
| Fever Without Source | 0.46 | 0.92 | 7 | 29 | −83.07 | 81.87 | 4.62E−05 |
| SBI | 0.90 | 0.44 | 44 | 12 | 0.53 | 2.23 | −7.90E−05 |
| Pathogen | | | | | | | |
| Adenovirus | 0.88 | 0.30 | 70 | 15 | 0.44 | 1.68 | −3.39E−05 |
| Coronavirus | 0.98 | 0.07 | 70 | 3 | 1.72 | 2.78 | −6.42E−05 |
| Parainfluenza virus | 0.95 | 0.47 | 70 | 12 | −0.05 | 3.66 | −7.42E−05 |
| Influenza A | 0.96 | 0.80 | 70 | 11 | −0.73 | 4.38 | −3.82E−05 |
| Influenza B | 1.00 | 0.67 | 70 | 4 | 1181.22 | 3149.69 | −1.00E−01 |
| RSV A/B | 0.94 | 0.75 | 70 | 10 | −0.35 | 3.86 | −4.76E−05 |
| Bocavirus 1/2/3/4 | 0.94 | 0.50 | 70 | 6 | −0.34 | 2.79 | 3.38E−05 |
| Enterovirus | 0.97 | 1.00 | 70 | 3 | 1.94 | 2.89 | −8.10E−05 |
| CMV/EBV | 0.99 | 0.50 | 70 | 3 | 0.35 | 4.46 | −4.10E−05 |
| Atypical bacteria | 0.21 | 0.97 | 10 | 87 | −2.19 | 1.87 | −9.91E−05 |
| *E. coli* | 0.63 | 0.96 | 11 | 30 | −108.02 | 109.64 | −1.48E−04 |

TABLE 1.4A(ii)-continued

| | PPV | NPV | B | V | Logistic regression coefficients Constant | CRP (μg/ml) | MX1 |
|---|---|---|---|---|---|---|---|
| Group A Strep | 0.18 | 0.99 | 4 | 86 | −100.46 | 99.67 | −1.35E−04 |
| GI viruses | 0.95 | 0.50 | 22 | 3 | −0.38 | 2.97 | 2.99E−05 |
| Chronic disease | | | | | | | |
| Diabetes | 0.95 | 0.43 | 23 | 4 | −102.68 | 105.97 | −9.82E−05 |
| Lung disease | 0.92 | 0.56 | 15 | 6 | −101.25 | 103.73 | −5.25E−05 |

Tables 1.4B(i) and 1.4B(ii) detail logistic regression models combining CRP at a fixed cutoff of 65 μg/ml and MX1 and their measures of accuracy in various indications and sub-groups. The columns of the tables are as defined for Table 1.1A-C above. Atypical bacteria include the bacteria listed above with respect to Tables 1.1A-C.

TABLE 1.4B(i)

| | AUC | MCC | Total accuracy | Sensitivity | Specificity |
|---|---|---|---|---|---|
| Bacterial vs Viral | 0.86 | 0.64 | 0.81 | 0.74 | 0.89 |
| Infectious vs Non-infectious | 0.89 | 0.40 | 0.84 | 0.84 | 0.83 |
| Syndrome | | | | | |
| LRTI | 0.93 | 0.78 | 0.88 | 0.82 | 1.00 |
| URTI | 0.88 | 0.59 | 0.83 | 0.83 | 0.82 |
| Fever Without Source | 0.91 | 0.69 | 0.89 | 0.86 | 0.90 |
| SBI | 0.93 | 0.60 | 0.86 | 0.84 | 0.92 |

TABLE 1.4B(i)-continued

| | AUC | MCC | Total accuracy | Sensitivity | Specificity |
|---|---|---|---|---|---|
| Pathogen | | | | | |
| Adenovirus | 0.76 | 0.30 | 0.77 | 0.79 | 0.67 |
| Coronavirus | 0.80 | −0.14 | 0.90 | 0.90 | 1.00 |
| Parainfluenza virus | 0.86 | 0.50 | 0.78 | 0.76 | 0.92 |
| Influenza A | 0.93 | 0.55 | 0.84 | 0.81 | 1.00 |
| Influenza B | 0.96 | 0.41 | 0.88 | 0.87 | 1.00 |
| RSV A/B | 0.94 | 0.55 | 0.88 | 0.87 | 0.90 |
| Bocavirus 1/2/3/4 | 0.81 | 0.35 | 0.78 | 0.77 | 0.83 |
| Enterovirus | 0.96 | 0.39 | 0.93 | 0.93 | 1.00 |
| CMV/EBV | 0.66 | 0.18 | 0.74 | 0.74 | 0.67 |
| Atypical bacteria | 0.81 | 0.34 | 0.80 | 0.70 | 0.82 |
| *E. coli* | 0.90 | 0.57 | 0.78 | 0.91 | 0.73 |
| Group A Strep | 0.92 | 0.26 | 0.77 | 1.00 | 0.76 |
| GI viruses | 0.86 | 0.24 | 0.72 | 0.68 | 1.00 |
| Chronic disease | | | | | |
| Diabetes | 0.88 | 0.54 | 0.78 | 0.74 | 1.00 |
| Lung disease | 0.98 | 0.67 | 0.95 | 1.00 | 0.83 |

TABLE 1.4B(ii)

| | PPV | NPV | B | V | Logistic regression coefficients Constant | CRP (μg/ml) | MX1 |
|---|---|---|---|---|---|---|---|
| Bacterial vs Viral | 0.88 | 0.76 | 117 | 107 | −0.18 | 3.32 | −5.99E−05 |
| Infectious vs Non-infectious | 0.97 | 0.41 | 224 | 29 | −0.40 | 101.16 | 1.98E−04 |
| Syndrome | | | | | | | |
| LRTI | 1.00 | 0.75 | 39 | 21 | −0.62 | 103.58 | −3.00E−05 |
| URTI | 0.75 | 0.89 | 18 | 28 | 0.61 | 2.51 | −1.50E−04 |
| Fever Without Source | 0.67 | 0.96 | 7 | 29 | −3.21 | 3.95 | −2.93E−06 |
| SBI | 0.97 | 0.61 | 44 | 12 | 1.39 | 4.79 | −1.44E−04 |
| Pathogen | | | | | | | |
| Adenovirus | 0.92 | 0.40 | 70 | 15 | 1.11 | 1.93 | −4.57E−05 |
| Coronavirus | 1.00 | 0.30 | 70 | 3 | 3.25 | 1.99 | −7.72E−05 |
| Parainfluenza virus | 0.98 | 0.39 | 70 | 12 | 1.44 | 3.56 | −6.57E−05 |
| Influenza A | 1.00 | 0.46 | 70 | 11 | 1.95 | 102.48 | −1.06E−04 |
| Influenza B | 1.00 | 0.31 | 70 | 4 | 3.55 | 101.66 | −1.36E−04 |
| RSV A/B | 0.98 | 0.50 | 70 | 10 | 2.07 | 102.49 | −1.12E−04 |
| Bocavirus 1/2/3/4 | 0.98 | 0.24 | 70 | 6 | 0.88 | 2.72 | 3.14E−05 |
| Enterovirus | 1.00 | 0.38 | 70 | 3 | 3.94 | 101.44 | −1.42E−04 |
| CMV/EBV | 0.98 | 0.10 | 70 | 3 | 2.06 | 1.82 | 7.02E−06 |
| Atypical bacteria | 0.30 | 0.96 | 10 | 87 | −1.20 | 2.16 | −1.12E−04 |
| *E. coli* | 0.56 | 0.96 | 11 | 30 | 0.74 | 3.29 | −2.43E−04 |
| Group A Strep | 0.16 | 1.00 | 4 | 86 | −1.63 | 2.39 | −1.67E−04 |
| GI viruses | 1.00 | 0.30 | 22 | 3 | 0.26 | 101.74 | 4.32E−05 |
| Chronic disease | | | | | | | |
| Diabetes | 1.00 | 0.40 | 23 | 4 | 0.39 | 102.17 | 1.22E−06 |
| Lung disease | 0.94 | 1.00 | 15 | 6 | 3.92 | 106.38 | −2.50E−04 |

Tables 1.4C(i) and 1.4C(ii) detail logistic regression models combining CRP at a fixed cutoff of 80 μg/ml and MX1 and their measures of accuracy in various indications and sub-groups. The columns of the tables are as defined for Table 1.1A-C above. Atypical bacteria include the bacteria listed above with respect to Tables 1.1A-C.

TABLE 1.4C(i)

| | AUC | MCC | Total accuracy | Sensitivity | Specificity |
|---|---|---|---|---|---|
| Bacterial vs Viral | 0.86 | 0.63 | 0.78 | 0.73 | 0.84 |
| Infectious vs Non-infectious | 0.88 | 0.39 | 0.83 | 0.83 | 0.83 |
| Syndrome | | | | | |
| LRTI | 0.92 | 0.76 | 0.87 | 0.80 | 1.00 |
| URTI | 0.87 | 0.57 | 0.83 | 0.83 | 0.82 |
| Fever Without Source | 0.82 | 0.65 | 0.89 | 0.71 | 0.93 |
| SBI | 0.92 | 0.67 | 0.84 | 0.80 | 1.00 |
| Pathogen | | | | | |
| Adenovirus | 0.80 | 0.39 | 0.72 | 0.70 | 0.80 |
| Coronavirus | 0.77 | −0.15 | 0.92 | 0.91 | 1.00 |
| Parainfluenza virus | 0.90 | 0.45 | 0.84 | 0.86 | 0.75 |
| Influenza A | 0.91 | 0.49 | 0.86 | 0.87 | 0.82 |
| Influenza B | 0.94 | 0.38 | 0.82 | 0.81 | 1.00 |
| RSV A/B | 0.91 | 0.49 | 0.83 | 0.81 | 0.90 |
| Bocavirus 1/2/3/4 | 0.85 | 0.39 | 0.75 | 0.73 | 1.00 |
| Enterovirus | 0.94 | 0.33 | 0.89 | 0.89 | 1.00 |
| CMV/EBV | 0.64 | 0.15 | 0.90 | 0.93 | 0.33 |
| Atypical bacteria | 0.80 | 0.21 | 0.63 | 0.80 | 0.61 |
| *E. coli* | 0.93 | 0.57 | 0.78 | 0.91 | 0.73 |
| Group A Strep | 0.83 | 0.09 | 0.80 | 0.50 | 0.81 |
| GI viruses | 0.86 | 0.20 | 0.68 | 0.64 | 1.00 |
| Chronic disease | | | | | |
| Diabetes | 0.82 | 0.47 | 0.70 | 0.65 | 1.00 |
| Lung disease | 0.98 | 0.67 | 0.95 | 1.00 | 0.83 |

TABLE 1.4C(ii)

| | | | | | Logistic regression coefficients | | |
|---|---|---|---|---|---|---|---|
| | PPV | NPV | B | V | Constant | CRP (μg/ml) | MX1 |
| Bacterial vs Viral | 0.83 | 0.74 | 117 | 107 | −0.15 | 3.59 | −5.42E−05 |
| Infectious vs Non-infectious | 0.97 | 0.39 | 224 | 29 | −0.32 | 101.12 | 1.97E−04 |
| Syndrome | | | | | | | |
| LRTI | 1.00 | 0.72 | 39 | 21 | −0.34 | 103.45 | −4.00E−05 |
| URTI | 0.75 | 0.89 | 18 | 28 | 0.92 | 2.71 | −1.64E−04 |
| Fever Without Source | 0.71 | 0.93 | 7 | 29 | −2.73 | 3.52 | 7.26E−06 |
| SBI | 1.00 | 0.57 | 44 | 12 | 0.31 | 102.70 | −3.93E−05 |
| Pathogen | | | | | | | |
| Adenovirus | 0.94 | 0.36 | 70 | 15 | 1.01 | 2.24 | −3.34E−05 |
| Coronavirus | 1.00 | 0.33 | 70 | 3 | 3.38 | 1.56 | −6.79E−05 |
| Parainfluenza virus | 0.95 | 0.47 | 70 | 12 | 1.55 | 101.97 | −6.50E−05 |
| Influenza A | 0.97 | 0.50 | 70 | 11 | 1.79 | 101.98 | −7.78E−05 |
| Influenza B | 1.00 | 0.24 | 70 | 4 | 3.26 | 101.00 | −1.00E−04 |
| RSV A/B | 0.98 | 0.41 | 70 | 10 | 1.79 | 101.90 | −7.35E−05 |
| Bocavirus 1/2/3/4 | 1.00 | 0.24 | 70 | 6 | 0.81 | 101.30 | 3.99E−05 |
| Enterovirus | 1.00 | 0.27 | 70 | 3 | 3.56 | 100.72 | −1.01E−04 |
| CMV/EBV | 0.97 | 0.17 | 70 | 3 | 2.18 | 1.53 | 1.50E−05 |
| Atypical bacteria | 0.19 | 0.96 | 10 | 87 | −0.88 | 2.44 | −1.31E−04 |
| *E. coli* | 0.56 | 0.96 | 11 | 30 | 1.72 | 5.30 | −3.97E−04 |
| Group A Strep | 0.11 | 0.97 | 4 | 86 | −1.05 | 2.24 | −1.95E−04 |
| GI viruses | 1.00 | 0.27 | 22 | 3 | 0.13 | 101.74 | 5.87E−05 |
| Chronic disease | | | | | | | |
| Diabetes | 1.00 | 0.33 | 23 | 4 | 0.88 | 101.82 | −1.44E−05 |
| Lung disease | 0.94 | 1.00 | 15 | 6 | 3.92 | 106.38 | −2.50E−04 |

Table 1.5A summarizes the differences between the accuracy measures of logistic regression models combining CRP and MX1 in cutoff independent manner (described in Tables 1.1A and 1.1B) and logistic regression models combining CRP at a fixed cutoff of 20 μg/ml and MX1 (described in Tables 1.4A(i) and 1.4A(ii)) in various indications and sub-groups. In the table, positive numbers indicate improvement of cutoff independent models compared to cutoff dependent models. The columns of the tables are as defined for Table 1.1A-C above. Atypical bacteria include the bacteria listed above with respect to Tables 1.1A-C.

TABLE 1.5A

| | AUC | MCC | Total accuracy | Sensitivity | Specificity | PPV | NPV |
|---|---|---|---|---|---|---|---|
| Bacterial vs Viral | 0.12 | 0.16 | 0.10 | 0.07 | 0.13 | 0.11 | 0.09 |
| Infectious vs Non-infectious | 0.02 | 0.02 | 0.01 | 0.01 | 0.00 | 0.00 | 0.02 |
| Syndrome | | | | | | | |
| LRTI | 0.18 | 0.23 | 0.13 | 0.08 | 0.24 | 0.13 | 0.16 |
| URTI | 0.11 | 0.21 | 0.11 | 0.28 | 0.00 | 0.08 | 0.16 |
| Fever Without Source | 0.15 | 0.09 | 0.14 | 0.00 | 0.17 | 0.38 | 0.01 |
| SBI | 0.20 | 0.33 | 0.11 | 0.07 | 0.25 | 0.08 | 0.17 |
| Pathogen | | | | | | | |
| Adenovirus | 0.19 | 0.28 | 0.05 | 0.00 | 0.27 | 0.06 | 0.09 |
| Coronavirus | 0.14 | 0.13 | 0.22 | 0.23 | 0.00 | 0.01 | 0.11 |
| Parainfluenza virus | 0.14 | 0.02 | 0.07 | 0.07 | 0.08 | 0.02 | 0.19 |
| Influenza A | 0.14 | 0.09 | −0.01 | −0.06 | 0.27 | 0.04 | −0.15 |
| Influenza B | 0.00 | 0.35 | 0.03 | 0.03 | 0.00 | 0.00 | 0.33 |
| RSV A/B | 0.13 | 0.21 | −0.04 | −0.10 | 0.40 | 0.06 | −0.22 |
| Bocavirus 1/2/3/4 | 0.28 | 0.14 | 0.00 | −0.04 | 0.50 | 0.04 | 0.00 |
| Enterovirus | 0.15 | 0.52 | −0.07 | −0.10 | 0.67 | 0.03 | −0.70 |
| CMV/EBV | −0.06 | −0.31 | −0.03 | −0.03 | 0.00 | 0.00 | −0.17 |
| Atypical bacteria | 0.06 | 0.14 | 0.18 | −0.10 | 0.21 | 0.16 | 0.00 |
| *E. coli* | 0.09 | 0.20 | 0.10 | 0.00 | 0.13 | 0.21 | 0.01 |
| Group A Strep | 0.04 | 0.05 | −0.03 | 0.00 | −0.03 | −0.03 | 0.00 |
| GI viruses | 0.20 | −0.27 | 0.04 | 0.05 | 0.00 | 0.00 | 0.17 |
| Chronic disease | | | | | | | |
| Diabetes | 0.14 | −0.28 | −0.07 | −0.13 | 0.25 | 0.05 | −0.07 |
| Lung disease | 0.16 | 0.28 | 0.14 | 0.20 | 0.00 | 0.02 | 0.28 |

Table 1.5B summarizes the differences between the accuracy measures of logistic regression models combining CRP and MX1 in cutoff independent manner (described in Tables 1.1A and 1.1B) and logistic regression models combining CRP at a fixed cutoff of 65 μg/ml and MX1 (described in Tables 1.4B(i) and 1.4B(ii)) in various indications and sub-groups. In the table, positive numbers indicate improvement of cutoff independent models compared to cutoff dependent models. The columns of the tables are as defined for Table 1A-B above. Atypical bacteria include the bacteria listed above with respect to Tables 1A-B.

TABLE 1.5B

| | AUC | MCC | Total accuracy | Sensitivity | Specificity | PPV | NPV |
|---|---|---|---|---|---|---|---|
| Bacterial vs Viral | 0.05 | 0.01 | 0.03 | 0.10 | −0.05 | −0.03 | 0.07 |
| Infectious vs Non-infectious | 0.08 | 0.20 | 0.06 | 0.05 | 0.07 | 0.01 | 0.12 |
| Syndrome | | | | | | | |
| LRTI | 0.05 | −0.09 | 0.00 | 0.05 | −0.10 | −0.06 | 0.04 |
| URTI | 0.03 | −0.04 | 0.00 | 0.06 | −0.03 | −0.02 | 0.03 |
| Fever Without Source | 0.06 | −0.11 | 0.03 | −0.14 | 0.07 | 0.17 | −0.03 |
| SBI | 0.01 | 0.03 | 0.00 | 0.00 | 0.00 | 0.00 | 0.00 |
| Pathogen | | | | | | | |
| Adenovirus | 0.08 | 0.10 | −0.02 | −0.06 | 0.13 | 0.03 | −0.01 |
| Coronavirus | 0.11 | 0.35 | −0.04 | −0.03 | −0.33 | −0.02 | −0.12 |
| Parainfluenza virus | 0.09 | 0.01 | 0.14 | 0.17 | −0.08 | −0.01 | 0.27 |
| Influenza A | 0.05 | 0.22 | 0.09 | 0.10 | 0.00 | 0.00 | 0.19 |
| Influenza B | 0.04 | 0.59 | 0.12 | 0.13 | 0.00 | 0.00 | 0.69 |
| RSV A/B | 0.04 | 0.12 | 0.01 | 0.00 | 0.10 | 0.02 | 0.03 |
| Bocavirus 1/2/3/4 | 0.14 | 0.03 | 0.15 | 0.16 | 0.00 | 0.00 | 0.26 |
| Enterovirus | 0.00 | 0.03 | −0.03 | −0.03 | 0.00 | 0.00 | −0.08 |

TABLE 1.5B-continued

| | AUC | MCC | Total accuracy | Sensitivity | Specificity | PPV | NPV |
|---|---|---|---|---|---|---|---|
| CMV/EBV | 0.20 | 0.00 | 0.19 | 0.20 | 0.00 | 0.00 | 0.23 |
| Atypical bacteria | 0.06 | 0.04 | 0.04 | 0.00 | 0.05 | 0.06 | 0.00 |
| *E. coli* | 0.07 | 0.20 | 0.15 | 0.00 | 0.20 | 0.28 | 0.01 |
| Group A Strep | 0.00 | −0.02 | 0.03 | −0.25 | 0.05 | −0.01 | −0.01 |
| GI viruses | 0.03 | 0.00 | 0.20 | 0.27 | −0.33 | −0.05 | 0.37 |
| Chronic disease | | | | | | | |
| Diabetes | −0.01 | −0.36 | −0.04 | −0.04 | 0.00 | 0.00 | −0.04 |
| Lung disease | 0.02 | 0.00 | −0.05 | −0.07 | 0.00 | 0.00 | −0.17 |

Table 1.5C summarizes the differences between the accuracy measures of logistic regression models combining CRP and MX1 in cutoff independent manner (described in Tables 1.1A and 1.1B) and logistic regression models combining CRP at a fixed cutoff of 80 μg/ml and MX1 (described in Tables 1.4C(i) and 1.4C(ii)) in various indications and sub-groups. In the table, positive numbers indicate improvement of cutoff independent models compared to cutoff dependent models. The columns of the tables are as defined for Table 1.1A-C above. Atypical bacteria include the bacteria listed above with respect to Tables 1.1A-C.

TABLE 1.5C

| | AUC | MCC | Total accuracy | Sensitivity | Specificity | PPV | NPV |
|---|---|---|---|---|---|---|---|
| Bacterial vs Viral | 0.06 | 0.01 | 0.06 | 0.12 | 0.00 | 0.02 | 0.10 |
| Infectious vs Non-infectious | 0.08 | 0.20 | 0.07 | 0.07 | 0.07 | 0.01 | 0.14 |
| Syndrome | | | | | | | |
| LRTI | 0.05 | −0.06 | 0.02 | 0.08 | −0.10 | −0.06 | 0.07 |
| URTI | 0.04 | −0.01 | 0.00 | 0.06 | −0.03 | −0.02 | 0.03 |
| Fever Without Source | 0.15 | −0.06 | 0.03 | 0.00 | 0.03 | 0.12 | 0.00 |
| SBI | 0.02 | −0.04 | 0.02 | 0.05 | −0.08 | −0.03 | 0.04 |
| Pathogen | | | | | | | |
| Adenovirus | 0.04 | 0.01 | 0.02 | 0.03 | 0.00 | 0.00 | 0.02 |
| Coronavirus | 0.13 | 0.36 | −0.06 | −0.04 | −0.33 | −0.02 | −0.15 |
| Parainfluenza virus | 0.05 | 0.06 | 0.07 | 0.07 | 0.08 | 0.02 | 0.19 |
| Influenza A | 0.08 | 0.28 | 0.06 | 0.04 | 0.18 | 0.03 | 0.15 |
| Influenza B | 0.06 | 0.62 | 0.18 | 0.19 | 0.00 | 0.00 | 0.77 |
| RSV A/B | 0.07 | 0.17 | 0.06 | 0.06 | 0.10 | 0.02 | 0.12 |
| Bocavirus 1/2/3/4 | 0.10 | −0.02 | 0.17 | 0.20 | −0.17 | −0.02 | 0.26 |
| Enterovirus | 0.02 | 0.10 | 0.01 | 0.01 | 0.00 | 0.00 | 0.03 |
| CMV/EBV | 0.21 | 0.03 | 0.03 | 0.01 | 0.33 | 0.02 | 0.17 |
| Atypical bacteria | 0.07 | 0.17 | 0.22 | −0.10 | 0.25 | 0.18 | 0.00 |
| *E. coli* | 0.05 | 0.20 | 0.15 | 0.00 | 0.20 | 0.28 | 0.01 |
| Group A Strep | 0.09 | 0.16 | 0.00 | 0.25 | −0.01 | 0.04 | 0.01 |
| GI viruses | 0.03 | 0.04 | 0.24 | 0.32 | −0.33 | −0.05 | 0.39 |
| Chronic disease | | | | | | | |
| Diabetes | 0.06 | −0.28 | 0.04 | 0.04 | 0.00 | 0.00 | 0.03 |
| Lung disease | 0.02 | 0.00 | −0.05 | −0.07 | 0.00 | 0.00 | −0.17 |

Table 1.6A summarizes measures of accuracy in distinguishing between bacterial and viral patients of combinations of CRP and MX1 at different cutoffs.

TABLE 1.6A

| CRP cutoff (μg/ml) | MX1 cutoff (ng/ml) | Sensitivity | Specificity | PPV | NPV | Total accuracy |
|---|---|---|---|---|---|---|
| 20 | 40 | 0.22 | 1.00 | 1.00 | 0.64 | 0.68 |
| 20 | 45 | 0.28 | 1.00 | 1.00 | 0.66 | 0.70 |

TABLE 1.6A-continued

| CRP cutoff (μg/ml) | MX1 cutoff (ng/ml) | Sensitivity | Specificity | PPV | NPV | Total accuracy |
|---|---|---|---|---|---|---|
| 20 | 50 | 0.28 | 1.00 | 1.00 | 0.66 | 0.70 |
| 20 | 55 | 0.31 | 1.00 | 1.00 | 0.67 | 0.71 |
| 20 | 60 | 0.34 | 1.00 | 1.00 | 0.68 | 0.73 |
| 20 | 65 | 0.34 | 1.00 | 1.00 | 0.68 | 0.73 |
| 20 | 70 | 0.34 | 1.00 | 1.00 | 0.68 | 0.73 |

TABLE 1.6A-continued

| CRP cutoff (μg/ml) | MX1 cutoff (ng/ml) | Sensitivity | Specificity | PPV | NPV | Total accuracy |
|---|---|---|---|---|---|---|
| 20 | 75 | 0.38 | 1.00 | 1.00 | 0.69 | 0.74 |
| 20 | 80 | 0.38 | 1.00 | 1.00 | 0.69 | 0.74 |
| 20 | 85 | 0.41 | 1.00 | 1.00 | 0.70 | 0.75 |
| 20 | 90 | 0.41 | 1.00 | 1.00 | 0.70 | 0.75 |
| 20 | 95 | 0.41 | 1.00 | 1.00 | 0.70 | 0.75 |
| 20 | 100 | 0.41 | 1.00 | 1.00 | 0.70 | 0.75 |
| 20 | 110 | 0.47 | 1.00 | 1.00 | 0.73 | 0.78 |

TABLE 1.6A-continued

| CRP cutoff (μg/ml) | MX1 cutoff (ng/ml) | Sensitivity | Specificity | PPV | NPV | Total accuracy |
|---|---|---|---|---|---|---|
| 20 | 120 | 0.47 | 1.00 | 1.00 | 0.73 | 0.78 |
| 20 | 130 | 0.47 | 1.00 | 1.00 | 0.73 | 0.78 |
| 20 | 140 | 0.47 | 1.00 | 1.00 | 0.73 | 0.78 |
| 20 | 150 | 0.47 | 1.00 | 1.00 | 0.73 | 0.78 |
| 20 | 160 | 0.47 | 0.98 | 0.94 | 0.72 | 0.77 |
| 20 | 170 | 0.47 | 0.98 | 0.94 | 0.72 | 0.77 |
| 20 | 180 | 0.47 | 0.98 | 0.94 | 0.72 | 0.77 |
| 20 | 190 | 0.47 | 0.98 | 0.94 | 0.72 | 0.77 |
| 20 | 200 | 0.47 | 0.98 | 0.94 | 0.72 | 0.77 |
| 65 | 40 | 0.06 | 1.00 | 1.00 | 0.60 | 0.61 |
| 65 | 45 | 0.09 | 1.00 | 1.00 | 0.61 | 0.62 |
| 65 | 50 | 0.09 | 1.00 | 1.00 | 0.61 | 0.62 |
| 65 | 55 | 0.13 | 1.00 | 1.00 | 0.62 | 0.64 |
| 65 | 60 | 0.13 | 1.00 | 1.00 | 0.62 | 0.64 |
| 65 | 65 | 0.13 | 1.00 | 1.00 | 0.62 | 0.64 |
| 65 | 70 | 0.13 | 1.00 | 1.00 | 0.62 | 0.64 |
| 65 | 75 | 0.16 | 1.00 | 1.00 | 0.63 | 0.65 |
| 65 | 80 | 0.16 | 1.00 | 1.00 | 0.63 | 0.65 |
| 65 | 85 | 0.19 | 1.00 | 1.00 | 0.63 | 0.66 |
| 65 | 90 | 0.19 | 1.00 | 1.00 | 0.63 | 0.66 |
| 65 | 95 | 0.19 | 1.00 | 1.00 | 0.63 | 0.66 |
| 65 | 100 | 0.19 | 1.00 | 1.00 | 0.63 | 0.66 |
| 65 | 110 | 0.22 | 1.00 | 1.00 | 0.64 | 0.68 |
| 65 | 120 | 0.22 | 1.00 | 1.00 | 0.64 | 0.68 |
| 65 | 130 | 0.22 | 1.00 | 1.00 | 0.64 | 0.68 |
| 65 | 140 | 0.22 | 1.00 | 1.00 | 0.64 | 0.68 |
| 65 | 150 | 0.22 | 1.00 | 1.00 | 0.64 | 0.68 |
| 65 | 160 | 0.22 | 0.98 | 0.88 | 0.64 | 0.66 |
| 65 | 170 | 0.22 | 0.98 | 0.88 | 0.64 | 0.66 |
| 65 | 180 | 0.22 | 0.98 | 0.88 | 0.64 | 0.66 |
| 65 | 190 | 0.22 | 0.98 | 0.88 | 0.64 | 0.66 |
| 65 | 200 | 0.22 | 0.98 | 0.88 | 0.64 | 0.66 |
| 20 | 40 | 0.22 | 1.00 | 1.00 | 0.64 | 0.68 |
| 25 | 40 | 0.19 | 1.00 | 1.00 | 0.63 | 0.66 |
| 30 | 40 | 0.19 | 1.00 | 1.00 | 0.63 | 0.66 |
| 35 | 40 | 0.13 | 1.00 | 1.00 | 0.62 | 0.64 |
| 40 | 40 | 0.13 | 1.00 | 1.00 | 0.62 | 0.64 |
| 45 | 40 | 0.13 | 1.00 | 1.00 | 0.62 | 0.64 |
| 50 | 40 | 0.06 | 1.00 | 1.00 | 0.60 | 0.61 |
| 55 | 40 | 0.06 | 1.00 | 1.00 | 0.60 | 0.61 |
| 60 | 40 | 0.06 | 1.00 | 1.00 | 0.60 | 0.61 |
| 65 | 40 | 0.06 | 1.00 | 1.00 | 0.60 | 0.61 |
| 70 | 40 | 0.06 | 1.00 | 1.00 | 0.60 | 0.61 |
| 75 | 40 | 0.06 | 1.00 | 1.00 | 0.60 | 0.61 |
| 80 | 40 | 0.06 | 1.00 | 1.00 | 0.60 | 0.61 |
| 20 | 200 | 0.47 | 0.98 | 0.94 | 0.72 | 0.77 |
| 25 | 200 | 0.44 | 0.98 | 0.93 | 0.71 | 0.75 |
| 30 | 200 | 0.44 | 0.98 | 0.93 | 0.71 | 0.75 |
| 35 | 200 | 0.38 | 0.98 | 0.92 | 0.69 | 0.73 |
| 40 | 200 | 0.38 | 0.98 | 0.92 | 0.69 | 0.73 |
| 45 | 200 | 0.38 | 0.98 | 0.92 | 0.69 | 0.73 |
| 50 | 200 | 0.25 | 0.98 | 0.89 | 0.65 | 0.68 |
| 55 | 200 | 0.25 | 0.98 | 0.89 | 0.65 | 0.68 |
| 60 | 200 | 0.22 | 0.98 | 0.88 | 0.64 | 0.66 |
| 65 | 200 | 0.22 | 0.98 | 0.88 | 0.64 | 0.66 |
| 70 | 200 | 0.22 | 0.98 | 0.88 | 0.64 | 0.66 |
| 75 | 200 | 0.22 | 0.98 | 0.88 | 0.64 | 0.66 |
| 80 | 200 | 0.22 | 0.98 | 0.88 | 0.64 | 0.66 |

Table 1.6B summarizes measures of accuracy in distinguishing between bacterial and viral patients of combinations of CRP and MX1 when applying lower CRP cutoff for ruling out bacterial infections and higher cutoff for ruling in bacterial infections.

TABLE 1.6B

| CRP cutoff# 1 (μg/ml) | CRP cutoff# 2 (μg/ml) | MX1 cutoff (ng/ml) | Sensitivity | Specificity | PPV | NPV | Total accuracy |
|---|---|---|---|---|---|---|---|
| 20 | 80 | 40 | 0.59 | 0.93 | 0.86 | 0.76 | 0.79 |
| 20 | 65 | 40 | 0.63 | 0.93 | 0.87 | 0.78 | 0.81 |

Table 1.7 details a set of coefficients for a logistic regression model distinguishing between bacterial (or mixed) and viral patients, combining MX1 and RSAD2 in cutoff independent manner for distinguishing between bacterial (n=87) and viral (n=81) patients. The accuracy measures AUC, MCC, Total accuracy, Sensitivity, Specificity, PPV and NPV are 0.74, 0.3, 0.7, 0.67, 0.73, 0.73 and 0.67, respectively.

TABLE 1.7

| Logistic regression coefficients | | | | |
|---|---|---|---|---|
| Constant | MX1 | RSAD2 | Min δ | Max δ |
| 0.67976 | 5.63E−06 | −0.0001 | −6.8 | 6.3 |

Table 1.8 details a set of coefficients for a logistic regression model distinguishing between bacterial (or mixed) and viral patients, combining MX1 and TRAIL in cutoff independent manner for distinguishing between bacterial (n=87) and viral (n=81) patients. The accuracy measures AUC, MCC, Total accuracy, Sensitivity, Specificity, PPV and NPV are 0.93, 0.7, 0.85, 0.85, 0.85, 0.85, 0.86, respectively.

TABLE 1.8

| Logistic regression coefficients | | | | |
|---|---|---|---|---|
| Constant | MX1 | TRAIL (pg/ml) | Min δ | Max δ |
| 2.7042 | 2.44E−05 | −0.05052 | −73.1 | 27.1 |

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

REFERENCES

Bhowmik, A., T. A. Seemungal, R. J. Sapsford, and J. A. Wedzicha. 2000. "Relation of Sputum Inflammatory Markers to Symptoms and Lung Function Changes in COPD Exacerbations." *Thorax* 55 (2): 114-20.

Bossuyt, Patrick M, Johannes B Reitsma, David E Bruns, Constantine A Gatsonis, Paul P Glasziou, Les M Irwig, David Moher, Drummond Rennie, Henrica C. W De Vet, and Jeroen G Lijmer. 2003. "The STARD Statement for Reporting Studies of Diagnostic Accuracy: Explanation and Elaboration." *Annals of Internal Medicine* 138 (1): W1-12.

Engelmann, Ilka, Francois Dubos, Pierre-Emmanuel Lobert, Claire Houssin, Vanessa Degas, Anne Sardet, Anne Decoster, Anny Dewilde, Alain Martinot, and Didier Hober. 2015. "Diagnosis of Viral Infections Using Myxovirus Resistance Protein A (MxA)." *Pediatrics* 135 (4): e985-93. doi:10.1542/peds.2014-1946.

Hoogendoorn, M. 2011. "Economic Impact of COPD: Empirical and Model-Based Studies on the Cost-Effectiveness of Treatment Options." *Journal of Neurophysiology—J NEUROPHYSIOL.*

Hurst, John R., Jørgen Vestbo, Antonio Anzueto, Nicholas Locantore, Hana Müllerova, Ruth Tal-Singer, Bruce Miller, et al. 2010. "Susceptibility to Exacerbation in Chronic Obstructive Pulmonary Disease." *The New England Journal of Medicine* 363 (12): 1128-38. doi:10.1056/NEJMoa0909883.

Kim, Victor, Parag Desai, John D. Newell, Barry J. Make, George R. Washko, Edwin K. Silverman, James D. Crapo, Surya P. Bhatt, Gerard J. Criner, and COPDGene Investigators. 2014. "Airway Wall Thickness Is Increased in COPD Patients with Bronchodilator Responsiveness." *Respiratory Research* 15: 84. doi:10.1186/s12931-014-0084-3.

Lin, Chii-Lan, Leung-Kei Siu, Jung-Chung Lin, Chien-Ying Liu, Chih-Feng Chian, Chun-Nin Lee, and Feng-Yee Chang. 2011. "MAnnose-Binding Lectin Gene Polymorphism Contributes to Recurrence of Infective Exacerbation in Patients with Copd." *Chest* 139 (1): 43-51. doi: 10.1378/chest.10-0375.

Molyneaux, Philip L., Patrick Mallia, Michael J. Cox, Joseph Footitt, Saffron A. G. Willis-Owen, Daniel Homola, Maria-Belen Trujillo-Torralbo, et al. 2013. "Outgrowth of the Bacterial Airway Microbiome after Rhinovirus Exacerbation of Chronic Obstructive Pulmonary Disease." *American Journal of Respiratory and Critical Care Medicine* 188 (10): 1224-31. doi:10.1164/rccm.201302-03410C.

Oved, Kfir, Asi Cohen, Olga Boico, Roy Navon, Tom Friedman, Liat Etshtein, Or Kriger, et al. 2015. "A Novel Host-Proteome Signature for Distinguishing between Acute Bacterial and Viral Infections." *PLoS ONE* 10 (3): e0120012. doi:10.1371/journal.pone.0120012.

Rutjes, A W S, J B Reitsma, A Coomarasamy, K S Khan, and P M M Bossuyt. 2007. "Evaluation of Diagnostic Tests When There Is No Gold Standard. A Review of Methods." *Health Technology Assessment* (*Winchester, England*) 11 (50): iii, ix-51.

Salvi, Sundeep. 2015. "The Silent Epidemic of COPD in Africa." *The Lancet. Global Health* 3 (1): e6-7. doi:10.1016/S2214-109X(14)70359-6.

Sethi, Sanjay, Nancy Evans, Brydon J. B. Grant, and Timothy F. Murphy. 2002. "New Strains of Bacteria and Exacerbations of Chronic Obstructive Pulmonary Disease." *The New England Journal of Medicine* 347 (7): 465-71. doi:10.1056/NEJMoa012561.

Taylor, A. E., T. K. Finney-Hayward, J. K. Quint, C. M. R. Thomas, S. J. Tudhope, J. A. Wedzicha, P. J. Barnes, and L. E. Donnelly. 2010. "Defective Macrophage Phagocytosis of Bacteria in COPD." *The European Respiratory Journal* 35 (5): 1039-47. doi: 10.1183/09031936.00036709.

Wild, D. 2005. *The Immunoassay Handbook*. Third Edition.

Wirth U., and Muller D. 2002. "Post-Translational Modification Detection Using Metastable Ions in Reflector Matrix-Assisted Laser Desorption/ionization-Time of Flight Mass Spectrometry." *Proteomics* 2 (10): 1445-51.

Woodhead, M., F. Blasi, S. Ewig, J. Garau, G. Huchon, M. leven, A. Ortqvist, et al. 2011. "Guidelines for the Management of Adult Lower Respiratory Tract Infections—Full Version." *Clinical Microbiology and Infection* 17: E1-59. doi:10.1111/j.1469-0691.2011.03672.x.

Zhang, Xin, Dan Liu, You-Ning Liu, Rui Wang, and Li-Xin Xie. 2015. "The Accuracy of Presepsin (sCD14-ST) for the Diagnosis of Sepsis in Adults: A Meta-Analysis." *Critical Care* 19 (1): 323. doi:10.1186/s13054-015-1032-4.

Sambursky R and Shapiro N, "Evaluation of a combined MxA and CRP point-of-care immunoassay to identify viral and/or bacterial immune response in patients with acute febrile respiratory infection," Eur Clin Respir J., 2015; 2:28245.

What is claimed is:

1. A method of analyzing biological data, the method comprising:

obtaining biological data containing at least an expression level of MX dynamin-like GTPase 1 (MX1) and an expression level of C-reactive protein (CRP) in the blood of a subject;

calculating by a hardware processor a distance between a segment of a curved line and an axis defined by a direction, said distance being calculated perpendicularly to said axis, between a point on said axis and a corresponding point over said curved line, said points being defined by a coordinate δ along said direction, wherein said coordinate δ, once calculated, equals $a_0+a_1X+a_2Z_{MX1}$, and wherein said X is a value of said CRP in μg/ml, and said $Z_{MX1}$ is a z-score of said MX1 relative to a group of subjects previously diagnosed with a bacterial infection;

storing said distance in a memory;

by said hardware processor, correlating said distance to the presence of, absence of, or likelihood that the subject has, a bacterial infection;

generating on a graphical user interface an output of said presence, absence or likelihood;

obtaining said likelihood based on said distance;

comparing said likelihood to a predetermined threshold; and treating the subject for said bacterial infection with an antibiotic agent when said likelihood is above said predetermined threshold;

wherein at least 90% of said segment is between a lower bound line $f(\delta)-\varepsilon_0$ and an upper bound line $f(\delta)+\varepsilon_1$, wherein said $f(\delta)$ equals $1/(1+\exp(-\delta))$, wherein each of said $\varepsilon_0$ and said $\varepsilon_1$ is less than 0.5, and wherein $a_0$ is from about −2.4 to about −1.9, $a_1$ is from about 0.04 to about 0.05, and $a_2$ is from about −0.39 to about −0.43.

2. The method according to claim 1, wherein at least one of said MX1 and said CRP is measured by an immunoassay.

3. The method according to claim 1, wherein at least one of said MX1 and CRP is measured by lateral flow immunoassay (LFIA).

4. The method according to claim 1, wherein at least one of said MX1 and CRP is measured by automated immunoassay.

5. The method according to claim 1, wherein at least one of said MX1 and CRP is measured by enzyme-linked immunosorbent assay (ELISA).

6. The method according to claim 1, being executed for distinguishing between a viral infection and a co-infection including both bacterial and viral infections.

7. The method according to claim 1, wherein said subject has an infection selected from the group consisting of a lower respiratory tract infection, and an upper respiratory tract infection.

8. The method according to claim 1, wherein said subject has a fever without identifiable source.

9. The method according to claim 1, wherein said subject has a serious bacterial infection.

10. The method according to claim 1, wherein said subject is suspected as having at least one of Adenovirus, Coronavirus, Parainfluenza virus, Influenza A, Influenza B, respiratory syncytial virus A, respiratory syncytial virus B, Bocavirus, Enterovirus, Cytomegalovirus (CMV)/Epstein bar virus (EBV).

11. The method according to claim 1, wherein said subject is suspected as having *Mycoplasma pneumoniae*.

12. The method according to claim 1, wherein said subject is suspected as having at least one of *E. coli*, Group A Strep.

13. The method according to claim 1, wherein said subject is suspected as having GI virus selected from the group consisting of Rota Virus, Astrovirus, Enteric Adenovirus, Norovirus G I and G II.

14. The method according to claim 1, wherein said subject is suspected as having at least one of *Streptococcus pneumoniae, Staphylococcus aureus* and lung disease.

15. The method according to claim 1, further comprising obtaining an expression level of Neutrophil gelatinase-associated lipocalin (NGAL), wherein said likelihood is based also on said expression level of said NGAL.

16. The method according to claim 1, further comprising obtaining an expression level of procalcitonin (PCT), wherein said likelihood is based also on said expression level of said PCT.

17. The method according to claim 1, wherein the subject has Chronic Obstructive Pulmonary Disease (COPD) and the method comprises determining whether said subject is in an infectious exacerbation state or a non-infectious exacerbation state.

18. The method according to claim 1, further comprising obtaining an age of the subject, and correcting said likelihood based on said age.

19. The method according to claim 1, wherein at least one of the expression levels is a protein expression level.

20. The method according to claim 1, wherein at least one of the expression levels is an RNA expression level.

21. The method according to claim 1, further comprising obtaining said likelihood based on said distance, comparing said likelihood to a predetermined threshold, and prescribing treatment to said subject based on said comparison.

22. The method according to claim 1, wherein the blood is a blood sample which is a fraction of whole blood.

23. The method according to claim 1, wherein said calculating and said correlating is executed by a computer remote from the subject.

24. The method according to claim 1, wherein said calculating and said correlating is executed by a computer near the subject.

25. The method according to claim 1, wherein said calculating and said correlating is executed by a cloud computing resource of a cloud computing facility.

26. The method according to claim 1, wherein said obtaining biological data comprises loading a blood sample of the subject onto a cartridge containing reagents for detecting CRP and MX1 in the blood sample, loading said cartridge to a system configured for measuring said expression levels from said cartridge, and receiving said expression levels from said system.

27. The method according to claim 1, further comprising obtaining an expression level of TNF Related Apoptosis Inducing Ligand (TRAIL), wherein said likelihood is based also on said expression level of said TRAIL.

28. A method of analyzing biological data, the method comprising:

obtaining biological data containing at least an expression level of MX dynamin-like GTPase 1 (MX1) and an expression level of C-reactive protein (CRP) in the blood of a subject;

calculating by a hardware processor a distance between a segment of a curved line and an axis defined by a direction, said distance being calculated perpendicularly to said axis, between a point on said axis and a corresponding point over said curved line, said points being defined by a coordinate δ along said direction, wherein said coordinate δ, once calculated, equals $a_0+a_1X+a_2Y$, and wherein said X is a value of said CRP in μg/ml, and said Y is a value of said MX1 in ng/ml;

storing said distance in a memory;

by said hardware processor, correlating said distance to the presence of, absence of, or likelihood that the subject has, a bacterial infection;

generating on a graphical user interface an output of said presence, absence or likelihood;

obtaining said likelihood based on said distance;

comparing said likelihood to a predetermined threshold; and treating the subject for said bacterial infection with an antibiotic agent when said likelihood is above said predetermined threshold;

wherein at least 90% of said segment is between a lower bound line $f(\delta)-\varepsilon_0$ and an upper bound line $f(\delta)+\varepsilon_1$, wherein said $f(\delta)$ equals $1/(1+\exp(-\delta))$, wherein each of said $\varepsilon_0$ and said $\varepsilon_1$ is less than 0.5, and wherein $a_0$ is from about 0.4 to about 0.5, $a_1$ is from about 0.015 to about 0.02, and $a_2$ is from about −0.0025 to about −0.0018.

29. A method of analyzing biological data, the method comprising:

obtaining biological data containing at least an expression level of MX dynamin-like GTPase 1 (MX1) and an expression level of C-reactive protein (CRP) in the blood of a subject;

calculating by a hardware processor a distance between a segment of a curved line and an axis defined by a direction, said distance being calculated perpendicularly to said axis, between a point on said axis and a corresponding point over said curved line, said points being defined by a coordinate δ along said direction, wherein said coordinate δ, once calculated, equals $a_0+a_1X+a_2Y$, and wherein said X is a value of said CRP in μg/ml, and said Y is a value of said MX1 when measured by flow cytometry;

storing said distance in a memory;

by said hardware processor, correlating said distance to the presence of, absence of, or likelihood that the subject has, a bacterial infection;

generating on a graphical user interface an output of said presence, absence or likelihood;

obtaining said likelihood based on said distance;

comparing said likelihood to a predetermined threshold; and treating the subject for said bacterial infection with an antibiotic agent when said likelihood is above said predetermined threshold;

wherein at least 90% of said segment is between a lower bound line $f(\delta)-\varepsilon_0$ and an upper bound line $f(\delta)+\varepsilon_1$, wherein said $f(\delta)$ equals $1/(1+\exp(-\delta))$, wherein each of said $\varepsilon_0$ and said $\varepsilon_1$ is less than 0.5, and wherein $a_0$ is from about −1.7 to about −1.4, $a_1$ is from about 0.03 to about 0.05, and $a_2$ is from about −5.8E-05 to about −4.7E-05.

* * * * *